United States Patent
Cooks et al.

(10) Patent No.: US 10,088,461 B2
(45) Date of Patent: Oct. 2, 2018

(54) ION GENERATION USING MODIFIED WETTED POROUS MATERIALS

(71) Applicant: Purdue Research Foundation, West Lafayette, IN (US)

(72) Inventors: Robert Graham Cooks, West Lafayette, IN (US); Zheng Ouyang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/710,072

(22) Filed: Sep. 20, 2017

(65) Prior Publication Data

US 2018/0017535 A1    Jan. 18, 2018

Related U.S. Application Data

(63) Continuation of application No. 15/359,031, filed on Nov. 22, 2016, now Pat. No. 9,797,872, which is a continuation of application No. 14/987,154, filed on Jan. 4, 2016, now Pat. No. 9,500,630, which is a continuation of application No. 14/512,579, filed on Oct. 13, 2014, now Pat. No. 9,230,792, which is a continuation of application No. 14/119,548, filed as application No. PCT/US2012/040521 on Jun. 1, 2012, now Pat. No. 8,895,918.

(60) Provisional application No. 61/492,933, filed on Jun. 3, 2011, provisional application No. 61/492,937, filed
(Continued)

(51) Int. Cl.
*H01J 49/00* (2006.01)
*G01N 30/95* (2006.01)
*G01N 33/49* (2006.01)
*G01N 30/91* (2006.01)

(52) U.S. Cl.
CPC ............. *G01N 30/95* (2013.01); *G01N 30/91* (2013.01); *G01N 33/49* (2013.01); *H01J 49/0031* (2013.01)

(58) Field of Classification Search
CPC ...... H01J 49/04; H01J 49/0431; H01J 27/022; G01N 2001/028; G01N 2035/00108
USPC ............. 250/281, 282, 288, 423 R, 424, 425
See application file for complete search history.

(56) References Cited

U.S. PATENT DOCUMENTS 8,895,918 B2 * 11/2014 Cooks .................. H01J 49/168
250/281
2008/0315083 A1 * 12/2008 Lubda ................ G01N 30/7266
250/288
(Continued)

FOREIGN PATENT DOCUMENTS

WO    WO 2010127059 A1 *  11/2010    .......... H01J 49/0431
WO    WO 2012170301 A1 *  12/2012    .......... H01J 49/0431

*Primary Examiner* — Michael Maskell
(74) *Attorney, Agent, or Firm* — Brown Rudnick LLP; Adam M. Schoen

(57) ABSTRACT

The invention generally relates to ion generation using modified wetted porous materials. In certain aspects, the invention generally relates to systems and methods for ion generation using a wetted porous substrate that substantially prevents diffusion of sample into the substrate. In other aspects, the invention generally relate to ion generation using a wetted porous material and a drying agent. In other aspects, the invention generally relates to ion generation using a modified wetted porous substrate in which at least a portion of the porous substrate includes a material that modifies an interaction between a sample and the substrate.

16 Claims, 91 Drawing Sheets

Related U.S. Application Data on Jun. 3, 2011, provisional application No. 61/492,947, filed on Jun. 3, 2011.

(56) References Cited

U.S. PATENT DOCUMENTS

| | | | |
|---|---|---|---|
| 2010/0035245 A1* | 2/2010 | Stiene | B01L 3/502707 435/6.12 |
| 2010/0075359 A1* | 3/2010 | Toranto | C12Q 1/26 435/28 |
| 2011/0210265 A1* | 9/2011 | Lozano | F03H 1/0012 250/423 R |
| 2012/0119079 A1* | 5/2012 | Ouyang | H01J 49/0431 250/282 |
| 2013/0330714 A1* | 12/2013 | Cooks | C12Q 1/04 435/5 |
| 2014/0008529 A1* | 1/2014 | Ouyang | H01J 49/0431 250/282 |
| 2014/0008532 A1* | 1/2014 | Ouyang | H01J 49/0431 250/287 |
| 2014/0054809 A1* | 2/2014 | Lozano | H01J 37/08 264/28 |
| 2014/0234891 A1* | 8/2014 | Mao | A61B 10/0045 435/30 |
| 2017/0125228 A1* | 5/2017 | Bango | H01J 49/0445 |

* cited by examiner

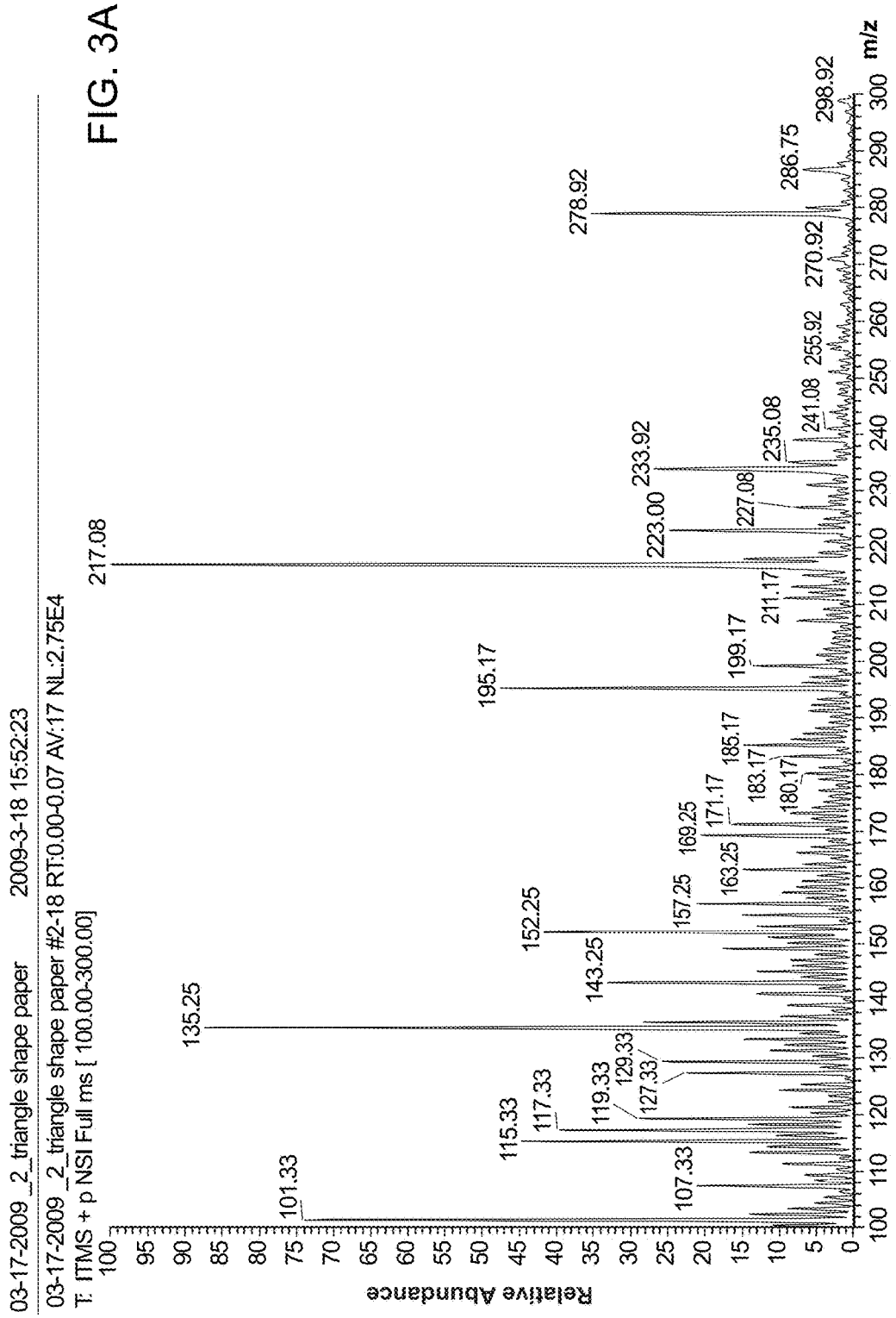

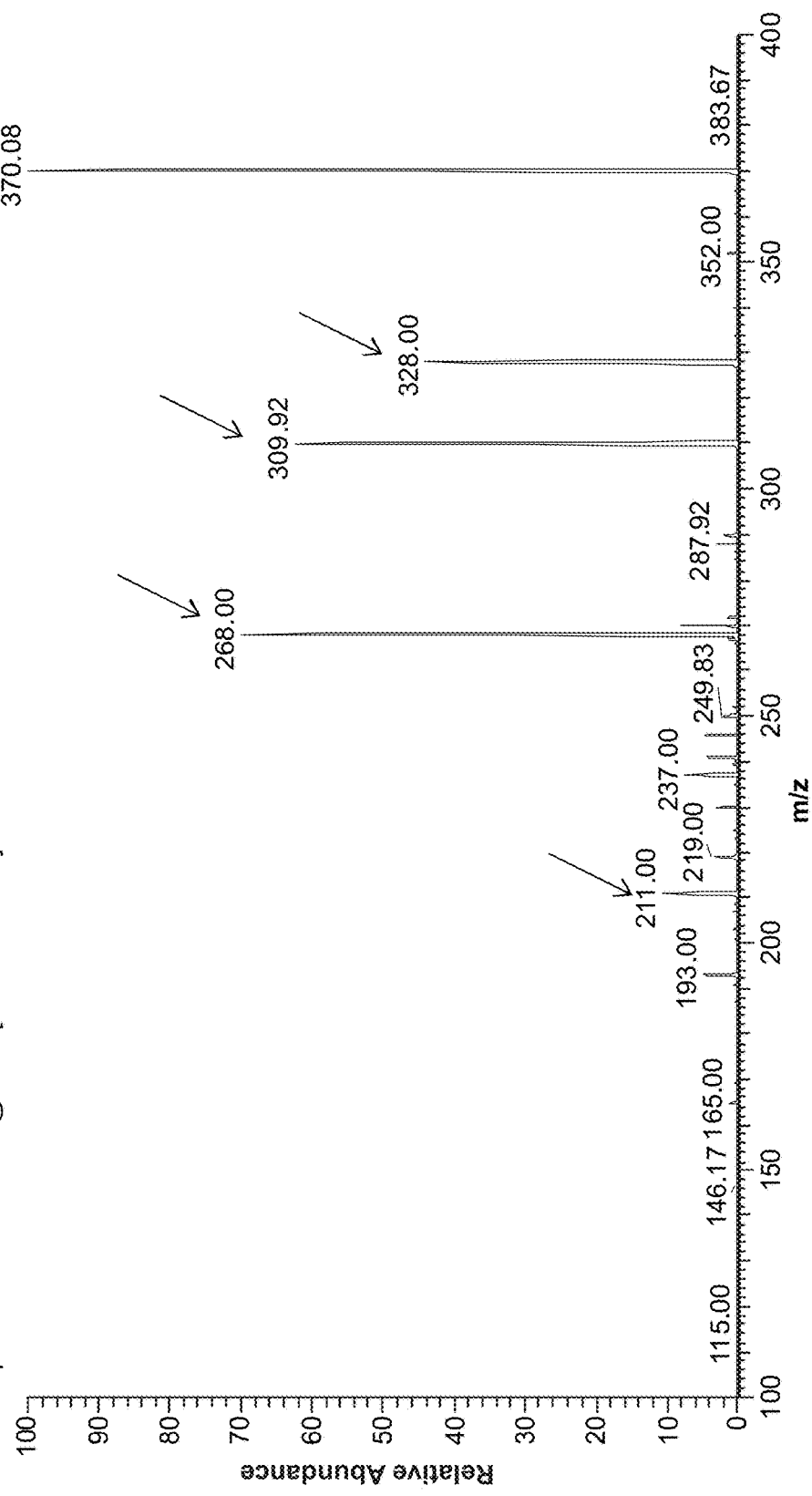

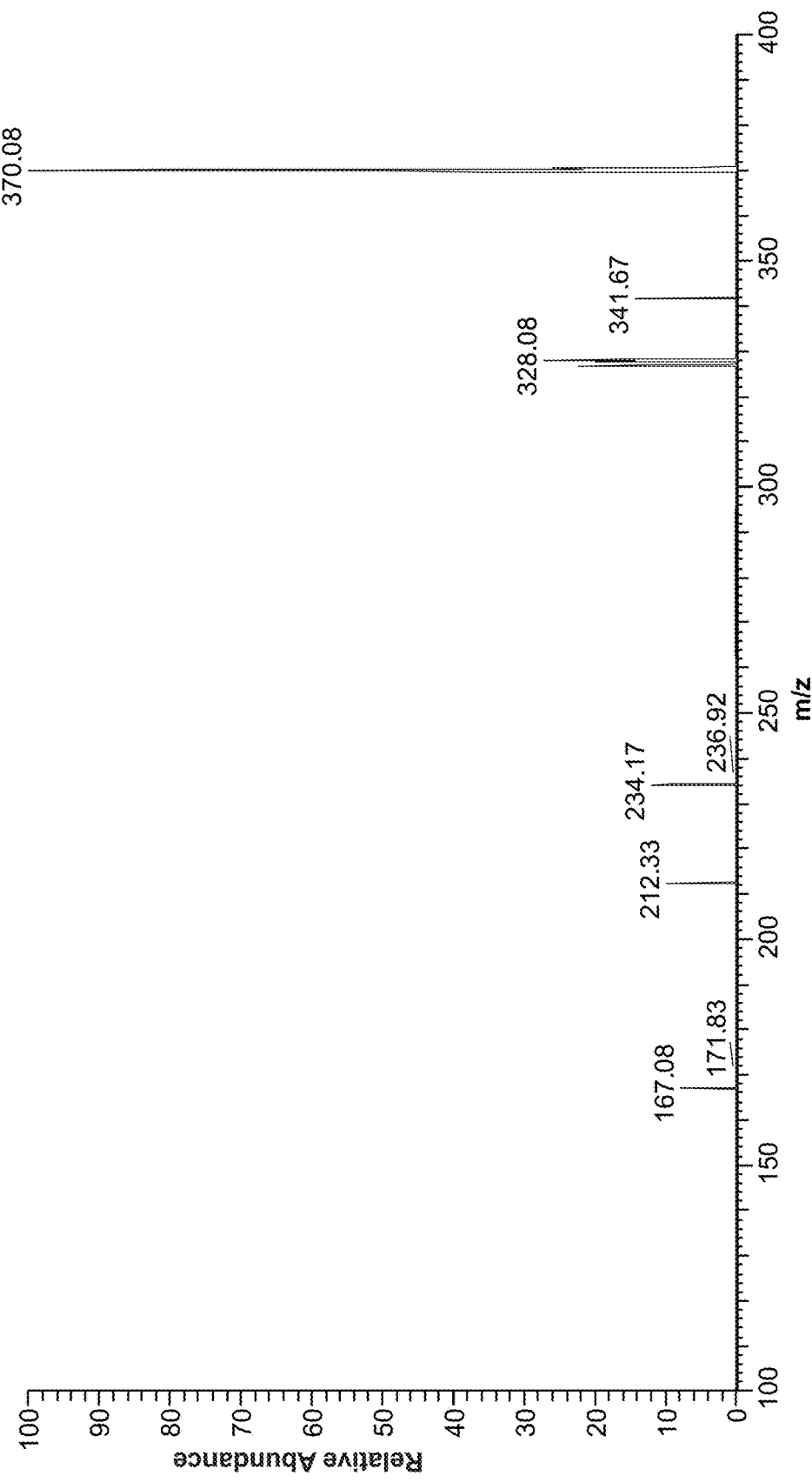

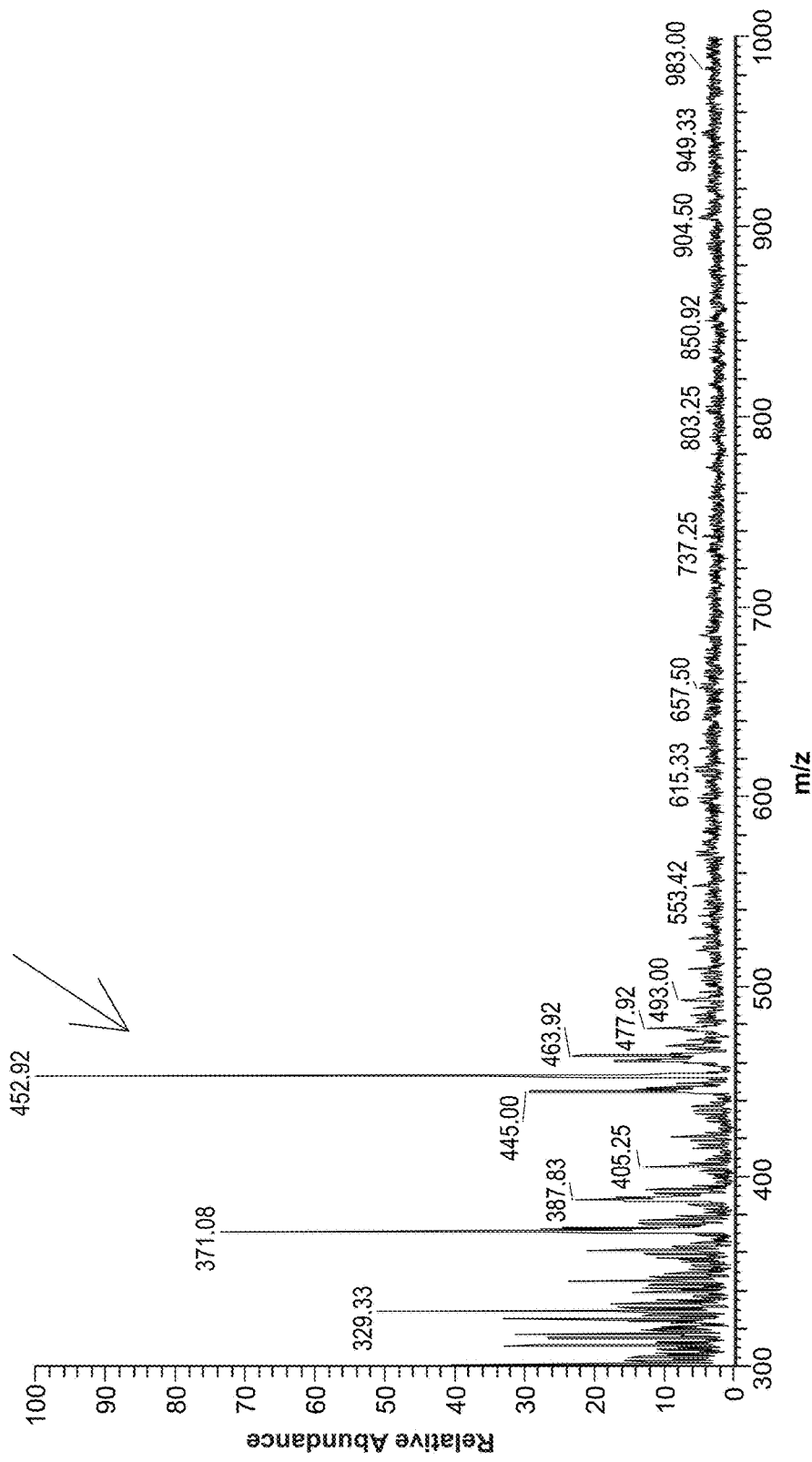

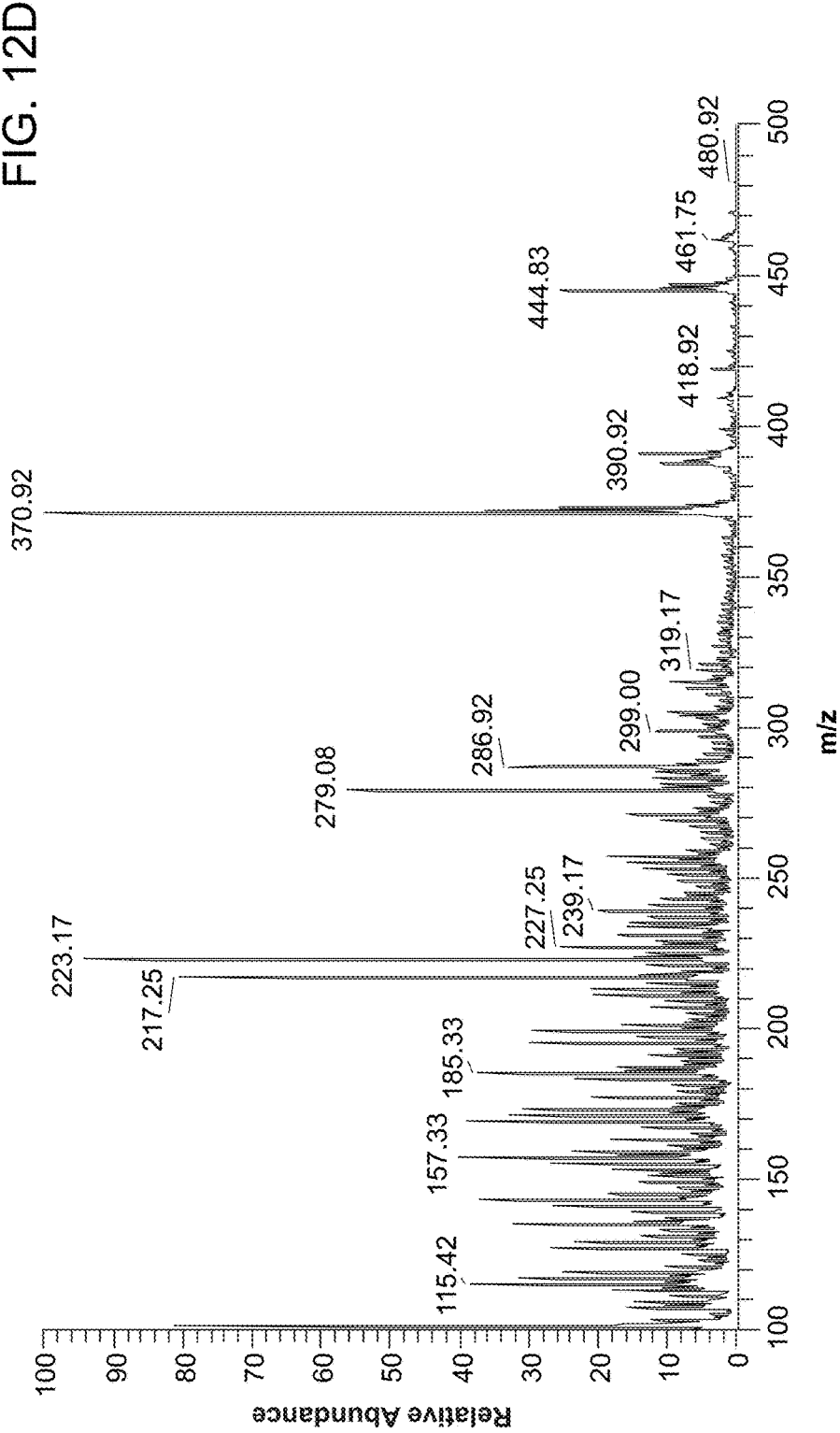

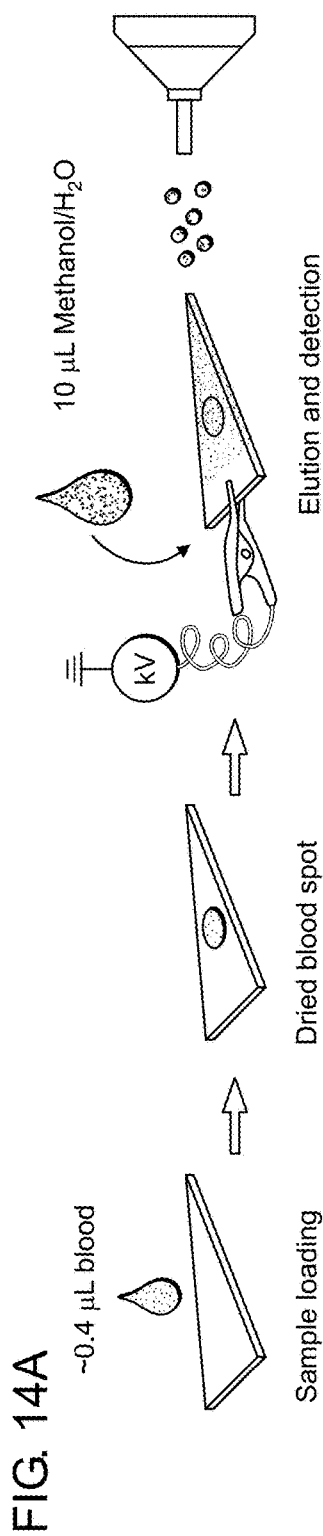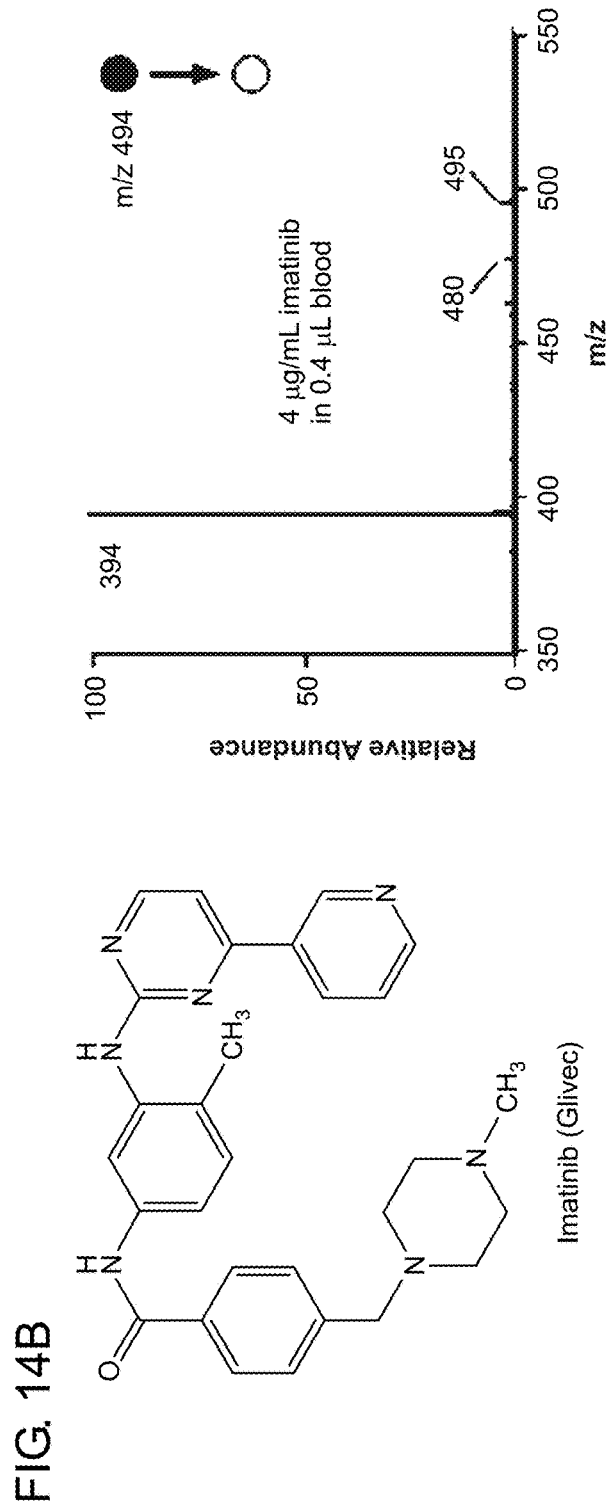
FIG. 14A
FIG. 14B

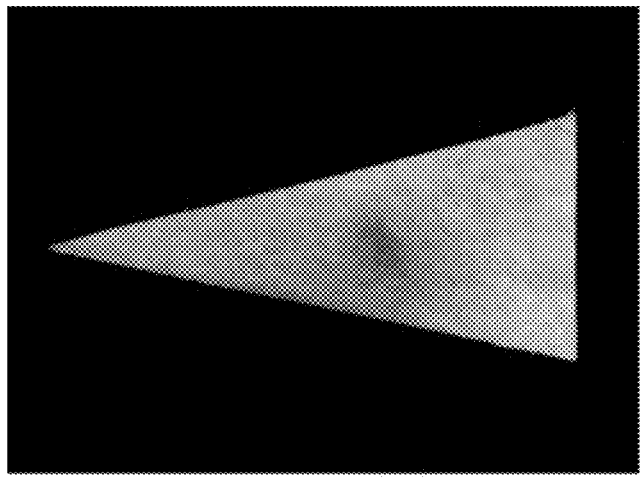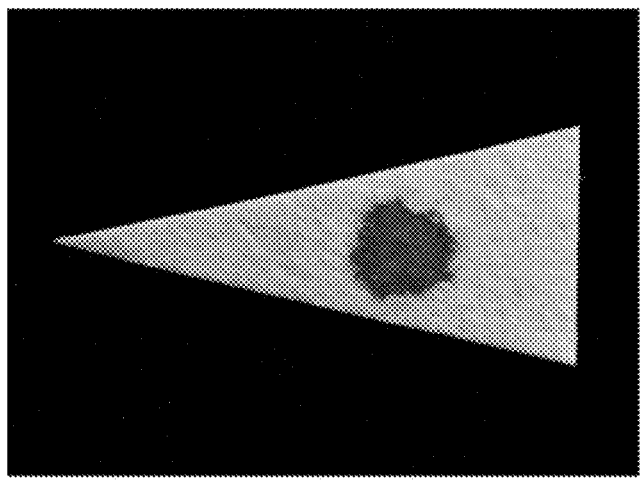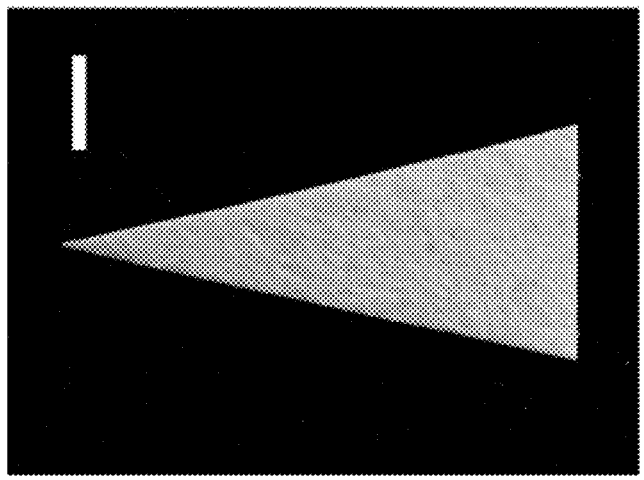
FIG. 23A

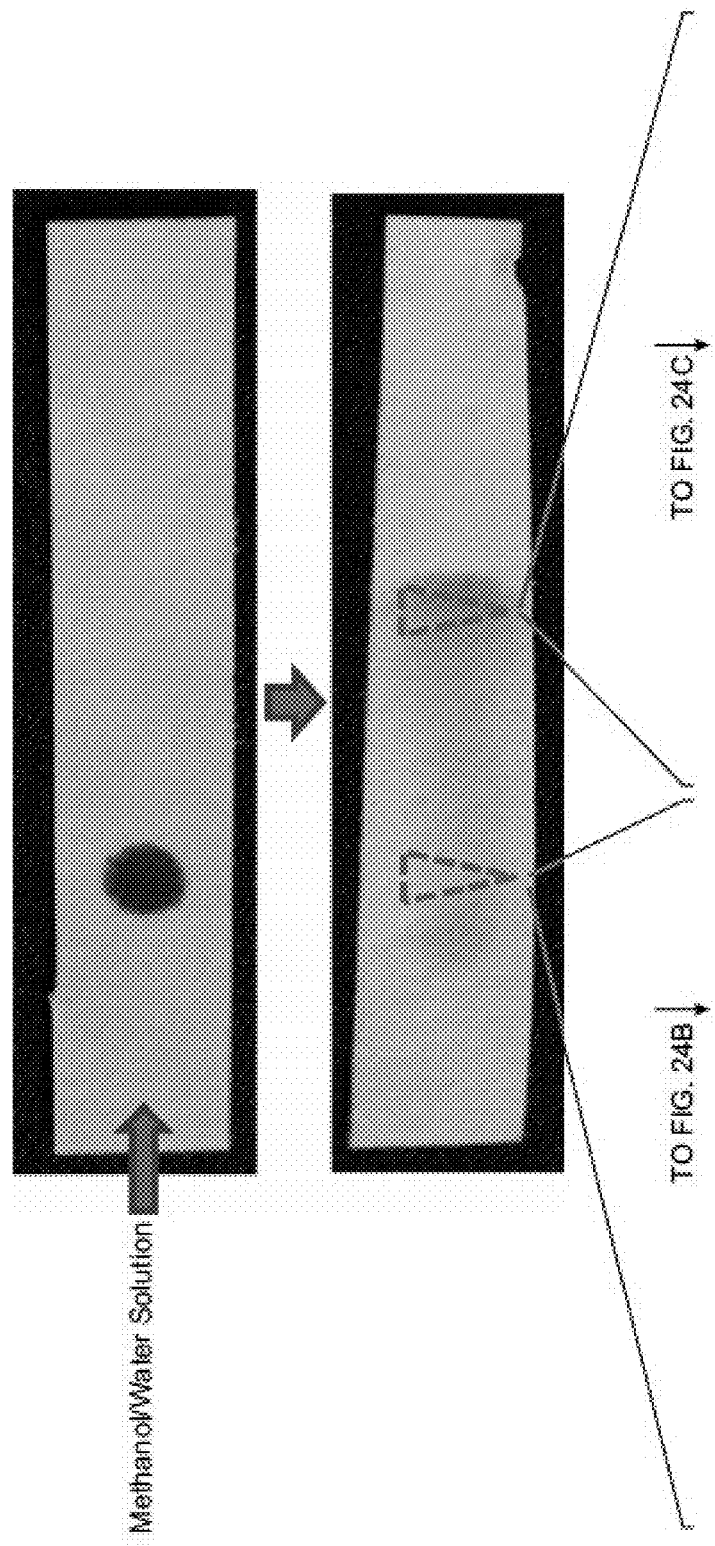

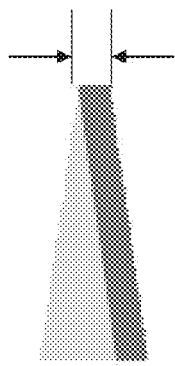
FIG. 25C
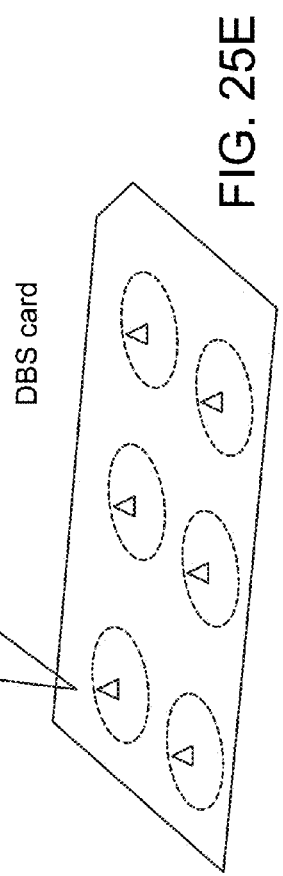
FIG. 25E
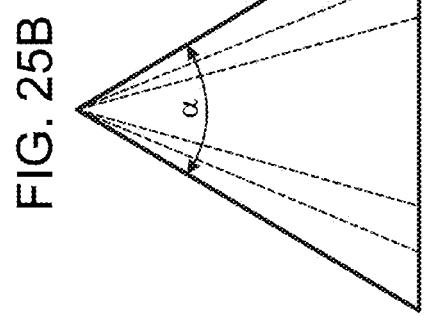
FIG. 25B
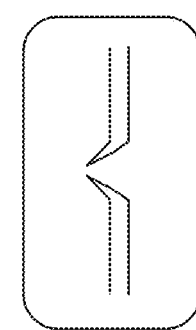
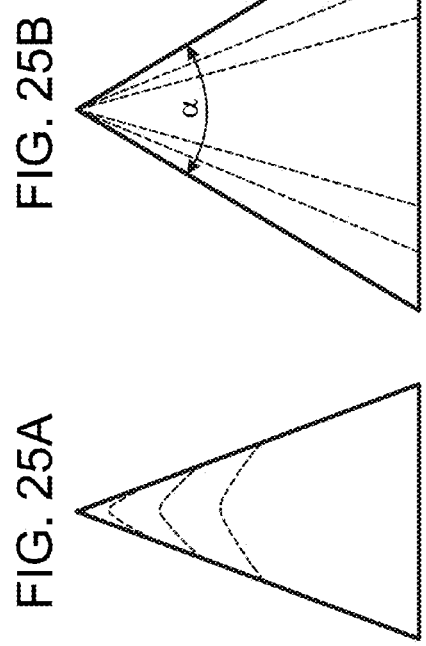
FIG. 25A
FIG. 25D

| tip1 | tip2 | tip3 | tip4 | tip5 | tip6 |
|------|------|------|------|------|------|
| Blank | Cocaine | Blank | Caffeine | Blank | Cocaine |

FIG. 29C  Lipids on tumor section
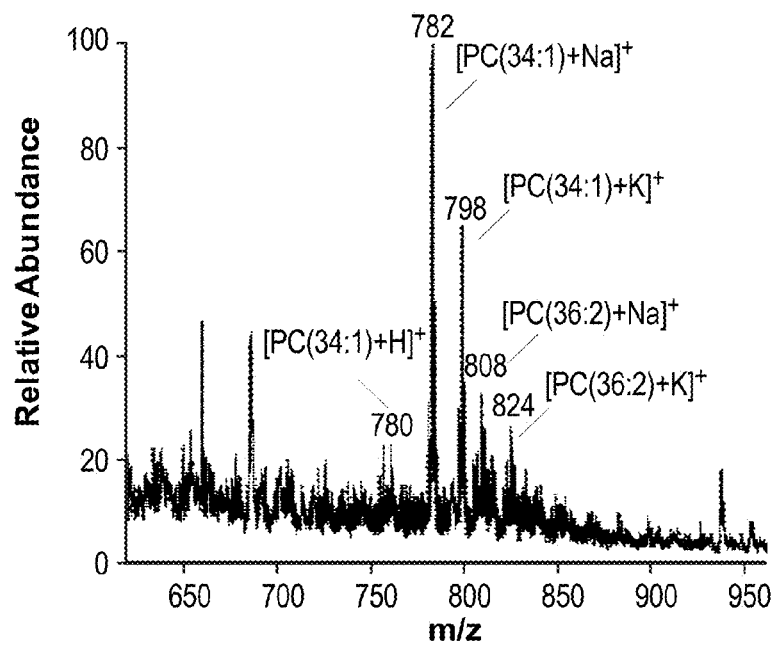
FIG. 29D  Lipids on non-tumor section
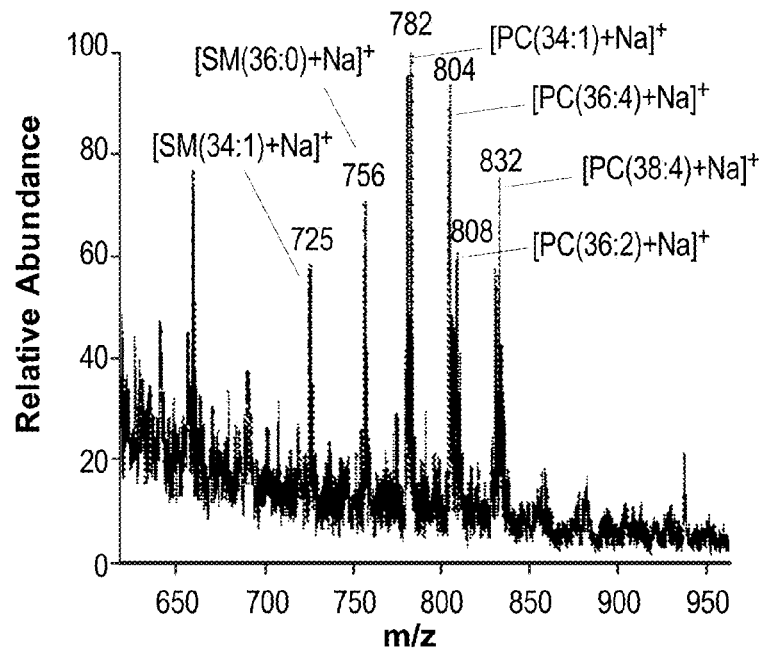

Drop the blood

Volume Control by overflowing

Dissolving IS membrane

DBS w/ IS on paper

FIG. 34A
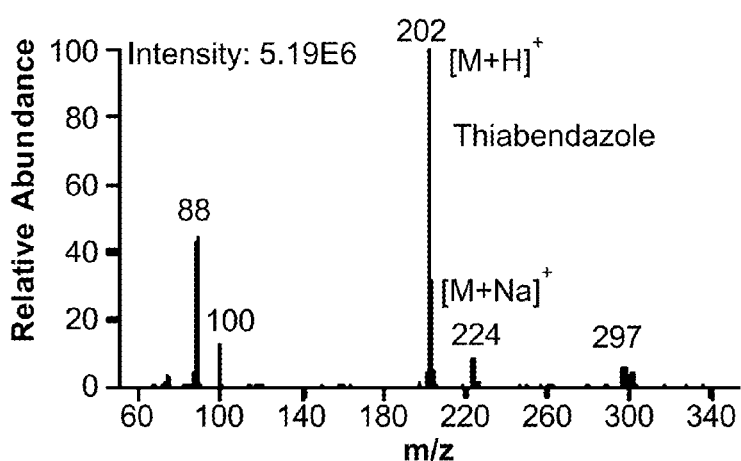
FIG. 34B
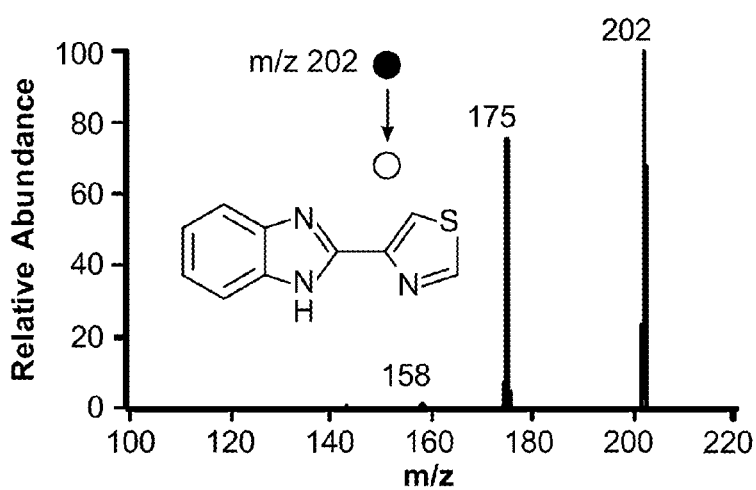
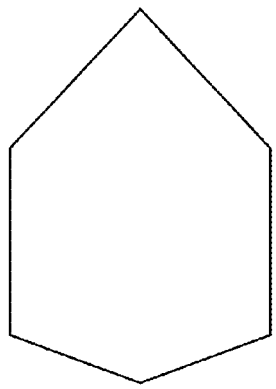
FIG. 35

Spot Blood → Apply Solvent

Load Drying Agent → Spot Blood → Apply Solvent

● MgSO4, 2 mins
□ Air Dry, 2 hrs

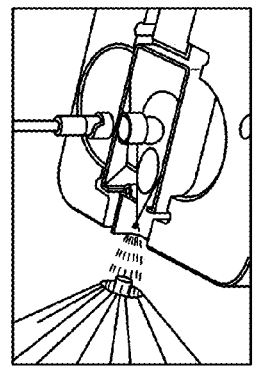
4. Spot Blood, Perform Paper Spray
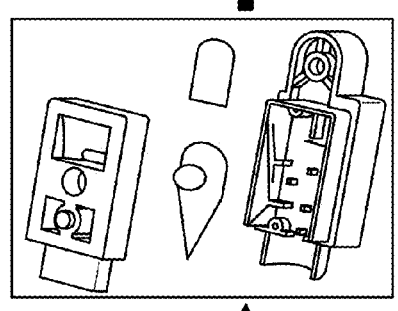
3. Cut paper and load into cartridge
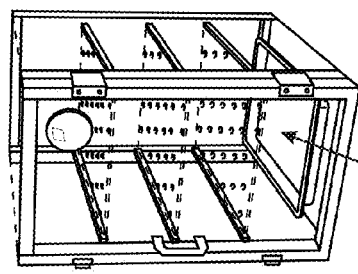
2. Store paper in desiccator
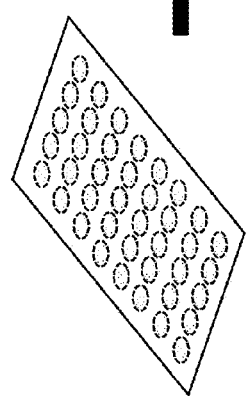
1. Pre-load paper with drying agent and internal standard
FIG. 39

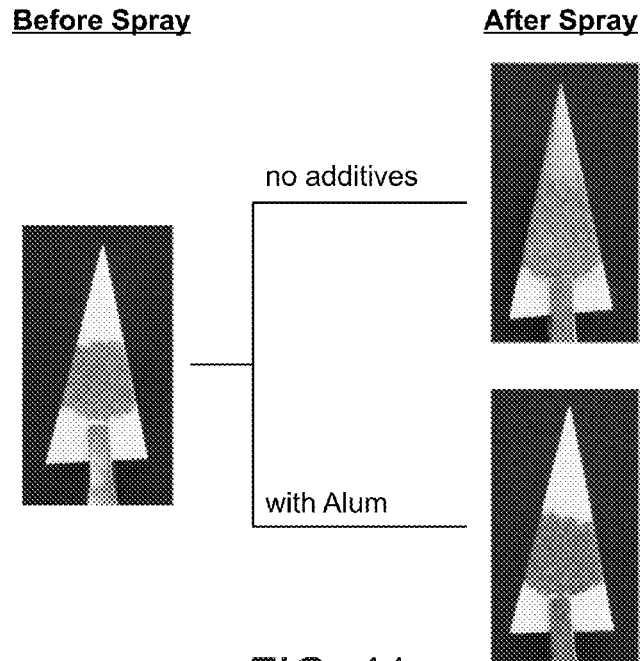
FIG. 41
FIG. 42A
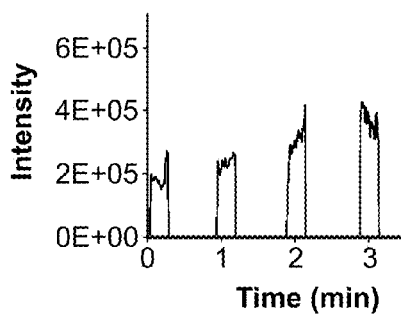
FIG. 42B
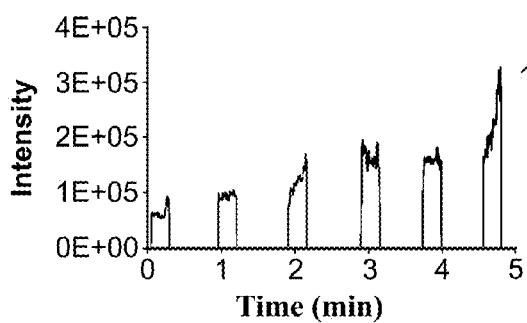
FIG. 42C
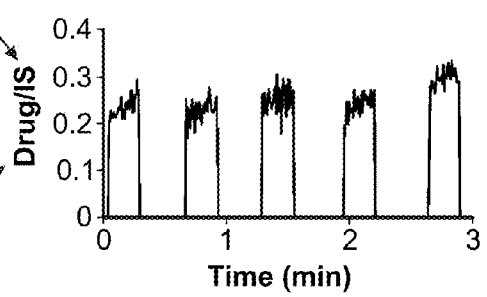

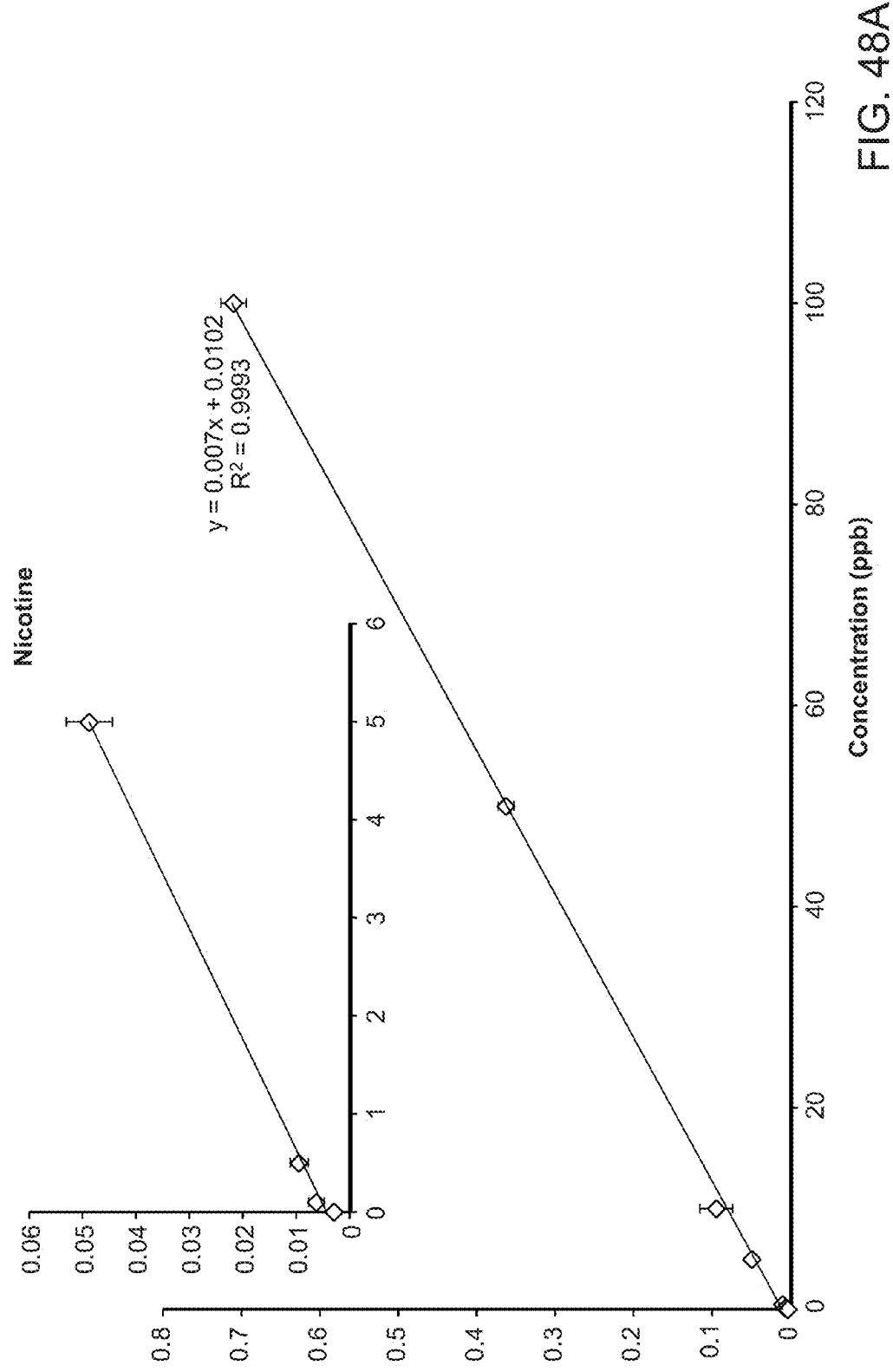

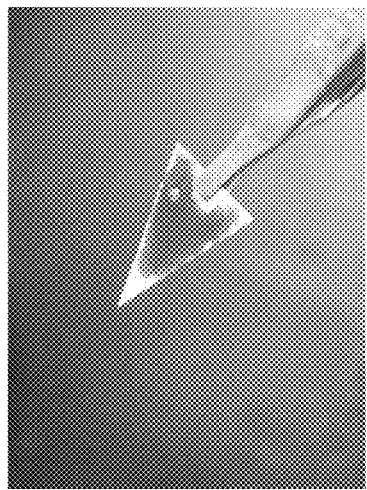
FIG. 52B Before spray
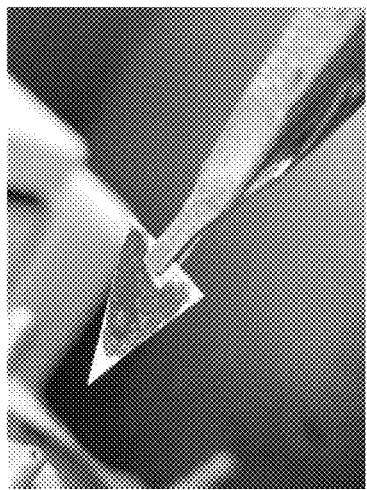
FIG. 52D After spray
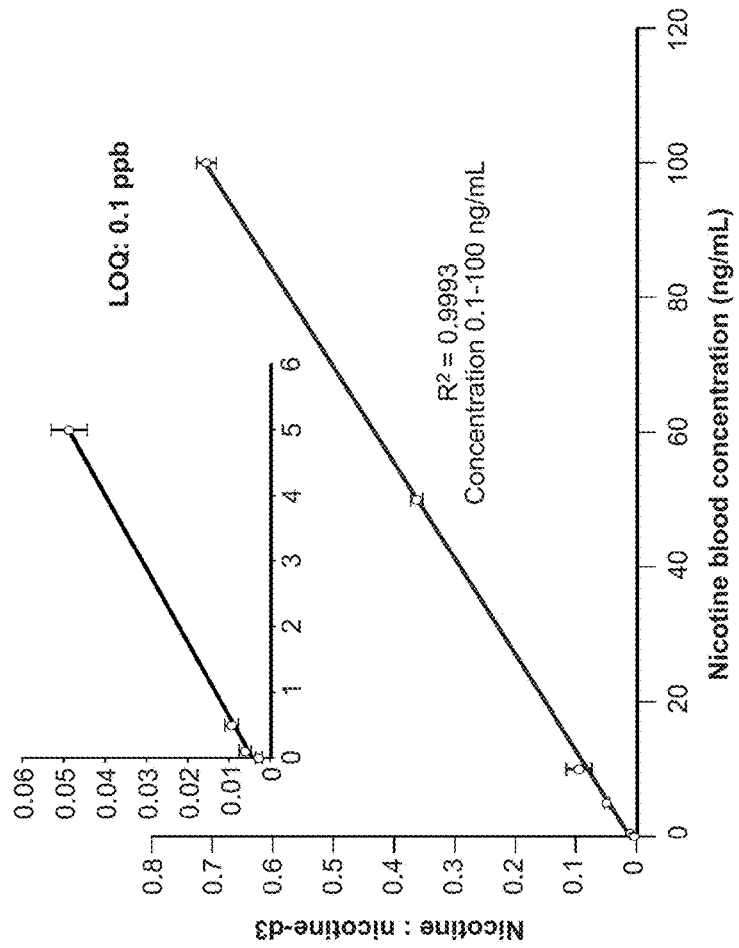
FIG. 52C

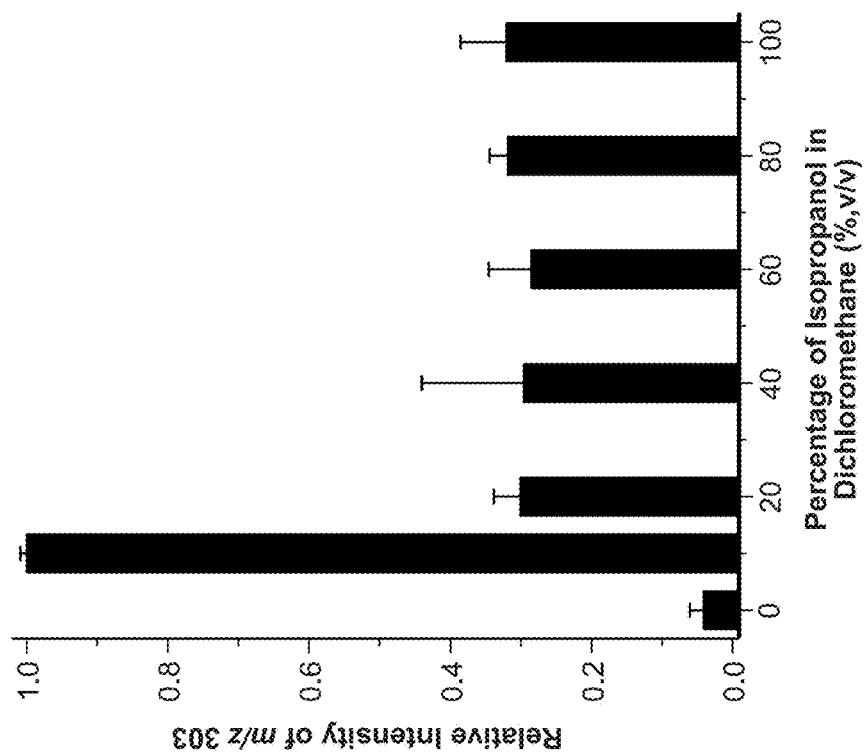
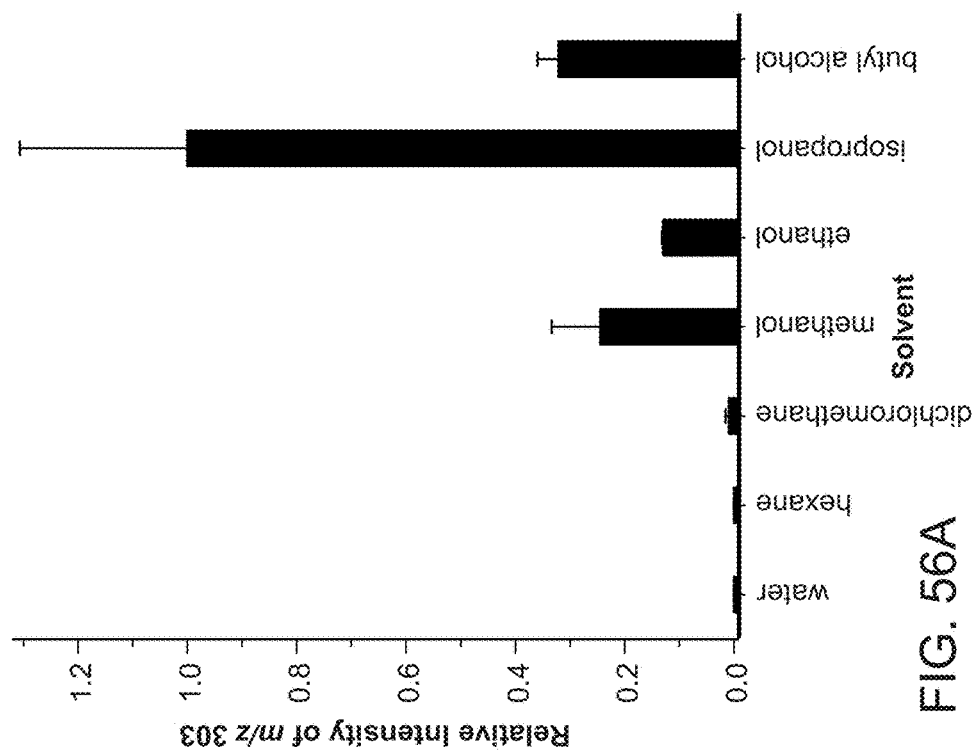
FIG. 56B
FIG. 56A

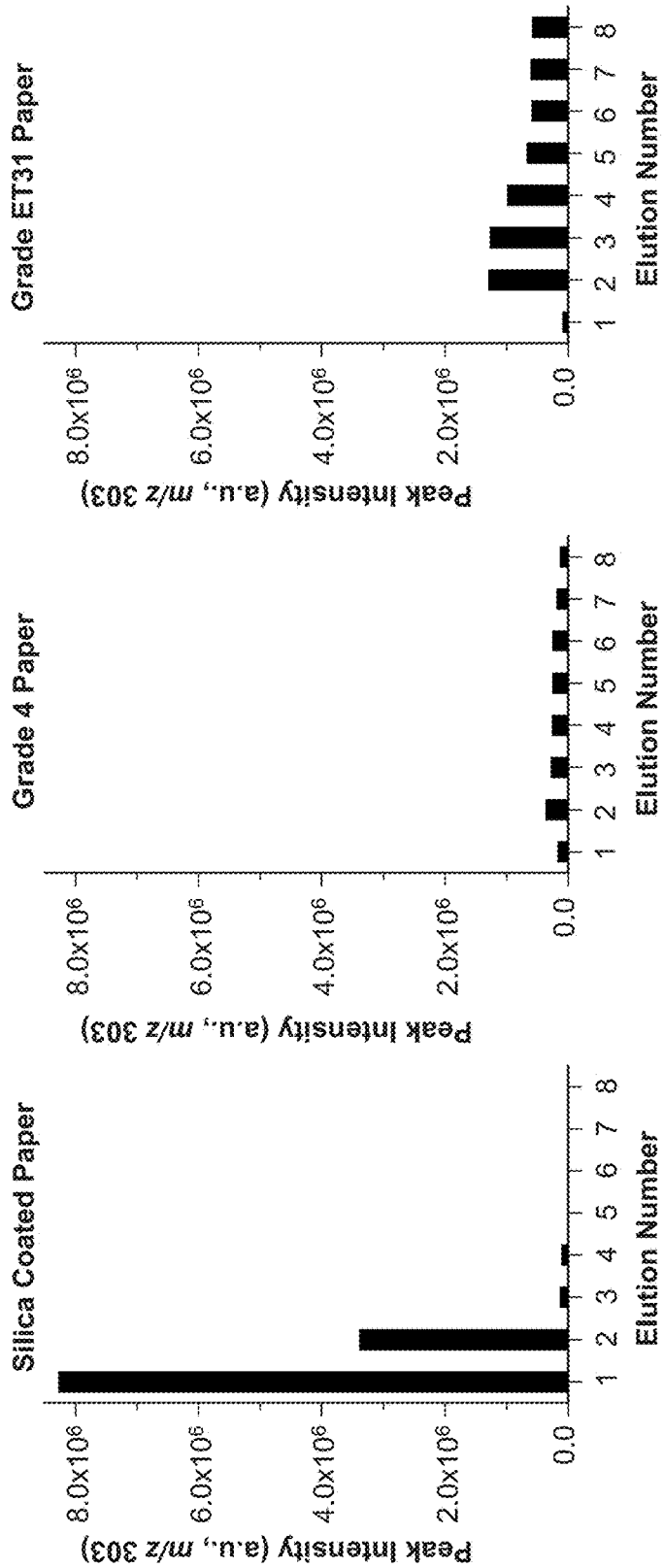

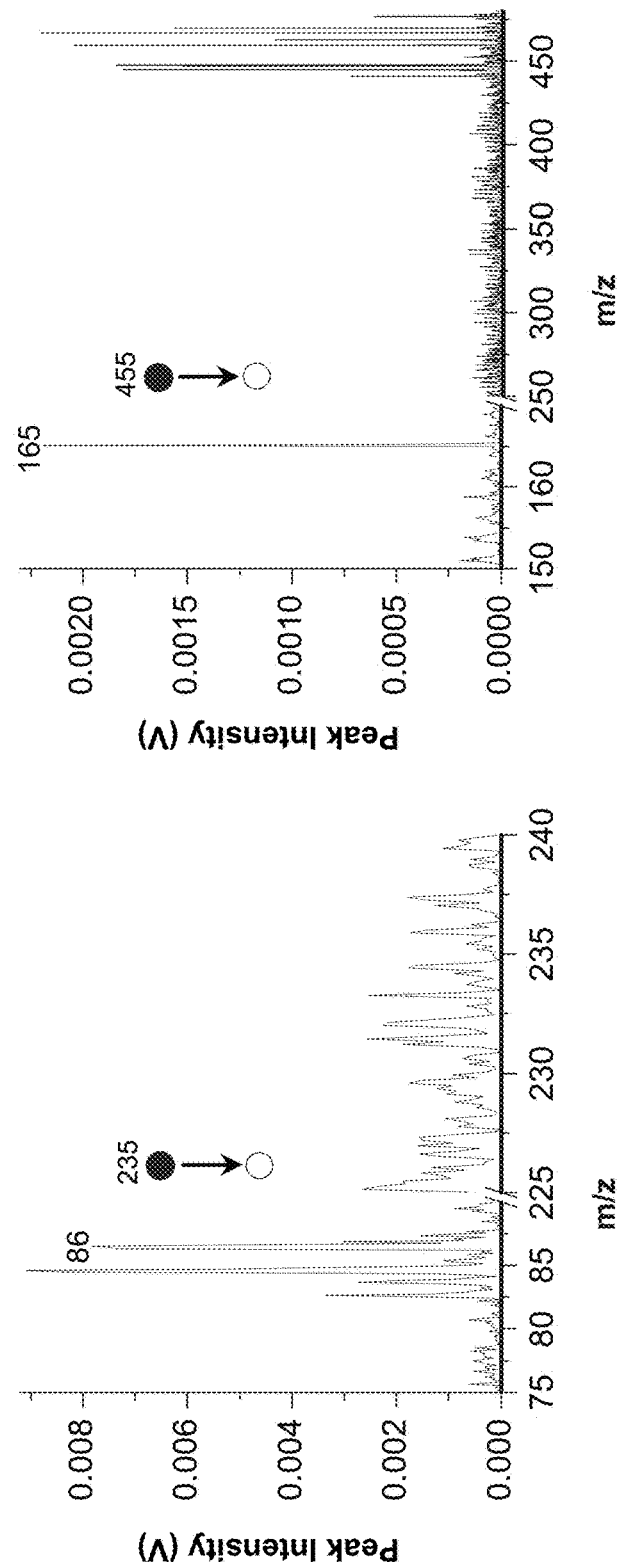

ION GENERATION USING MODIFIED WETTED POROUS MATERIALS

RELATED APPLICATIONS

The present application is a continuation of U.S. nonprovisional application Ser. No. 15/359,031, filed Nov. 22, 2016, which is a is a continuation of U.S. nonprovisional application Ser. No. 14/987,154, filed Jan. 4, 2016, which is a is a continuation of U.S. nonprovisional application Ser. No. 14/512,579, filed Oct. 13, 2014, which is a continuation of U.S. nonprovisional application Ser. No. 14/119,548, filed Nov. 22, 2013, which is a 35 U.S.C. § 371 national phase application of PCT application number PCT/US12/40521, filed Jun. 1, 2012, which claims the benefit of and priority to U.S. provisional patent application Ser. No. 61/492,933, filed Jun. 3, 2011, U.S. provisional patent application Ser. No. 61/492,937, filed Jun. 3, 2011, and U.S. provisional patent application Ser. No. 61/492,947, filed Jun. 3, 2011, the content of each of which is incorporated by reference herein in its entirety.

GOVERNMENT INTEREST

This invention was made with government support under RR031246 and EB009459 awarded by the National Institutes of Health. The government has certain rights in the invention.

TECHNICAL FIELD

The invention generally relates to systems and methods for mass spectrometry analysis of samples.

BACKGROUND

Biofluids (e.g., complex mixtures such as blood, saliva, or urine) are routinely separated using chromatography before the MS measurement in order to minimize suppression effects on analyte ionization and to pre-concentrate the analytes. Recently, systems and methods have been developed that allow for sample preparation and pre-treatment to be combined with the ionization process (See Ouyang et al., WO 2010/127059).

These systems and methods use wetted porous material, named paper spray ionization, for direct, qualitative and quantitative analysis of complex biofluids ("paper spray"). Analyte transport is achieved by wicking in a porous material with a macroscopically sharp point and a high electric field is used to perform ionization and chemical analysis of compounds present in biological samples. Pneumatic assistance is not required to transport the analyte: a voltage is simply applied to the wet paper, held in front of a mass spectrometer.

SUMMARY

The inventions herein generally relate to various modifications to the wetted porous material used in the paper spray process described above. Such modified substrates lend themselves to more efficient analysis of certain samples as well as improved analytical results for those samples.

In certain aspects, the invention generally relates to systems and methods for ion generation using a wetted porous substrate that substantially prevents diffusion of sample into the substrate. Paper spray has been applied for analysis of biofluids, such as dried blood spots. Generally, the whole blood is deposited onto hydrophilic chromatography paper and dried to form a dried blood spot. The liquid blood is hydrophilic, and when it is dropped onto a hydrophilic porous sample substrate, such as chromatography paper, the fresh blood sample diffuses into the substrate. When the whole blood is dried on the paper substrate, the microstructure of the paper substrate is modified. During the paper spray, the efficiency of the extraction of chemical from the dried blood spot is limited.

In these embodiments, systems and methods of the invention limit or prevent interaction of the sample with a porous substrate, thus allowing efficient transfer of the sample through the substrate for analysis. In these embodiments, the invention provides a mass spectrometry probe including at least one porous substrate connected to a high voltage source, in which the porous substrate includes a material that substantially prevents diffusion of a sample into the substrate. In certain embodiments, the porous substrate is discrete from a flow of solvent. The substrate may have any shape, although shapes having sharp points are preferred. Exemplary shapes include triangles or cones. The material for the porous substrate will depend on the properties of the sample to be analyzed. For example, when the sample is hydrophilic, the substrate is less hydrophilic than the sample. Alternatively, when the sample is hydrophobic, the substrate is less hydrophobic than the sample. An exemplary substrate for analyzing a biological fluid is silanized paper.

In other embodiments, the probe further includes a discrete amount of a solvent, e.g., a droplet or droplets, applied to the porous substrate. The solvent is capable of diffusing into the substrate. The solvent is applied as a droplet or droplets, and in an amount sufficient to wet the porous substrate. Once applied to the porous substrate, the solvent can assist transport of the sample through the porous material. The solvent can contain an internal standard. The solvent/substrate combination can allow for differential retention of sample components with different chemical properties. In certain embodiments, the solvent minimizes salt and matrix effects. In other embodiments, the solvent includes chemical reagents that allow for on-line chemical derivatization of selected analytes.

In another embodiment, the invention provides a system for analyzing a sample material including at least one porous substrate connected to a high voltage source, in which the porous substrate includes a material that substantially prevents diffusion of a sample into the substrate, and a mass analyzer. In certain embodiments, the porous substrate is discrete from a flow of solvent. The mass analyzer is for a mass spectrometer or a handheld mass spectrometer. Exemplary mass analyzers include a quadrupole ion trap, a rectalinear ion trap, a cylindrical ion trap, a ion cyclotron resonance trap, an orbitrap, a time of flight, a Fourier Transform ion cyclotron resonance, and sectors.

Another embodiment of the invention provides a method for analyzing a sample that involves contacting a sample to a porous substrate, in which the porous substrate includes a material that substantially prevents diffusion of the sample into the substrate, applying a solvent that is capable of diffusing into the substrate to the sample, resulting in diffusion of components of the sample into the substrate, applying a high voltage to the substrate to generate ions of the components that are expelled from the porous substrate, and analyzing the expelled ions. In certain embodiments, the porous substrate is kept separate from a flow of solvent. Exemplary samples include chemical species or biological species. In certain embodiments, the sample is a biological fluid, e.g., complex mixtures such as blood, saliva, or urine.

In certain embodiments, the solvent is capable of mixing with the sample. In other embodiments, the solvent is not capable of mixing with the sample but is capable of extracting the components from the sample. In certain embodiments, prior to applying the high voltage, the method further involves drying the substrate. In certain embodiments, analyzing involves providing a mass analyzer to generate a mass spectrum of analytes in the sample.

Another embodiment of the invention provides a method for analyzing blood that involves contacting a blood sample to a porous substrate, in which the porous substrate includes a material that substantially prevents diffusion of the blood sample into the substrate, applying to the blood sample a solvent that is capable of diffusing into the substrate, resulting in diffusion of components of the blood sample into the substrate, applying a high voltage to the substrate to generate ions of the components that are expelled from the porous substrate, and analyzing the expelled ions. In certain embodiments, the porous substrate is kept separate from a flow of solvent. In certain embodiments, the solvent is capable of mixing with the blood sample. In other embodiments, the solvent is not capable of mixing with the blood sample but is capable of extracting the components (e.g., proteins) from the blood sample. In certain embodiments, prior to applying the high voltage, the method further involves drying the substrate to produce a dried blood spot.

Another embodiment of the invention provides a method for analyzing a protein from a blood sample that involves contacting a blood sample comprising at least one protein to a porous substrate, in which the porous substrate includes a material that substantially prevents diffusion of the blood sample into the substrate, applying to the blood sample a solvent that is capable of diffusing into the substrate, resulting in diffusion of the protein into the substrate, applying a high voltage to the substrate to generate ions of the protein that are expelled from the porous substrate, and analyzing the expelled ions. In certain embodiments, the porous substrate is kept separate from a flow of solvent.

Other aspects of the invention generally relate to ion generation using a wetted porous material and a drying agent. As previously mentioned, paper spray has been applied for analysis of biofluids, such as dried blood spots. One current method for analyzing a dried blood spot involves spotting 15 microliters of drug-spiked blood onto Whatman 31ETF card paper, and allowing it to air dry for at least 2 hours. This drying time is important, otherwise the blood can run through the paper during analysis, thus reducing the efficiency of the paper spray.

These aspects of the invention combine a drying agent with the porous substrate used in paper spray in order to rapidly dry a sample that is applied to the substrate. Rapid drying decreases waiting time and allows for sample analysis within approximately two to five minutes of applying a sample to the substrate. With respect to analysis of biological fluids, probes, systems, and methods of the invention provide a point-of-care device for rapid and convenient use. In a particular embodiment, probes, systems, and methods of the invention use anhydrous salts to dry and thus restrict flow of liquid blood during paper spray analysis.

In certain embodiments, the invention provides a mass spectrometry probe including at least one porous substrate connected to a high voltage source, in which the porous substrate includes a drying agent. Any drying agent that is compatible with the sample and does not interfere with analysis by mass spectrometry may be used. An exemplary drying agent is an anhydrous salt. In certain embodiments, the porous substrate also includes an internal standard.

In certain embodiments, the porous substrate is discrete (i.e., separate or disconnected from) from a flow of solvent. Instead, a sample is either spotted onto the porous substrate or the porous substrate is wetted and used to swab a surface containing the sample. The porous substrate with spotted or swabbed sample is then wetted and connected to a high voltage source to produce ions of the sample which are subsequently analyzed. The sample is transported through the porous substrate without the need of a separate solvent flow.

Probes, systems, and methods of the invention combine sample preparation and pre-treatment with the ionization process needed for mass analysis of samples. Probes, systems, and methods of the invention allow for rapid and direct analysis of chemicals in raw biological samples of complex matrices, such as biofluids and tissues, without sample preparation. In particular embodiments, probes, systems, and methods of the invention allow for the analysis of a dried spots of blood or urine.

Exemplary porous materials include paper, e.g., filter paper, or PVDF membrane. The porous material can be of any shape. In certain embodiments, the porous material is provided as a triangular piece or cone.

In certain embodiments, the probe further includes a discrete amount of a solvent, e.g., a droplet or droplets, applied to the porous material. The solvent is applied as a droplet or droplets, and in an amount sufficient to wet the porous material. Once applied to the porous material, the solvent can assist transport of the sample through the porous material. The solvent can contain an internal standard. The solvent/substrate combination can allow for differential retention of sample components with different chemical properties. In certain embodiments, the solvent minimizes salt and matrix effects. In other embodiments, the solvent includes chemical reagents that allow for on-line chemical derivatization of selected analytes.

Another embodiment of the invention provides a system for analyzing a sample material including at least one porous substrate connected to a high voltage source, in which the porous substrate includes a drying agent, and a mass analyzer. In certain embodiments, the porous substrate is discrete from a flow of solvent. The mass analyzer is for a mass spectrometer or a handheld mass spectrometer. Exemplary mass analyzers include a quadrupole ion trap, a rectalinear ion trap, a cylindrical ion trap, a ion cyclotron resonance trap, an orbitrap, a time of flight, a Fourier Transform ion cyclotron resonance, and sectors.

Another embodiment of the invention provides a method for analyzing a sample that involves contacting a sample to a porous substrate, in which the porous substrate includes a drying agent, applying a high voltage to the porous material to generate ions of an analyte in the sample that are expelled from the porous material, and analyzing the expelled ions. In certain embodiments, the porous substrate is kept separate from a flow of solvent. In certain embodiments, methods of the invention further involve, prior to applying the high voltage, drying the substrate. In certain embodiments, methods of the invention further involve applying a solvent to the substrate. The solvent is applied as a droplet or droplets, and in an amount sufficient to wet the porous material. Once applied to the porous material, the solvent can assist transport of the sample through the porous material. In certain embodiments, analyzing involves providing a mass analyzer to generate a mass spectrum of analytes in the sample. Exemplary samples include chemical species or biological species. In certain embodiments, the sample is a biological fluid, e.g., complex mixtures such as blood, saliva, or urine.

Another embodiment of the invention involves contacting a blood sample to a porous substrate, in which the porous substrate includes a drying agent, drying the blood sample on the substrate, applying a solvent to the substrate, applying a high voltage to the substrate to generate ions of the components that are expelled from the porous substrate, and analyzing the expelled ions. In certain embodiments, applying the solvent and the high voltage occur simultaneously. In certain embodiments, applying the solvent and the high voltage occur sequentially.

Other aspects of the invention generally relate to ion generation using a modified wetted porous substrate. These aspects of the invention recognize that the porous material used in paper spray plays an important role in determining the resolution of target compounds from complex samples and also in determining the transfer efficiency of analyte ions. Accordingly, embodiments of the invention provide a mass spectrometry probe that includes at least one porous substrate connected to a high voltage source, in which at least a portion of the porous substrate includes a material that modifies an interaction between a sample and the substrate. In certain embodiments, the porous substrate is discrete from a flow of solvent. Exemplary porous substrates include paper, e.g., filter paper, or PVDF membrane. The porous material can be of any shape. In certain embodiments, the porous material is provided as a triangular piece or cone.

In these embodiments, the material may be any material that modifies the interaction between the sample and the substrate. In certain embodiments, the material modifies the interaction between the sample and substrate during sample deposition. In other embodiments, the material modifies the interaction between the sample and substrate during sample elution. The material may coat at least a portion of the substrate. Alternatively, the material may impregnate at least a portion of the substrate. In certain embodiments, the material is silica. In particular embodiments, the silica coats a surface of the substrate.

In certain embodiments, the probe further includes a discrete amount of a solvent, e.g., a droplet or droplets, applied to the porous material. The solvent is applied as a droplet or droplets, and in an amount sufficient to wet the porous material. Once applied to the porous material, the solvent can assist transport of the sample through the porous material. The solvent can contain an internal standard. The solvent/substrate combination can allow for differential retention of sample components with different chemical properties. In certain embodiments, the solvent minimizes salt and matrix effects. In other embodiments, the solvent includes chemical reagents that allow for on-line chemical derivatization of selected analytes.

Another embodiment of the invention provides a system for analyzing a sample material including at least one porous substrate connected to a high voltage source, in which at least a portion of the porous substrate includes a material that modifies an interaction between a sample and the substrate, and a mass analyzer. In certain embodiments, the porous substrate is discrete from a flow of solvent. The mass analyzer is for a mass spectrometer or a handheld mass spectrometer. Exemplary mass analyzers include a quadrupole ion trap, a rectalinear ion trap, a cylindrical ion trap, a ion cyclotron resonance trap, an orbitrap, a time of flight, a Fourier Transform ion cyclotron resonance, and sectors.

Another embodiment of the invention provides a method for analyzing a sample that involves contacting a sample to a porous substrate, in which at least a portion of the porous substrate includes a material that modifies an interaction between a sample and the substrate, applying a high voltage to the porous material to generate ions of an analyte in the sample that are expelled from the porous material, and analyzing the expelled ions. In certain embodiments, the porous substrate is kept separate from a flow of solvent. Exemplary samples include chemical species or biological species. In certain embodiments, the sample is a biological fluid, e.g., complex mixtures such as blood, saliva, or urine.

Another embodiment of the invention provides a method for analyzing blood that involves contacting a blood sample to a porous substrate, in which at least a portion of the porous substrate comprises a silica coating that modifies an interaction between the blood sample and the substrate, applying a high voltage to the porous substrate to generate ions of an analyte in the blood sample that are expelled from the porous substrate, and analyzing the expelled ions.

BRIEF DESCRIPTION OF THE FIGURES

FIG. 3A is a MS spectrum of caffeine (concentration: 10 ppm, volume: 10 μl, solvent: MeOH/$H_2$O/HOAc (50:49:1, v/v/v)) using probes of the invention.

FIG. 8A MS/MS spectrum shows heroin can be detected from raw urine sample by a "spot" method. FIG. 8B shows the MS/MS spectrum of the urine spot without heroin.

FIG. 10A is a MS spectrum showing that caffeine was detected in urine from a person who consumed coffee. FIG. 10B is a MS spectrum showing that caffeine was not detected in urine from a person who had not consumed any coffee.

FIGS. 11A-B are MS spectra showing the difference between peptide analysis (10 ppm of bradykinin 2-9) on (FIG. 11A) paper triangle and (FIG. 11B) PVDF membrane using the same parameters (~2 kV, Solvent: MeOH:$H_2O$=1:1).

FIGS. 12A-D shows direct MS spectra of plant tissues using sliced tissues of four kinds of plants. (FIG. 12A) Onion, (FIG. 12B) Spring onion, and two different leaves (FIG. 12C) and (FIG. 12D).

FIG. 13A direct analysis of onion without sample preparation. FIG. 13B using standard solution.

FIG. 14A is a picture showing dried blood spot analysis on paper; 0.4 µL of whole blood is applied directly to a triangular section of chromatography paper (typically height 10 mm, base 5 mm). A copper clip holds the paper section in front of the inlet of an LTQ mass spectrometer (Thermo Fisher Scientific, San Jose, Calif.) and a DC voltage (4.5 kV) is applied to the paper wetted with 10 µL methanol/water (1:1 v/v). FIG. 14B shows the molecular structure of imatinib (GLEEVEC) and paper spray tandem mass spectrum of 0.4 µL whole blood containing 4 µg/mL imatinib. Imatinib is identified and quantified (inset) by the MS/MS transition m/z 494→m/z 394 (inset).

(FIG. 19A) 3 µm, (FIG. 19B) 4-7 µm, (FIG. 19C) 8 µm, and (FIG. 19D) 11 µm, (FIG. 19E) glass fiber paper and (FIG. 19F) chromatography paper). The spray voltage was 4.5 kV.

FIGS. 22A-B are mass spectra of COCA-COLA (cola drink), which was directly analyzed on paper in both of (A) positive and (B) negative mode. FIG. 22C is a mass spectrum of caffeine. FIG. 22D is a mass spectrum of potassium benzoate. FIG. 22E is a mass spectrum of acesulfame potassium. FIG. 22F is a mass spectrum of caffeine detected from urine. FIG. 22G is a mass spectrum of heroin detected directly from a desktop surface after swabbing of the surface by probes of then invention.

FIG. 23A shows images of a probe of the invention used for blood analysis. In this embodiment, the porous material is paper. The panel on the left is prior to spotting with whole blood. The panel in the middle is after spotting with whole blood and allowing the spot to dry. The panel on the right is after methanol was added to the paper and allowed to travel through the paper. The panel on the right shows that the methanol interacts with the blood spot, causing analytes to travel to the tip of the paper for ionization and analysis.

FIGS. 24A-C show analysis of two dyes, methylene blue (m/z 284) and methyl violet (m/z 358.5), separated by TLC. Dye mixture solution (0.1 µl of a 1 mg/mL solution) was applied onto the chromatography paper (4 cm×0.5 cm) and dried before TLC and paper spray MS analysis.

FIGS. 25A-E show different shapes, thicknesses, and angles for probes of the invention. FIG. 25A shows sharpness. FIG. 25B shows angle of the tip. FIG. 25C shows thickness of the paper. FIG. 25D shows a device with multiple spray tips. FIG. 25E shows a DBS card with micro spray tips fabricated with sharp needles.

FIG. 26A shows a MS spectrum for 5 µg/mL. FIG. 26B shows a MS/MS spectrum for 5 ng/mL.

FIGS. 29B-D are mass spectra showing different chemicals detected in the tissue.

FIGS. 34A-B show mass spectra of agrochemicals that are present on a lemon peel purchased from a grocery store and swabbed with paper.

FIG. 35 shows a design of a substrate for paper spray with multiple corners. The angle of the corner to be used for spray is smaller than that of other corners.

FIG. 39 is a schematic showing work flow for paper spray analysis of blood using a drying agent.

FIG. 41 is a photograph showing paper spray mass spectrometry of 10 μL whole blood with and without alum, a coagulant which was pre-spotted to clot the blood during analysis.

FIGS. 42A-C show paper spray mass spectrometry of five individual samples of 50 ng/mL pazopanib (in 10 μL fresh blood) and 5 μL of 500 ng/mL $^2H_3{}^{13}C$-pazopanib (pre-spotted). Total mass of pazopanib and $^2H_3{}^{13}C$-pazopanib deposited onto the paper was 500 pg and 2.5 ng, respectively. (FIG. 42A) SRM ion chronogram of $^2H_3{}^{13}C$-pazopanib (m/z 442.1→361.1). (FIG. 42B) SRM ion chronogram of pazopanib (m/z 438.1→357.1). (FIG. 42C) Drug-to-internal standard ratio over time.

FIG. 48A is a graph showing quantitation of nicotine from fresh bovine whole blood.

FIGS. 52B and D: The blood film on the printer paper before and after spray. FIG. 52C: Quantitative analysis of fresh liquid blood spiked with nicotine (0.1 ng/mL-100 ng/mL) and its internal standard nicotine-d3 (100 ng/mL). Inset plot shows low concentration range. The bars represent the standard deviation of analysis for three replicates at different nicotine concentrations.

FIG. 56A Effect of spray solvent on the analysis of verapamil [(M+H)+, m/z 455, product ion, m/z 303] and (FIG. 56B) effect of isopropanol percentage in dichloromethane on the signal of verapamil with a triple quadrupole. Silica-coated paper substrate used. The peak intensity is an average of total ion chronogram values. The concentration of verapamil in the blood sample was 500 ng mL−1.

FIGS. 57A-F are graphs showing a comparison of the elution behavior of verapamil with silica coated paper and chromatography papers: (i) verapamil in pure water (5 μL, 500 ng mL−1) deposited onto surface of (FIG. 57A) silica coated paper, (FIG. 57B) Grade 4 chromatography paper and (FIG. 57C) ET31 chromatography paper; (ii) verapamil in blood (5 μL, 500 ng mL−1) deposited onto surface of (FIG. 57D) silica coated paper and (FIG. 57E) Grade 4 chromatography paper and (FIG. 57F) Grade ET31 chromatography paper. Note: the experiments were performed after the paper had dried. Solvent for silica coated paper was 9:1 dichloromethane/isopropanol, chromatography paper 9:1 methanol/water. a.u.: arbitrary units.

DETAILED DESCRIPTION

The invention generally relates to ion generation using modified wetted porous materials. In certain aspects, the invention generally relates to systems and methods for ion generation using a wetted porous substrate that substantially prevents diffusion of sample into the substrate. In other aspects, the invention generally relate to ion generation using a wetted porous material and a drying agent. In other aspects, the invention generally relates to ion generation using a modified wetted porous substrate in which at least a portion of the porous substrate includes a material that modifies an interaction between a sample and the substrate.

Figure 1A:
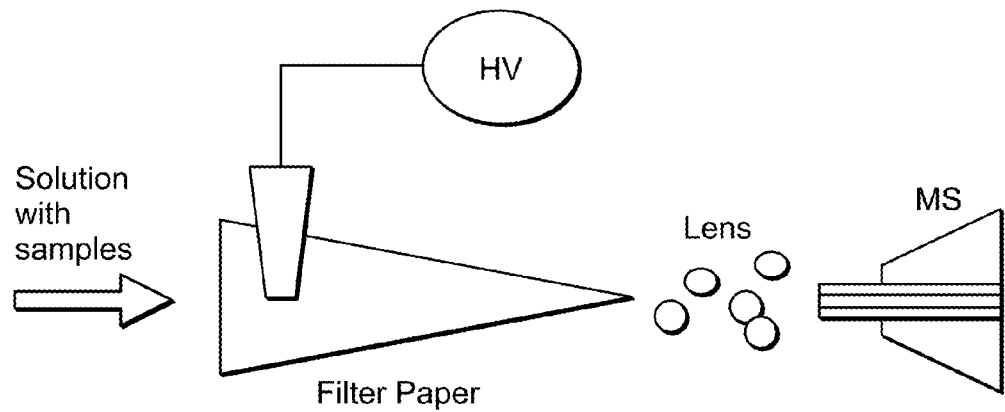
FIG. 1A is a drawing of a sample solution being fed to a piece of paper for electrospray ionization.
Figure 1B:
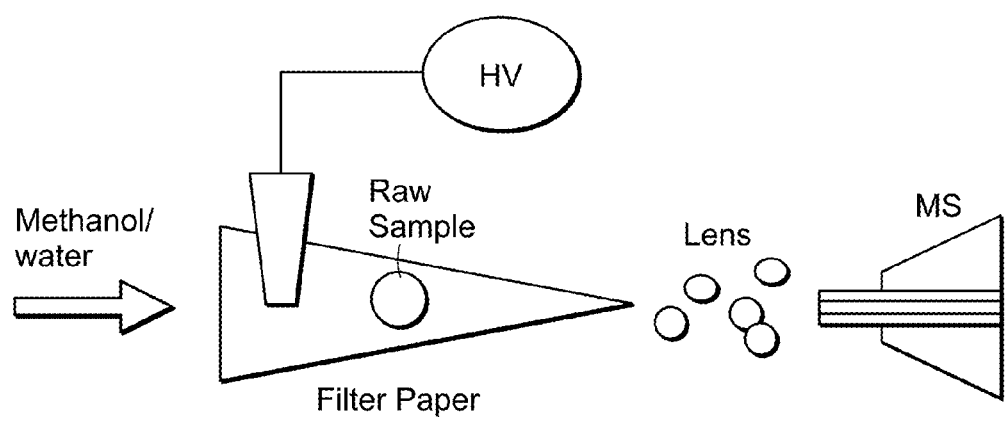
FIG. 1B is a drawing of a sample solution pre-spotted onto the paper and a droplet of solvent being subsequently supplied to the paper for electrospray ionization.

A method of generating ions from fluids and solids for mass spectrometry analysis is described. Porous materials, such as paper (e.g. filter paper or chromatographic paper) or other similar materials are used to hold and transfer liquids and solids, and ions are generated directly from the edges of the material when a high electric voltage is applied to the material (FIG. 1). In certain embodiments, the porous material is kept discrete (i.e., separate or disconnected) from a flow of solvent, such as a continuous flow of solvent. Instead, sample is either spotted onto the porous material or swabbed onto it from a surface including the sample. In other embodiments, the paper substrate is directly connected to a continuous flow of solvent. Further description is provided for example in Ouyang et al., WO 2010/127059, the content of which is incorporated by reference herein in its entirety.

In certain embodiments, the porous material is any cellulose-based material. In other embodiments, the porous material is a non-metallic porous material, such as cotton, linen wool, synthetic textiles, or plant tissue. In still other embodiments, the porous material is paper. Advantages of paper include: cost (paper is inexpensive); it is fully commercialized and its physical and chemical properties can be adjusted; it can filter particulates (cells and dusts) from liquid samples; it is easily shaped (e.g., easy to cut, tear, or fold); liquids flow in it under capillary action (e.g., without external pumping and/or a power supply); and it is disposable.

In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 µm), Grade 2 (8 µm), Grade 595 (4-7 µm), and Grade 6 (3 µm), Pore size will not only influence the transport of liquid inside the spray materials, but could also affect the formation of the Taylor cone at the tip. The optimum pore size will generate a stable Taylor cone and reduce liquid evaporation. The pore size of the filter paper is also an important parameter in filtration, i.e., the paper acts as an online pretreatment device. Commercially available ultrafiltration membranes of regenerated cellulose, with pore sizes in the low nm range, are designed to retain particles as small as 1000 Da. Ultra filtration membranes can be commercially obtained with molecular weight cutoffs ranging from 1000 Da to 100,000 Da.

In certain embodiments, the substrate includes a material that substantially prevents diffusion of a sample into the substrate. The material for the porous substrate will depend on the properties of the sample to be analyzed. For example, when the sample is hydrophilic, the substrate is less hydrophilic than the sample. Alternatively, when the sample is hydrophobic, the substrate is less hydrophobic than the sample. Thus the sample remains substantially on top of the substrate until an appropriate solvent is applied to the substrate. The solvent is capable of diffusing into the substrate. The solvent interacts with the sample, causing the sample or components of the sample to diffuse into the substrate. In certain embodiments, the solvent is capable of mixing with the sample and both the solvent and the sample diffuse into the substrate. In other embodiments, the solvent is not capable of mixing with the sample but is capable of extracting the components from the sample that diffuse into the substrate along with the solvent.

In other embodiments, the porous material includes a drying agent in order to rapidly dry a sample that is applied to the substrate. Any drying agent that is compatible with the sample and does not interfere with analysis by mass spectrometry may be used. An exemplary drying agent is an anhydrous salt, such as magnesium sulfate, sodium sulfate, sodium carbonate, or calcium chloride. Other exemplary drying agents include blood coagulants, such as alum powder. In certain embodiments, the porous substrate also includes an internal standard. Rapid drying decreases waiting time and allows for sample analysis within approximately two to five minutes of applying a sample to the substrate. With respect to analysis of biological fluids, such a substrate allows for a point-of-care device for rapid and convenient use.

In other embodiments, the substrate includes a material that modifies an interaction between the sample and the substrate. The material may be any material that modifies the interaction between the sample and the substrate. In certain embodiments, the material modifies the interaction between the sample and substrate during sample deposition. In other embodiments, the material modifies the interaction between the sample and substrate during sample elution. The material may coat at least a portion of the substrate. Alternatively, the material may impregnate at least a portion of the substrate. In certain embodiments, the material is silica. In particular embodiments, the silica coats a surface of the substrate.

The substrate is then connected to a high voltage source to produce ions of the sample which are subsequently mass analyzed. The sample is transported through the porous material without the need of a separate solvent flow. Pneumatic assistance is not required to transport the analyte; rather, a voltage is simply applied to the porous material that is held in front of a mass spectrometer.

In certain embodiments, the porous material is integrated with a solid tip having a macroscopic angle that is optimized for spray. In these embodiments, the porous material is used for filtration, pre-concentration, and wicking of the solvent containing the analytes for spray at the solid type.

Probes of the invention work well for the generation of micron scale droplets simply based on using the high electric field generated at an edge of the porous material. In particular embodiments, the porous material is shaped to have a macroscopically sharp point, such as a point of a triangle, for ion generation. Probes of the invention may have different tip widths. In certain embodiments, the probe tip width is at least about 5 µm or wider, at least about 10 µm or wider, at least about 50 µm or wider, at least about 150 µm or wider, at least about 250 µm or wider, at least about 350 µm or wider, at least about 400µ or wider, at least about 450 µm or wider, etc. In particular embodiments, the tip width is at least about 350 µm or wider. In other embodiments, the probe tip width is about 400 μm. In other embodiments, probes of the invention have a three dimensional shape, such as a conical shape.

As mentioned above, no pneumatic assistance is required to transport the droplets. Ambient ionization of analytes is realized on the basis of these charged droplets, offering a simple and convenient approach for mass analysis of solution-phase samples.

Sample solution is directly applied on the porous material held in front of an inlet of a mass spectrometer without any pretreatment. Then the ambient ionization is performed by applying a high potential on the wetted porous material. In certain embodiments, the porous material is paper, which is a type of porous material that contains numerical pores and microchannels for liquid transport. The pores and microchannels also allow the paper to act as a filter device, which is beneficial for analyzing physically dirty or contaminated samples.

In other embodiments, the porous material is treated to produce microchannels in the porous material or to enhance the properties of the material for use as a probe of the invention. For example, paper may undergo a patterned silanization process to produce microchannels or structures on the paper. Such processes involve, for example, exposing the surface of the paper to tridecafluoro-1,1,2,2-tetrahydrooctyl-1-trichlorosilane to result in silanization of the paper. In other embodiments, a soft lithography process is used to produce microchannels in the porous material or to enhance the properties of the material for use as a probe of the invention. In other embodiments, hydrophobic trapping regions are created in the paper to pre-concentrate less hydrophilic compounds.

Hydrophobic regions may be patterned onto paper by using photolithography, printing methods or plasma treatment to define hydrophilic channels with lateral features of 200~1000 μm. See Martinez et al. (*Angew. Chem. Int. Ed.* 2007, 46, 1318-1320); Martinez et al. (*Proc. Natl Acad. Sci. USA* 2008, 105, 19606-19611); Abe et al. (*Anal. Chem.* 2008, 80, 6928-6934); Bruzewicz et al. (*Anal. Chem.* 2008, 80, 3387-3392); Martinez et al. (*Lab Chip* 2008, 8, 2146-2150); and Li et al. (*Anal. Chem.* 2008, 80, 9131-9134), the content of each of which is incorporated by reference herein in its entirety. Liquid samples loaded onto such a paper-based device can travel along the hydrophilic channels driven by capillary action.

Another application of the modified surface is to separate or concentrate compounds according to their different affinities with the surface and with the solution. Some compounds are preferably absorbed on the surface while other chemicals in the matrix prefer to stay within the aqueous phase. Through washing, sample matrix can be removed while compounds of interest remain on the surface. The compounds of interest can be removed from the surface at a later point in time by other high-affinity solvents. Repeating the process helps desalt and also concentrate the original sample.

In certain embodiments, methods and systems of the invention use a porous material, e.g., paper, to hold and transport analytes for mass spectral analysis. Analytes in samples are pre-concentrated, enriched and purified in the porous material in an integrated fashion for generation of ions with application of a high voltage to the porous material. In certain embodiments, a discrete amount of transport solution (e.g., a droplet or a few droplets) is applied to assist movement of the analytes through the porous material. In certain embodiments, the analyte is already in a solution that is applied to the porous material. In such embodiments, no additional solvent need be added to the porous material. In other embodiments, the analyte is in a powdered sample that can be easily collected by swabbing a surface. Systems and methods of the invention allow for analysis of plant or animal tissues, or tissues in living organisms.

Methods and systems of the invention can be used for analysis of a wide variety of small molecules, including epinephrine, serine, atrazine, methadone, roxithromycin, cocaine and angiotensin I. All display high quality mass and MS/MS product ion spectra (see Examples below) from a variety of porous surfaces. Methods and systems of the invention allow for use of small volumes of solution, typically a few μL, with analyte concentrations on the order of 0.1 to 10 μg/mL (total amount analyte 50 pg to 5 ng) and give signals that last from one to several minutes.

Methods and systems of the invention can be used also for analysis of a wide variety of biomolecules, including proteins and peptides. Methods of the invention can also be used to analyze oligonucleotides from gels. After electrophoretic separation of oligonucleotides in the gel, the band or bands of interest are blotted with porous material using methods known in the art. The blotting results in transfer of at least some of the oligonucleotides in the band in the gel to the porous material. The porous material is then connected to a high voltage source and the oligonucleotides are ionized and sprayed into a mass spectrometer for mass spectral analysis.

Methods and systems of the invention can be used for analysis of complex mixtures, such as whole blood or urine. The typical procedure for the analysis of pharmaceuticals or other compounds in blood is a multistep process designed to remove as many interferences as possible prior to analysis. First, the blood cells are separated from the liquid portion of blood via centrifugation at approximately 1000×g for 15 minutes (Mustard, J. F.; Kinlough-Rathbone, R. L.; Packham, M. A. *Methods in Enzymology*; Academic Press, 1989). Next, the internal standard is spiked into the resulting plasma and a liquid-liquid or solid-phase extraction is performed with the purpose of removing as many matrix chemicals as possible while recovering nearly all of the analyte (Buhrman, D. L.; Price, P. I.; Rudewicz, P. J. *Journal of the American Society for Mass Spectrometry* 1996, 7, 1099-1105). The extracted phase is typically dried by evaporating the solvent and then resuspended in the a solvent used as the high performance liquid chromatography (HPLC) mobile phase (Matuszewski, B. K.; Constanzer, M. L.; Chavez-Eng, C. M., Ithaca, N.Y., Jul. 23-25, 1997; 882-889). Finally, the sample is separated in the course of an HPLC run for approximately 5-10 minutes, and the eluent is analyzed by electrospray ionization-tandem mass spectrometry (Hopfgartner, G.; Bourgogne, E. *Mass Spectrometry Reviews* 2003, 22, 195-214).

Methods and systems of the invention avoid the above sample work-up steps. Methods and systems of the invention analyze a dried blood spots in a similar fashion, with a slight modification to the extraction procedure. First, a specialized device is used to punch out identically sized discs from each dried blood spot. The material on these discs is then extracted in an organic solvent containing the internal standard (Chace, D. H.; Kalas, T. A.; Naylor, E. W. *Clinical Chemistry* 2003, 49, 1797-1817). The extracted sample is dried on the paper substrate, and the analysis proceeds as described herein.

Examples below show that methods and systems of the invention can directly detect individual components of complex mixtures, such as caffeine in urine, 50 pg of cocaine on a human finger, 100 pg of heroin on a desktop surface, and hormones and phospholipids in intact adrenal tissue, without the need for sample preparation prior to analysis (See Examples below). Methods and systems of the invention allow for simple imaging experiments to be performed by examining, in rapid succession, needle biopsy tissue sections transferred directly to paper.

Analytes from a solution are applied to the porous material for examination and the solvent component of the solution can serve as the electrospray solvent. In certain embodiments, analytes (e.g., solid or solution) are pre-spotted onto the porous material, e.g., paper, and a solvent is applied to the material to dissolve and transport the analyte into a spray for mass spectral analysis.

In certain embodiments, a solvent is applied to the porous material to assist in separation/extraction and ionization. Any solvents may be used that are compatible with mass spectrometry analysis. In particular embodiments, favorable solvents will be those that are also used for electrospray ionization. Exemplary solvents include combinations of water, methanol, acetonitrile, and THF. The organic content (proportion of methanol, acetonitrile, etc. to water), the pH, and volatile salt (e.g. ammonium acetate) may be varied depending on the sample to be analyzed. For example, basic molecules like the drug imatinib are extracted and ionized more efficiently at a lower pH. Molecules without an ionizable group but with a number of carbonyl groups, like sirolimus, ionize better with an ammonium salt in the solvent due to adduct formation.

In certain embodiments, a multi-dimensional approach is undertaken. For example, the sample is separated along one dimension, followed by ionization in another dimension. In these embodiments, separation and ionization can be individually optimized, and different solvents can be used for each phase.

In other embodiments, transporting the analytes on the paper is accomplished by a solvent in combination with an electric field. When a high electric potential is applied, the direction of the movement of the analytes on paper is found to be related to the polarity of their charged forms in solution. Pre-concentration of the analyte before the spray can also be achieved on paper by placing an electrode at a point on the wetted paper. By placing a ground electrode near the paper tip, a strong electric field is produced through the wetted porous material when a DC voltage is applied, and charged analytes are driven forward under this electric field. Particular analytes may also be concentrated at certain parts of the paper before the spray is initiated.

In certain embodiments, chemicals are applied to the porous material to modify the chemical properties of the porous material. For example, chemicals can be applied that allow differential retention of sample components with different chemical properties. Additionally, chemicals can be applied that minimize salt and matrix effects. In other embodiments, acidic or basic compounds are added to the porous material to adjust the pH of the sample upon spotting. Adjusting the pH may be particularly useful for improved analysis of biological fluids, such as blood. Additionally, chemicals can be applied that allow for on-line chemical derivatization of selected analytes, for example to convert a non-polar compound to a salt for efficient electrospray ionization.

In certain embodiments, the chemical applied to modify the porous material is an internal standard. The internal standard can be incorporated into the material and released at known rates during solvent flow in order to provide an internal standard for quantitative analysis. In other embodiments, the porous material is modified with a chemical that allows for pre-separation and pre-concentration of analytes of interest prior to mass spectrum analysis.

The spray droplets can be visualized under strong illumination in the positive ion mode and are comparable in size to the droplets emitted from a nano-electrospray ion sources (nESI). In the negative ion mode, electrons are emitted and can be captured using vapor phase electron capture agents like benzoquinone. Without being limited by any particular theory or mechanism of action, it is believed that the high electric field at a tip of the porous material, not the fields in the individual fluid channels, is responsible for ionization.

The methodology described here has desirable features for clinical applications, including neotal screening, therapeutic drug monitoring and tissue biopsy analysis. The procedures are simple and rapid. The porous material serves a secondary role as a filter, e.g., retaining blood cells during analysis of whole blood. Significantly, samples can be stored on the porous material and then analyzed directly from the stored porous material at a later date without the need transfer from the porous material before analysis. Systems of the invention allow for laboratory experiments to be performed in an open laboratory environment.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The following examples are intended to further illustrate certain embodiments of the invention, and are not to be construed to limit the scope of the invention. Examples herein show that mass spectrometry probes of the invention can ionize chemical and biological samples, allowing for subsequent mass analysis and detection. An exemplary probe was constructed as a paper triangle, which was used to generate micron scale droplets by applying a high potential on the paper. The analytes were ionized from these electrically charged droplets and transported into a conventional mass spectrometer.

Examples below show that a wide range of samples could be directly analyzed in the ambient environment by probes of the invention in both of pure state and complex mixtures. The results showed that paper-based spray has the following benefits: it operated without sheath gas, i.e., few accessories were required for in situ analysis; biological samples (dried blood, urine) could be stored on the precut filter papers for months before analysis; filter paper minimized matrix effects seen with electrospray or nano electrospray in many samples (blood cells, salt and proteins) and enhanced the MS signal of chemicals in complex samples; powdered samples were easily collected by swabbing surfaces using paper pieces and then directly analyzed; the paper could be pretreated to contain internal standards that were released at known rates during solvent flow in quantitative analysis; and the paper could be pretreated to contain matrix suppression or absorption sites or to perform ion exchange or to allow on-line chemical derivatization of selected analytes.

Detection of most analytes was achieved as low as ppb levels (when examined as solutions) or in the low ng to pg range (when solids were examined) and the detection time was less than one minute. Certain Examples below provide a protocol for analyzing a dried blood spot, which can also be used for in situ analysis of whole blood samples. The dried blood spot method is also demonstrated to be compatible with the storage and transport of blood sample for blood screening and other clinical tests.

Devices of the invention integrated the capabilities of sampling, pre-separation, pre-concentration and ionization. Methods and systems of the invention simplify the problem of sample introduction in mass analyzers.

Example 1: Construction of an MS Probe

Filter paper was cut into triangular pieces with dimensions of 10 mm long and 5 mm wide and used as a sprayer (FIG. 1). A copper clip was attached to the paper, and the paper was oriented to face an inlet of a mass spectrometer (FIG. 1). The copper clip was mounted on a 3D moving stage to accurately adjust its position. A high voltage was applied to the copper clip and controlled by a mass spectrometer to generate analyte ions for mass detection.

Samples were directly applied to the paper surface that served as a sample purification and pre-concentration device. Filter paper allowed liquid samples to move through the hydrophilic network driven by capillary action and electric effects and to transport them to the tip of the paper. Separation could take place during this transport process. Sample solution was sprayed from the tip and resulted in ionization and MS detection when a high voltage (~4.5 kV) was applied to the paper surface.

All experiments were carried out with a Finnigan LTQ mass spectrometer (Thermo Electron, San Jose, Calif.). The typical temperature of the capillary inlet was set at 150° C. while 30° C. for heroin detection. The lens voltage was set at 65 V for sample analysis and 240 V for survival yield experiment. Tandem mass spectra were collected using collision-induced dissociation (CID) to identify analytes in tested samples, especially for complex mixtures and blood samples.

Example 2: Spray Generation

Spray was produced by applying a high potential on the wetted paper triangle. One paper triangle was placed in front of the inlet of LTQ with its sharp tip facing to the inlet, separated by 3 mm or more. Typically, 10 uL sample solution was applied to wet the paper triangle. The solution can wet or saturate the paper or form a thin layer of liquid film on the surface of the paper. A high potential (3-5 kV) was applied between the paper triangle and mass inlet to generate an electric field, which induced a charge accumulation on the liquid at the tip of paper triangle. The increasing coulombic force breaks the liquid to form charged droplets and then the solvent evaporated during the flight of droplets from the paper tip to the mass analyzer. Paper spray required no sheath gas, heating or any other assistance to remove the solvent.

When liquid accumulated on the paper triangle, a Taylor cone was observed at the tip when examined with a microscope. The droplets formed were clearly visible under strong illumination. The Taylor cone and visible spray disappeared after a short time of evaporation and spray. However, the mass signal lasted for a much longer period (several minutes). This revealed that the paper triangle could work in two modes for mass analysis. In a first mode, the liquid was transported inside the paper at a rate faster than the liquid could be consumed as spray at the paper tip, resulting in a large cone being formed at the paper tip and droplets being generated. In a second mode, the liquid transport inside the paper was not able to move at a rate fast enough to keep up with the spray consumption, and droplets were not visible. However, it was observed that ionization of analytes did take place. The first mode provided ESI like mass spectra and the second mode provided spectra with some of the features APCI spectra. In the latter case, the paper triangle played a role analogous to a conductive needle to generate a high electric field to ionize the molecules in the atmosphere. It was observed that the mass signal in the first mode was stronger than the mass signal in the second mode by approximately two orders of magnitude under the conditions and for the samples tested.

Example 3: Probe Considerations a. Probe Materials

A number of porous materials were tested to generate charged droplets for mass spectrometry. The materials were shaped into triangles having sharp tips and sample solution was then applied to the constructed probes. Data herein show that any hydrophilic and porous substrate could be used successfully, including cotton swab, textile, plant tissues as well as different papers. The porous network or microchannels of these materials offered enough space to hold liquid and the hydrophilic environment made it possible for liquid transport by capillary action. Hydrophobic and porous substrates could also be used successfully with properly selected hydrophobic solvents.

For further investigation, six kinds of commercialized papers were selected and qualitatively tested to evaluate their capabilities in analyte detection. Filter papers and chromatography paper were made from cellulose, while glass microfiber filter paper was made from glass microfiber. FIG. 19 shows the mass spectra of cocaine detection on those papers. The spectrum of glass fiber paper (FIG. 19 panel E) was unique because the intensity of background was two orders of magnitude lower than other papers and the cocaine peak (m/z, 304) could not be identified.

It was hypothesized that the glass fiber paper was working on mode II and prohibiting efficient droplet generation, due to the relative large thickness (~2 mm). This hypothesis was proved by using a thin layer peeled from glass fiber paper for cocaine detection. In that case, the intensity of the background increased and a cocaine peak was observed. All filter papers worked well for cocaine detection, (FIG. 19 panels A-D). Chromatography paper showed the cleanest spectrum and relative high intensity of cocaine (FIG. 19 panel F).

b. Probe Shape and Tip Angle

Figure 27A:
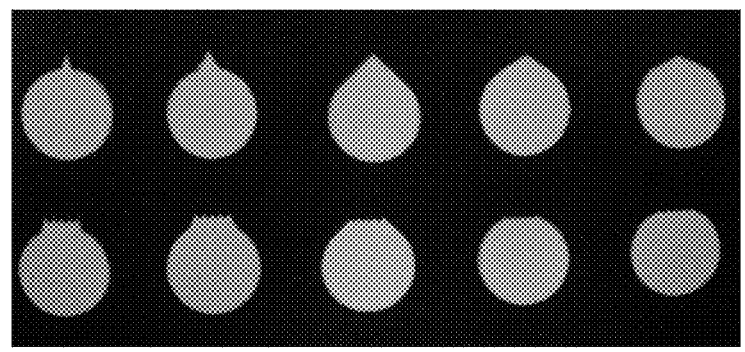
FIG. 27A is a picture showing different tip angles for probes of the invention. From left to right, the angles are 30, 45, 90, 112, 126 degree, respectively.
Figure 27B:
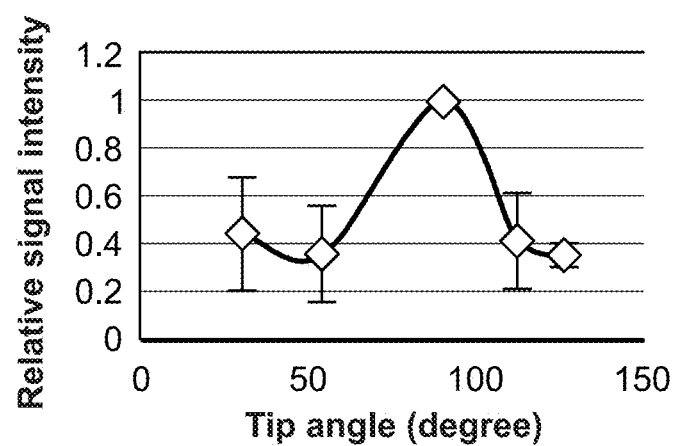
FIG. 27B is a graph showing the effect of angle on MS signal intensity. All MS signals were normalized to the MS signal using the 90 degree tip.

Many different probe shapes were investigated with respect to generating droplets. A preferred shape of the porous material included at least one tip. It was observed that the tip allowed ready formation of a Taylor cone. A probe shape of a triangle was used most often. As shown in FIG. 25 panels (A-C), the sharpness of the tip, the angle of the tip (FIG. 27 panels A and B), and the thickness of the paper substrate could effect the spray characteristics. The device of a tube shape with multiple tips (FIG. 25 panel D) is expected to act as a multiple-tip sprayer, which should have improved spray efficiency. An array of micro sprayers can also be fabricated on a DBS card using sharp needles to puncture the surface (FIG. 25 panel E).

Example 4: Configuration of Probe with Inlet of a Mass Spectrometer

Figure 20A:
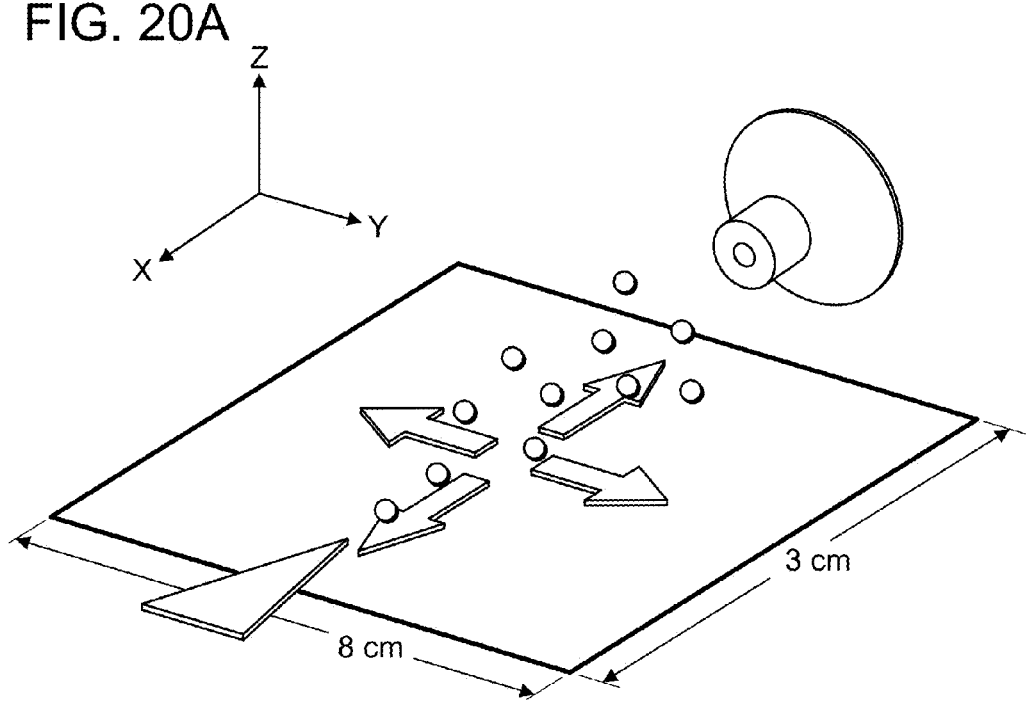
FIG. 20A shows a schematic setup for characterizing the spatial distribution of paper spray.
Figure 20B:
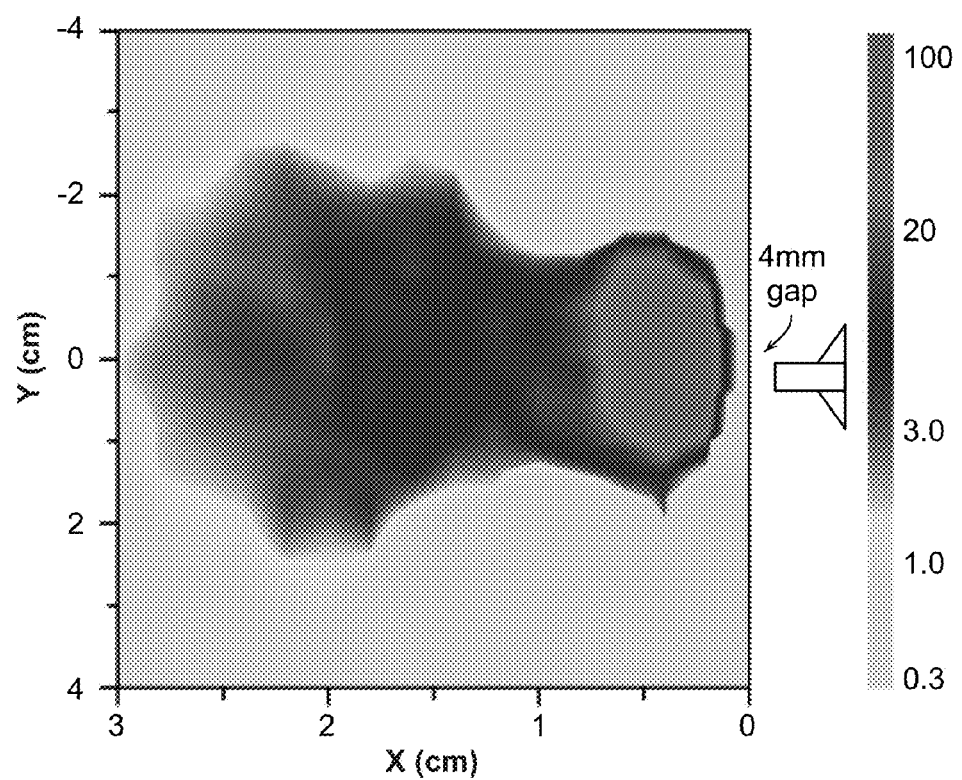
FIG. 20B is a 2D contour plot showing the relative intensity of m/z 304 when the probe is moved in the x-y plane with respect to the inlet of the mass spectrometer.
Figure 20C:
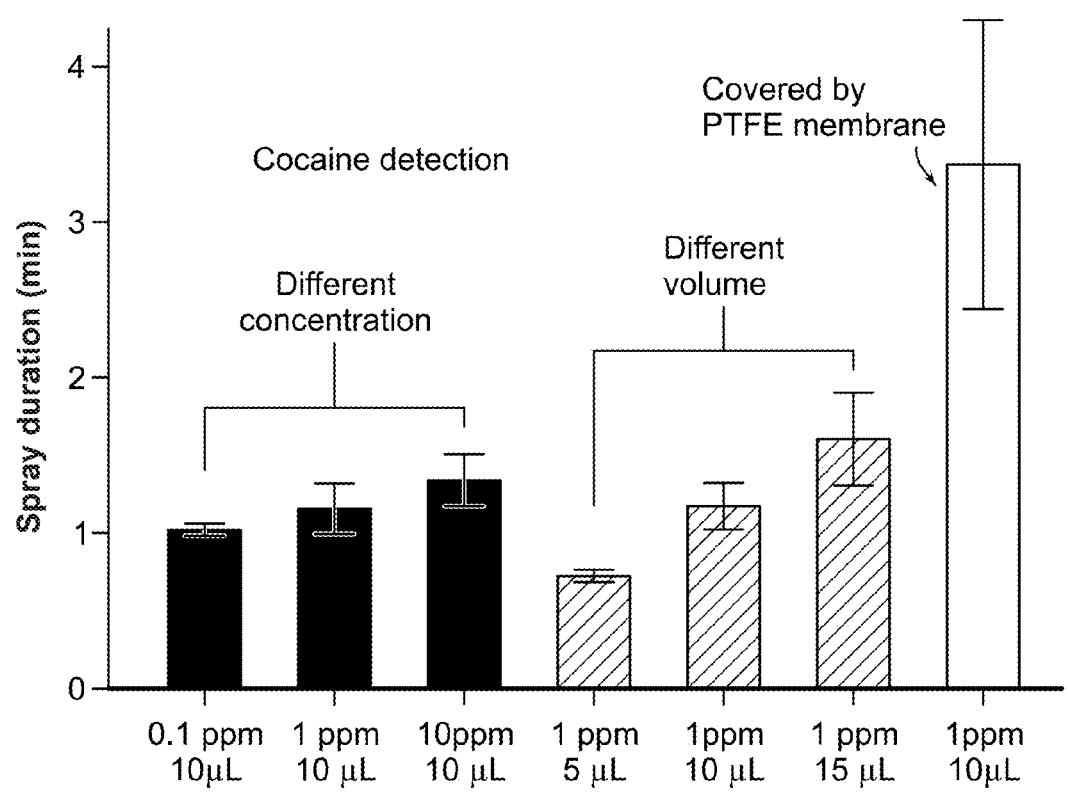
FIG. 20C is a graph showing signal duration of m/z 304 when loading cocaine solution on paper with different concentrations or volumes, or sealed by Teflon membrane.
Figure 21A:
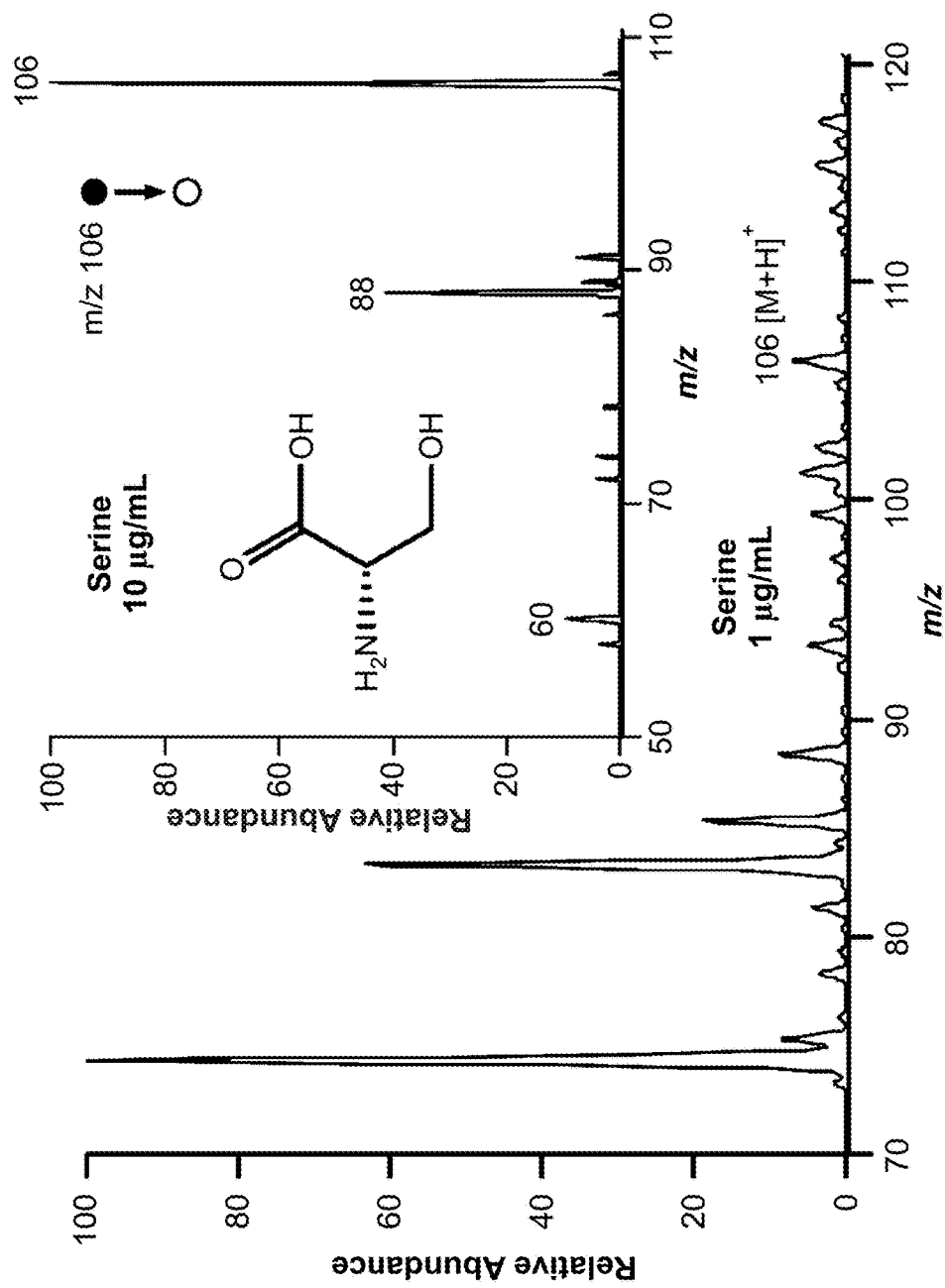
FIGS. 21A-D are a set of MS spectra of pure chemical solutions and their corresponding MS/MS spectra. Spectra were obtained for (FIG. 21A) serine, (FIG. 21B) methadone, (FIG. 21C) roxithromycin, and (FIG. 21D) bradykinin 2-9.
Figure 21B:
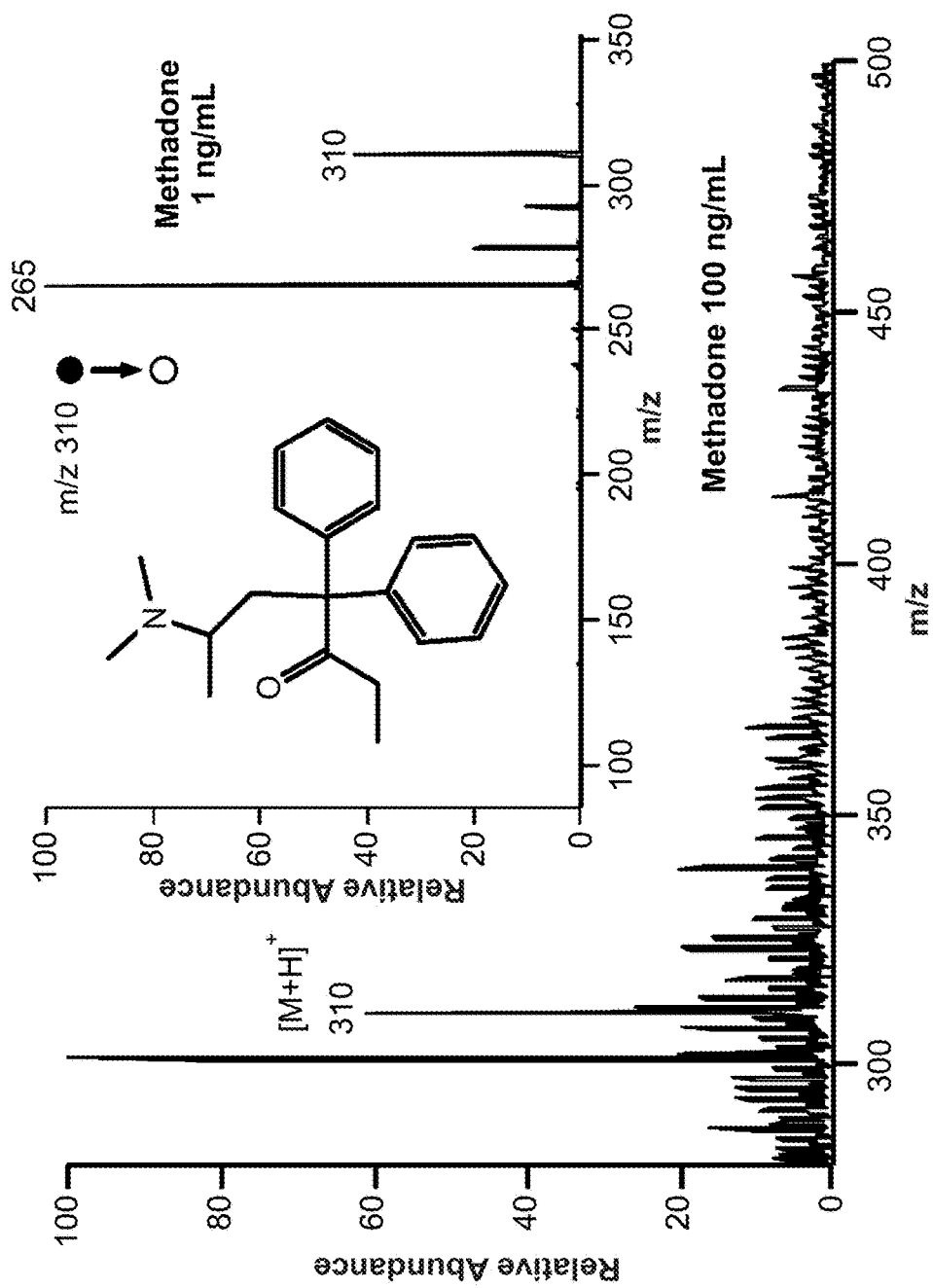
Figure 21C:
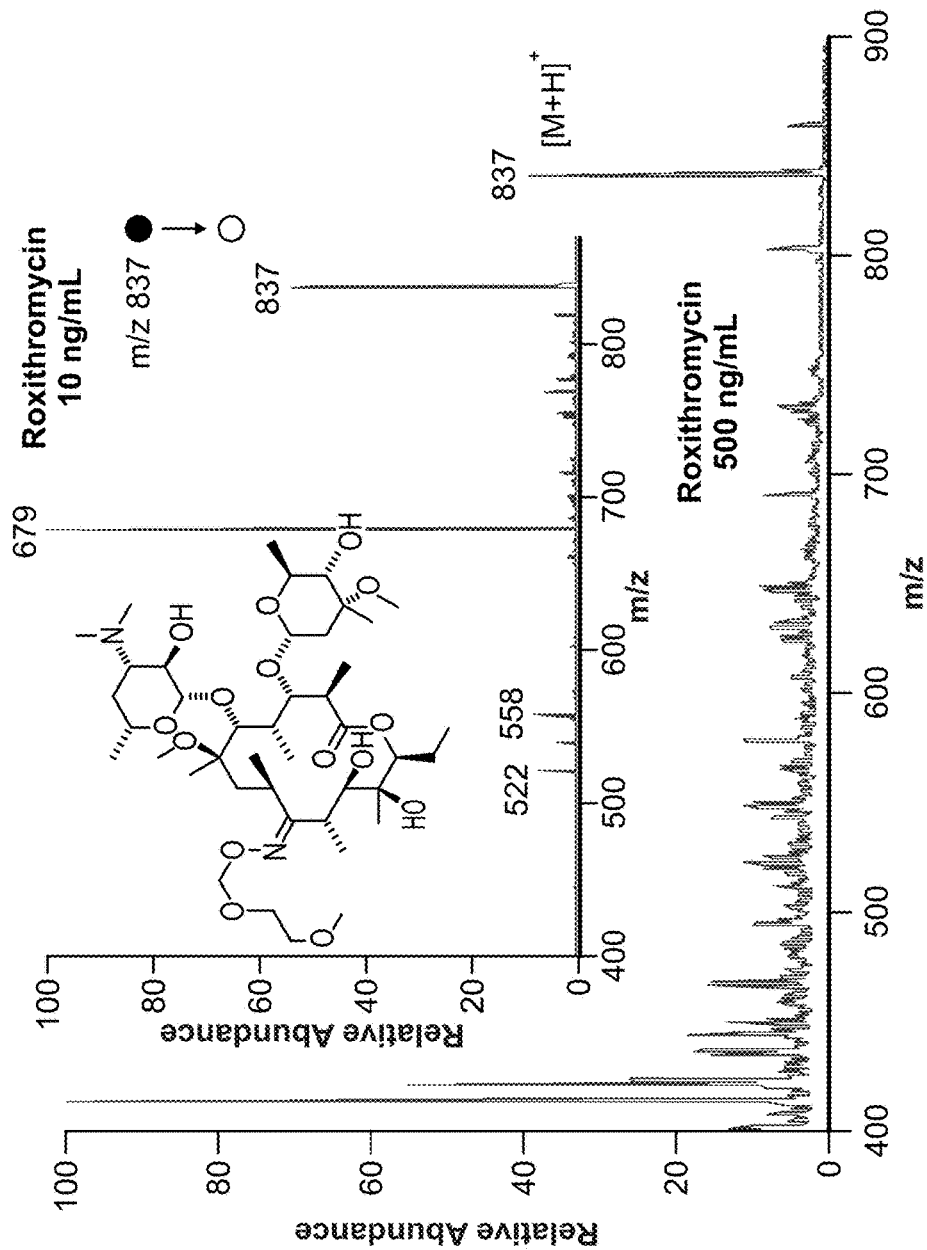
Figure 21D:
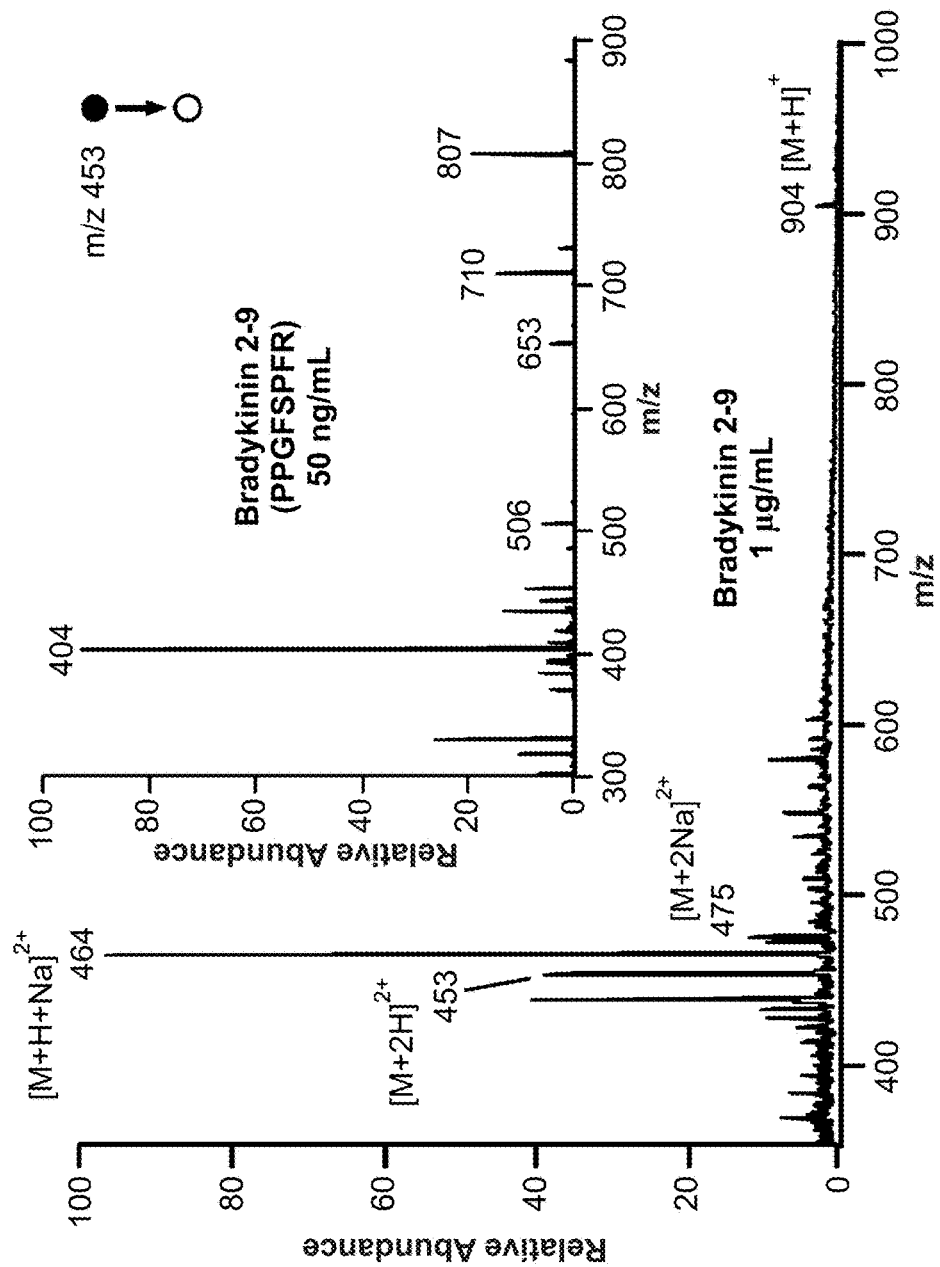
Figure 22A:
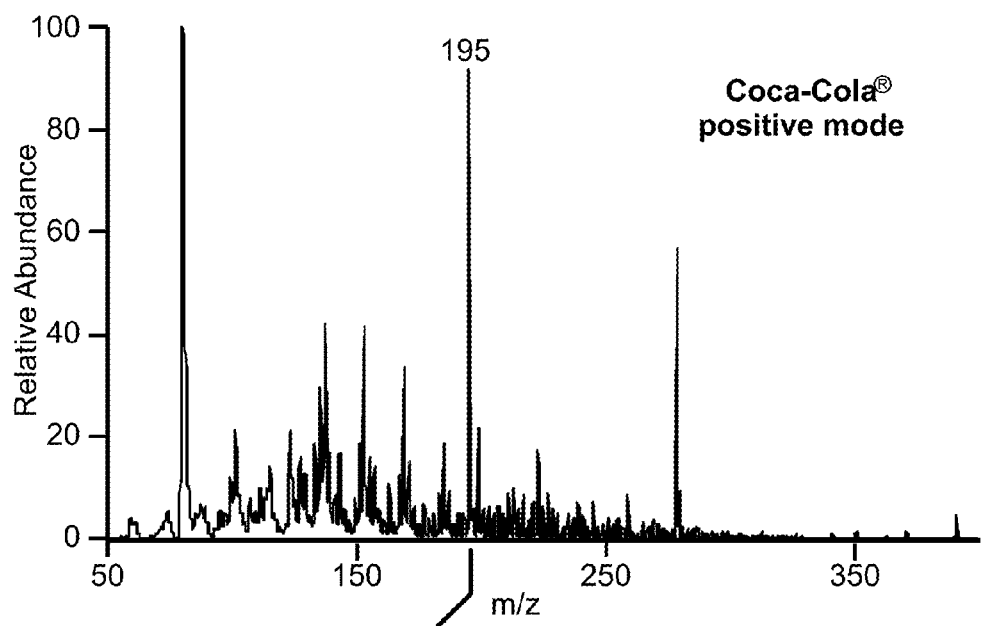
FIGS. 22A-G are a set of mass spectra showing analysis of chemicals from complex mixtures and direct analysis from surfaces without sample preparation.
Figure 22C:
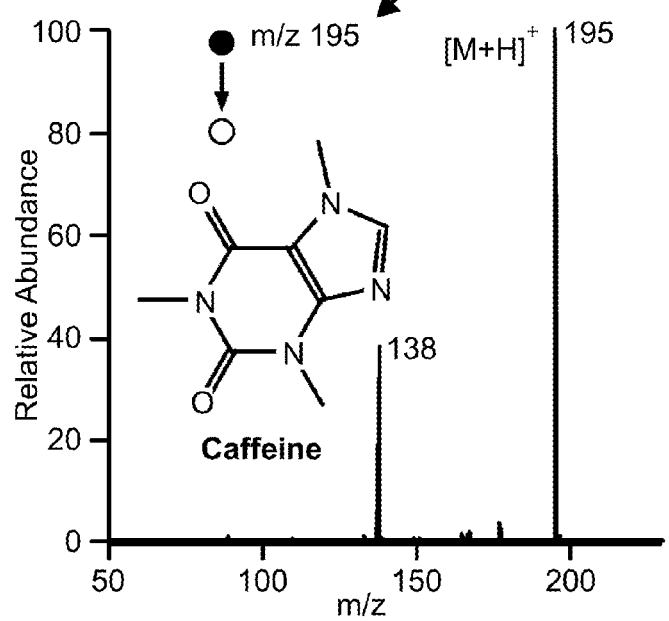
Figure 22B:
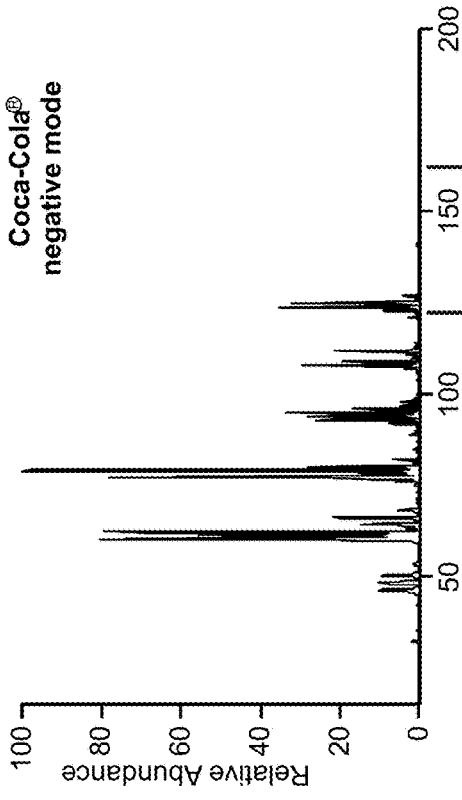
Figure 22E:
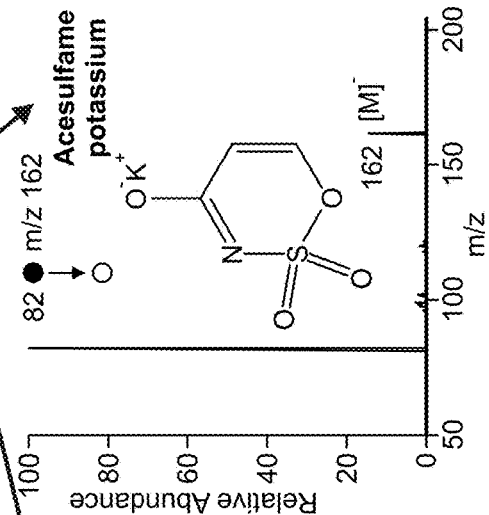
Figure 22D:
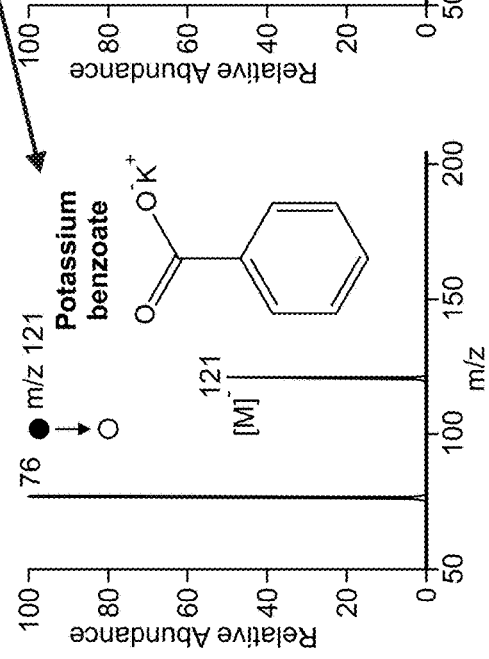
Figure 22F:
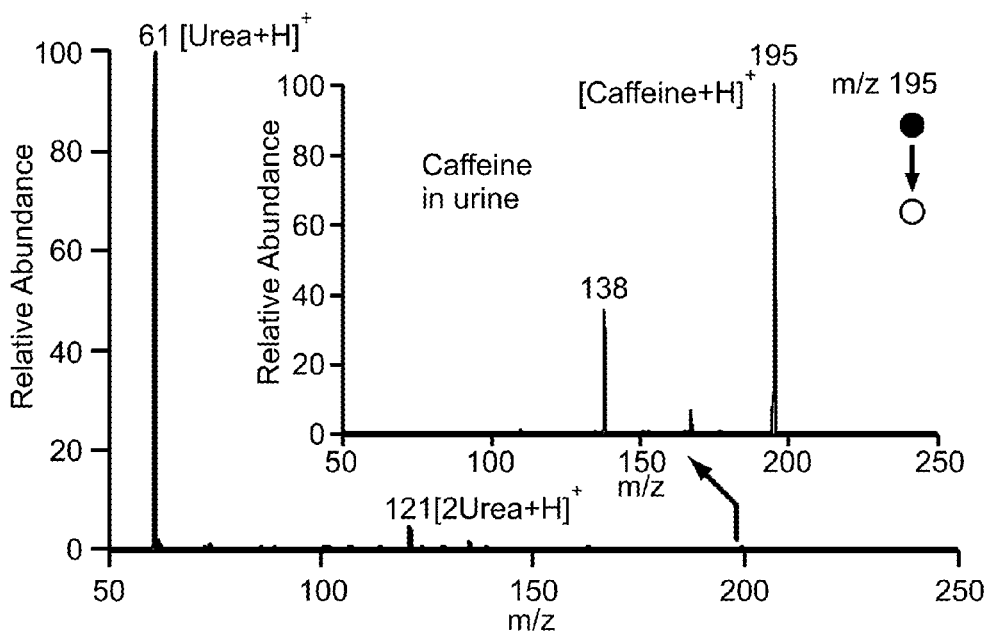
Figure 22G:
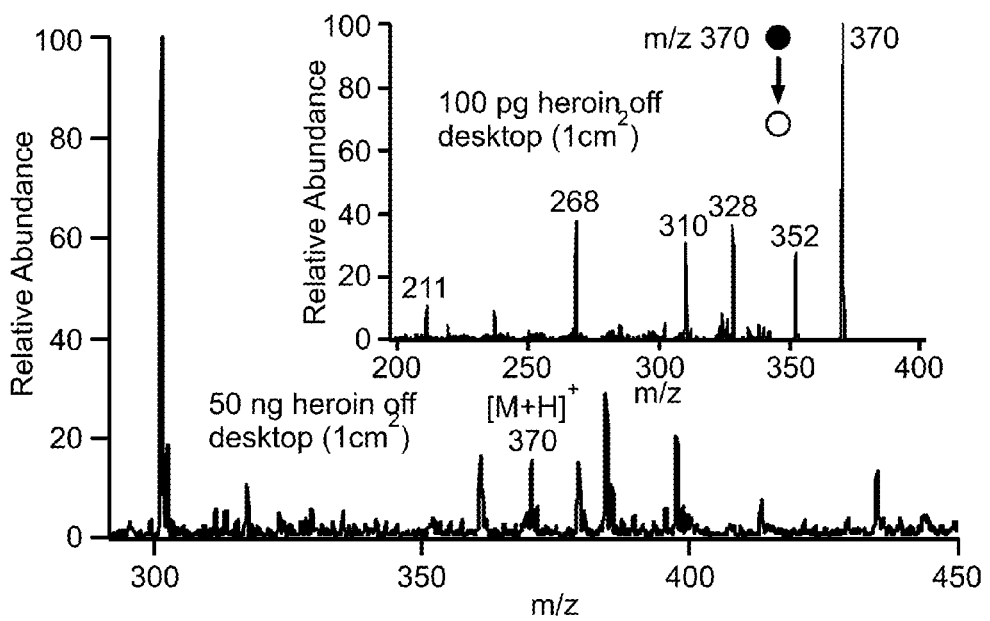

A paper triangle was mounted on a 2D moving stage to determine how the mass signal was affected by the relative positions of the paper triangle and the mass spectrometer inlet. The paper triangle was moved 8 cm in the y-direction in a continuous manner and 3 cm in the x-direction with a 2 mm increment for each step (FIG. 20 panel A). Cocaine solution (1 ug/mL, methanol/water, 1:1 v/v) was continuously fed onto the paper surface. The mass spectrum was continuously recorded during the entire scan. A contour plot of the peak intensity of protonated cocaine (m/z, 304) was created from the normalized data extracted from the mass spectrum (FIG. 20 panel B). The contour plot shows that it was not necessary for the paper triangle to be placed directly in-line with the inlet of the mass spectrometer to generate droplets.

Spray duration was also tested (FIG. 20 Panel C). Paper triangles (size 10 mm, 5 mm) were prepared. First, 10 uL solutions were applied on the paper triangles with different concentration of 0.1, 1 and 10 ug/mL. The spray time for each paper was just slightly varied by the difference of concentration. After that, 1 ug/mL cocaine solutions were applied on the paper triangles with different volumes of 5 uL, 10 uL and 15 uL. The spray times showed a linear response followed by the increasing sample volumes.

In another test, the paper was sealed with a PTFE membrane to prevent evaporation of solution, which prolonged the spray time by about three times. These results indicate that paper spray offers long enough time of spray for data acquisition even using 5 uL solution, and the intensity of signal is stable during the entire spray period.

Example 5: Separation and Detection

Figure 24B:
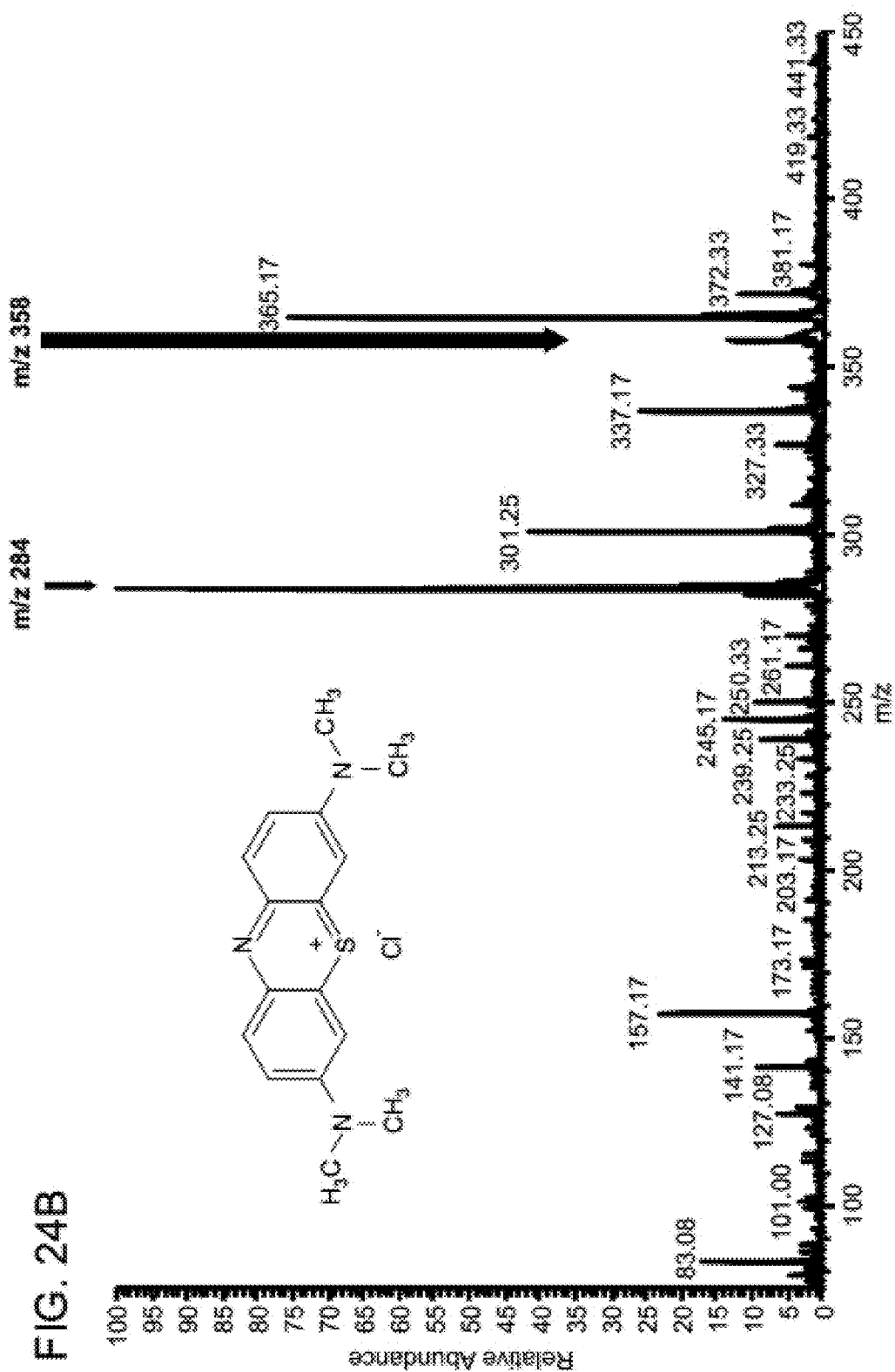
Figure 24C:
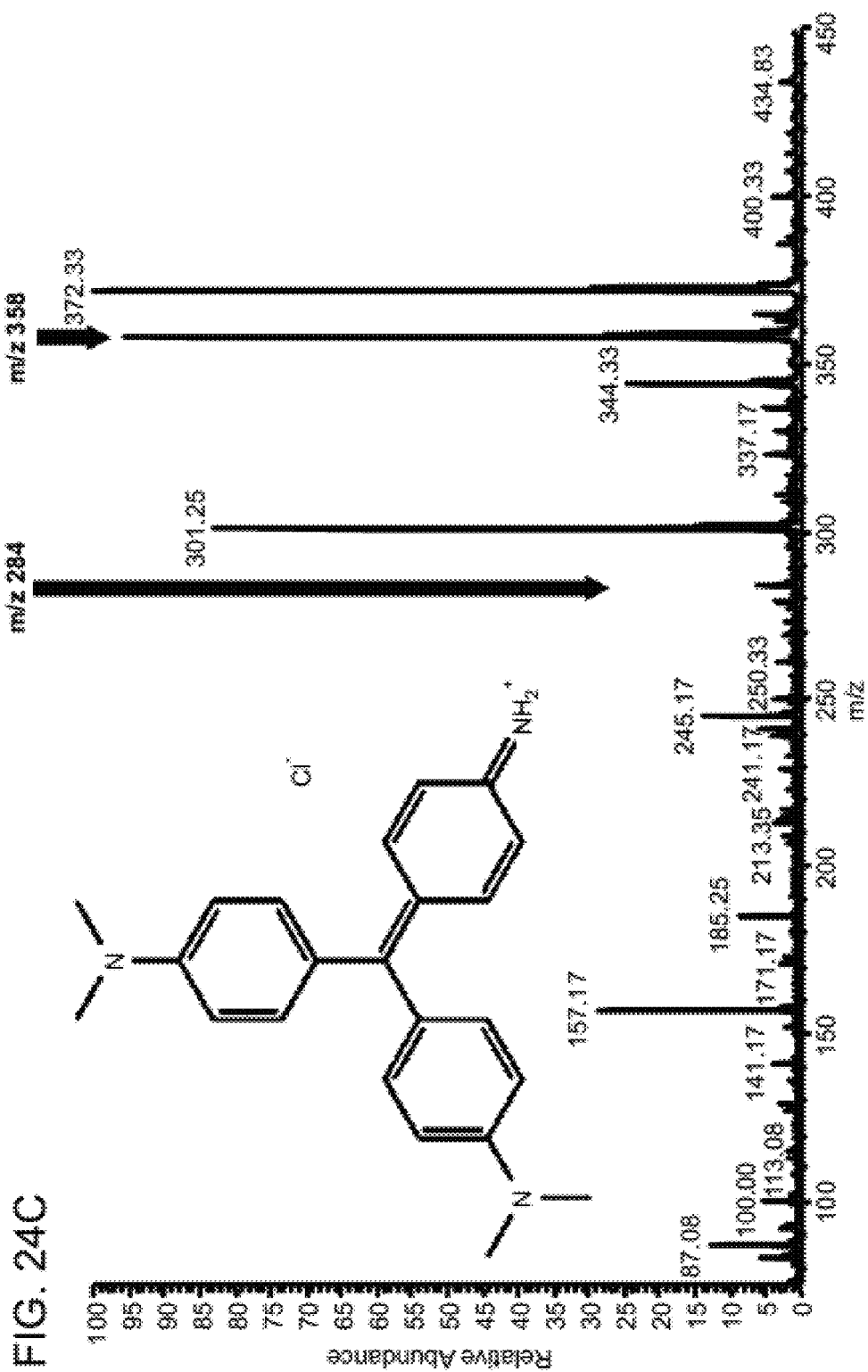
Figure 26A:
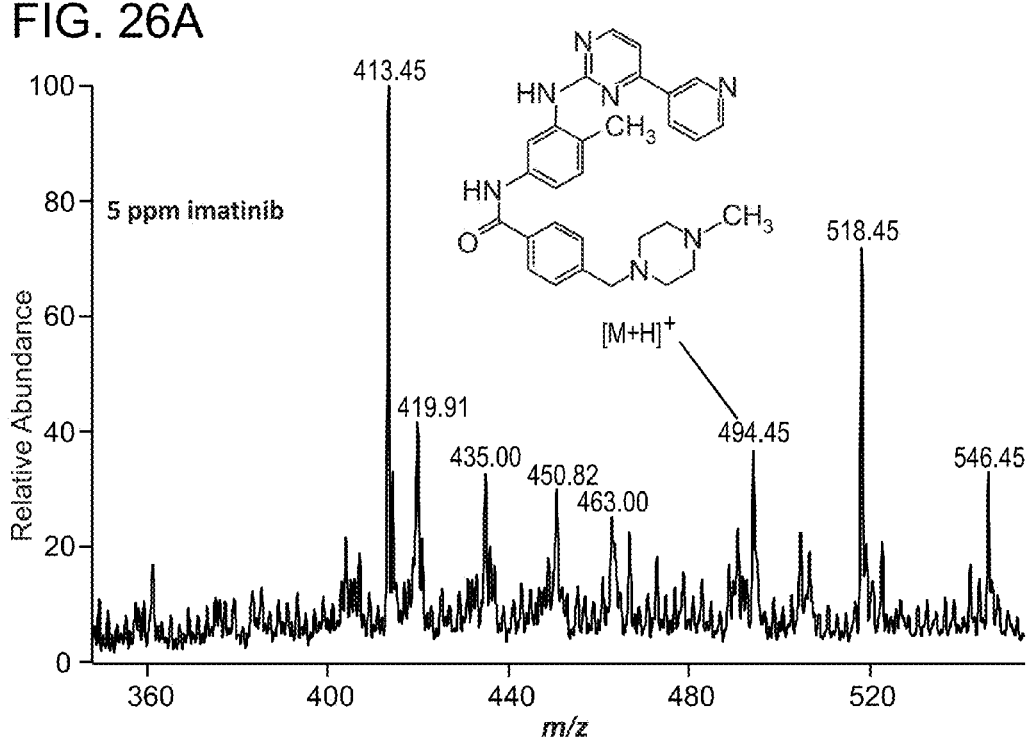
FIGS. 26A-B are a set of mass spectra of imatinib from human serum using direct spray from a C4 zip-tip of conical shape. Human serum samples (1.5 µL each) containing imatinib were passed through the porous C4 extraction material three times and then 3 µL methanol was added onto the zip-tip with 4 kV positive DC voltage applied to produce the spray.
Figure 26B:
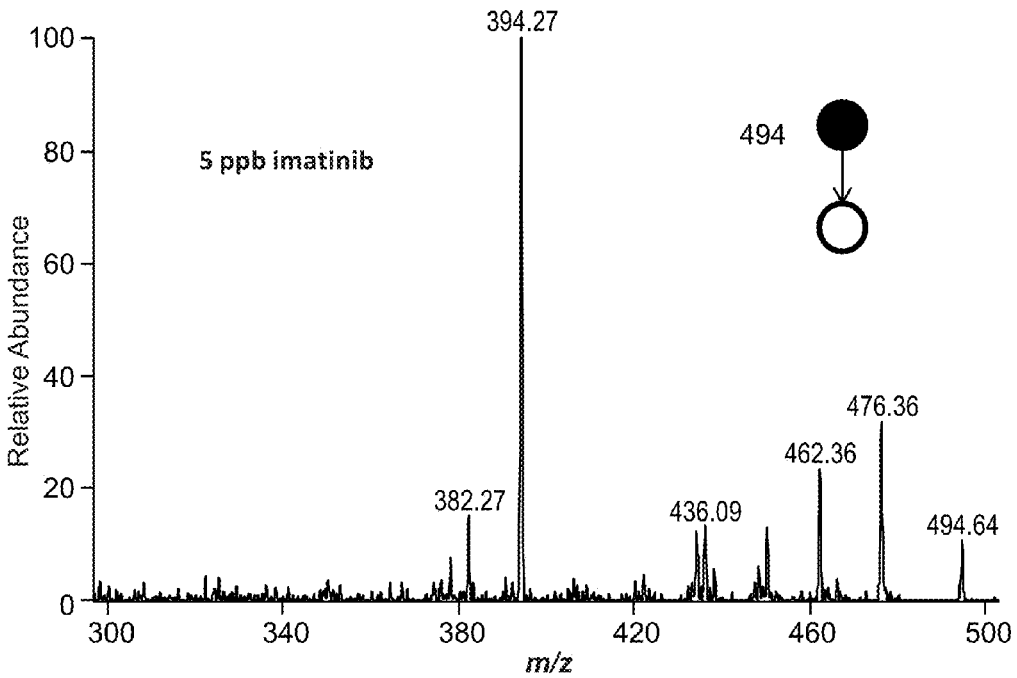

Probes of the invention include a porous material, such as paper, that can function to both separate chemicals in biological fluids before in situ ionization by mass spectrometry. In this Example, the porous material for the probe was chromatography paper. As shown in FIG. 24, a mixture of two dyes was applied to the paper as a single spot. The dyes were first separated on the paper by TLC (thin layer chromatograph) and the separated dyes were examined using MS analysis by methods of the invention with the paper pieces cut from the paper media (FIG. 24). Data show the separate dyes were detected by MS analysis (FIG. 24).

The chromatography paper thus allowed for sample collection, analyte separation and analyte ionization. This represents a significant simplification of coupling chromatography with MS analysis. Chromatography paper is a good material for probes of the invention because such material has the advantage that solvent movement is driven by capillary action and there is no need for a syringe pump. Another advantage is that clogging, a serious problem for conventional nanoelectrospray sources, is unlikely due to its multi-porous characteristics. Therefore, chromatography paper, a multi-porous material, can be used as a microporous electrospray ionization source.

Example 6: Pure Compounds: Organic Drugs, Amino Acids, and Peptides

As already described, probes and methods of the invention offer a simple and convenient ionization method for mass spectrometry. Paper triangles were spotted with different compounds and connected to a high voltage source to produce ions. All experiments were carried out with a Finnigan LTQ mass spectrometer (Thermo Electron, San Jose, Calif.). Data herein show that a variety of chemicals could be ionized in solution phase, including amino acid, therapeutic drugs, illegal drugs and peptides.

Figure 2A:
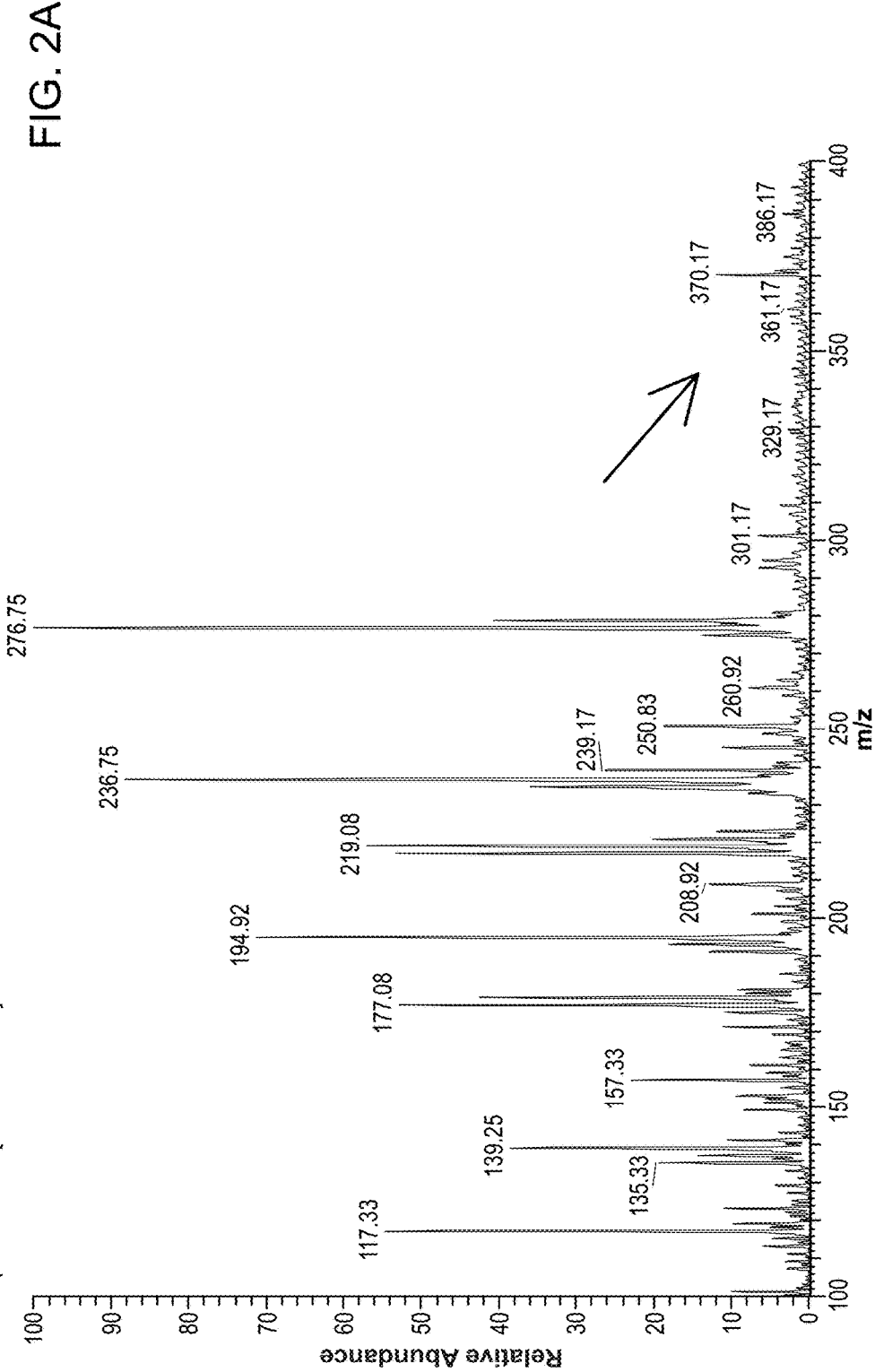
FIG. 2A is a MS spectrum of heroin (concentration: 1 ppm, volume: 10 μl, solvent: MeOH/$H_2$O/HOAc (50:49:1, v/v/v)) using probes of the invention.
Figure 2B:
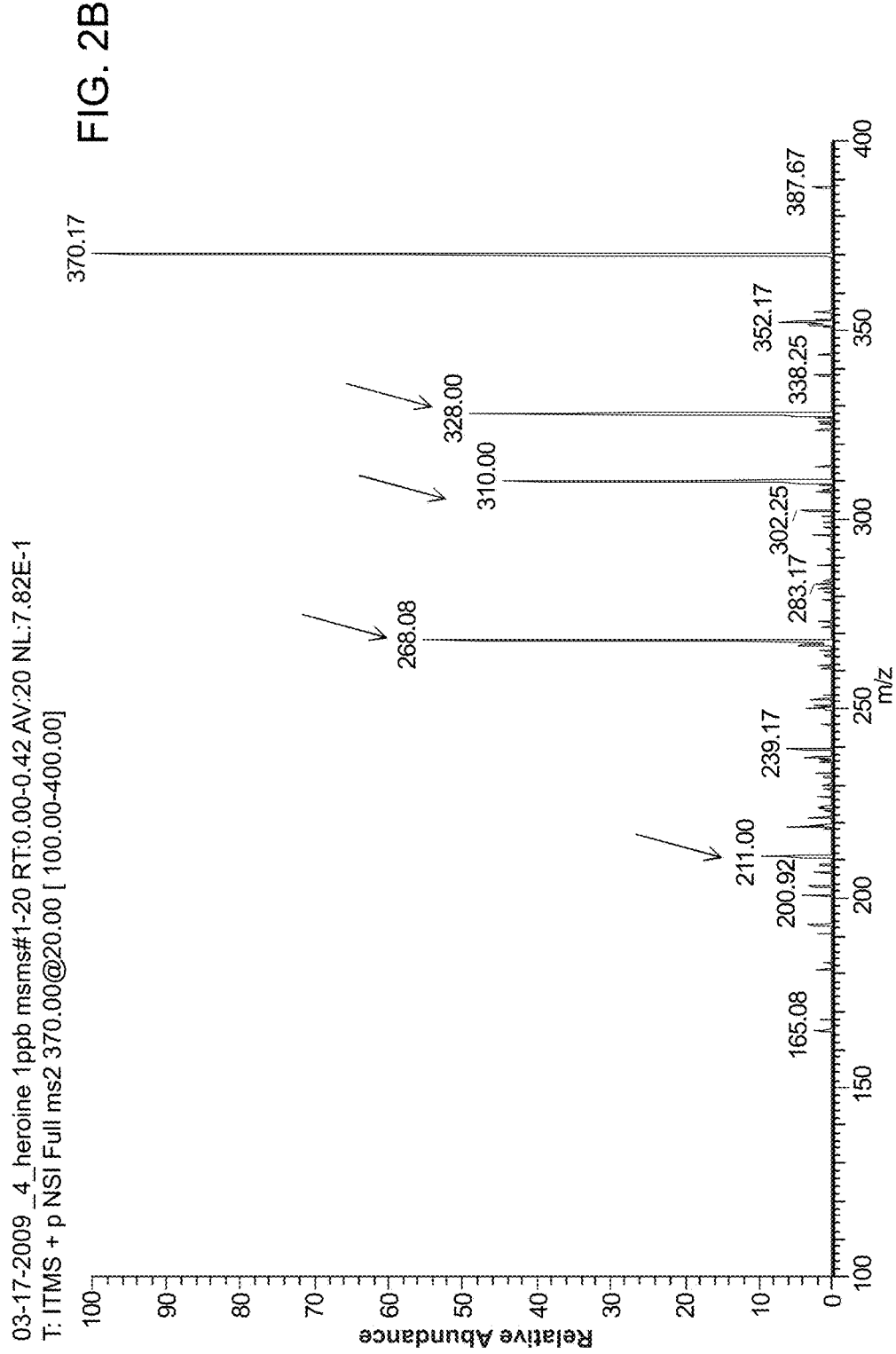
FIG. 2B is a MS/MS spectrum of heroin (concentration: 1 ppb, volume: 10 μl, solvent: MeOH/$H_2$O/HOAc (50:49:1, v/v/v)).

FIG. 2 panel (A) shows an MS spectrum of heroin (concentration: 1 ppm, volume: 10 µl, solvent: MeOH/$H_2O$/HOAc (50:49:1, v/v/v)) using probes of the invention. FIG. 2 panel (B) shows MS/MS spectrum of heroin (concentration: 1 ppb, volume: 10 µl solvent: MeOH/$H_2O$/HOAc (50:49:1, v/v/v)).

Figure 3B:
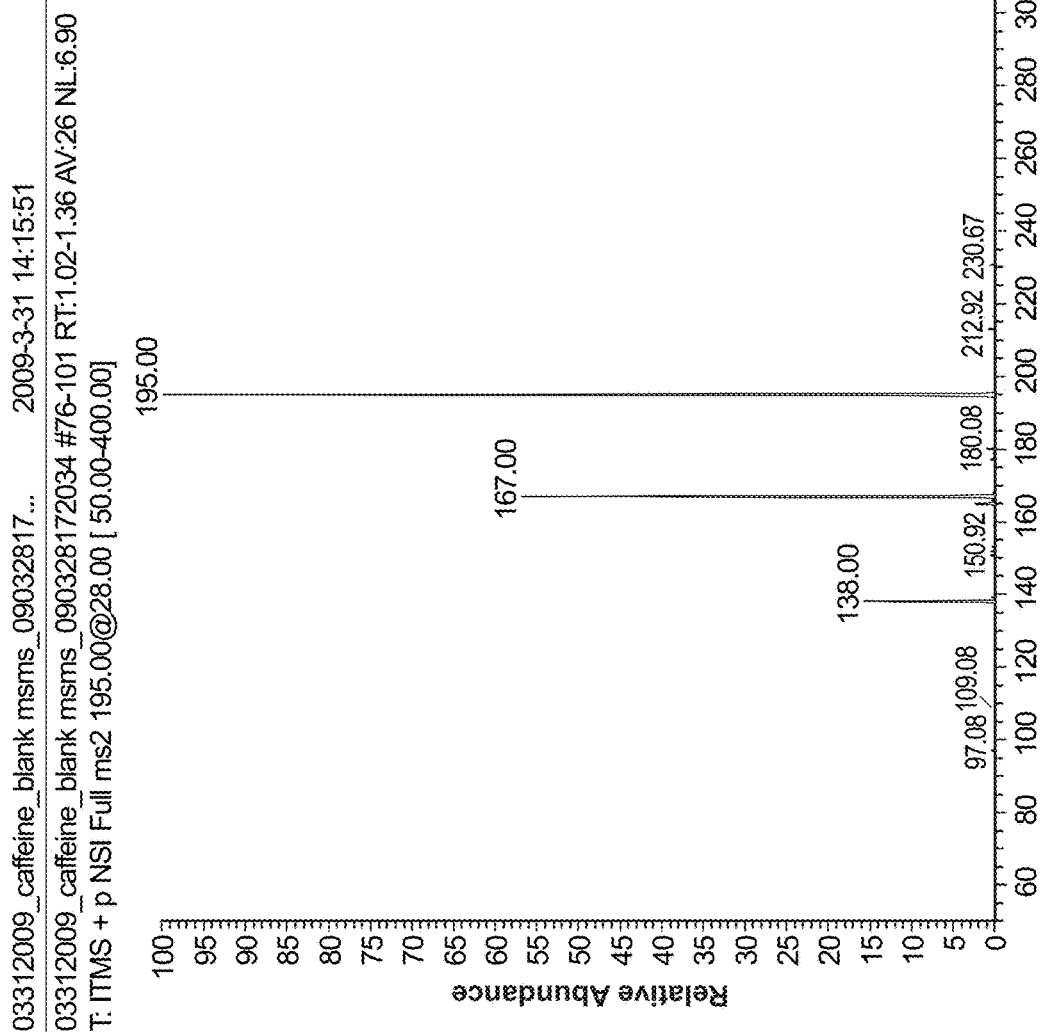
FIG. 3B is a MS/MS spectrum of caffeine (concentration: 10 ppb, volume: 10 μl, solvent: MeOH/$H_2$O/HOAc (50:49:1, v/v/v)).

FIG. 3 panel (A) shows MS spectrum of caffeine (concentration: 10 ppm, volume: 10 µl solvent: MeOH/$H_2O$/HOAc (50:49:1, v/v/v)) using probes of the invention. FIG. 3 panel (B) shows MS/MS spectrum of caffeine (concentration: 10 ppb, volume: 10 µl solvent: MeOH/$H_2O$/HOAc (50:49:1, v/v/v)). Peak 167 also exists in the blank spectrum with solvent and without caffeine.

Figure 4A:
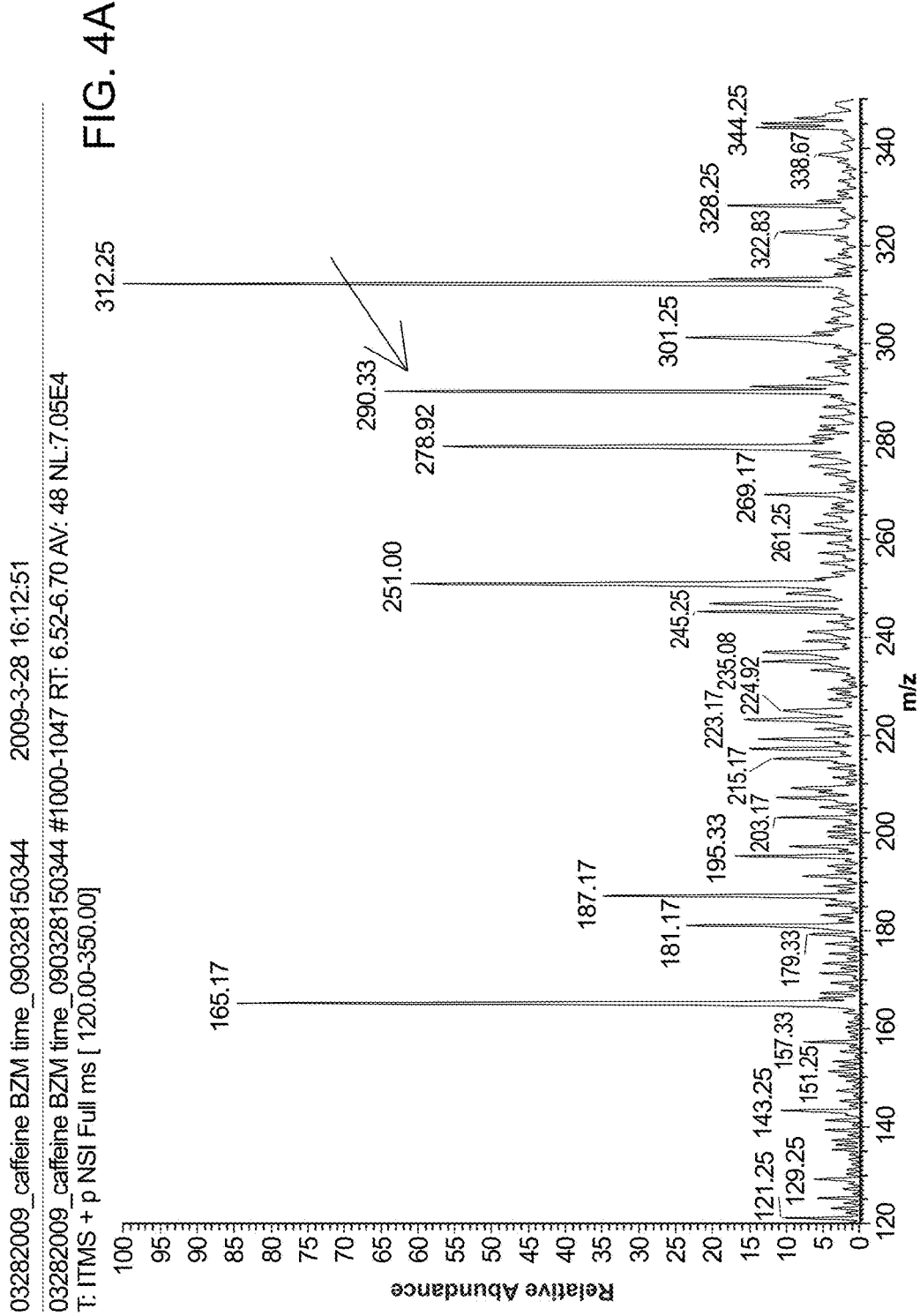
FIG. 4A is a MS spectrum of benzoylecgonine (concentration: 10 ppm, volume: 10 μl, solvent: MeOH/$H_2$O/HOAc (50:49:1, v/v/v)) using probes of the invention.
Figure 4B:
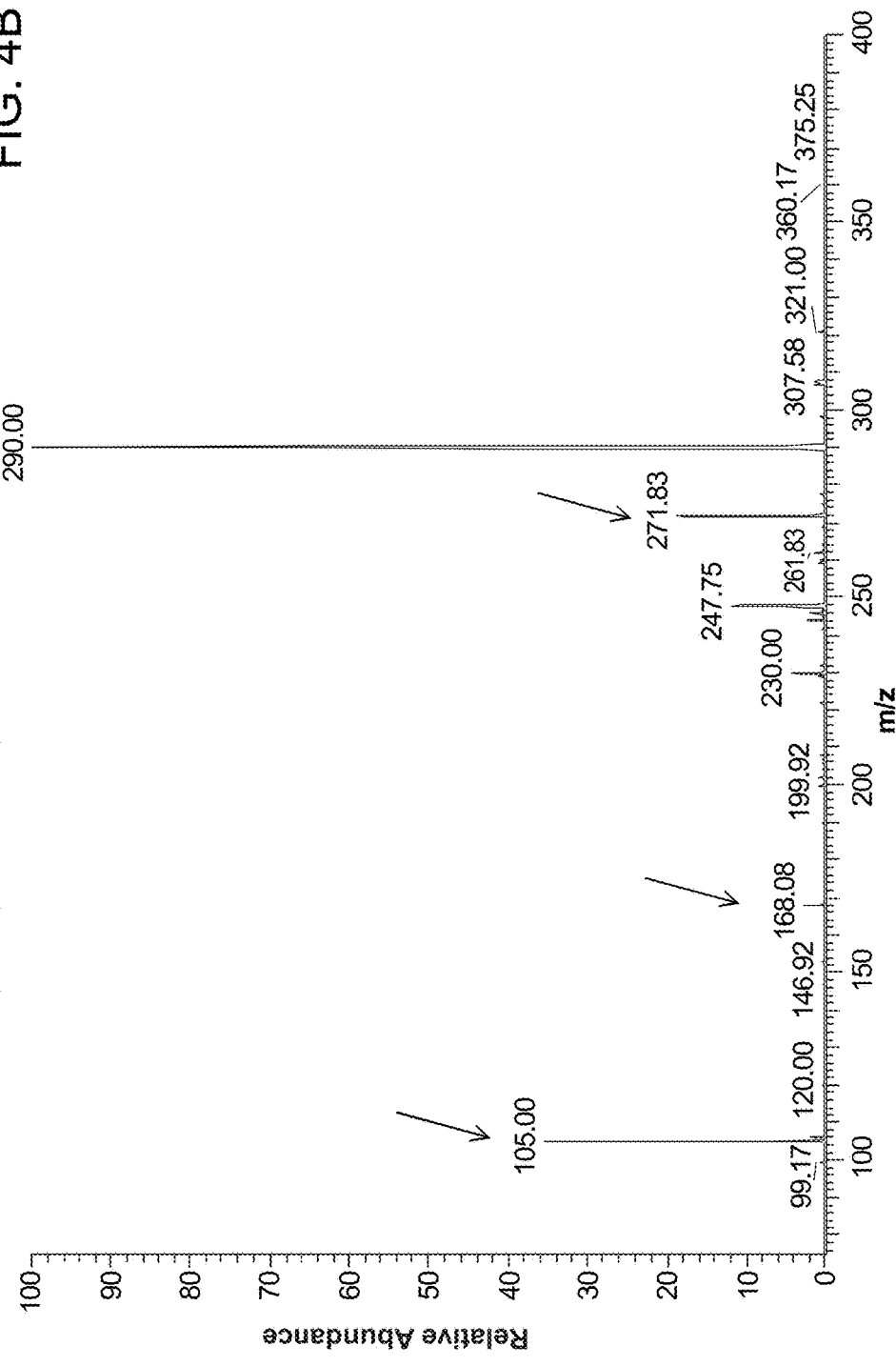
FIG. 4B is a MS/MS spectrum of benzoylecgonine (concentration: 10 ppb, volume: 10 μl, solvent: MeOH/$H_2$O/HOAc (50:49:1, v/v/v)).

FIG. 4 panel (A) shows MS spectrum of benzoylecgonine (concentration: 10 ppm, volume: 10 µl, solvent: MeOH/$H_2O$/HOAc (50:49:1, v/v/v)) using probes of the invention. FIG. 4 panel (B) shows MS/MS spectrum of benzoylecgonine (concentration: 10 ppb, volume: 10 µl, solvent: MeOH/$H_2O$/HOAc (50:49:1, v/v/v)).

Figure 5A:
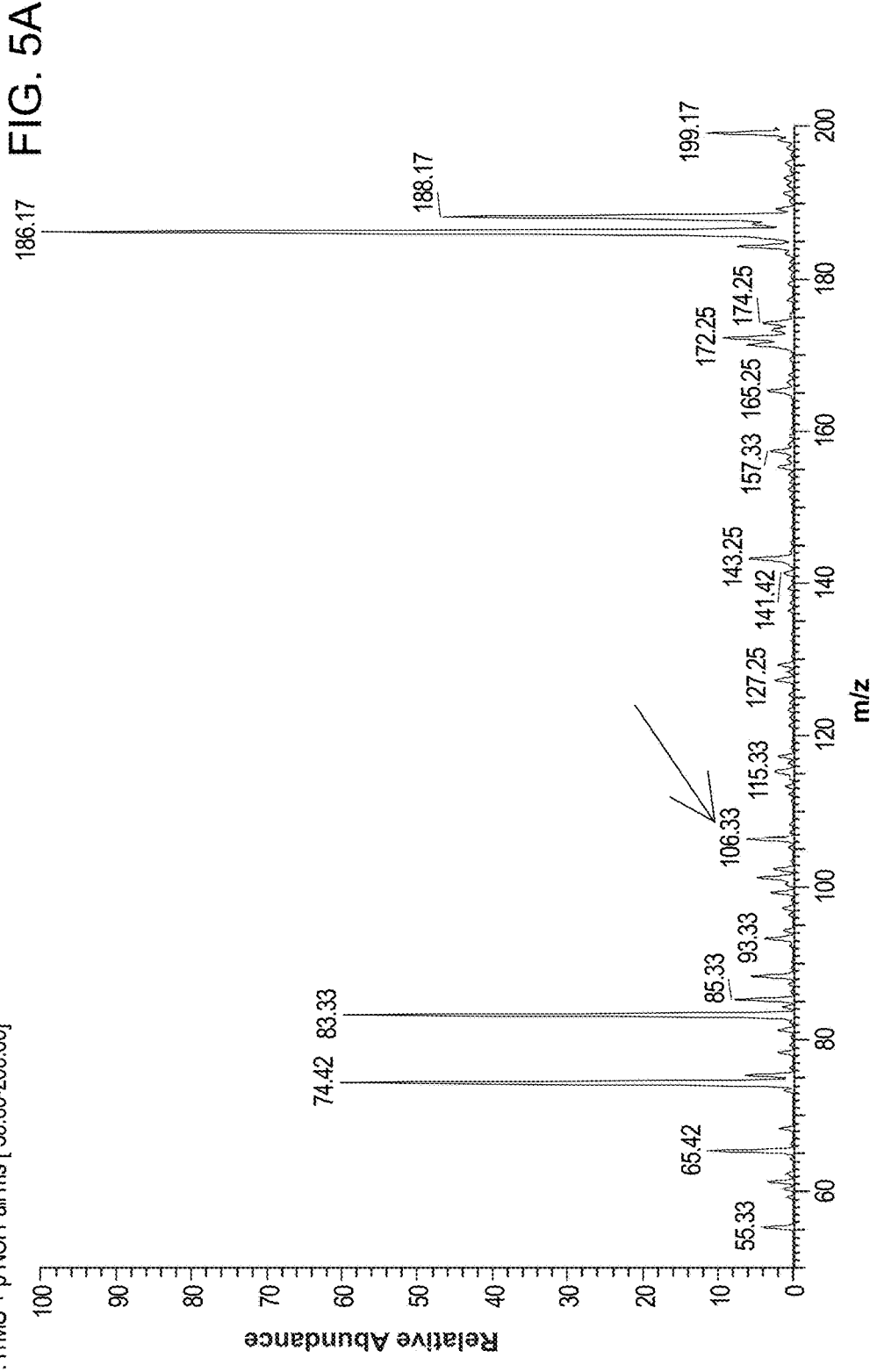
FIG. 5A is a MS spectrum of serine (concentration: 1 ppm, volume: 10 μl, solvent: MeOH/$H_2$O/HOAc (50:49:1, v/v/v)) using probes of the invention.
Figure 5B:
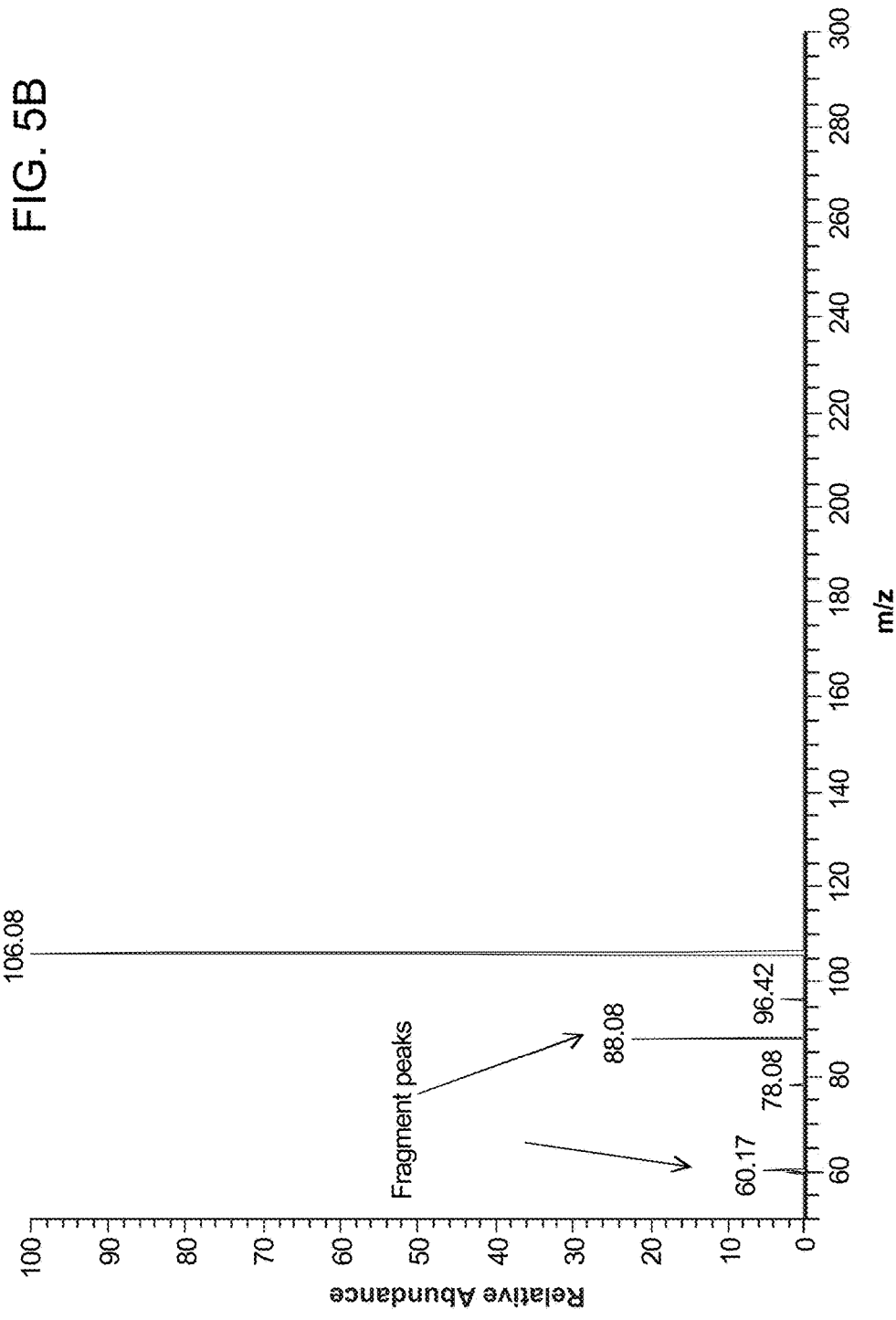
FIG. 5B is a MS/MS spectrum of serine (concentration: 100 ppb, volume: 10 μl, solvent: MeOH/$H_2$O/HOAc (50:49:1, v/v/v)).

FIG. 5 panel (A) shows MS spectrum of serine (concentration: 1 ppm, volume: 10 µl, solvent: MeOH/$H_2O$/HOAc (50:49:1, v/v/v)) using probes of the invention. FIG. 5 panel (B) shows MS/MS spectrum of serine (concentration: 100 ppb, volume: 10 µl, solvent: MeOH/$H_2O$/HOAc (50:49:1, v/v/v)). Peak 74 and 83 also exist in the blank spectrum with solvent and without serine. FIG. 21 panel (A) shows MS spectrum of serine (m/z, 106) using probes of the invention. Panel (A) also shows MS/MS spectrum of serine (m/z, 106).

FIG. 21 Panel (B) shows MS spectrum of methadone (m/z, 310) using probes of the invention. Panel (B) also shows MS/MS spectrum of methadone (m/z, 310). Panel (C) shows MS spectrum of roxithromycin (m/z, 837) using probes of the invention. Panel (B) also shows MS/MS spectrum of roxithromycin (m/z, 837).

Figure 6A:
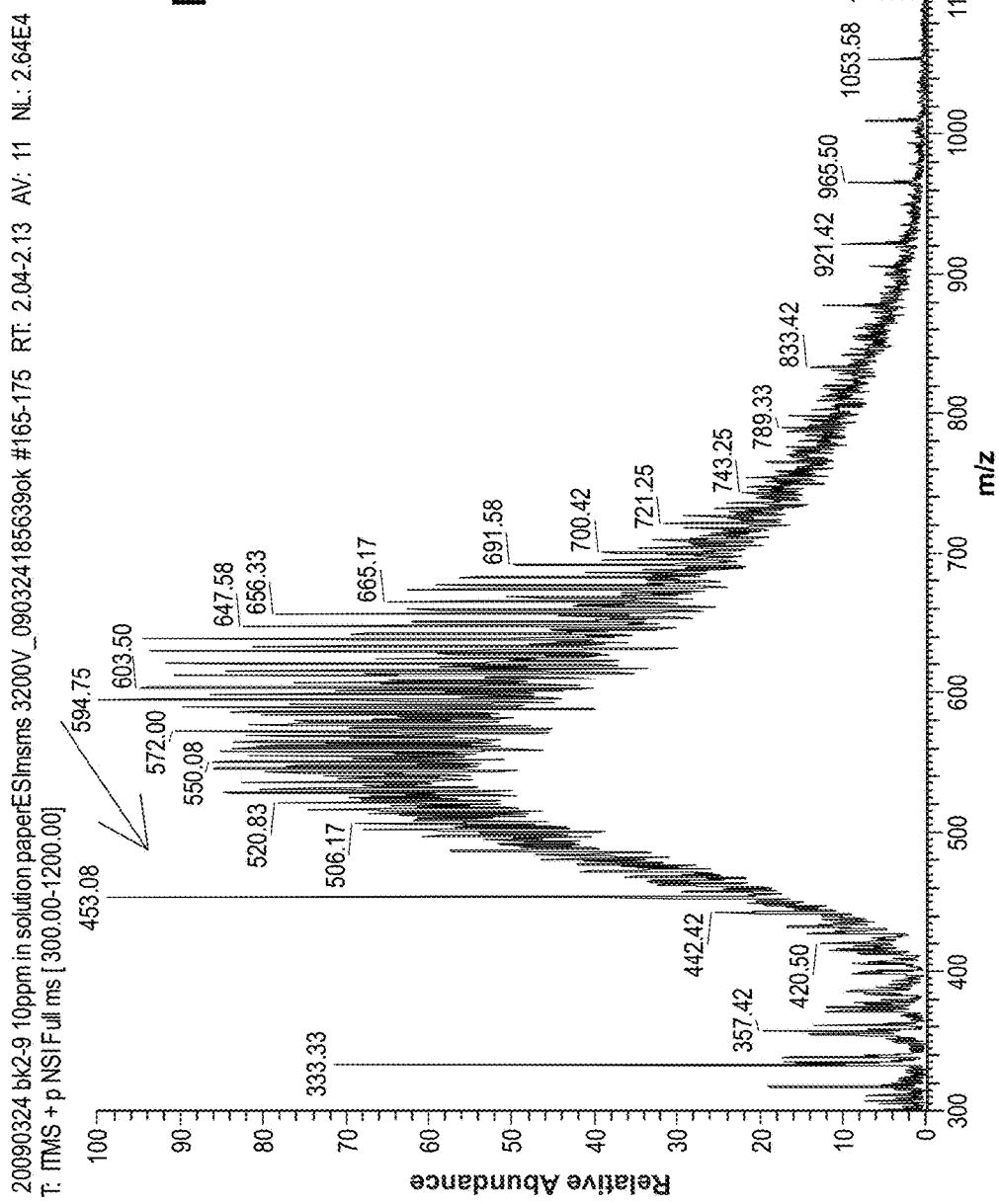
FIG. 6A is a MS spectrum of peptide bradykinin2-9 (concentration: 10 ppm, volume: 10 μl, solvent: MeOH/$H_2$O/HOAc (50:49:1, v/v/v)) using probes of the invention.
Figure 6B:
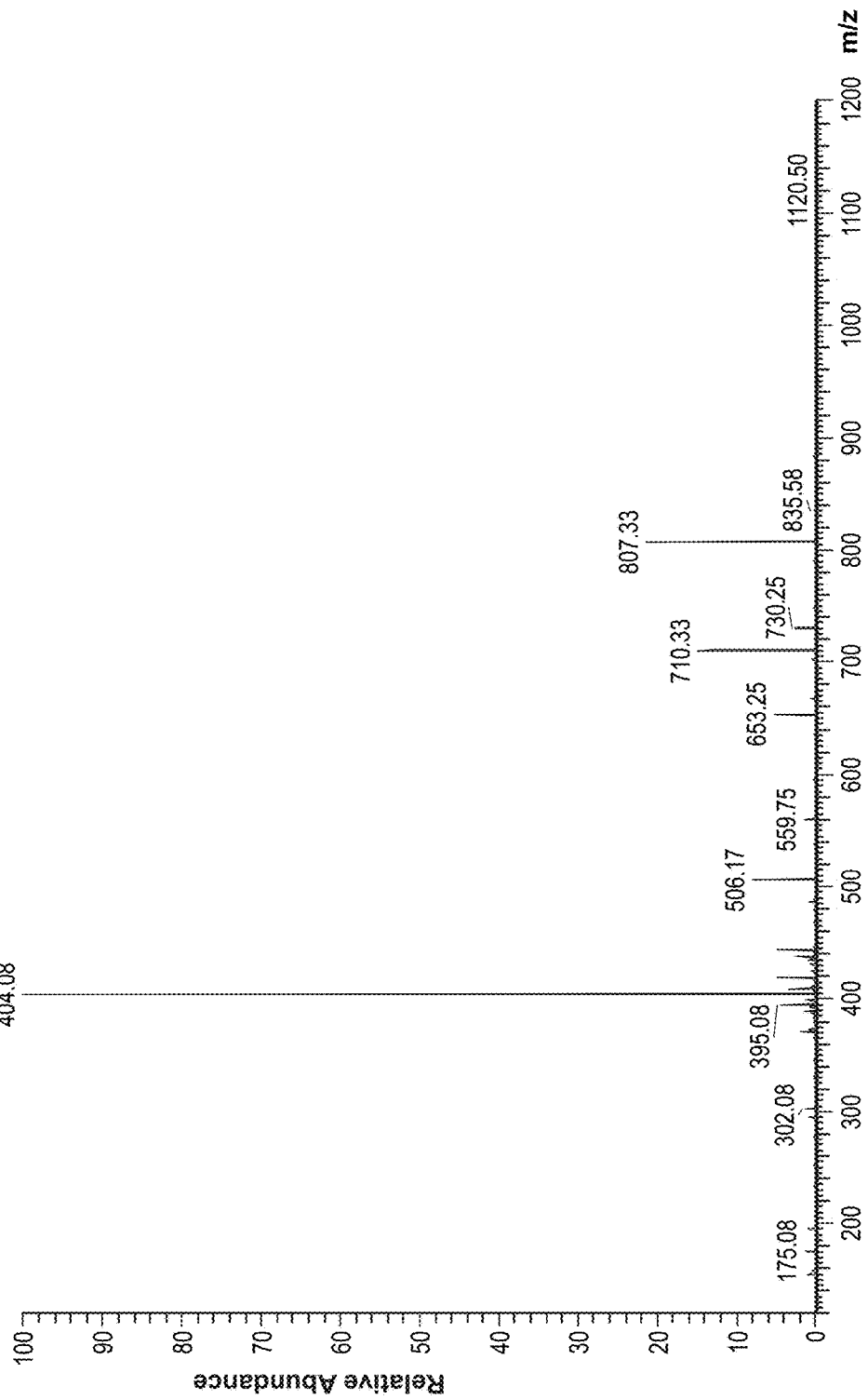
FIG. 6B is a MS/MS spectrum of bradykinin2-9 (concentration: 1 ppm, volume: 10 μl, solvent: MeOH/$H_2$O/HOAc (50:49:1, v/v/v)).

FIG. 6 panel (A) shows MS spectrum of peptide bradykinin2-9 (concentration: 10 ppm, volume: 10 µl, solvent: MeOH/$H_2O$/HOAc (50:49:1, v/v/v)) using probes of the invention. FIG. 6 panel (B) shows MS/MS spectrum of bradykinin2-9 (concentration: 1 ppm, volume: 10 µl, solvent: MeOH/$H_2O$/HOAc (50:49:1, v/v/v)). The hump in the spectrum is assumed to be caused by polymers, such as polyethylene glycol (PEG), which are frequently added to materials in industry. FIG. 21 panel (D) shows MS spectrum of bradykinin 2-9 (m/z, 453) using probes of the invention. Panel (D) also shows MS/MS spectrum of bradykinin 2-9 (m/z, 453). Panel D further shows adduct ions [M+H] (m/z, 904), [M+2H]$^{2+}$ (m/z, 453), [M+H+Na]$^{2+}$ (m/z, 464) and [M+2Na]$^{2+}$ (m/z, 475). The m/z 453 peak was double charged adduct ion confirmed by the MS/MS spectrum.

Figure 11A:
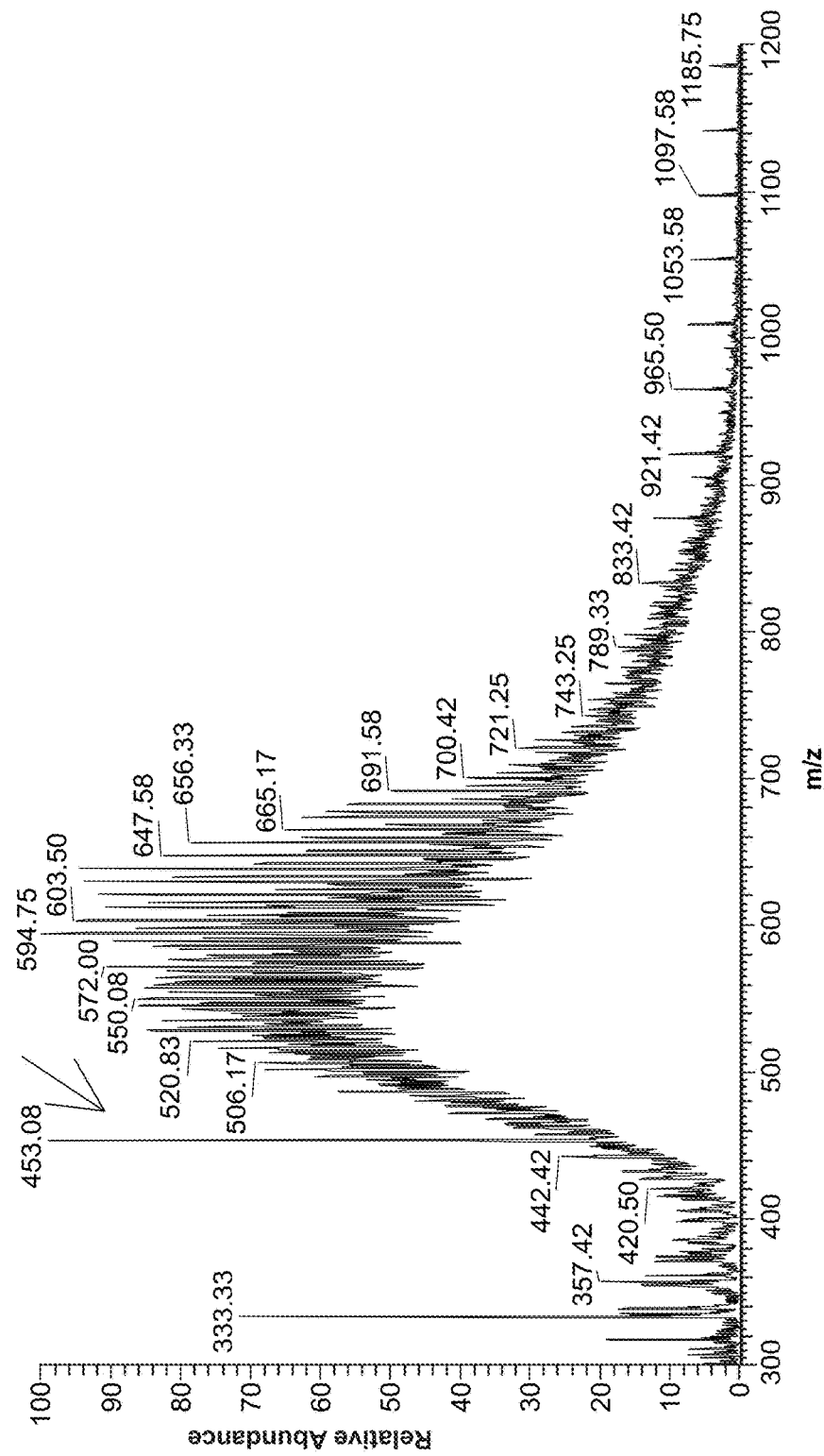

FIG. 11 is an MS spectra showing the difference between peptide analysis (10 ppm of bradykinin 2-9) on (A) paper slice and (B) PVDF membrane using the same parameters (~2 kV, Solvent: MeOH:$H_2O$=1:1).

Data herein show that probes of the invention work well over the mass/charge range from 50 to over 1000 for detection of pure compounds. Data further shows that detection was achieved down to as low as 1 ng/mL for most chemicals, including illegal drugs, such as heroin, cocaine and methadone.

Example 7: Complex Mixtures

Complex mixtures such as urine, blood, and cola drink were examined using methods, devices, and systems of the invention. All experiments were carried out with a Finnigan LTQ mass spectrometer (Thermo Electron, San Jose, Calif.).

Figure 7A:
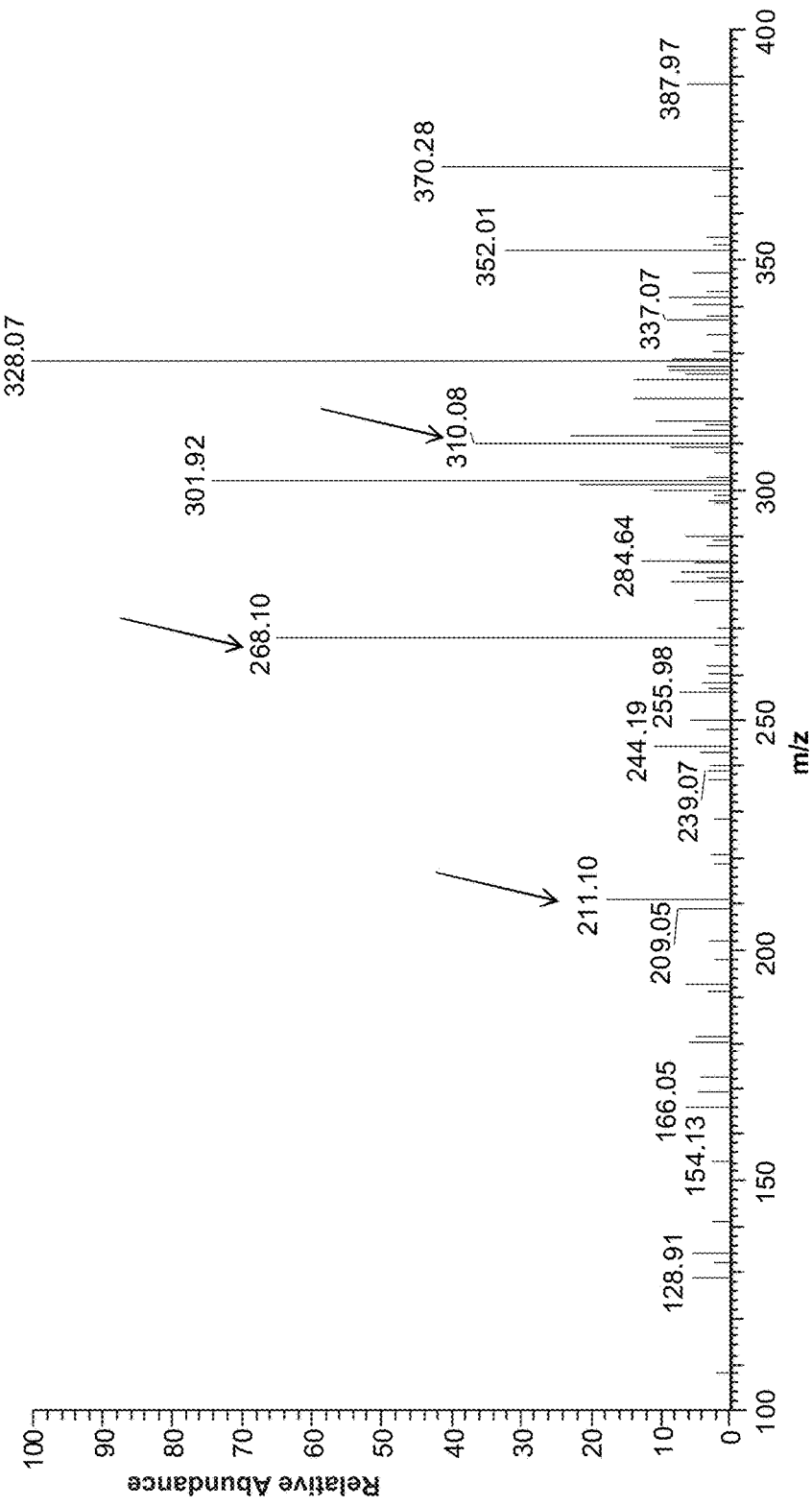
FIG. 7A is a MS/MS spectrum showing that heroin can be detected from whole blood sample by a "spot" method.
Figure 7B:
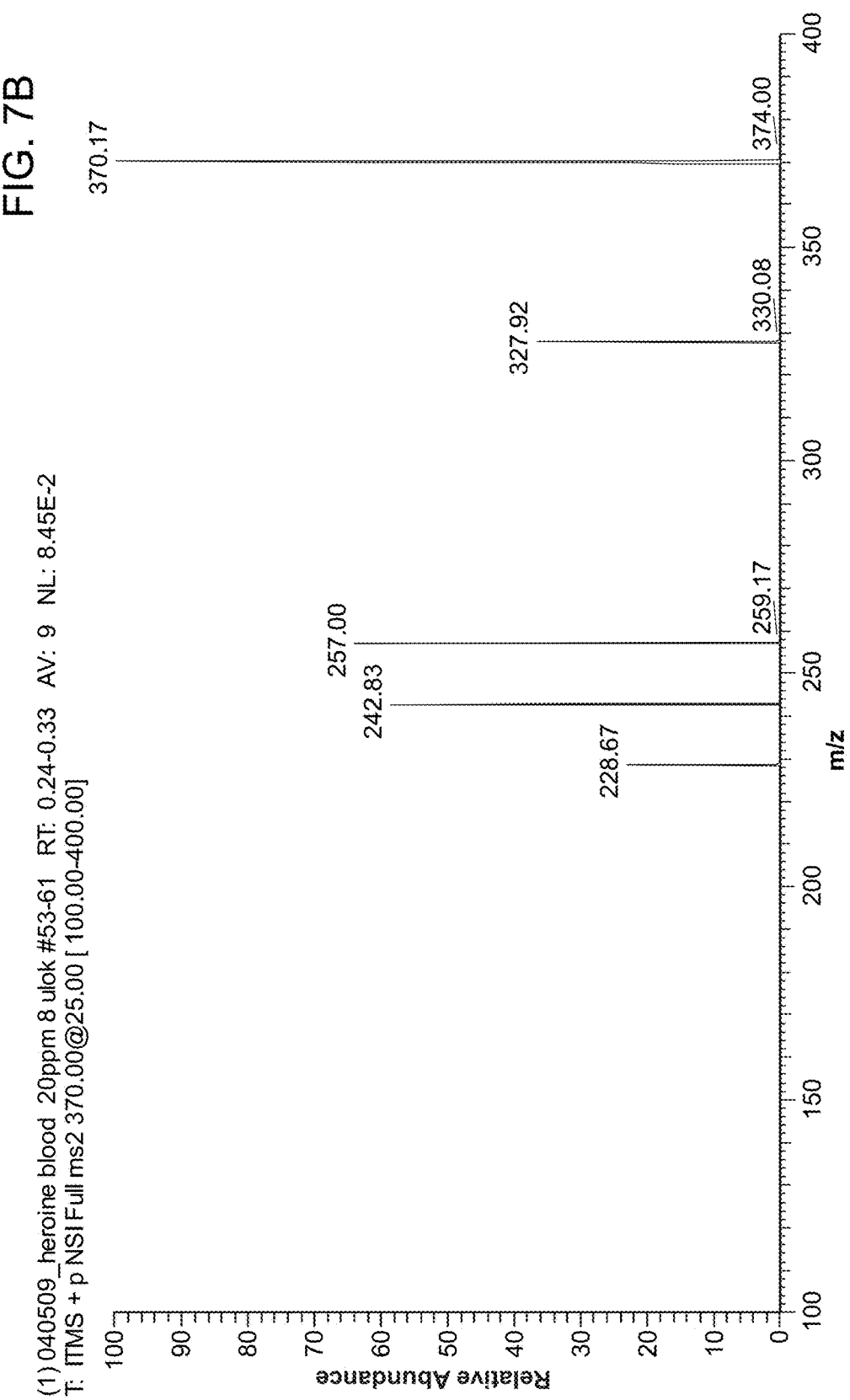
FIG. 7B shows the MS/MS spectrum of the blood spot without heroin.

FIG. 7 panel (A) shows an MS/MS spectrum that shows that heroin was detected from whole blood sample by a "spot" method. 0.4 μl of whole blood sample containing 200 ppb heroin was applied on the center of the triangle paper to form a 1 mm² blood spot. After the spot was dry, 10 μl of solvent (MeOH/H$_2$O/HOAc (50:49:1, v/v/v)) was applied to the rear end of the triangle paper. Due to the capillary effect, the solvent moved forward and dissolved the chemicals in the blood spot. Finally, electrospray occurred when the solvent reached the tip of the paper. To demonstrate the effectiveness of the "blood spot" method mentioned above, the whole blood was added on the paper for electrospray directly. MS/MS spectrum showed that heroin was not detected from 10 μl of whole blood sample, even when the concentration was as high as 20 ppm (FIG. 7 panel B).

FIG. 8 panel (A) shows an MS/MS spectrum that shows that heroin can be detected from raw urine sample by a "spot" method. 0.4 μl of raw urine sample containing 100 ppb heroin was applied on the center of the triangle paper to form a 1 mm² urine spot. After the spot was dry, 10 μl of solvent (MeOH/H$_2$O/HOAc (50:49:1, v/v/v)) was applied to the rear end of the triangle paper. Due to the capillary effect, the solvent moved forward and dissolved the chemicals in the blood spot. Finally, electrospray occurred when the solvent reached the tip of the paper. To demonstrate the effectiveness of the "spot" method mentioned above, the raw urine was added on the paper for electrospray directly. MS/MS spectrum showed heroin was not detected from 10 μl of raw urine sample when concentration was 100 ppb (FIG. 8 panel B).

Figure 9A:
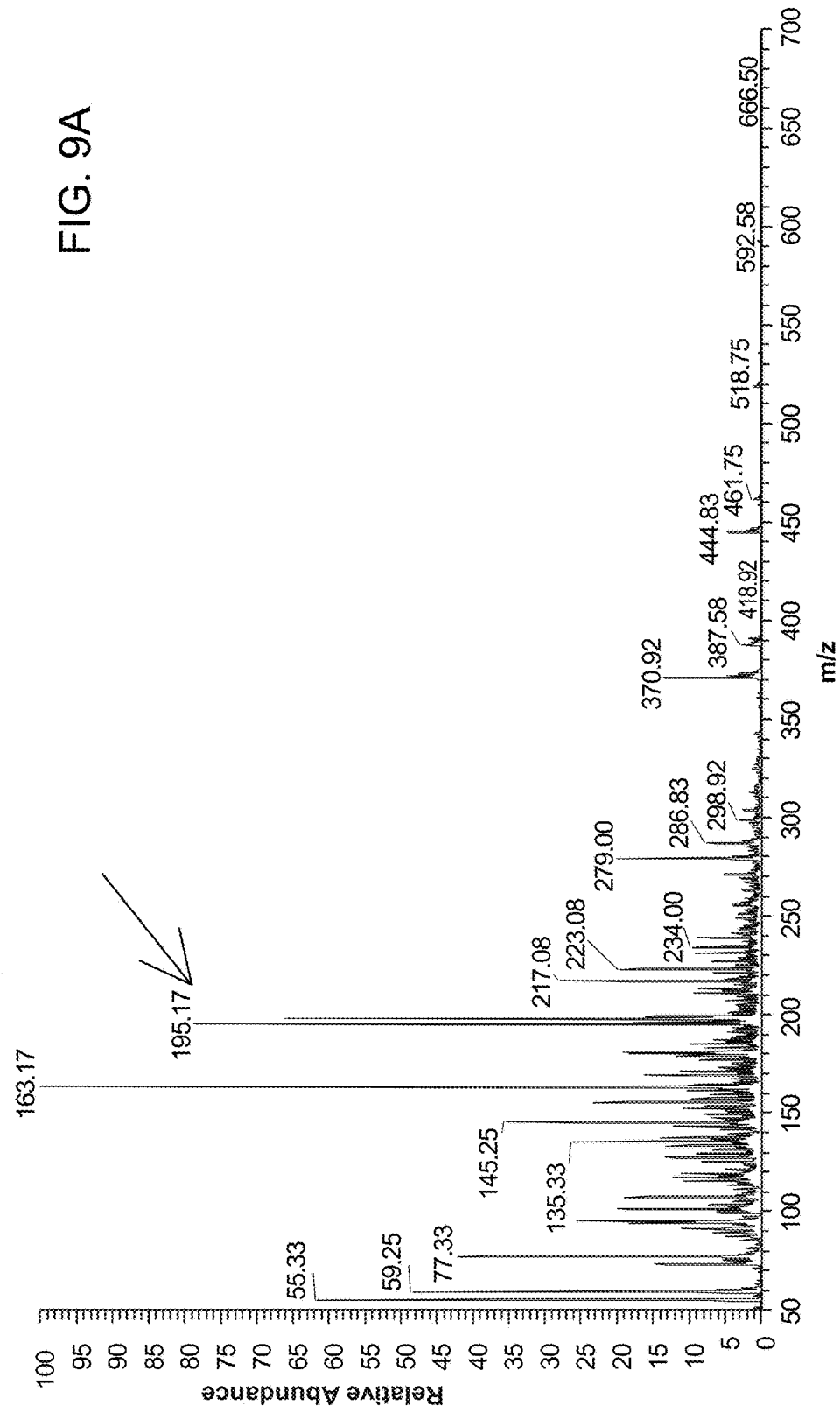
FIG. 9A is a MS spectrum showing the caffeine detected from a cola drink without sample preparation.
Figure 9B:
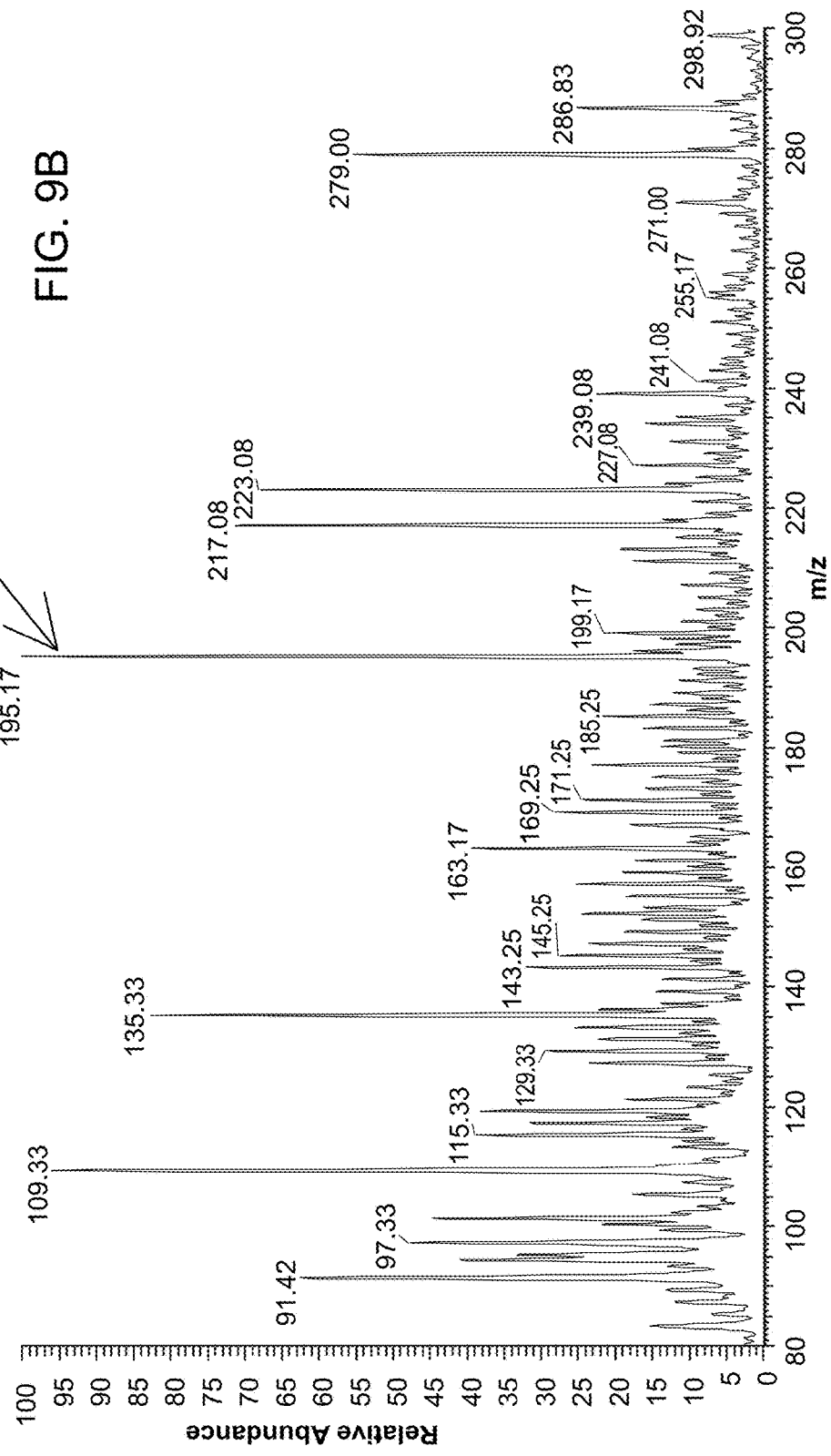
FIG. 9B is a MS spectrum showing caffeine detected from coffee powder. A paper slice was used to collect the coffee powder from a coffee bag by swabbing the surface.

FIG. 9 panel (A) is an MS spectrum showing that caffeine was detected from a cola drink without sample preparation. FIG. 9 panel (B) is an MS spectrum showing that caffeine was detected from coffee powder. A paper triangle was used to collect the coffee powder from a coffee bag by swabbing the surface.

FIG. 22 panels (A-B) show the spectra of COCA-COLA (cola drink), analyzed in positive mode and negative mode, respectively. The peak of protonated caffeine, m/z 195, identified in MS/MS spectrum, was dominated in the mass spectrum in positive mode due to the high concentration of caffeine (100 ug/mL) in this drink (Panel C). Two high concentrated compounds, potassium benzoate and acesulfame potassium were identified in the MS/MS spectrum in negative mode (Panels D-E).

FIG. 22 panel F shows spectra of caffeine in urine from a person who had drunk COCA-COLA (cola drink) two hours before the urine collection. Urine typically contains urea in very high concentration, which is also easily ionized. Therefore, protonated urea [m/z, 61] and urea dimmer [m/z, 121] dominated the MS spectrum. However, the protonated caffeine was identified in the MS/MS spectrum, which showed good signal to noise ratio in the urine sample.

Figure 10A:
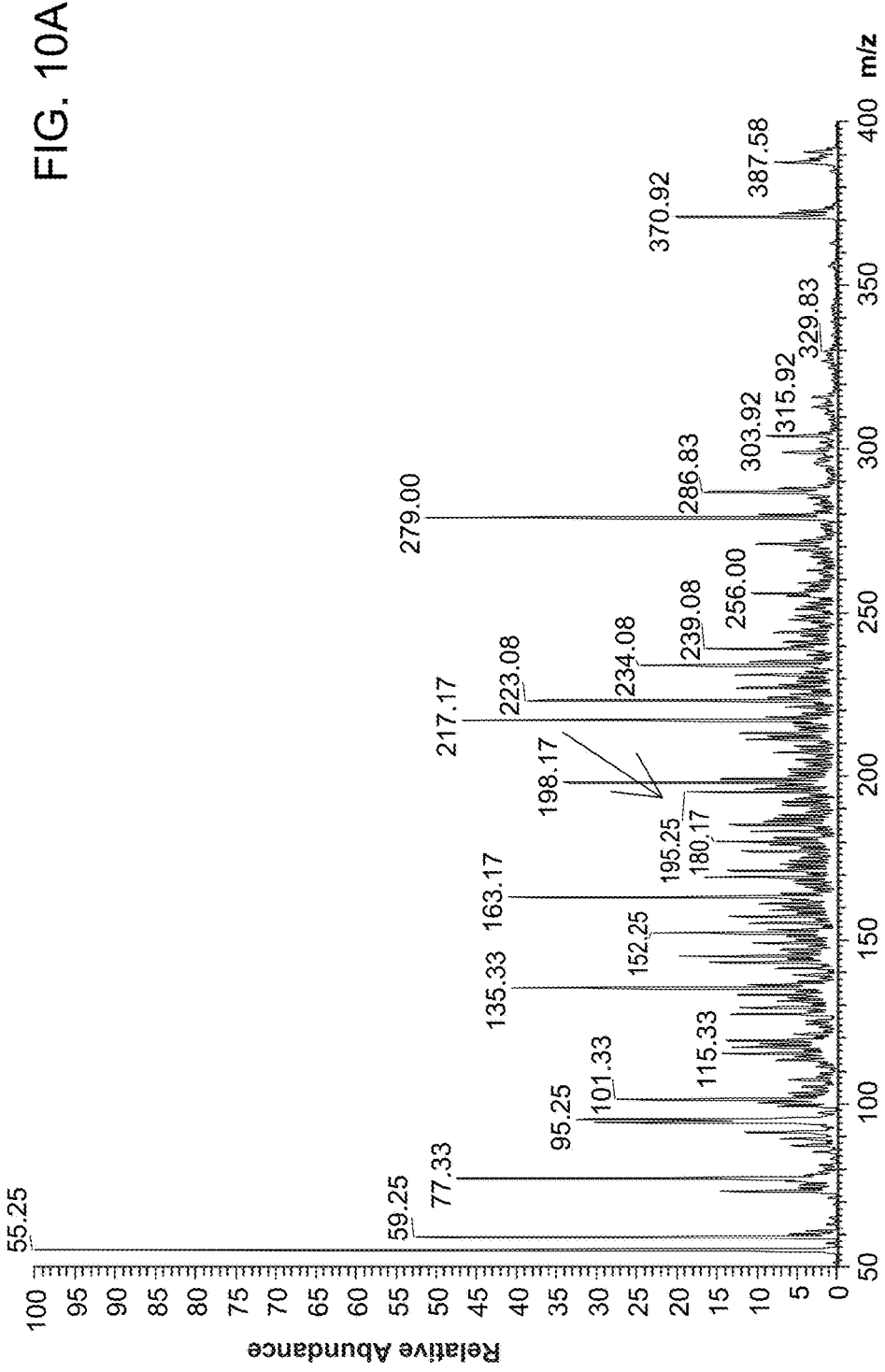
FIGS. 10A-B shows MS spectra of urine analysis without sample preparation.
Figure 10B:
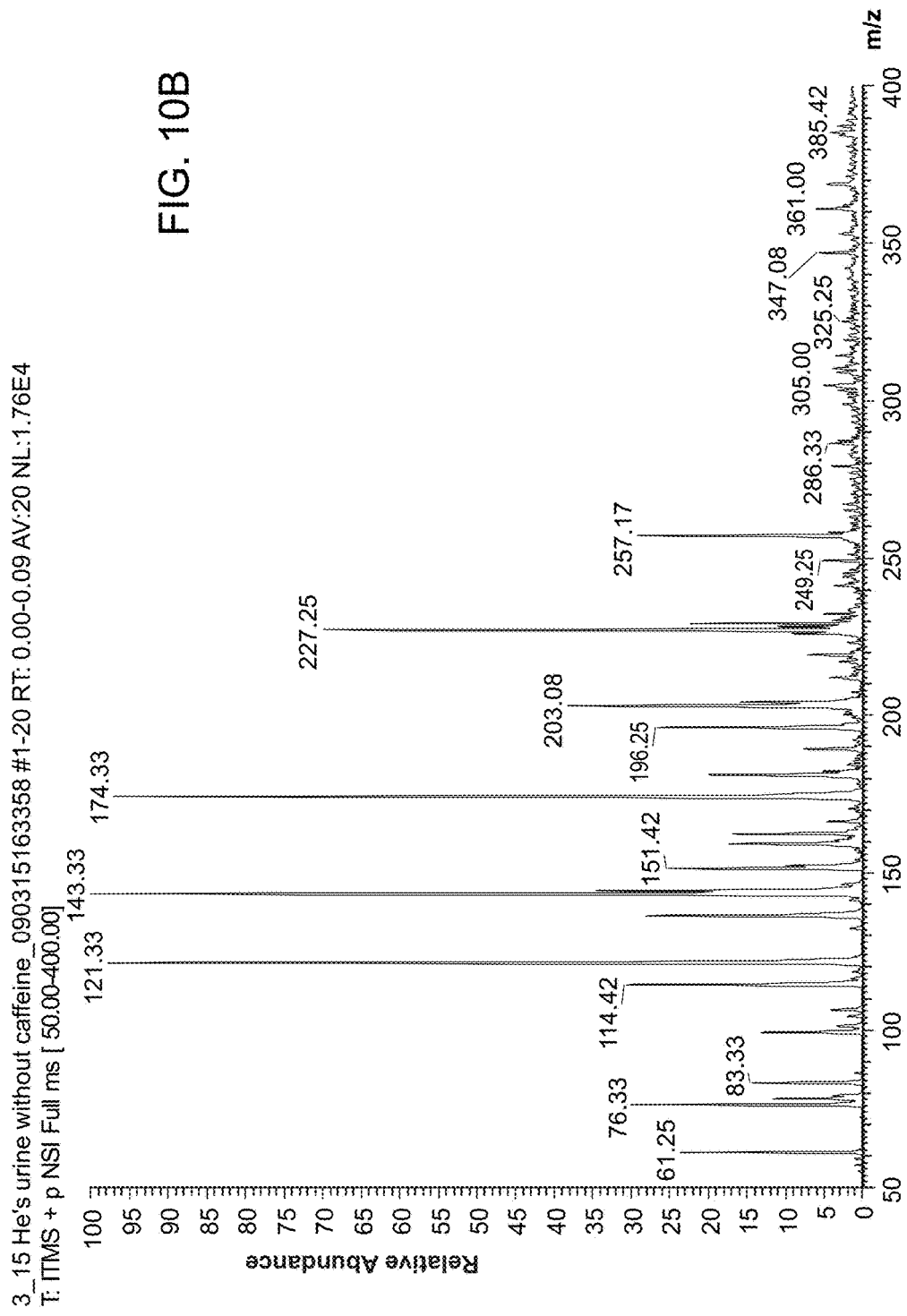

FIG. 10 shows MS spectra of urine taken for analysis without sample preparation. FIG. 10 panel (A) is a mass spectra of caffeine that was detected in urine from a person who had consumed coffee. FIG. 10 panel (B) is a mass spectra showing that caffeine was not detected in urine from a person who had not consumed any coffee.

FIG. 22 panel G shows the MS spectrum of heroin (m/z, 370) collected as a swabbed sample. A 5 uL solution containing 50 ng heroin was spotted on a 1 cm² area of a desktop. The paper triangle was wetted and used to swab the surface of the desktop. The paper triangle was then connected to the high voltage source for mass detection. This data shows that probes of the invention can have dual roles of ionization source as well as a sampling device for mass detection. Trace sample on solid surface could be simply collected by swabbing the surface using probes of the invention. Dust and other interferences were also collected on the paper triangle, but the heroin could be directly detected from this complex matrix.

Example 8: Plant Tissue Direct Analysis by ESI Without Extraction

Figure 12A:
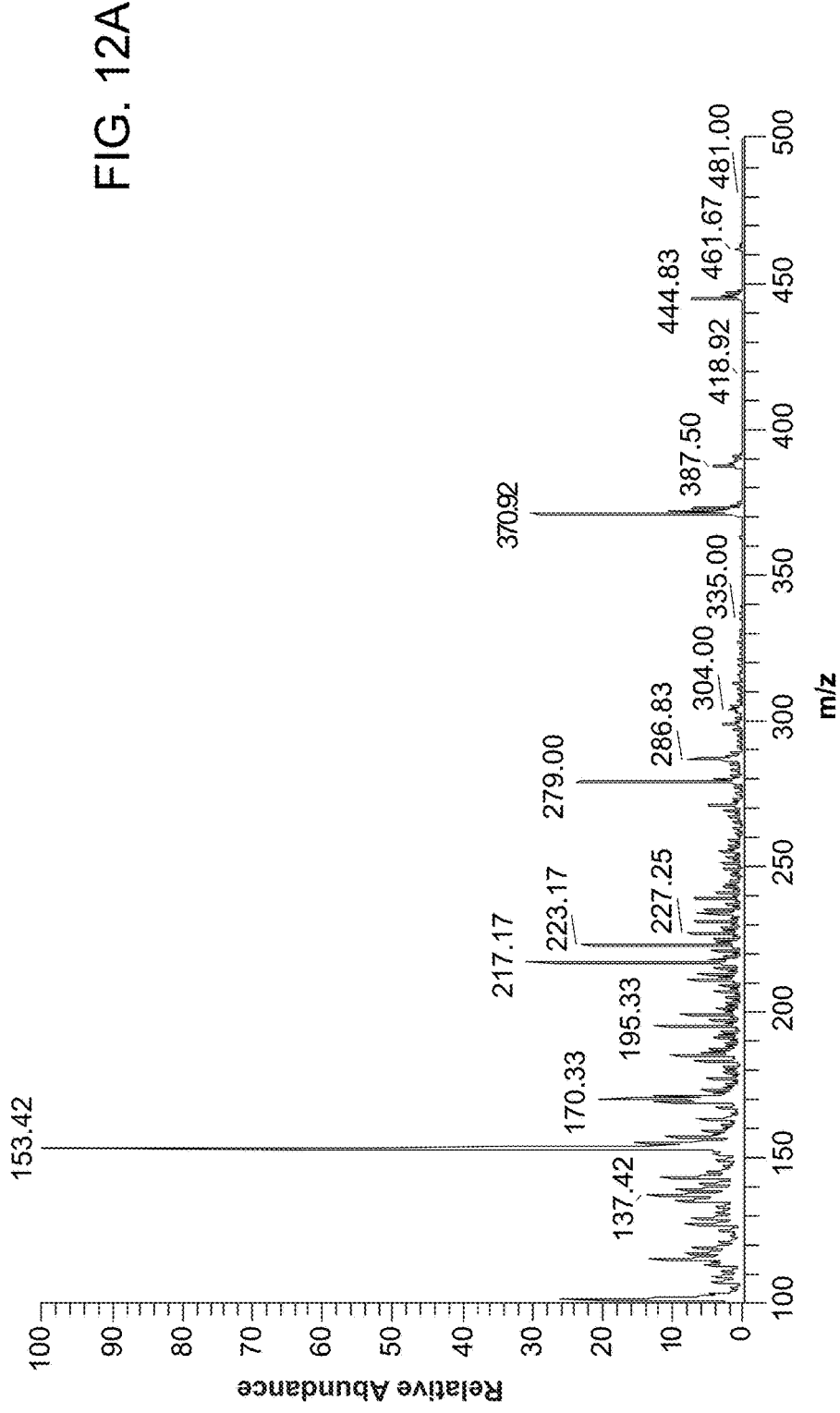
Figure 12B:
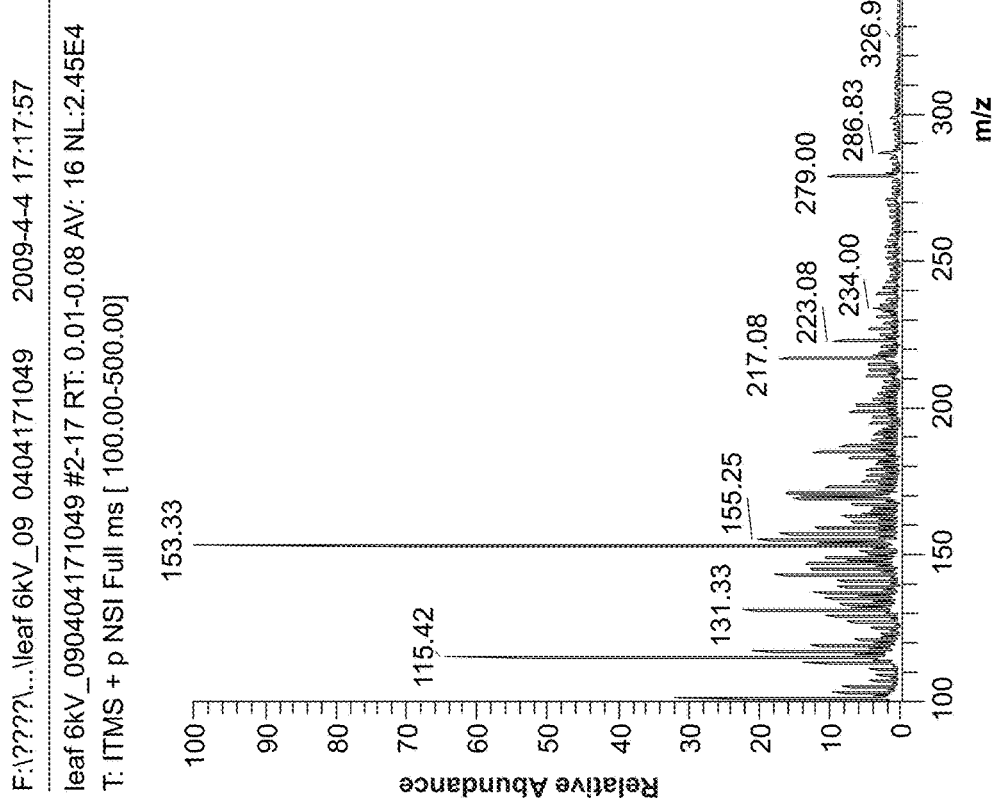
Figure 12C:
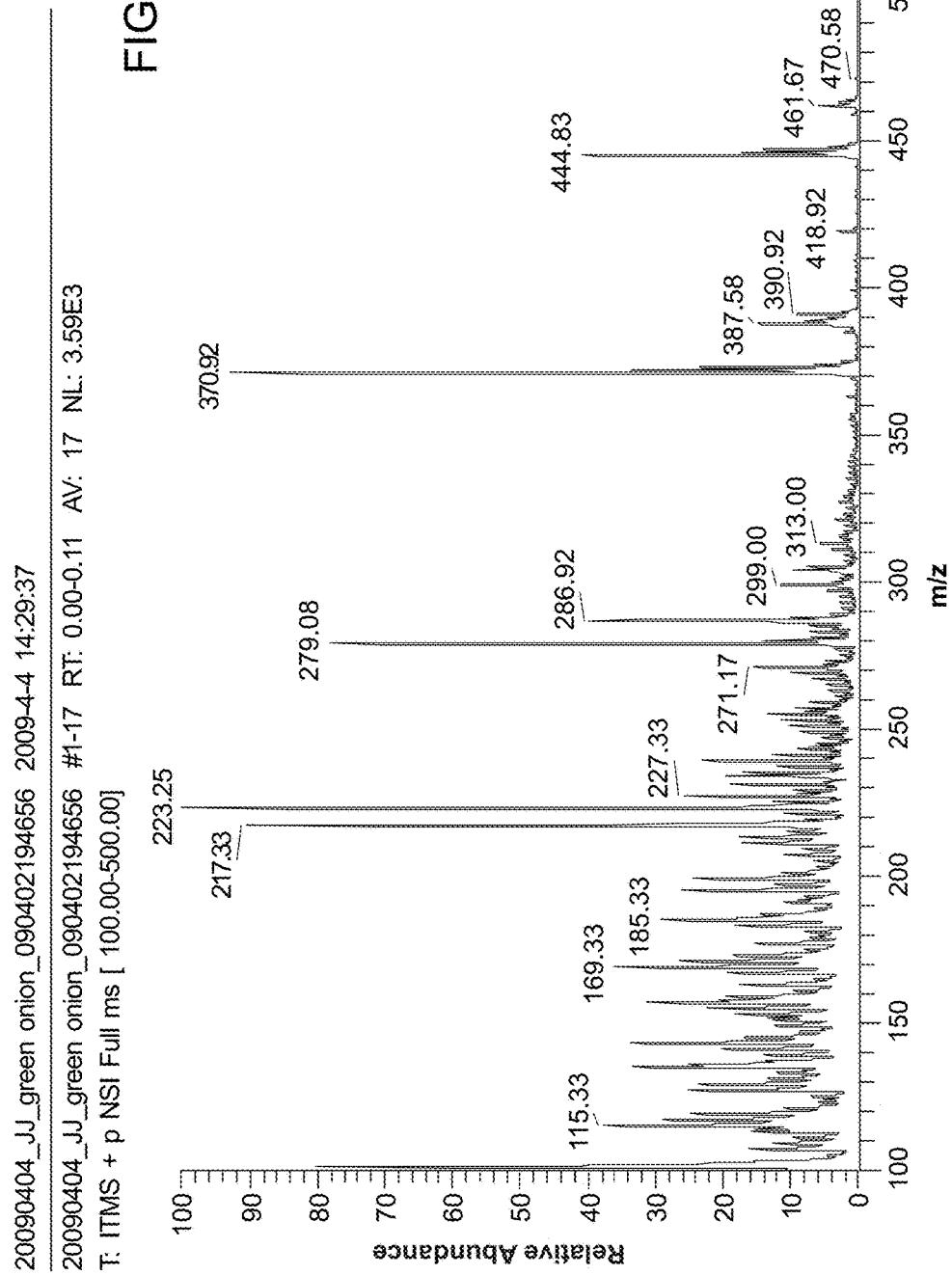

FIG. 12 shows direct MS spectra of plant tissues using sliced tissues of four kinds of plants. (A) Onion, (B) Spring onion, and two different leaves (C) and (D).

Figure 13A:
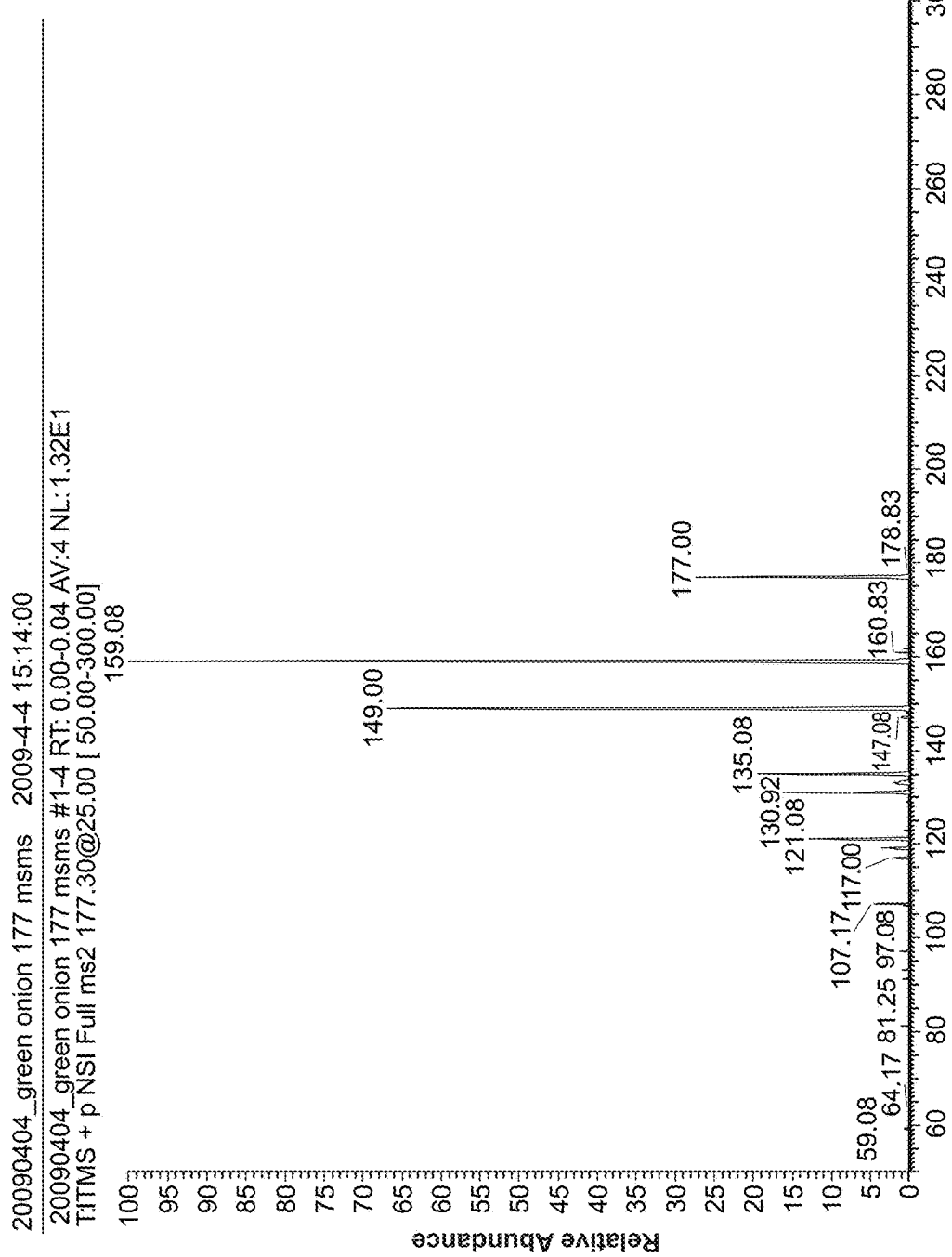
FIGS. 13A-B show MS/MS spectra of Vitamin C.
Figure 13B:
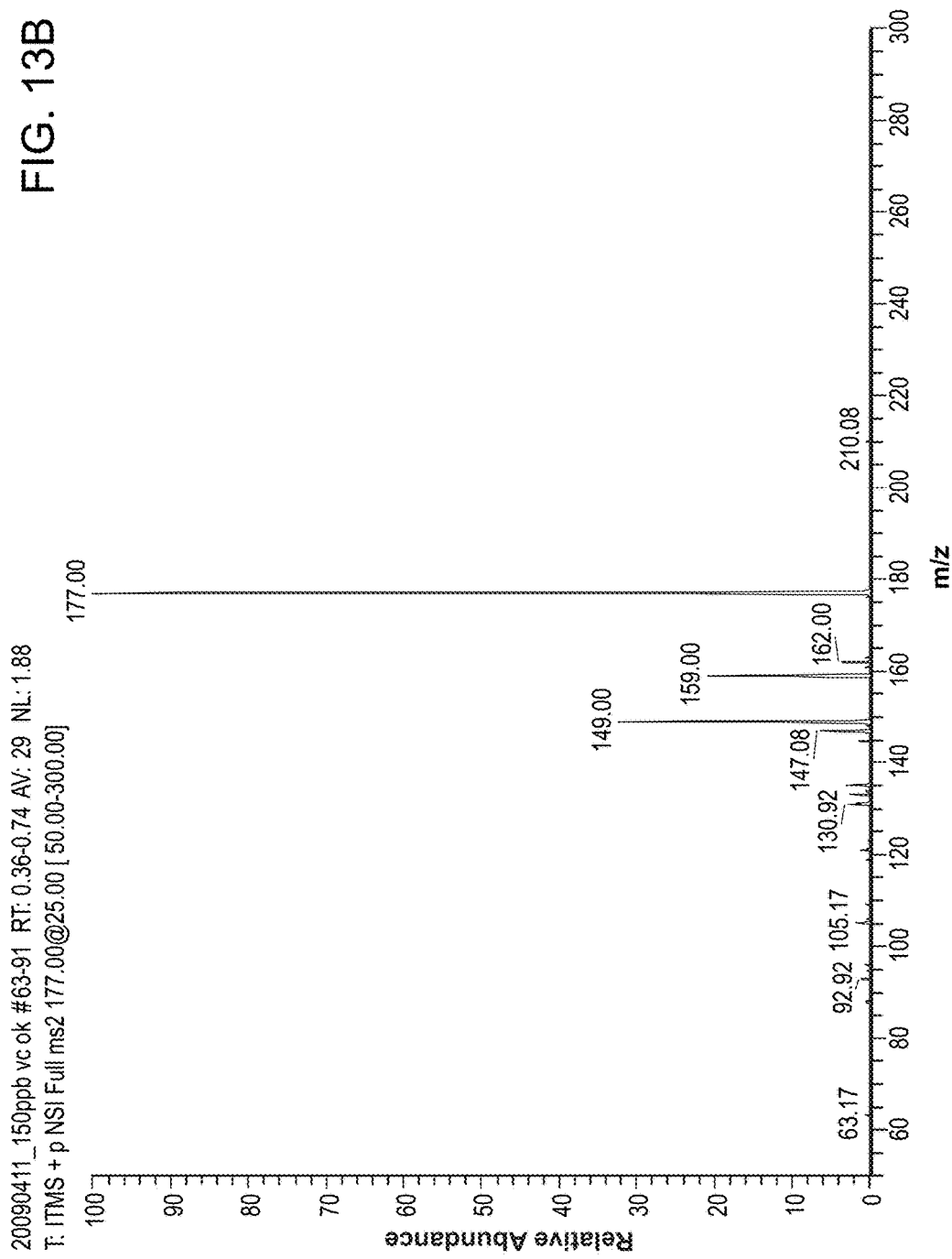

FIG. 13 shows an MS/MS spectra of Vitamin C analysis (A) direct analysis of onion without sample preparation, (B) using standard solution.

Example 9: Whole Blood and Other Biofluids

Body fluids, such as plasma, lymph, tears, saliva, and urine, are complex mixtures containing molecules with a wide range of molecular weights, polarities, chemical properties, and concentrations. Monitoring particular chemical components of body fluids is important in a number of different areas, including clinical diagnosis, drug development, forensic toxicology, drugs of abuse detection, and therapeutic drug monitoring. Tests of blood, including the derived fluids plasma and serum, as well as on urine are particularly important in clinical monitoring.

A wide variety of chemicals from blood are routinely monitored in a clinical setting. Common examples include a basic metabolic panel measuring electrolytes like sodium and potassium along with urea, glucose, and creatine and a lipid panel for identifying individuals at risk for cardiovascular disease that includes measurements of total cholesterol, high density lipoprotein (HDL), low density lipoprotein (LDL), and triglycerides. Most laboratory tests for chemicals in blood are actually carried out on serum, which is the liquid component of blood separated from blood cells using centrifugation. This step is necessary because many medical diagnostic tests rely on colorimetric assays and therefore require optically clear fluids. After centrifugation, detection of the molecule of interest is carried in a number of ways, most commonly by an immunoassay, such as an enzyme-linked immunosorbent assay (ELISA) or radioimmunoas say (RIA), or an enzyme assay in which the oxidation of the molecule of interest by a selective enzyme is coupled to a reaction with a color change, such as the tests for cholesterol (oxidation by cholesterol oxidase) or glucose (oxidation by glucose oxidase).

There is considerable interest in the pharmaceutical sciences in the storage and transportation of samples of whole blood as dried blood spots on paper (N. Spooner et al. *Anal Chem.*, 2009, 81, 1557). Most tests for chemicals found in blood are carried out on a liquid sample, typically serum or plasma isolated from the liquid whole blood. The required storage, transportation, and handling of liquid blood or blood components present some challenges. While blood in liquid form is essential for some tests, others can be performed on blood or other body fluids that have been spotted onto a surface (typically paper) and allowed to dry.

Figure 23B:
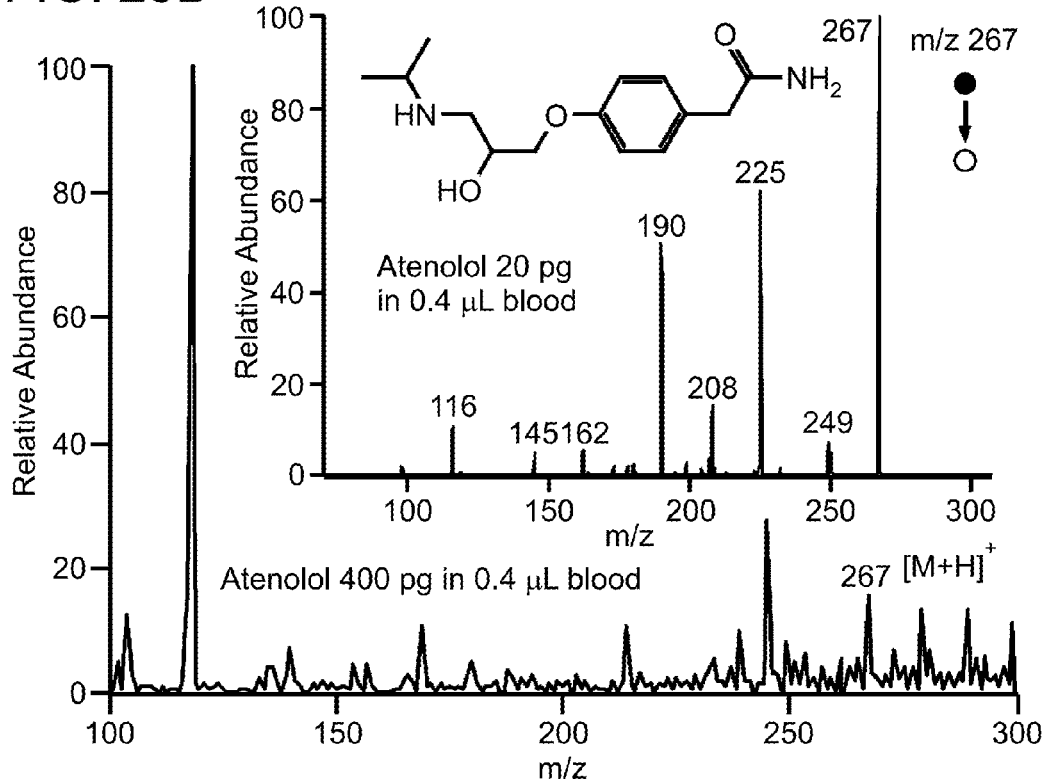
FIG. 23B is a mass spectrum of Atenolol from whole blood.
Figure 23C:
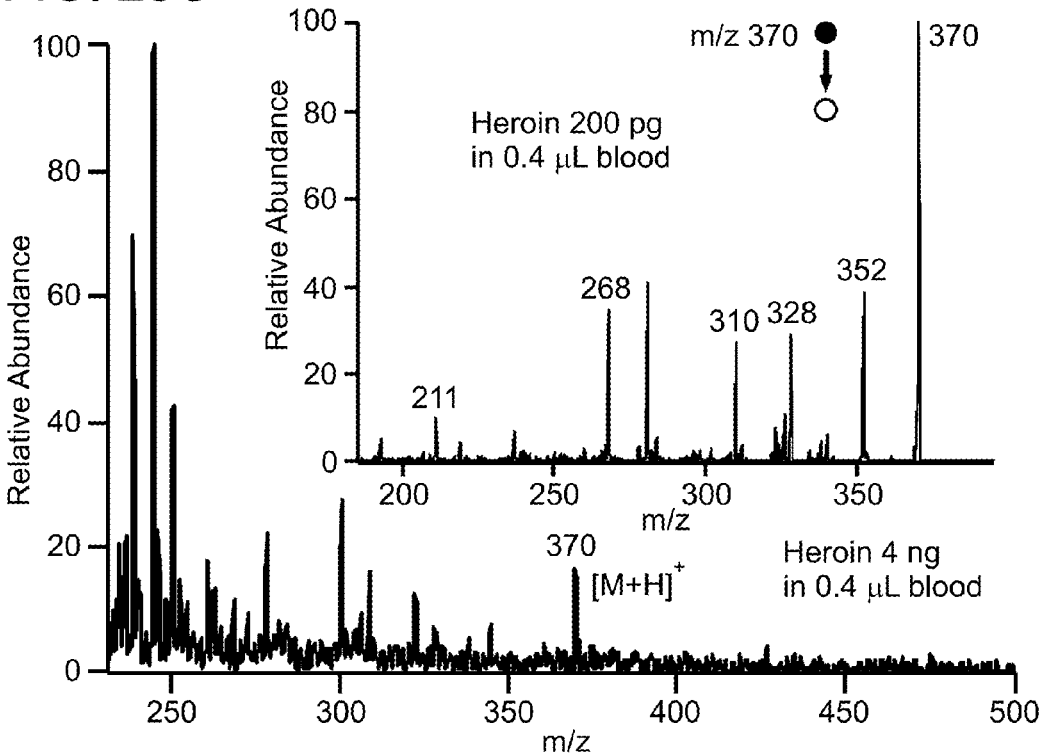
FIG. 23C is a mass spectrum of heroin from whole blood.

Probes and methods of the invention can analyze whole blood without the need for any sample preparation. The sample was prepared as follows. 0.4 uL blood was directly applied on the center of paper triangle and left to dry for about 1 min. to form a dried blood spot (FIG. 23 panel A). 10 uL methanol/water (1:1, v/v) was applied near the rear end of the paper triangle. Driven by capillary action, the solution traveled across the paper wetting it throughout its depth. As the solution interacted with the dried blood spot, the analytes from the blood entered the solution and were transported to the tip of the probe for ionization (FIG. 23 panel A). The process of blood sample analysis was accomplished in about 2 min.

Different drugs were spiked into whole blood and the blood was applied to probes of the invention as described above. Detection of different drugs is described below.

Figure 14C:
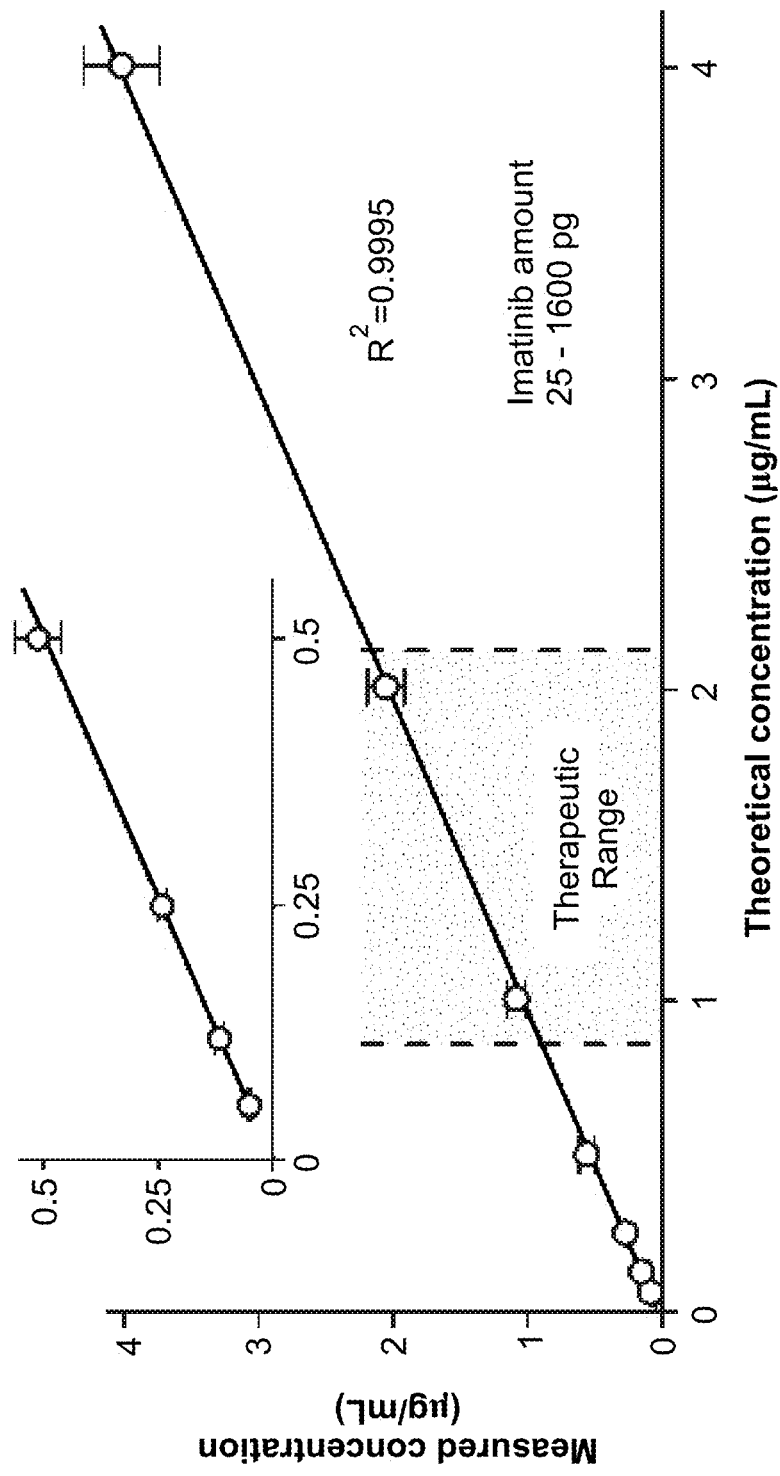
FIG. 14C shows a quantitative analysis of whole blood spiked with imatinib (62.5-4 µg/mL) and its isotopomers imatinib-d8 (1 µg/mL). Inset plot shows low concentration range.

Imatinib (GLEEVEC), a 2-phenylaminopyrimidine derivative, approved by the FDA for treatment of chronic myelogenous leukemia, is efficacious over a rather narrow range of concentrations. Whole human blood, spiked with imatinib at concentrations including the therapeutic range, was deposited on a small paper triangle for analysis (FIG. 14, panel A). The tandem mass spectrum (MS/MS, FIG. 14 panel B) of protonated imatinib, m/z 494, showed a single characteristic fragment ion. Quantitation of imatinib in whole blood was achieved using this signal and that for a known concentration of imatinib-d8 added as internal standard. The relative response was linear across a wide range of concentrations, including the entire therapeutic range (FIG. 14 panel C).

Atenolol, a β-blocker drug used in cardiovascular diseases, was tested using the dried blood spot method to evaluate paper spray for whole blood analysis. Atenolol was directly spiked into whole blood at desired concentrations and the blood sample was used as described above for paper spray. The protonated atenolol of 400 pg (1 ug/mL atenolol in 0.4 uL whole blood) in dried blood spot was shown in mass spectra, and the MS/MS spectra indicated that even 20 pg of atenolol (50 ug/mL atenolol in 0.4 uL whole blood) could be identified in the dried blood spot (FIG. 23 panel B).

FIG. 23 panel (C) is a mass spectra of heroin in whole blood. Data herein show that 200 pg heroin in dried blood spot could be detected using tandem mass.

Figure 18:
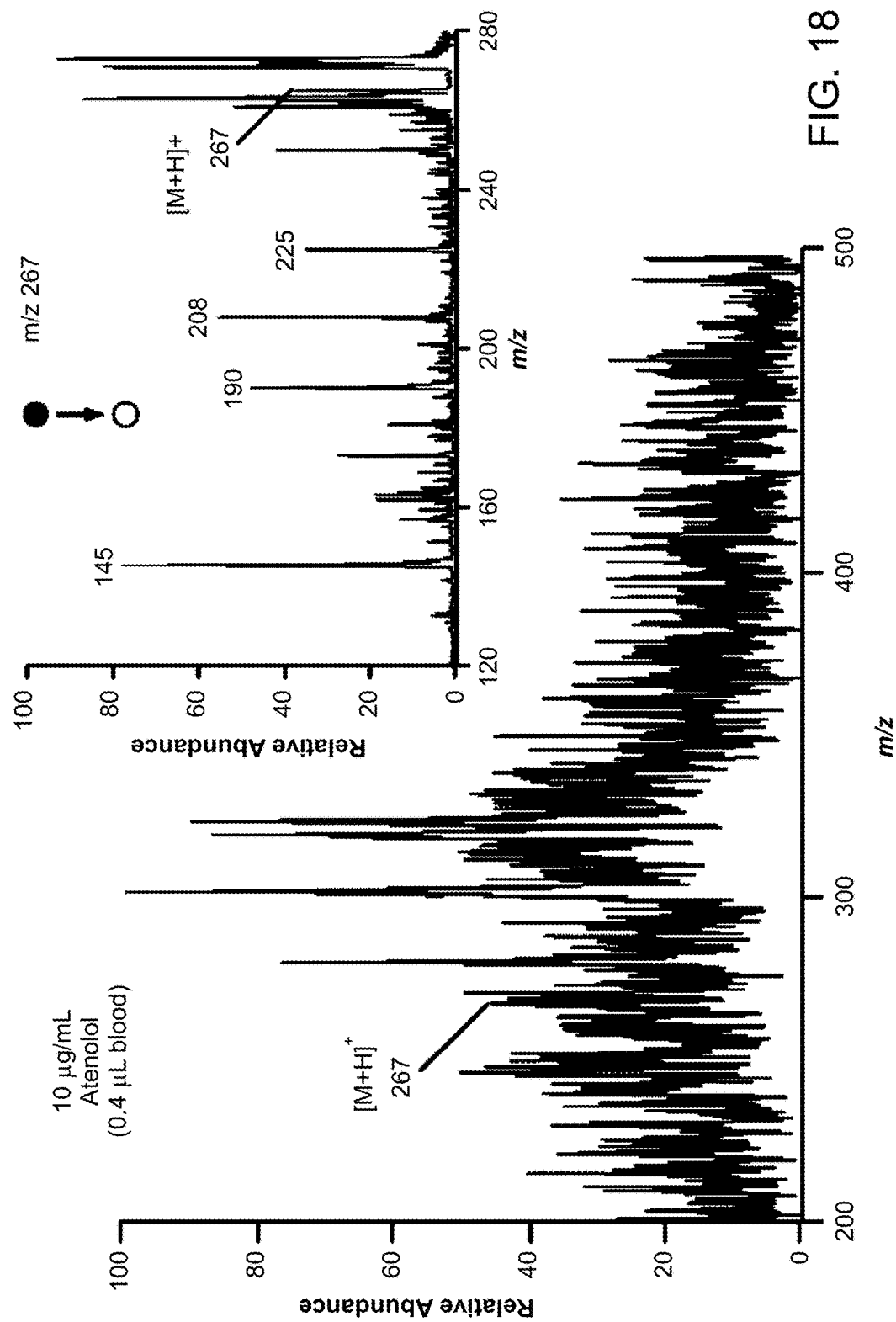
FIG. 18 is a mass spectrum of whole blood spiked with 10 µg/mL atenolol. The data was obtained by combining systems and methods of the invention with a handheld mass spectrometer.
Figure 19A:
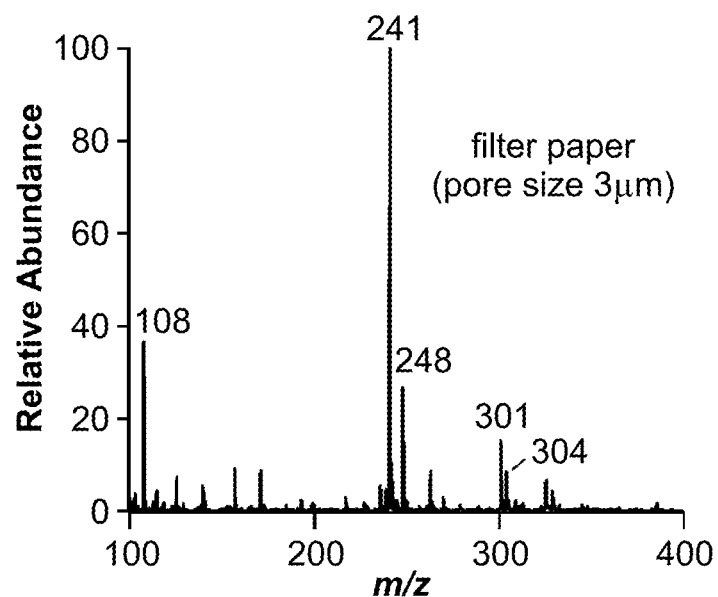
FIGS. 19A-F show mass spectra of cocaine sprayed from six different types of paper (Whatman filter paper with different pore sizes.
Figure 19B:
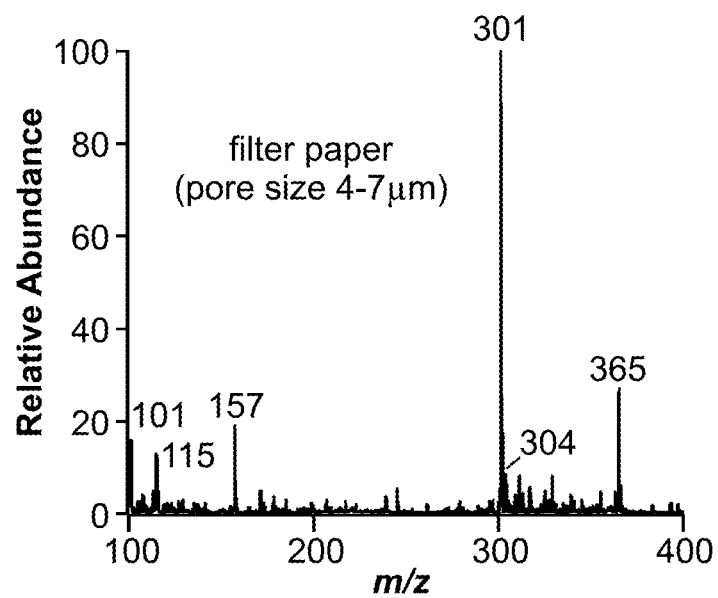
Figure 19C:
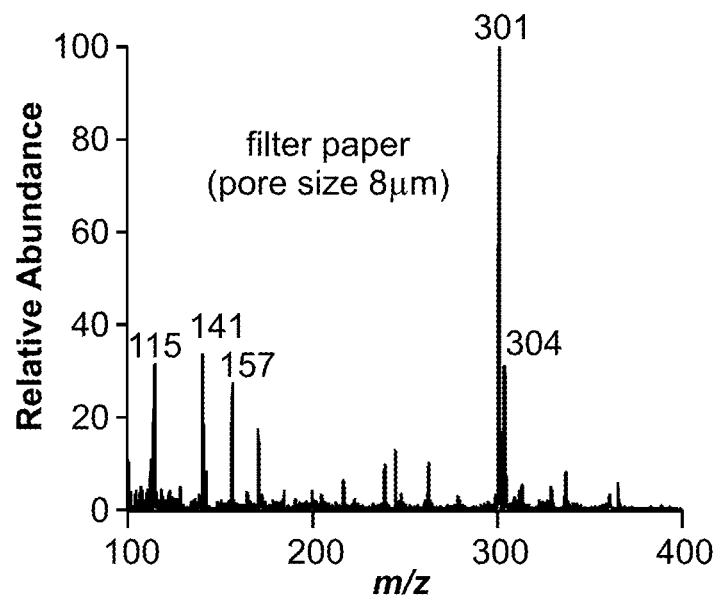
Figure 19D:
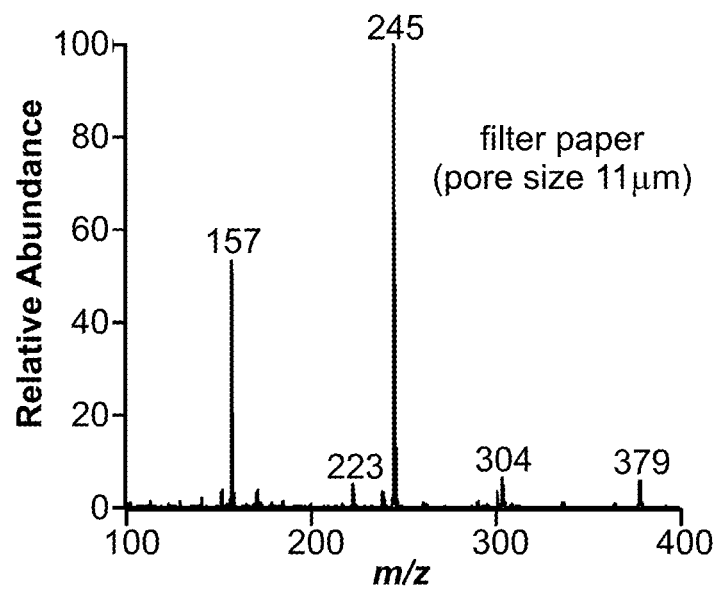
Figure 19E:
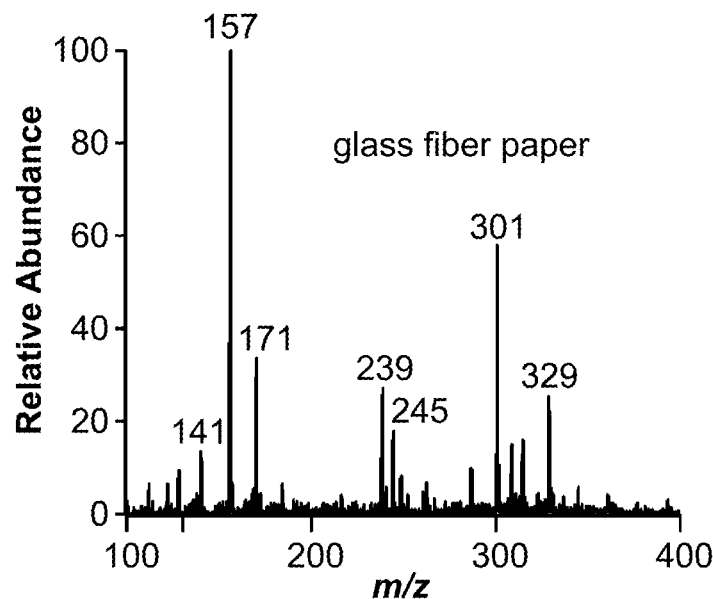
Figure 19F:
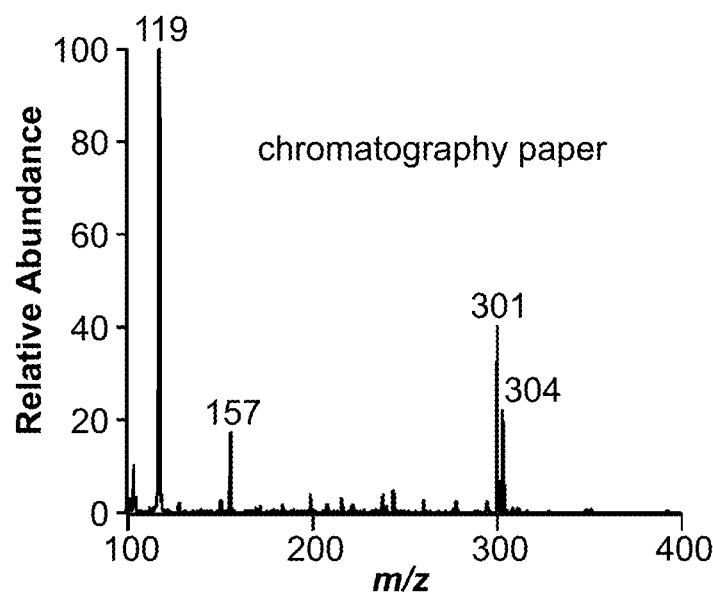

It was also observed that the paper medium served a secondary role as a filter, retaining blood cells. Significantly, samples were analyzed directly on the storage medium rather than requiring transfer from the paper before analysis. All experiments were done in the open lab environment. Two additional features indicated that the methodology had the potential to contribute to increasing the use of mass spectrometry in primary care facilities: blood samples for analysis were drawn by means of a pinprick rather than a canula; and the experiment was readily performed using a handheld mass spectrometer (FIG. 18 and Example 10 below).

Example 10: Handheld Mass Spectrometer

Systems and methods of the invention were compatible with a handheld mass spectrometer. Paper spray was performed using a handheld mass spectrometer (Mini 10, custom made at Purdue University). Analysis of whole blood spiked with 10 μg/mL atenolol. Methanol/water (1:1; 10 μL) was applied to the paper after the blood (0.4 uL) had dried (~1 min) to generate spray for mass detection (FIG. 18). The inset shows that atenolol could readily be identified in whole blood using tandem mass spectrum even when the atenolol amount is as low as 4 ng.

Example 11: Angiotensin I

Figure 15:
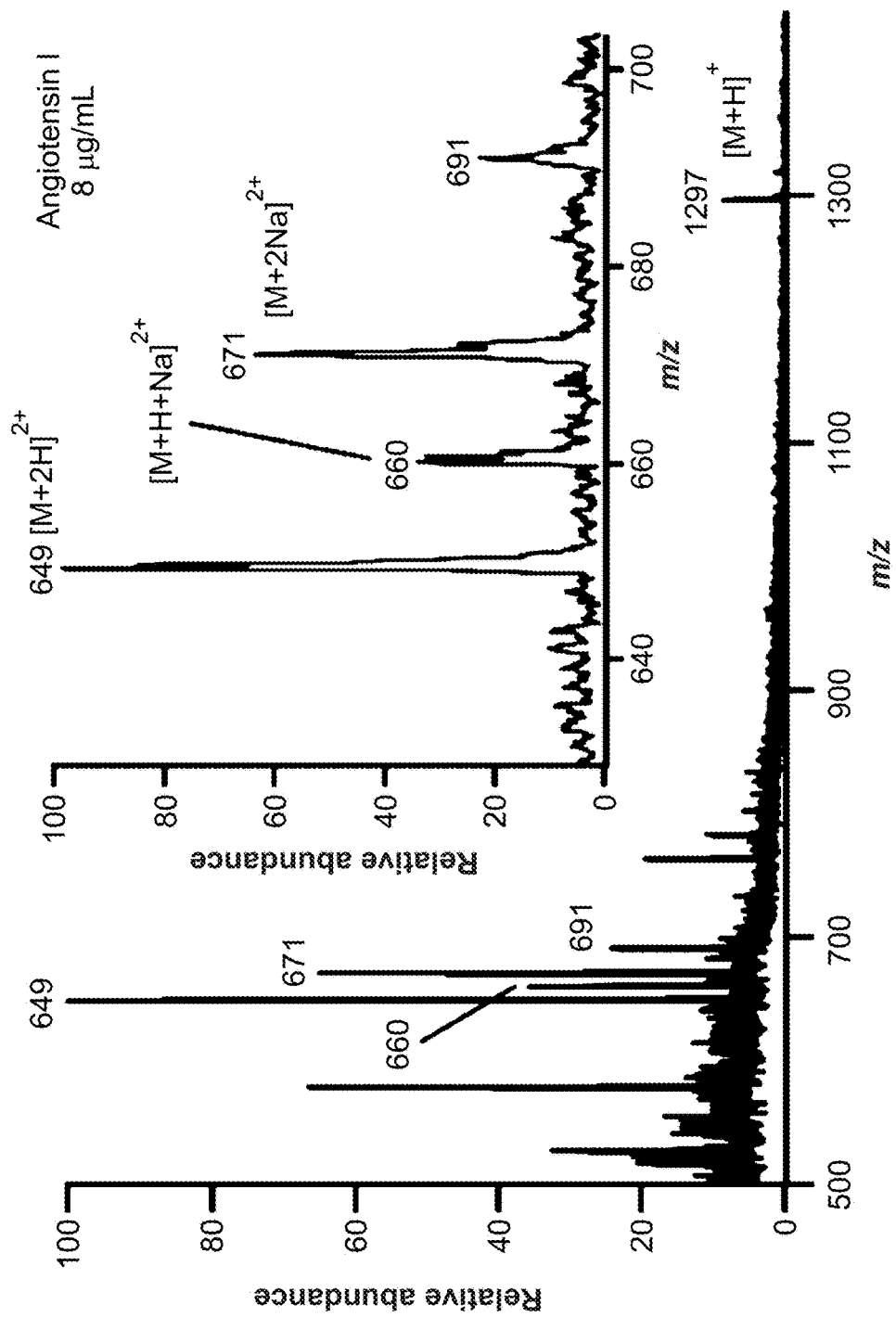
FIG. 15 is a paper spray mass spectrum of angiotensin I solution. The inset shows an expanded view over the mass range 630-700.

FIG. 15 is a paper spray mass spectrum of angiotensin I solution (Asp-Arg-Val-Tyr-Ile-His-Pro-Phe-His-Leu (SEQ ID NO: 1), 10 μL, 8 μg/mL in methanol/water, 1:1, v/v) on chromatography paper (spray voltage, 4.5 kV). The inset shows an expanded view over the mass range 630-700. The protonated ($[M+2H]^{2+}$) and sodium-adduct ions ($[M+H+Na]^{2+}$, $[M+2Na]^{2+}$) are the major ionic species.

Example 12: Agrochemicals on Fruit

Sample collection by paper wiping followed by analysis using probes of the invention was used for fast analysis of agrochemicals on fruit. Chromatography paper (3×3 cm) wetted with methanol was used to wipe a 10 $cm^2$ area on the peel of a lemon purchased from a grocery store. After the methanol had dried, a triangle was cut from the center of the paper and used for paper spray by applying 10 μL methanol/water solution. The spectra recorded (FIG. 34 panels A-B) show that a fungicide originally on the lemon peel, thiabendazole (m/z 202 for protonated molecular ion and m/z 224 for sodium adduct ion), had been collected onto the paper and could be identified easily with MS and confirmed using MS/MS analysis. Another fungicide imazalil (m/z 297) was also observed to be present.

Example 13: Tumor Sample

Systems and methods of the invention were used to analyze human prostate tumor tissue and normal tissue. Tumor and adjacent normal tissue sections were 15 μm thick and fixed onto a glass slide for an imaging study using desorption electrospray ionization (DESI). A metal needle was used to remove a 1 $mm^2$×15 μm volume of tissue from the glass slide from the tumor region and then from the normal region and place them onto the surface of the paper triangle for paper spray analysis.

Figure 17A:
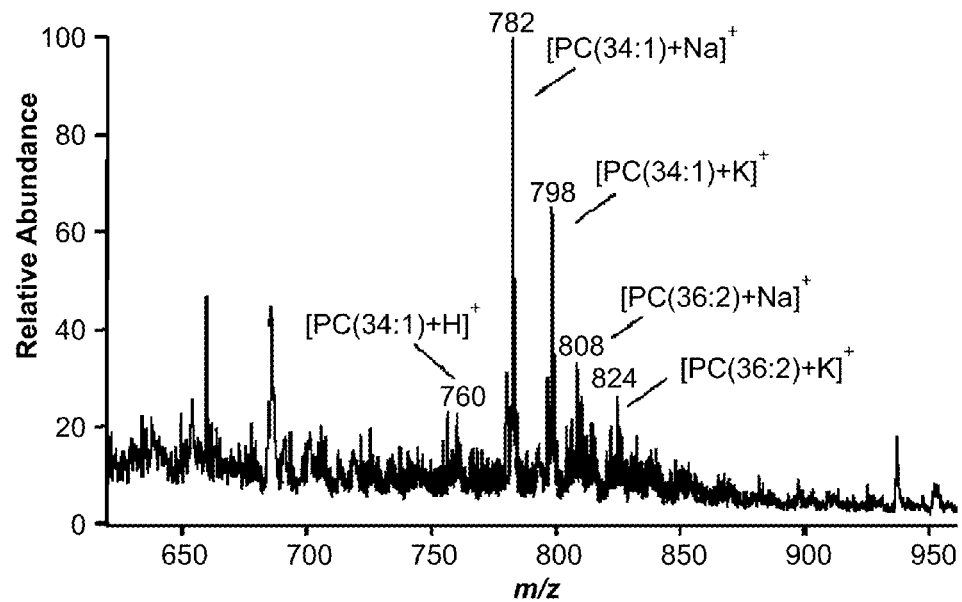
FIGS. 17A-B are mass spectra showing direct analysis of human prostate tumor tissue and normal tissue.
Figure 17B:
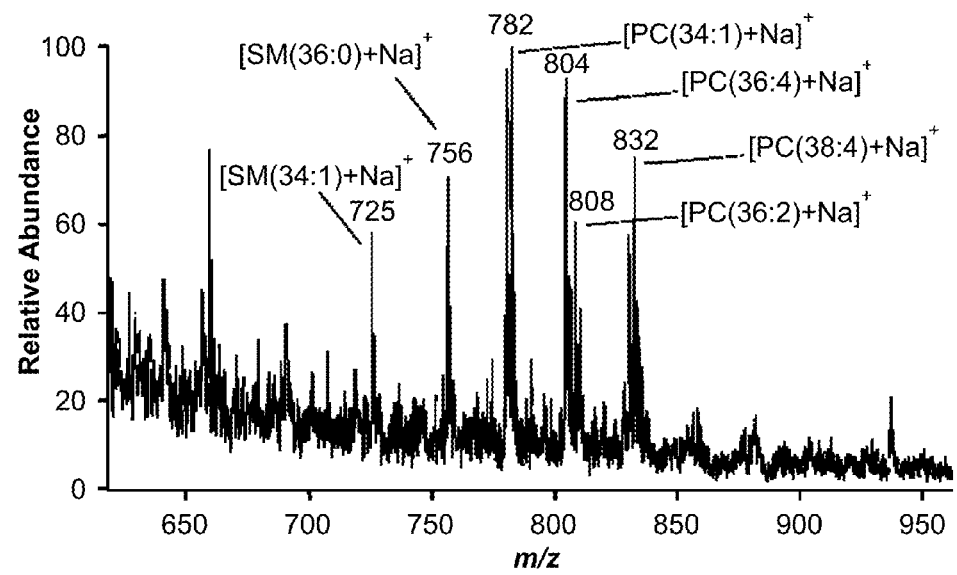

A droplet of methanol/water (1:1 v:v; 10 μl) was added to the paper as solvent and then 4.5 kV positive DC voltage applied to produce the spray. Phospholipids such as phosphatidylcholine (PC) and sphingomyelin (SM) were identified in the spectrum (FIG. 17 panels A and B). The peak of $[PC(34:1)+K]^+$ at m/z 798 was significantly higher in tumor tissue and peaks $[SM(34:1)+Na]^+$ at m/z 725, $[SM(36:0)+Na]^+$ at m/z 756, and $[SM(36:4)+Na]^+$ at m/z 804 were significantly lower compared with normal tissue.

Example 14: Therapeutic Drug Monitoring

The administration of a drug depends on managing the appropriate dosing guidelines for achievement of a safe and effective outcome. This guideline is established during clinical trials where the pharmacokinetics (PK) and pharmacodynamics (PD) of the drug are studied. Clinical trials use PK-PD studies to establish a standard dose, which may be fixed or adjusted according formulas using variables like body mass, body surface area, etc. However, the drug exposure, i.e. the amount of drug circulating over time, is influenced by a number of factors that vary from patient to patient. For example, an individuals' metabolic rate, the type and level of plasma proteins, and pre-existing conditions such as renal and/or hepatic impairment all play a role in affecting the exposure of the drug in vivo. Further, administration of a drug in combination with other medications may also affect exposure. As a result, it is often difficult to predict and prescribe an optimum regimen of drug administration.

Over- or underexposure to a drug can lead to toxic effects or decreased efficacy, respectively. To address these concerns, therapeutic drug monitoring (TDM) can be employed. TDM is the measurement of active drug levels in the body followed by adjustment of drug dosing or schedules to increase efficacy and/or decrease toxicity. TDM is indicated when the variability in the pharmacokinetics of a drug is large relative to the therapeutic window, and there is an established relationship between drug exposure and efficacy and/or toxicity. Another requirement for TDM is that a sufficiently precise and accurate assay for the active ingredient must be available. Immunoassays and liquid chromatography mass spectrometry (LC-MS) are commonly used methods for TDM. In comparison with immunoassay, LC-MS has advantages which include wide applicability, high sensitivity, good quantitation, high specificity and high throughput. Probes of the invention may be coupled with standard mass spectrometers for providing point-of-care therapeutic drug monitoring.

The drug Imatinib (GLEEVEC in USA and GLIVEC in Europe/Australia, for the treatment of chronic myelogenous leu-kemia) in a dried blood spot was analyzed using paper spray and a lab-scale LTQ mass spectrometer. Quantitation of Imatinib in whole blood was achieved using the MS/MS spectra with a known concentration of Imatinib-d8 being used as the internal standard (FIG. 14 panel C). The relative response was linear across a wide range of concentrations, including the entire therapeutic range (FIG. 14 panel C).

Example 15: High-Throughout Detection

Figure 28A:
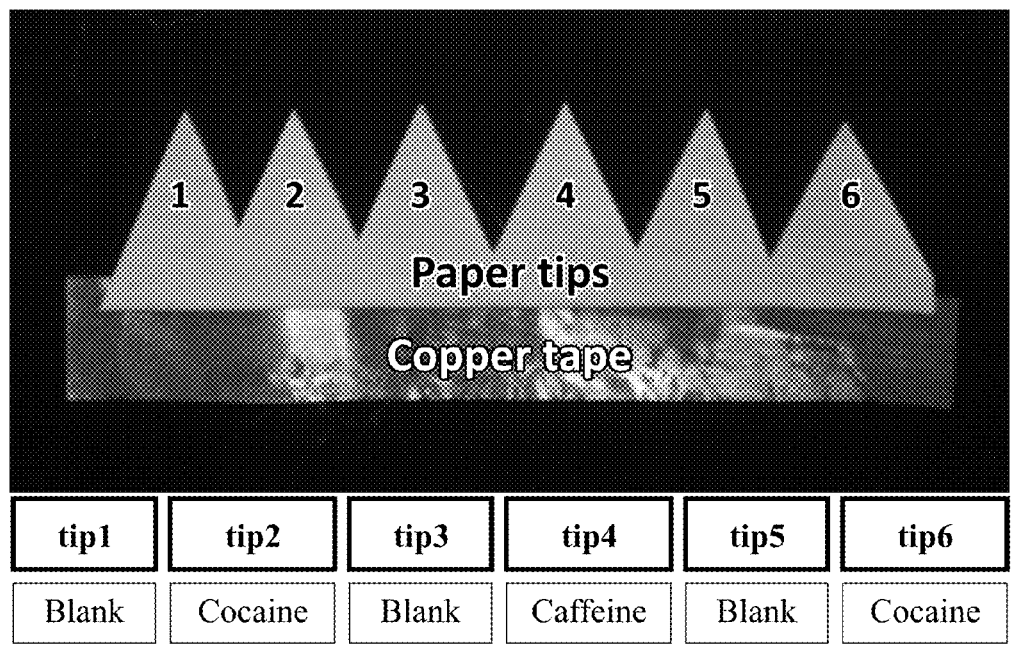
FIG. 28A is a picture of a high-throughput probe device of the invention.
Figure 28B:
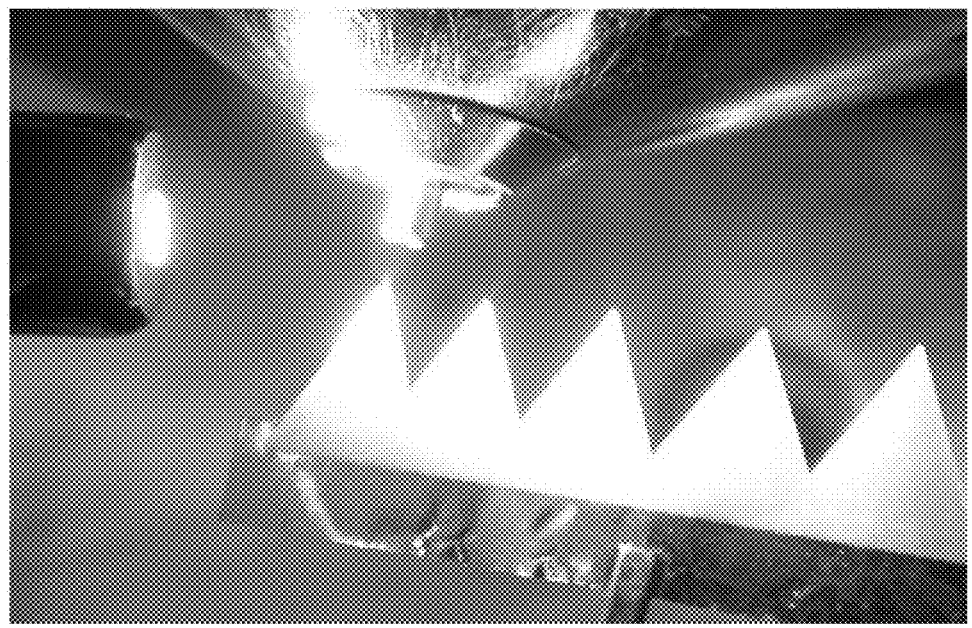
FIG. 28B shows spray from a single tip of the device into an inlet of a mass spectrometer.
Figure 28C:
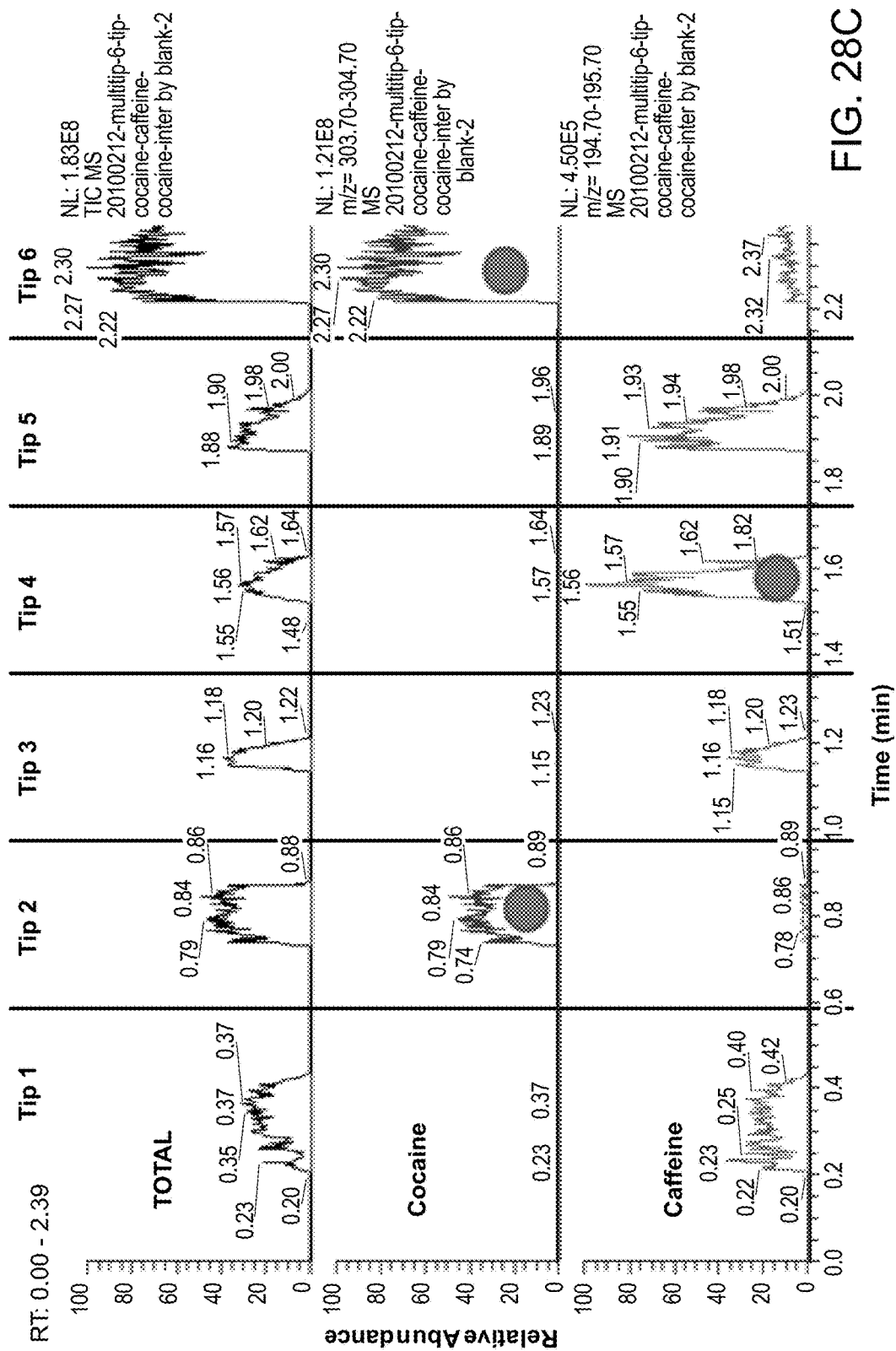
FIG. 28C is a set of mass spectra showing MS signal intensity in high-throughput mode.

Multiple-tip devices were fabricated and applied for high throughput analysis (FIG. 28 panel A). The multiple-tip device was a set of paper triangles all connected to a single copper strip (FIG. 28 panel A). An electrode was connected to the copper strip. Multiple samples were put on a single paper substrate and analyzed in series using the multiple-tip probe (FIG. 28 panels B-C). Each tip was pre-loaded with 0.2 uL methanol/water containing 100 ppm sample (cocaine or caffeine) and dried. Then the whole multiple-tip device was moved on a moving stage from left to right with constant velocity and 7 uL methanol/water was applied from the back part for each tip during movement.

To prevent the contaminant during spray, blanks were inserted between two sample tips. FIG. 28 panel (C) shows the signal intensity for the whole scanning. From total intensity, six tips gave six individual high signal peaks. For cocaine, peaks only appeared when tip 2 and tip 6 were scanned. For caffeine, the highest peak came from tip 4, which was consistent with the sample loading sequence.

Example 16: Tissue Analysis

Figure 16:
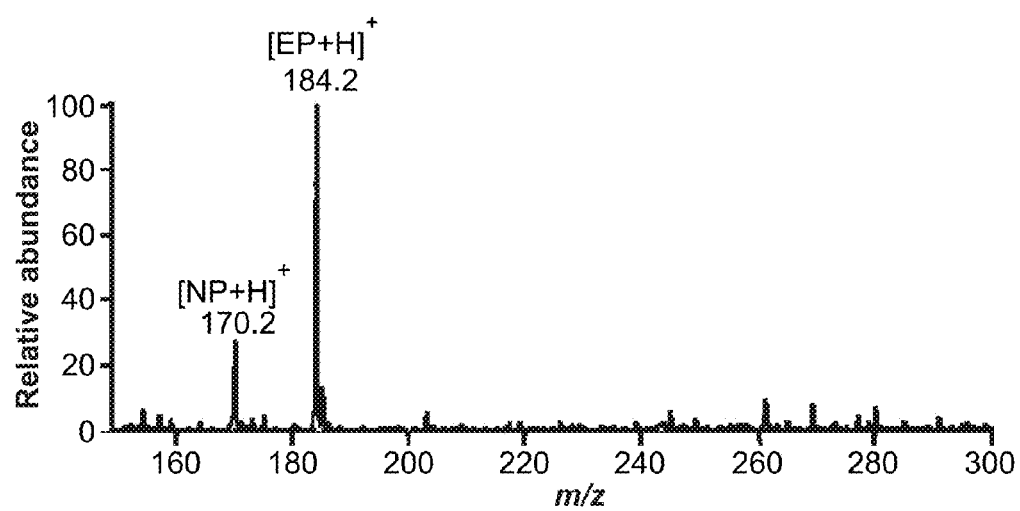
FIG. 16 is a mass spectrum showing direct analysis of hormones in animal tissue by probes of the invention.
Figure 29A:
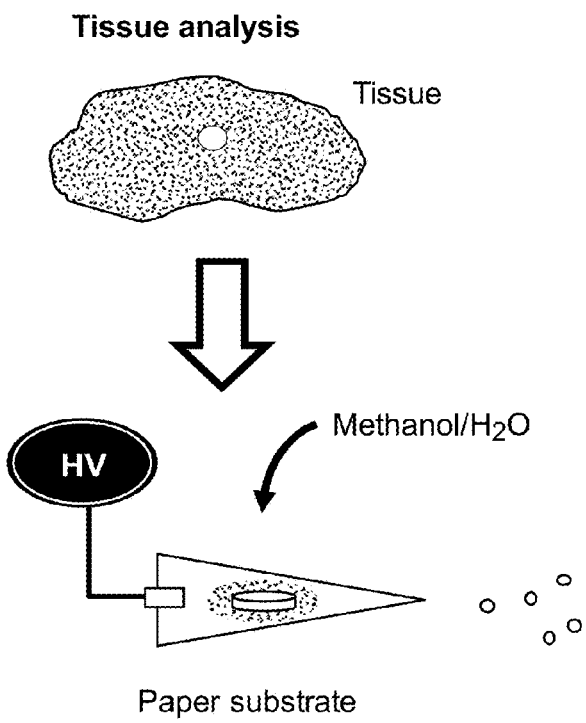
FIG. 29A is a schematic depicting a protocol for direct analysis of animal tissue using probes of the invention.
Figure 29B:
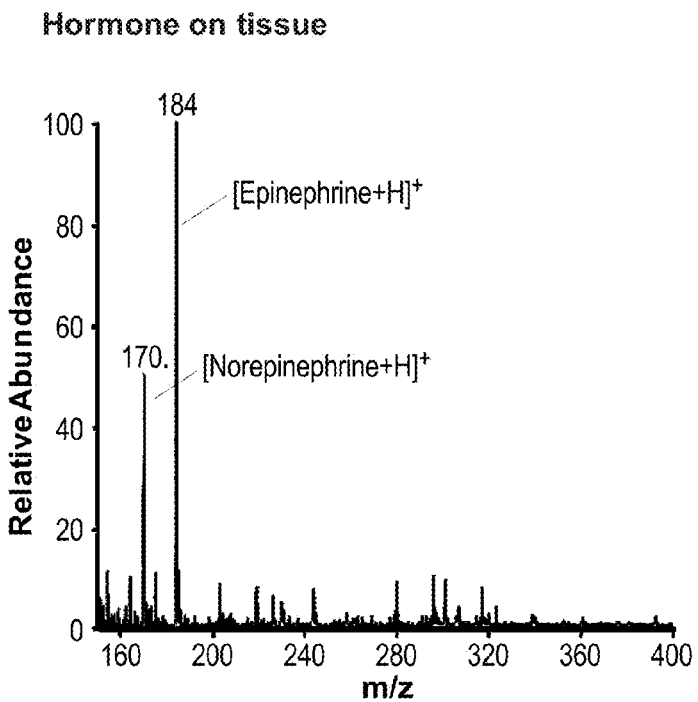

Direct analysis of chemicals in animal tissue using probes of the invention was performed as shown in FIG. 29 panel (A). A small sections of tissue were removed and placed on a paper triangle. Methanol/water (1:1 v:v; 10 µl) was added to the paper as solvent and then 4.5 kV positive DC voltage was applied to produce the spray for MS analysis. Protonated hormone ions were observed for porcine adrenal gland tissue (1 mm$^3$, Panel (B)). FIG. 16 is a mass spectrum showing direct analysis of hormones in animal tissue by paper spray. A small piece of pig adrenal gland tissue (1 mm×1 mm×1 mm) was placed onto the paper surface, MeOH/water (1:1 v:v; 10 µl) was added and a voltage applied to the paper to produce a spray. The hormones epinephrine and norepinephrine were identified in the spectrum; at high mass the spectrum was dominated by phospolipid signals.

Lipid profiles were obtained for human prostate tissues (1 mm$^2$×15 µm, Panel (C) & (D)) removed from the tumor and adjacent normal regions. Phospholipids such as phosphatidylcholine (PC) and sphingomyelin (SM) were identified in the spectra. The peak of $[PC(34:1)+K]^+$ at m/z 798 was significantly more intense in tumor tissue (panel C) and peaks $[SM(34:1)+Na]^+$ at m/z 725, $[SM(36:0)+Na]^+$ at m/z 756, and $[SM(36:4)+Na]^+$ at m/z 804 were significantly lower compared with normal tissue (panel D).

Example 17: On-Line Derivatization

For analysis of target analytes which have relatively low ionization efficiencies and relatively low concentrations in mixtures, derivatization is often necessary to provide adequate sensitivity. On-line derivatization can be implemented by adding reagents into the spray solution, such as methanol/water solutions containing reagents appropriate for targeted analytes. If the reagents to be used are stable on paper, they can also be added onto the porous material when the probes are fabricated.

As a demonstration, 5 µL methanol containing 500 ng betaine aldehyde chloride was added onto a paper triangle and allowed to dry to fabricate a sample substrate preloaded with a derivatization reagent for the analysis of cholesterol in serum. On-line charge labeling with betaine aldehyde (BA) through its reaction with hydroxyl groups has been demonstrated previously to be very effective for the identification of cholesterol in tissue (Wu et al., *Anal Chem*. 2009, 81:7618-7624). When the paper triangle was used for analysis, 2 µL human serum was spotted onto the paper to form a dried spot and then analyzed by using paper spray ionization. A 10 µL ACN/CHCl$_3$ (1:1 v:v) solution, instead of methanol/water, was used for paper spray to avoid reaction between the betaine aldehyde and methanol.

Figure 30A:
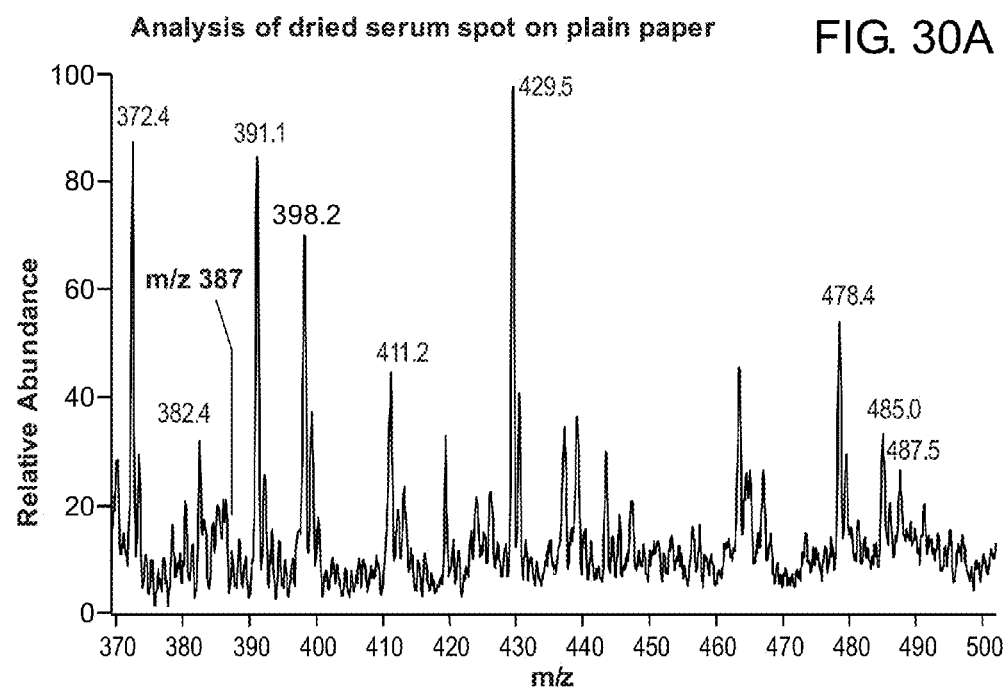
FIG. 30A shows a mass spectral analysis of a dried serum spot on plain paper.
Figure 30B:
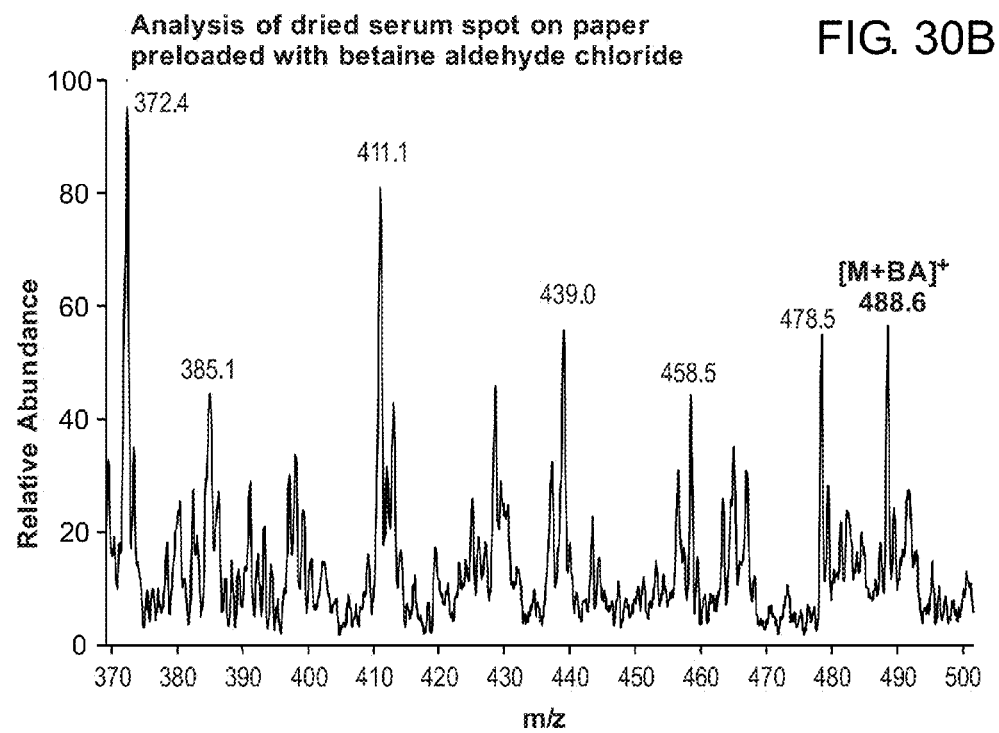
FIG. 30B shows a mass spectrum analysis of a dried serum sport on paper preloaded with betaine aldehyde (BA) chloride.
Figure 30C:
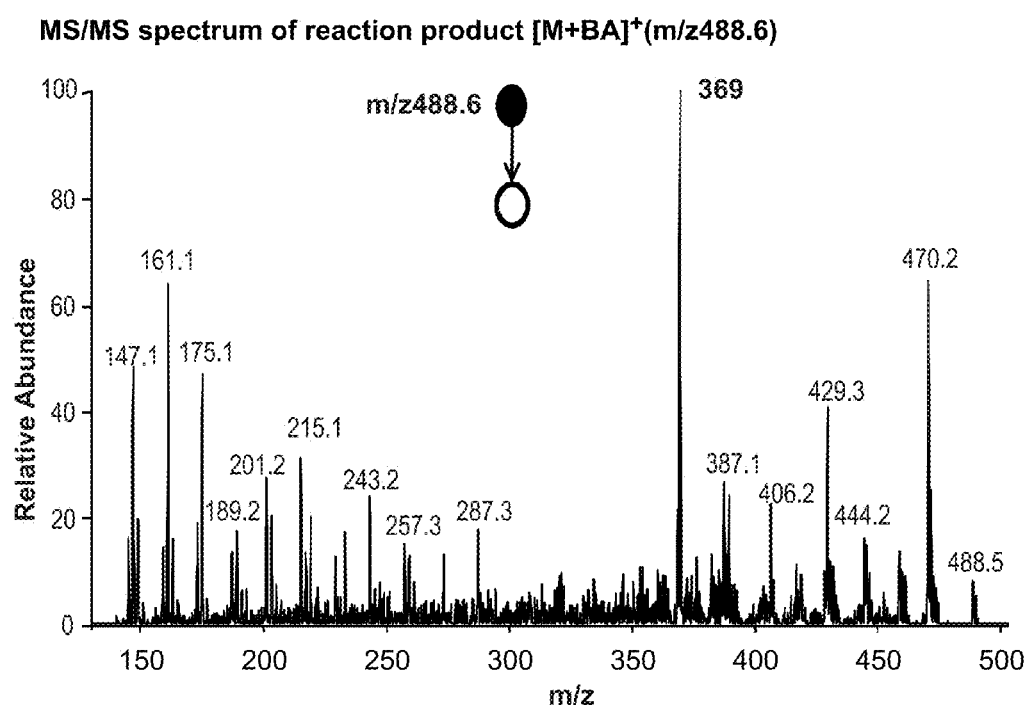
FIG. 30C shows a MS/MS analysis of reaction product [M+BA]$^+$ (m/z 488.6).

The comparison between analysis using a blank and a reagent-preloaded paper triangle is shown in FIG. 30 panels (A) and (B). Without the derivatization reagent, cholesterol-related peaks, such as protonated ion $[Chol+H]^+$ (m/z 387), water loss $[Chol+H-H_2O]^+$ (m/z 369), and sodium adduction $[Chol+Na]^+$ (m/z 409), were not observed (Panel A). With the derivatization reagent, the ion $[Chol+BA]^+$ was observed at m/z 488.6 (Panel B). MS/MS analysis was performed for this ion and a characteristic fragment ion m/z 369 was observed (Panel C).

Example 18: Peptide Pre-Concentration Using Modified Paper Spray Substrate

Pre-concentration of chemicals on the paper surface using photoresist treatment. Chromatography paper was rendered hydrophobic by treatment with SU-8 photoresist as described previously (Martinez et al., *Angew Chem Int. Ed.*, 2007, 46:1318-1320). Then 5 µl bradykinin 2-9 solution (100 ppm in pure H$_2$O) was applied on the paper surface. When the solution was dry, the paper was put into water and washed for 10 s. After washing, the paper triangle was held in front of the MS inlet, 10 µl pure MeOH was applied as solvent and the voltage was set at 4.5 kV for paper spray. The same experiment was done with untreated paper substrate for comparison.

Figure 31A:
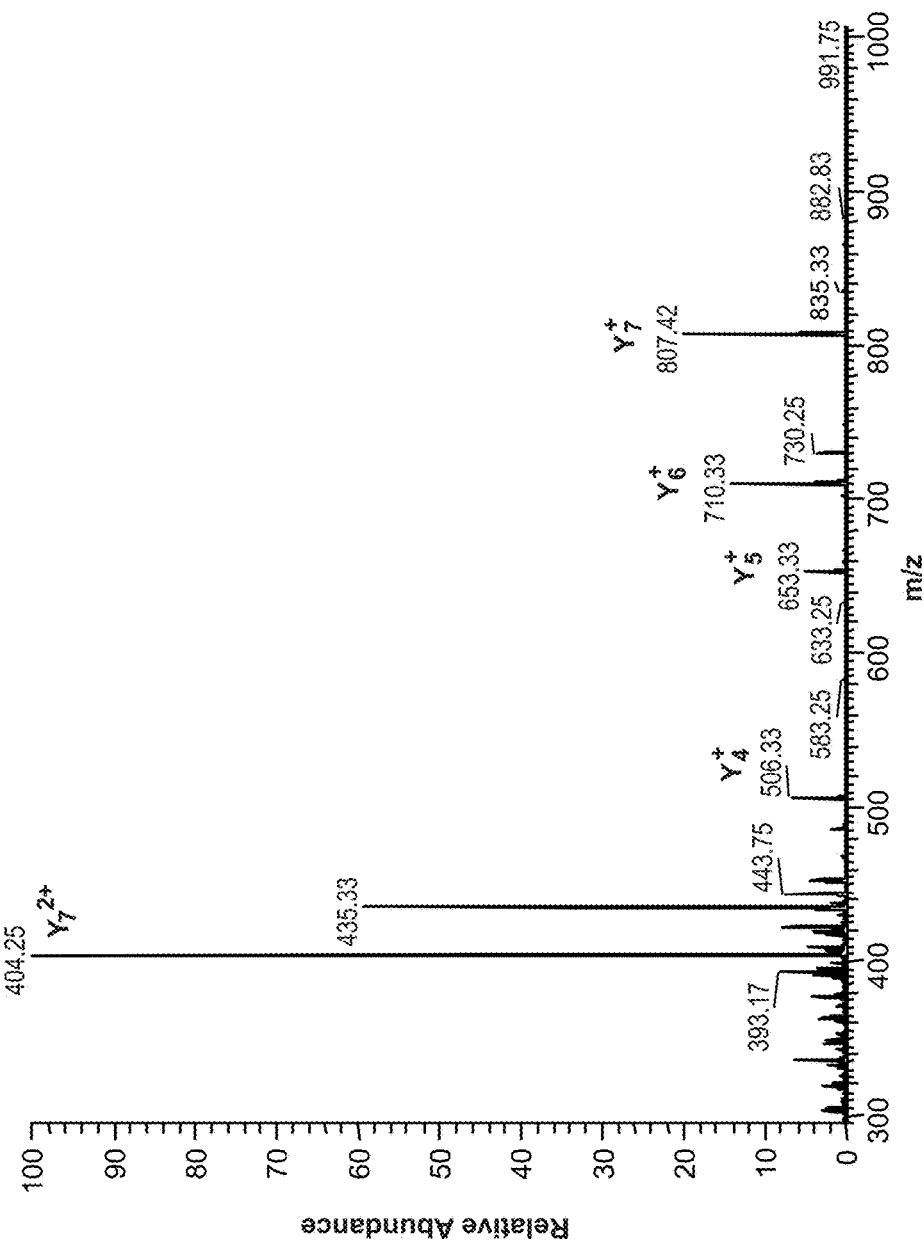
FIGS. 31A-B show MS/MS spectra recorded with modified (FIG. 31A) and unmodified (FIG. 31B) paper substrates.
Figure 31B:
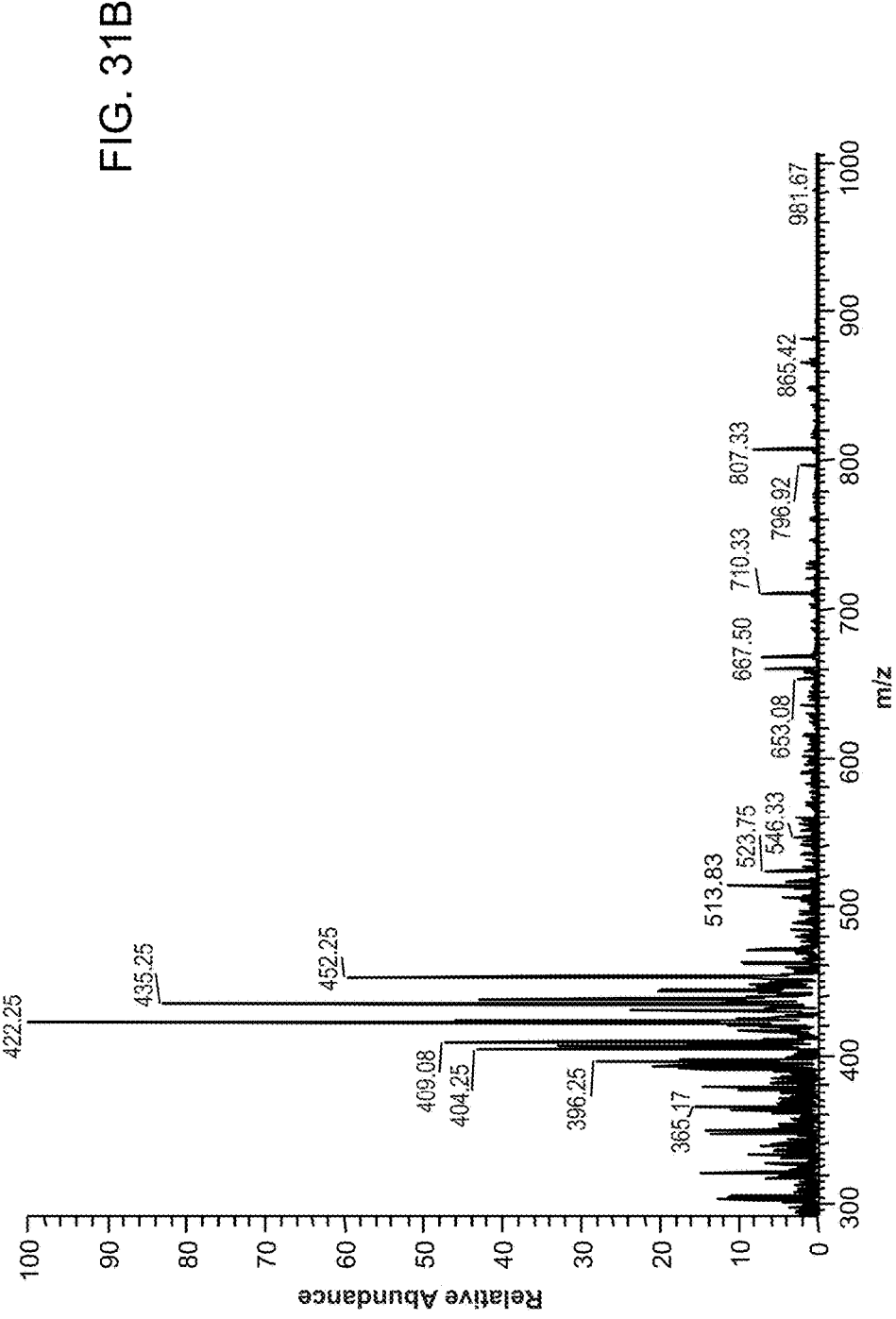

FIG. 31 panel (A) shows the tandem MS spectrum of bradykinin 2-9 from paper with photoresist treatment. The intensity of the most intense fragment ion 404 is 5.66E3. FIG. 31 panel (B) shows the tandem MS spectrum of bradykinin 2-9 from normal chromatography paper without photoresist treatment. The intensity of the most intense fragment ion 404 is only 1.41E1. These data show that the binding affinity between photoresist-treated chromatography paper and peptide is much higher than that between normal chromatography paper and peptide, thus more peptide can be kept on the paper surface after washing by water. When pure methanol is applied, these retained peptides will be desorbed and detected by MS. This method can be used to pre-concentrate hydrophobic chemicals on the paper surface, and other hydrophilic materials (e.g. salts) can also be removed from the paper surface.

Example 19: Inverted Polarities

The polarity of the voltage applied to the probe need not match that used in the mass analyzer. In particular, it is possible to operate the probes of the invention with a negative potential but to record the mass spectrum of the resulting positively changed ions. In negative ion mode, a large current of electrons (or solvated electrons) is produced in paper spray. These electrons, if of suitable energy, can be captured by molecules with appropriate electron affinities to generate radical anions.

Alternatively, these electrons might be responsible for electron ionization of the analyte to generate the radical cation or alternatively ESI might involve a solvent molecule which might then undergo charge exchange with the analyte to again generate the radical cation. If this process occurs with sufficient energy, characteristic fragment ions might be produced provided the radical cation is not collisionally deactivated before fragmentation can occur.

Figure 32:
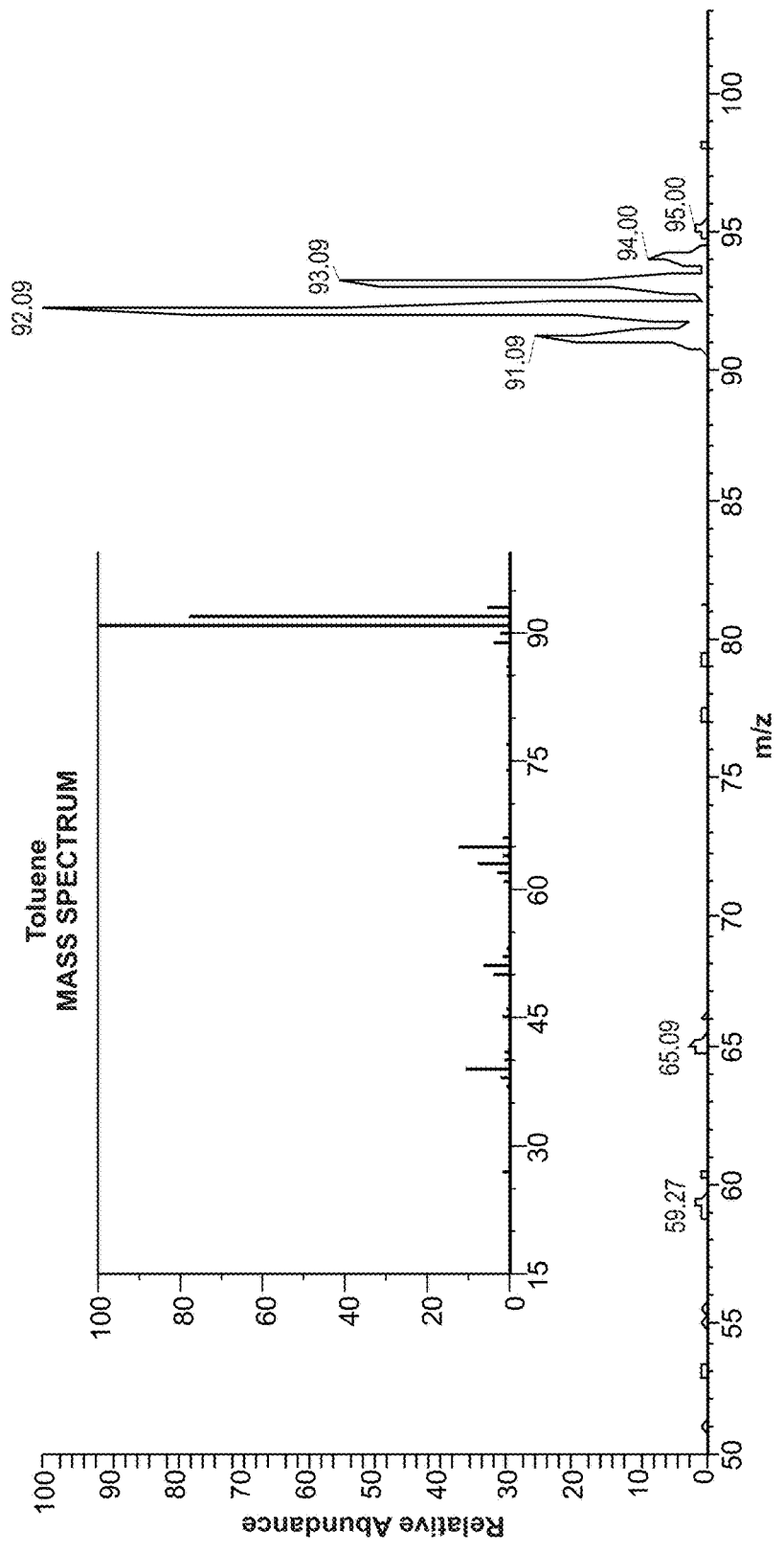
FIG. 32 is a mass spectrum showing that ions can be generated using a negative ion source potential but positively charged ions are mass-analyzed.

An experiment was done on a benchtop LTP using toluene vapor, with a probe of the invention conducted at −4.5 kV with methanol:water as solvent applied to the paper. The spectrum shown in FIG. 32 was recorded. One notes that ion/molecule reactions to give the protonated molecule, m/z 93 occur as expected at atmospheric pressure. One also notes however, the presence of the radical cation, m/z 92 and its characteristic fragments at m/z 91 and 65.

An interesting note is that the "EI" fragment ions were most easily produced when the source of toluene vapor was placed close to the MS inlet; i.e., in the cathodic region of the discharge between the paper tip and MS inlet. This suggests that direct electron ionization by energetic electrons in the "fall" region might be at least partly responsible for this behavior.

Example 20: Cartridge for Blood Analysis

Figure 33A:
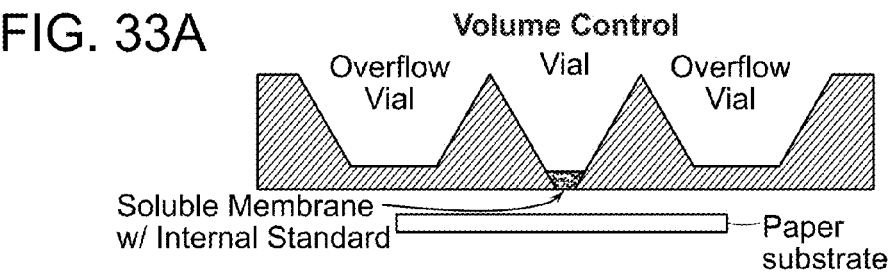
FIG. 33A is a schematic showing the design of a sample cartridge with volume control and overflowing vials. A soluble plug with internal standard chemical is used to block the bottom of the volume control vial.
Figure 33B:
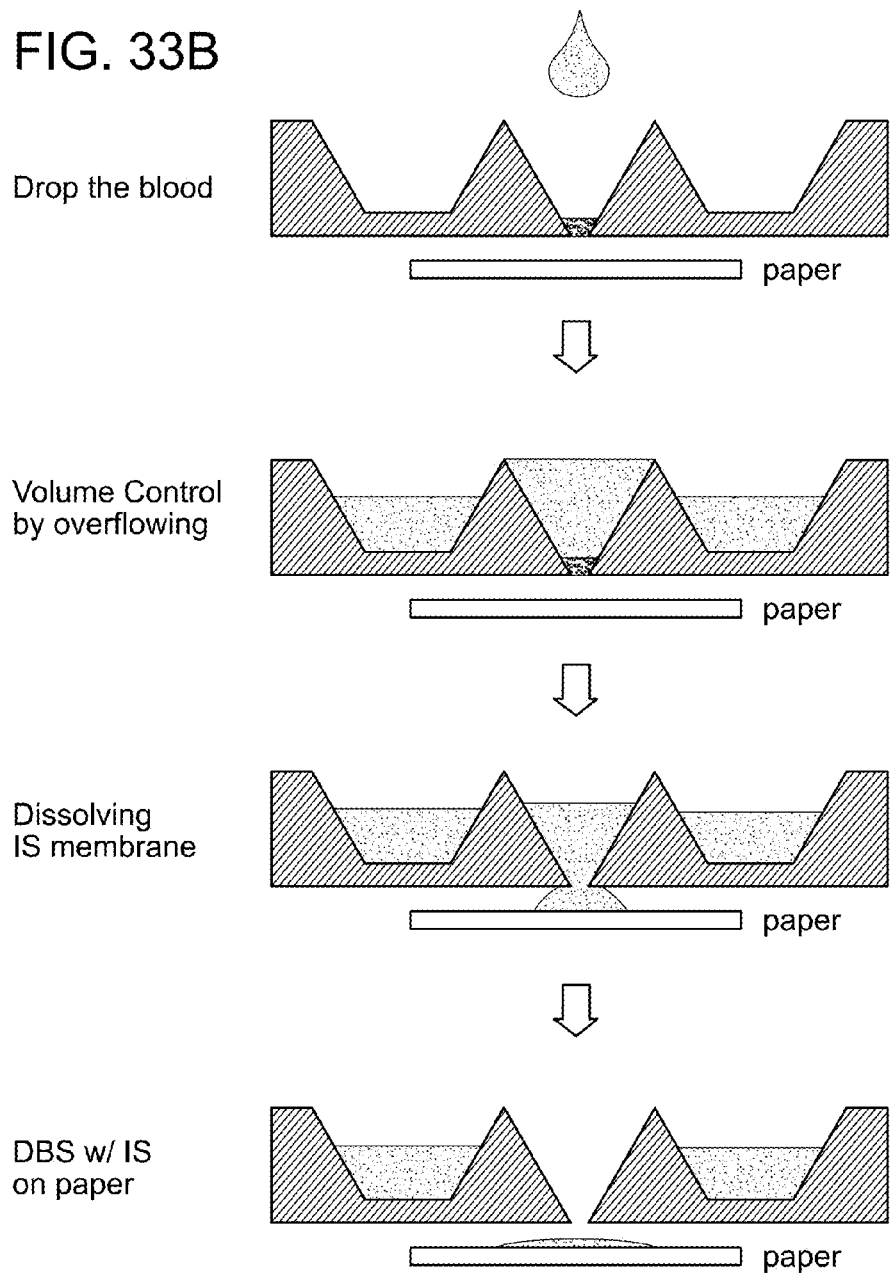
FIG. 33B shows a step-by-step process of applying blood samples onto the cartridge to prepare a dried blood spot on paper from a controlled volume of blood.
Figure 36A:
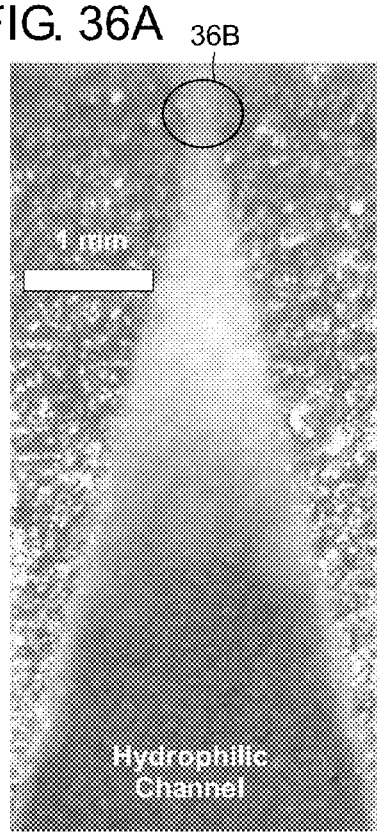
FIGS. 36A-B show a spray tip fabricated on a piece of chromatography paper using SU-8 2010 photoresist.
Figure 36B:
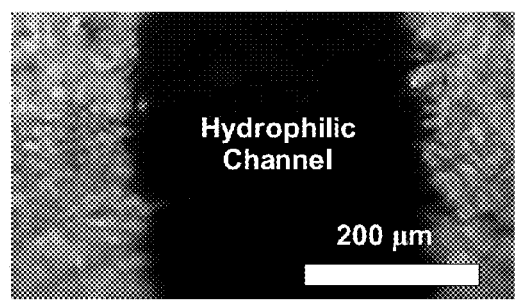
Figure 36C:
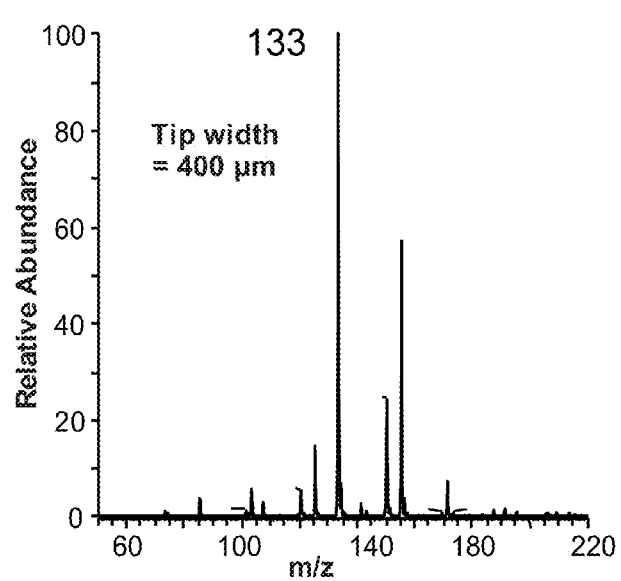
FIG. 36C shows a MS spectrum of methanol/water solution containing a mixture of asparagines.

FIG. 33 panel (A) shows an exemplary case for spotting blood onto porous material that will be used for mass spectral analysis. The cartridge can have a vial with a volume at the center and vials for overflows. A plug, such as a soluble membrane containing a set amount of internal standard chemical, is used to block the bottom of the vial for volume control. A drop of blood is placed in the vial (Panel B). The volume of the blood in the vial is controlled by flowing the extra blood into the overflow vials (Panel B). The blood in the vial is subsequently dissolved in the membrane at the bottom, mixing the internal standard chemical into the blood (Panel B). Upon dissolution of the plug, blood flows to the paper substrate, and eventually forms a dried blood spot having a controlled amount of sample and internal standard (Panel B).

Figure 37A:
FIGS. 37A-B are schematics showing result of applying solvent too early (<2 hours) to blood spot on paper (FIG. 37A) compared to methods of pre-loading the paper with a drying agent before spotting the blood, allowing for more rapid analysis (FIG. 37B).
Figure 37B:
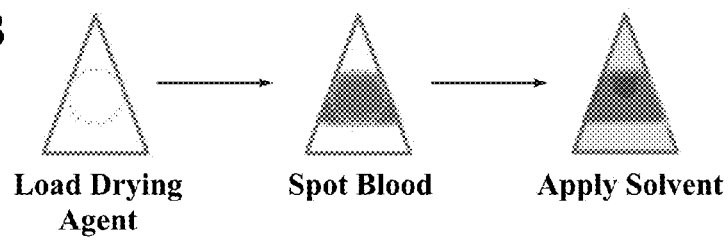

Example 21: Ion Generation Using Wetted Porous Material and a Drying Agent a. Solvent Applied to Liquid Blood on a Porous Substrate and Dried Blood on a Porous Substrate Systems and methods described herein use anhydrous salts (drying agents) to dry and thus restrict the flow of liquid blood during paper spray analysis. FIG. 37 panel (A) shows result of applying solvent too early (<2 hours) to blood spot on paper. The mixture of blood and solvent causes the blood to run through the paper and decreases the efficiency of the paper spray. FIG. 37 panel (B) shows systems and methods in which the porous substrate is pre-loaded with a drying agent before spotting the blood, allowing for more rapid analysis.

b. Drying Agent for Rapid Analysis of Whole Blood

Figure 38:
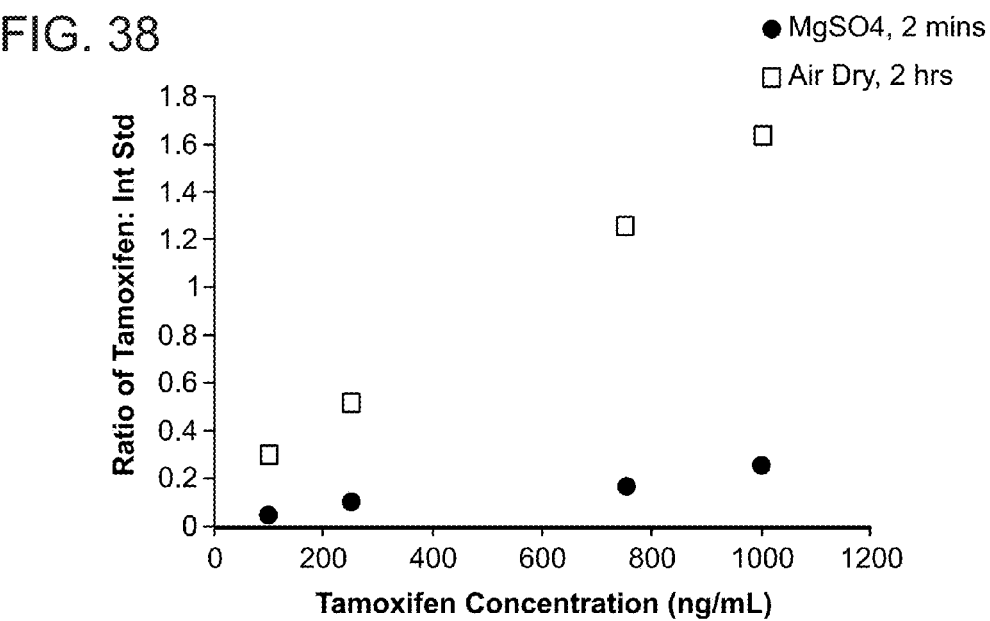
FIG. 38 is a graph showing calibration curves for Tamoxifen by the standard air-dry method versus quick analysis by pre-spotting $MgSO_4$.

A drying agent, such as magnesium sulfate, sodium sulfate, sodium carbonate, or calcium chloride is mixed and pre-spotted along with the internal standard, thus saving a sample preparation step. Another potential agent, is a blood coagulant such as alum powder. As is seen in FIG. 38 and in Table 1 below, the method of pre-spotting the internal standard and drying agent provided a very respectable limit of detection with significantly reduced drying times.

TABLE 1

| Drying Method | IS Method | RSD blank | RSD normal signal | LOD (ng/mL) |
| --- | --- | --- | --- | --- |
| 2 Hours Air | Mixed | 32% | 4% | 18 |
| MgSO$_4$ | Pre-spotted | 55% | 36% | 56 |

Further improvements include (i) drying/crystallizing the drying agent on the paper; (ii) drying agent choice; (iii) Compatibility with paper type, e.g. thickness & pore size; (iv) combination of a drying agent and oven drying.

In certain embodiments, a desiccator may be used to store the pre-loaded paper in a moisture-free atmosphere. Such a desiccator could be any container that contains the commercially-available Drierite. This scheme is shown in FIG. 39.

Example 22: Blood Coagulant as a Drying Agent

Paper spray mass spectrometry is applied to oncology drugs in fresh whole blood samples supported on filter paper substrates instead of dry blood as done previously. Addition of the coagulant alum clotted the blood and allowed for immediate sample analysis. The coagulant did not interfere with the function of the paper spray nor did it add features to the mass spectra. Quantitative analysis of therapeutic drugs in the blood was achieved utilizing internal standards which were pre-spotted onto the filter paper. Eight oncology drugs were examined, with lower limits of detection ranging between 0.5 and 17 ng/mL and linear dynamics ranges greater than two orders of magnitude. Inter-day accuracies of quality controls for pazopanib ranged from 102 to 118%, with imprecisions of 9 to 13%. This one-step method was conducted using 10 µL of blood, a drop of solvent, and took about 45 seconds per trial. These results indicate applicability to point-of-care therapeutic drug monitoring in a clinical setting.

a. Introduction

Every drug has an optimally effective therapeutic range, outside of which the drug is harmful or ineffective. Concentrations of active pharmaceutical compounds in a patient's circulatory system vary with the individual (A. Y. H. Lu, Drug Metab. Dispos., 1998, 26, 1217-1222). One procedure for determining the upper limit is to increase drug dosage until dose-limiting toxicity occurs. Alternative approaches include pharmacogenomics (W. E. Evans and M. V. Relling, Science, 1999, 286, 487-491; W. E. Evans and H. L. McLeod, N. Engl. J. Med., 2003, 348, 538-549; and W. E. Evans and M. V. Relling, Nature, 2004, 429, 464-468) and pharmacokinetic modeling (N. H. G. Holford and L. B. Sheiner, Clin Pharmacokinet, 1981, 6, 429-453; and L. E. Gerlowski and R. K. Jain, J. Pharm. Sci., 1983, 72, 1103-1127) which use genetics and statistics to account for the variation in uptake and metabolism of drugs. Another possibility is therapeutic drug monitoring (TDM), in which drug exposure levels within the body are measured directly by a quantitative method. Historically, immunoassays and high performance liquid chromatography with optical or mass spectrometric detection have been the methods-of-choice for therapeutic drug monitoring. Immunoassays have been used for decades for point-of-care monitoring of blood, and recent research has provided faster results for point-of-care applications (X. Yang, J. Janatova, J. M. Juenke, G. A. McMillin and J. D. Andrade, Anal. Biochem., 2007, 365, 222-229; and T. Tachi, T. Hase, Y. Okamoto, N. Kaji, T. Arima, H. Matsumoto, M. Kondo, M. Tokeshi, Y. Hasegawa and Y. Baba, Anal. Bioanal. Chem., 2011, 401, 2301-2305) by implementing microfluidic methods (B. Zheng and R. F. Ismagilov, Angew. Chem. Int. Ed., 2005, 44, 2520-2523). The ultimate goal for TDM is individualized dosing during treatment using a platform technology for fast, accurate, and inexpensive assays directly from untreated biofluid.

This Example shows the use of coagulants for rapid quantitative analysis of oncology drugs from fresh whole blood by paper spray mass spectrometry. Oncology drug analysis has been chosen as a model problem for point-of-care analysis due to the need for fast results during chemotherapy. The quantitative results herein show that paper spray has sufficient sensitivity and precision, with regard to clinical regulations, to provide the first one-step analysis of fresh whole blood for applications in point-of-care mass spectrometry.

b. Materials

Most drug standards were purchased from Sigma-Aldrich (St. Louis, Mo., USA) and used without any further purification. All organic solvents (HPLC grade) were purchased from VWR Scientific (Chicago, Ill., USA). Blood card paper (grade 31 ETF) was obtained as a sample from Whatman (Piscataway, N.J., USA). Bovine whole blood with potassium ethylene diamine tetraacetic acid ($K_2EDTA$) was purchased from Innovative Research (Novi, Mich., USA) and stored at 4° C.

c. Preparation of Samples

All stock solutions were prepared in methanol, and working solutions were prepared in 50:50 methanol/water. Spiked blood samples were prepared by adding the necessary quantity of working solution not to exceed 5% of the volume of blood (typically, addition of 50 □L 20× concentration solution to 950 □L of bovine whole blood). Before sample preparation, the blood was incubated to a temperature of 37° C. The blood standards were vortexed for 10 seconds and analyzed within 1 hour of preparation.

d. Mass Spectrometry and Paper Spray Ionization

Figure 40:
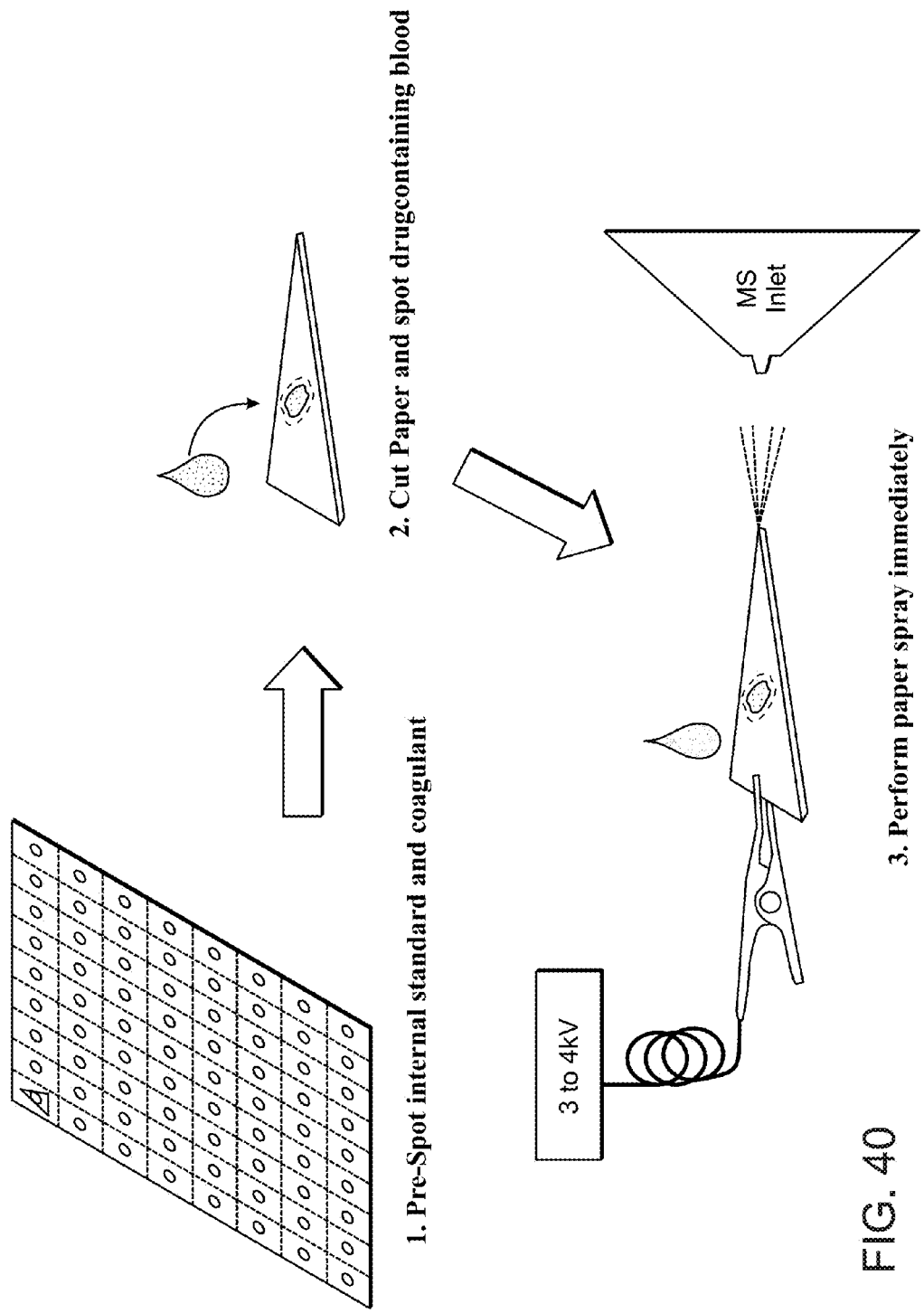
FIG. 40 is a schematic showing the mode of operation for point-of-care therapeutic drug monitoring of whole blood by paper spray mass spectrometry utilizing a coagulating agent.

FIG. 40 is a schematic showing the mode of operation for point-of-care therapeutic drug monitoring of whole blood by paper spray mass spectrometry utilizing a coagulating agent. Each sheet of Whatman 31ETF paper had a grid drawn with pencil, each pixel of which was 1 cm×2 cm in size (FIG. 40). A mixture of internal standard (500 ng/mL) and alum powder (60 mg/mL), dissolved in distilled water, was pipetted (5 µL) at the center of each of the marked grid boxes. After allowing the spots to dry in air for approximately 10 minutes, the pre-spotted paper sheet was cut into small triangles, measuring 8 mm at the base and 15 mm in height. The center of each triangle contained the pre-spotted alum and internal standard solution.

For blood sample analysis, the back edge of the paper triangle was held by a toothless copper alligator clip which was connected to the high voltage power supply (FIG. 40). The front tip of the paper was placed 5 mm away from the atmospheric pressure inlet of the mass spectrometer. The whole blood sample was then pipetted (10 µL) onto the center of the paper triangle. Pure methanol (or methanol with 0.1% sodium acetate for drugs that formed sodiated adducts) was applied slowly to the back end of the paper, behind the blood spot, until the solvent wicked through the blood and to the front tip of the triangle. The applied spray solvent was only enough to wet the entire blood spot and paper triangle and did not exceed 32 µL for each spray process. Since the solvent flows from the back to front tip, if not enough solvent is applied, no spray will occur. On the other hand, if too much solvent is applied, 1) the solvent may travel over the blood spot instead of through it, which reduces the analyte pick-up; 2) the solvent flow rate at the spray tip will be too high and cause the paper to eject very large droplets which do not evaporate properly. Following addition of the solvent, 3000 V was applied to the paper via the alligator clip, producing a spray current between 0.2 and 0.6 µA. The paper spray procedure left the blood spot stationary and intact, thus reinjection analysis was performed by applying solvent and a high voltage on the same sample for a second time.

Dried blood spot analysis was performed in the same fashion as fresh blood, but without the coagulant and with an extra two hours for blood drying, in accordance to the procedure of Manicke et al. (J. Am. Soc. Mass. Spectrom., 2011, 22, 1501-1507). All experiments were performed using a TSQ Quantum Access MAX (Thermo Scientific, San Jose, Calif., USA). Data collection was executed in selected reaction monitoring (SRM) mode (R. W. Kondrat and R. G. Cooks, Anal. Chem., 1978, 50, A81-A92), observing the desired fragment intensity for the drugs and internal standards by collision-induced dissociation (CID). Scan times were 250 ms, alternating between the drug and internal standard, and data were collected until the spray voltage was manually turned off at 15 seconds, totaling 30 scans for each fragment ion.

e. Data Analysis

The two sets of 30 scans were plotted as individual ion chronograms, showing ion current versus time for each fragment ion. The area under the curve corresponding to the drug was compared to that of the internal standard and used for quantitation. Limits of detection were determined using a calibration curve consisting of four trials each of 0, 50, 100, 500, and 1000 ng/mL drug standard solutions. Limits of detection were determined by multiplying the t-value (95% confidence) by the standard deviation of the blank, divided by the slope of the calibration curve determined by $1/x^2$ weighted linear least squares (G. L. Long and J. D. Winefordner, Anal. Chem., 1983, 55, A712-A724). Reported precision values are the relative standard deviation of concentration determined from multiple blood spots taken from a single blood sample. Accuracy is defined to be the measured concentration divided by the actual concentration multiplied by 100%.

f. Results

One of the primary challenges faced by rapid blood analysis with paper spray is the contamination of the spray tip by blood components. In the case of freshly-spotted blood that was not dried, oxygenated hemoglobin—the red component of blood—was seen to run to the tip (see FIG. 41). This phenomenon, which presumably indicated the movement of other proteins and cellular components toward the tip as well, prohibited formation of a stable Taylor cone using volumes of blood greater than 2 µL. Lower volumes of blood (<2 µL) can be analyzed in a few minutes (H. Wang, J. J. Liu, R. G. Cooks and Z. Ouyang, Angew. Chem. Int. Ed., 2010, 49, 877-880) but are less desirable due to poorer limits of detection and increased standard deviations. One requirement of a viable bioanalytical blood analysis method by paper spray, therefore, is that the red blood cells, proteins, and other sources of interference remain stationary on the paper. While this fixation occurs naturally in the case when dried blood spots are extracted with organic solvents, additional means are needed for freshly spotted blood.

One approach for the rapid paper spray analysis of fresh blood samples was the addition of coagulants to the paper. A pre-spotted coagulant, potash alum, quickly clotted the blood (within seconds) and allowed the spray solvent to wick through the blood spot and to the tip of the paper, dissolving analytes in the process (FIG. 41). Potash alum, more specifically potassium aluminum sulfate [$KNH_4(SO_4)_2.H_2O$], is a common product found in powdered alum which promotes flocculation in suspended colloids. Potash alum is also minimally soluble in methanol (a common and effective paper spray solvent) and does not produce any contaminant ions during mass spectrometry. Alum was the coagulant used in all of the following experiments.

g. Therapeutic Drug Monitoring

Two important parameters characterizing the method are precision and accuracy. The imprecision should not exceed a relative standard deviation of 15% (20% at the lower limit of quantitation). The inaccuracy of quality control samples likewise should not exceed ±15% (±20% at the lower limit of quantitation). Table 2 is a representative quality control table for analysis of pazopanib in blood, portraying the inter- and intra-day accuracy and reproducibility of the oncology drug assay (n=5 for each concentration, each day). Pazopanib is an anti-cancer drug which has been approved by the U.S. FDA.

The quality control results from Table 2 suggest that this method is a viable bioanalytical method for point-of-care therapeutic drug monitoring. Most of the quality control samples yielded a positive bias, which was most likely due to error in the sample preparation process. All of the inter-day percent accuracies and standard deviations for this data set produced errors under 15%, on average 10.8%. This is comparable to previous work on dried blood spots by paper spray with pre-spotted internal standards, which had about 10% relative standard deviations (N. E. Manicke, P. Abu-Rabie, N. Spooner, Z. Ouyang and R. G. Cooks, J. Am. Soc. Mass. Spectrom., 2011, 22, 1501-1507). The most unusual result, from 750 ng/mL on Day 1, seems especially erroneous and was most likely caused by experimental errors during the paper spray process.

TABLE 2

Quality control of pazopanib by paper spray analysis of 10 µL fresh whole blood

| Pazopanib concentration | Mean % Accuracy {Imprecision (% CV)} | | | |
|---|---|---|---|---|
| | Day 1 | Day 2 | Day 3 | Inter-day |
| 15 ng/mL (3 × LLOQ) | 113.0% {12.3%} | 110.9% {12.6%} | 129.3% {8.7%} | 117.7% {11.2%} |
| 50 ng/mL | 97.1% {13.5%} | 101.2% {3.9%} | 106.4% {10.8%} | 101.6% {9.4%} |
| 500 ng/mL | 107.7% {9.5%} | 111.6% {12.9%} | 103.7% {8.9%} | 107.6% {10.4%} |
| 750 ng/mL | 116.3% {16.5%} | 102.9% {7.5%} | 101.2% {12.4%} | 106.8% {12.1%} |

It is conceivable that in the course of point-of-care work, reanalysis of a sample will be needed due to instrument malfunction or required immediate result confirmation. Therefore, reinjection reproducibility was analyzed in which the solvent was reapplied and paper spray was performed on the same blood spot for a second time. In general, paper spray does not have high recovery of the analyte. That is, the amount of analyte extracted and sprayed from the paper toward the mass spectrometer is only a portion of the available analyte (Z. Zhang, W. Xu, N. E. Manicke, R. G. Cooks, Z. Ouyang, Anal. Chem., 2012, DOI: 10.1021/ac202058w). Although the relatively lower recovery contributed to poorer sensitivity, it did allow for reanalysis of the same blood spot. Table 3 shows how analyzing the same blood sample a second time did not affect the accuracy of the results, with the exception of the 10 ng/mL samples, the concentrations of which were less than three times the lower limit of quantitation.

TABLE 3

Reinjection of pazopanib standards from fresh blood paper spray mass spectrometry

| Pazopanib Concentration | Mean Drug/IS (n = 6) | | |
|---|---|---|---|
| | Injection 1 | Injection 2 | % Change |
| Blank | 0.0087 | 0.0084 | 3.4% |
| 10 ng/mL | 0.057 | 0.067 | 17.5% |
| 50 ng/mL | 0.253 | 0.251 | 0.8% |
| 100 ng/mL | 0.522 | 0.506 | 3.1% |
| 500 ng/mL | 3.114 | 3.029 | 2.7% |
| 1000 ng/mL | 5.713 | 5.754 | 0.7% |

It should be noted that the parameters for paper spray were chosen carefully for optimal performance. To achieve precision of better than 15%, it was necessary to use an isotopically-labeled internal standard due to the various affinities of the analytes for the substrate, as well as inefficiencies in ionization and ion transfer. In addition, although volumes of blood less than 5 µL clotted more efficiently, 10 µL of blood was typically used in order to improve the standard deviation of the method. It was difficult, for example, to control the blood volume, spot size, and spot shape for smaller volumes of micro-pipetted blood. An automated technique would allow for smaller blood volumes to be analyzed more reproducibly. The spray solvent, methanol, was chosen to achieve proper wicking through the paper, good analyte extraction, and low background noise. The background noise was reduced by using the lowest spray voltage possible, typically 3.0 kV.

FIG. 42 shows six consecutive trials (from different blood spots) of pazopanib. The method of pre-spotting the clotting agent and the internal standard resulted in a relative standard deviation of 9 to 12%. A key feature of the chronograms was that although the internal standard was pre-spotted, the peak shapes of the drug and the internal standard were similar, resulting in acceptable reproducibility.

A wide variety of oncology drugs was explored by the same method. These drugs varied in molecular weight from 261 g/mol (cyclophosphamide) to 854 g/mol (paclitaxel). There are many factors that affected the lower limits of detection for these drugs, including solubility in the spray solvent, affinity for the substrate and blood components, proton affinity (or $Na^+$ affinity in the case of the taxanes which form sodium ion adducts), background noise level, and selectivity of the SRM transition. A previous study demonstrated that matrix effects cause negligible analyte suppression within the therapeutic range for drugs by paper spray, and that paper spray MS measures the total drug concentration in blood (free plus bound drug) (N. E. Manicke, Q. A. Yang, H. Wang, S. Oradu, Z. Ouyang and R. G. Cooks, Int. J. Mass spectrom., 2011, 300, 123-129).

Oncology drugs pazopanib, tamoxifen, imatinib, cyclophosphamide, paclitaxel, docetaxel, topotecan, and irinotecan were each analyzed individually to determine lower limits of detections (LLOD's). As Table 4 shows, the method described herein for rapid drug analysis from fresh blood gave LLOD's ranging from 0.5 ng/mL for pazopanib, to 17 ng/mL for topotecan; all these values are in the same order of magnitude as the dried blood spot experiments by paper spray (N. E. Manicke, P. Abu-Rabie, N. Spooner, Z. Ouyang and R. G. Cooks, J. Am. Soc. Mass. Spectrom., 2011, 22, 1501-1507). The LLOD's were within one order of magnitude compared to previously-reported HPLC-MS/MS methods of therapeutic drugs.

Figure 43:
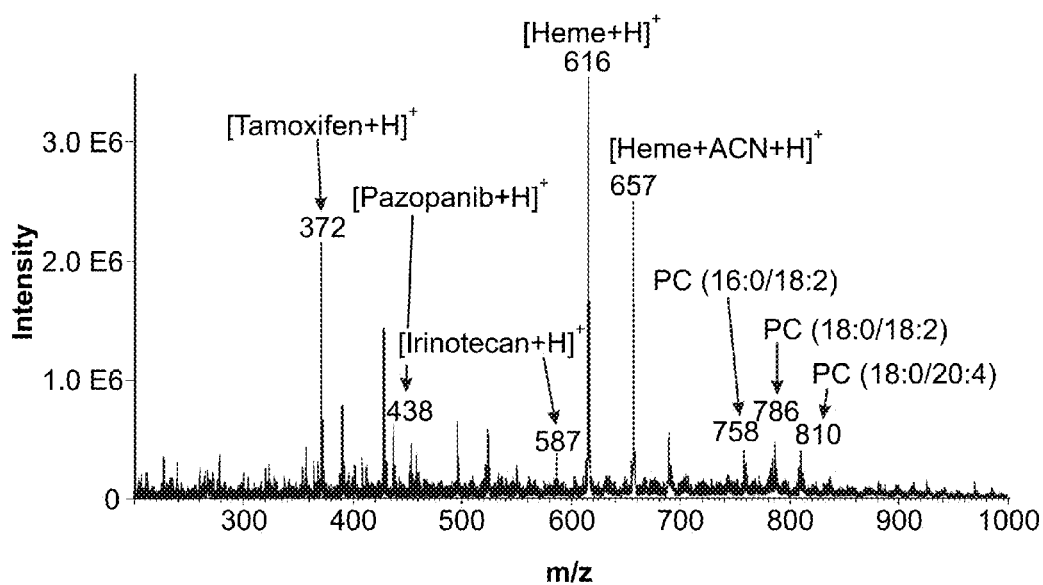
FIG. 43 shows paper spray mass spectrometry of 1 μg/mL tamoxifen, pazopanib, and irinotecan in 10 μL fresh whole blood with 0.45 mg of alum was pre-spotted. The spray solvent was 32 μL 50:50 methanol/acetonitrile (ACN) and +3.0 kV applied. Abbreviation PC denotes phosphatidylcholine.

When analyzing fresh blood, it was hypothesized that any biomolecules that are soluble in the spray solvent and ionizable by paper spray will be detected by the mass spectrometer. FIG. 43 shows that in addition to the drugs that were spiked into the blood, free heme was observed, as well as some common phospholipids. The presence of heme indicates that red blood cell lysis is occurring due to the solvent composition and/or paper spray conditions. It is reasonable to expect that future experiments may involve the analysis of lipids, proteins, and/or other biomolecules which would also be useful for point-of-care clinical diagnostics.

h. Conclusion

Quantitative analysis of oncology drugs by paper spray with alum, a coagulant, shows that this method has capabilities for point-of-care therapeutic drug monitoring. Utilizing a bench-top mass spectrometer, inter- and intra-day percent accuracies and imprecisions of quality controls and standards were within regulated guidelines (<15% error) using pre-spotted isotopically-labeled internal standards. The time span from blood spotting to results took under 60 seconds, due to the online extraction of paper spray and the coagulating ability of pre-spotted alum. The excellent limits of detection suggest that this method should be easily transferrable to a portable mass spectrometer where the larger blood volumes that can be handled quickly with the drying agent will be necessary for adequate analytical performance. The use of inexpensive expendables means that disposable cartridges could be used which would reduce sample contact and lower the potential risk for cross-contamination.

This method could also find a place in home-use applications, for example in an assisted living facility to ensure day-to-day medication levels. The small blood consumption by paper spray, several microliters, would also allow co-monitoring of blood by separate aliquots and analyzing electrolytes, blood gases, and glucose levels. In addition to therapeutic oncology drugs and metabolites, paper spray may be applied for analysis of biocompounds such as fatty acids, lipids, and proteins, as well as other applications including drugs of abuse, steroids, and human growth hormones.

Example 23: Ion Generation Using a Wetted Porous Substrate that Substantially Prevents Diffusion of Sample into the Substrate a. Analysis of Whole Blood When fresh (liquid) blood is dropped onto sample substrates of less hydrophobicity, such as print paper or

TABLE 4

Limits of detection for oncology chemotherapeutic drugs by paper spray mass spectrometry

| Drug | Therapeutic Range (ng/mL)[a] | Precursor Ion (m/z) | Fragment Ion (m/z) | Internal Standard (IS) | IS Precursor Ion | IS Fragment Ion | 15 µL Dried Blood Spot LLOD (ng/mL) | 10 µL Fresh Blood w/Alum LLOD (ng/mL) |
|---|---|---|---|---|---|---|---|---|
| Pazopanib | NA | 438.1 $[M + H]^+$ | 357.1 | $^2H_3{}^{13}C$-pazopanib | 442.1 $[M + H]^+$ | 361.1 | 1 | 0.5 |
| Tamoxifen | 35-45 | 372.2 $[M + H]^+$ | 72.2 | $^{13}C_2{}^{15}N$-tamoxifen | 375.2 $[M + H]^+$ | 75.2 | 13 | 8 |
| Imatinib | 900-1800 | 494.2 $[M + H]^+$ | 394.0 | imatinib-d8 | 502.2 $[M + H]^+$ | 394.0 | 1.2 | 9 |
| Cyclophosphamide | 10000-25000 | 261.0 $[M + H]^+$ | 140.0 | Ifosfamide | 261.0 $[M + H]^+$ | 154.0 | 13 | 11 |
| Paclitaxel | 85-1000 | 876.5 $[M + Na]^+$ | 307.9 | Docetaxel | 830.3 $[M + Na]^+$ | 549.2 | 15 | 12 |

[a]Therapeutic Ranges for plasma concentrations (R. Regenthal, M. Krueger, C. Koeppel and R. Preiss, J. Clin. Monitor Comp., 1999, 15, 529-544.)

Figure 44A:
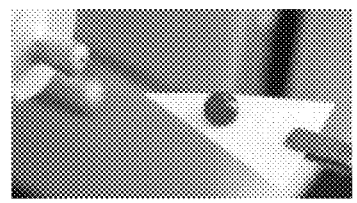
FIG. 44A is a photograph showing 10 μL bovine blood on print paper (Xerox 3R2047).
Figure 44B:
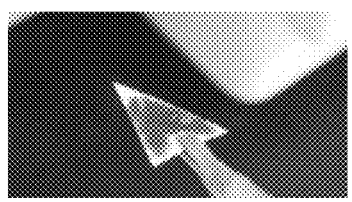
FIG. 44B Blood diffuses after 50 μL methanol with 1% acetic acid is applied onto the printing paper.

Silanized paper, the blood drop stays on the top of the substrate without diffusing into the porous substrate (FIG. 44A). When a solvent of proper hydrophobicity is dropped on the substrate with the blood droplet, the blood defuses with the solvent (FIG. 44B).

Figure 45:
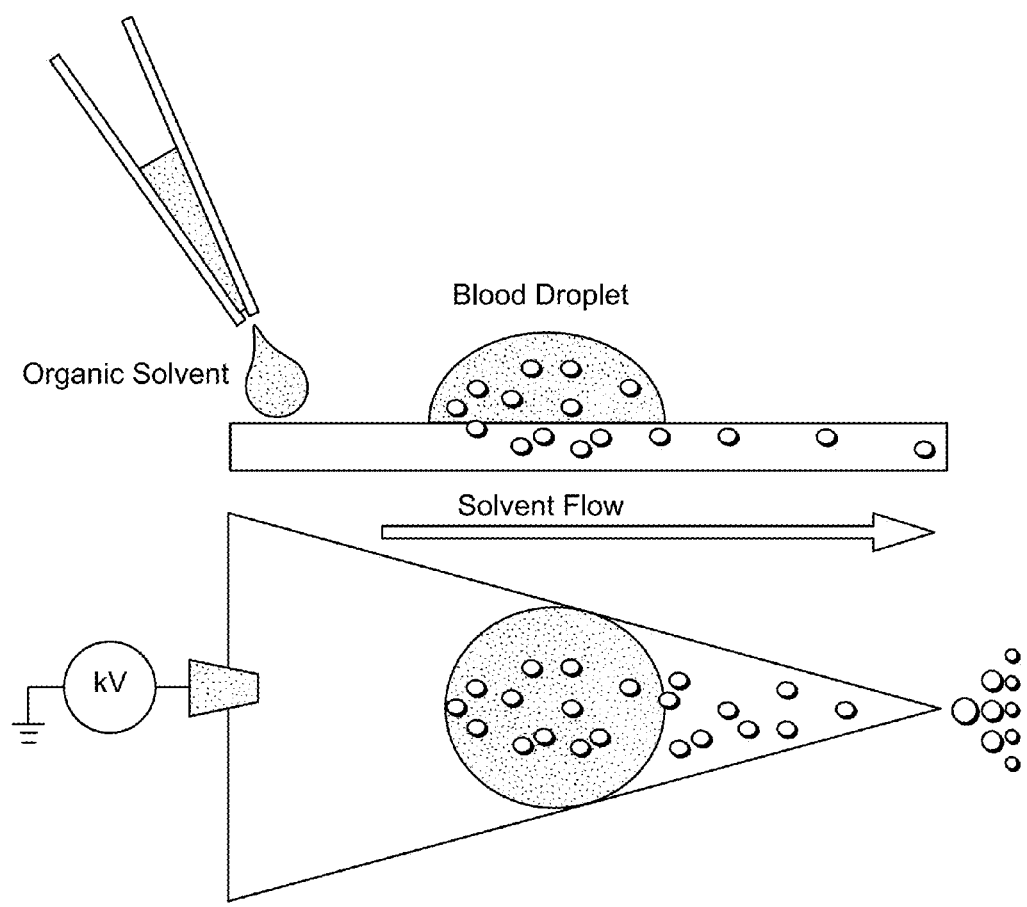
FIG. 45 is a schematic showing chemical extraction from fresh whole blood.

The solvent can extract the chemicals from the blood and also facilitate the spray to generate ions from the substrate (FIG. 45). Certain chemicals could be selectively extracted from the whole blood while most other chemicals stay on the paper substrate reducing the matrix effect and contamination to the mass spectrometer. When a high voltage is applied onto the paper triangle, the charged droplets containing the chemicals will be sprayed from the tip of the triangle, as shown in FIG. 45.

b. Direct Detection of Proteins from Whole Fresh Blood

Even though there is a large amount of proteins in whole blood, it is difficult to detect any protein spectra from a dried blood spot using chromatography paper. Without being limited by any particular theory or mechanism of action, it is believed that when blood is dried on paper, the proteins in the blood could be denatured and combine strongly with the substrate especially if the substrate is polar.

Figure 46A:
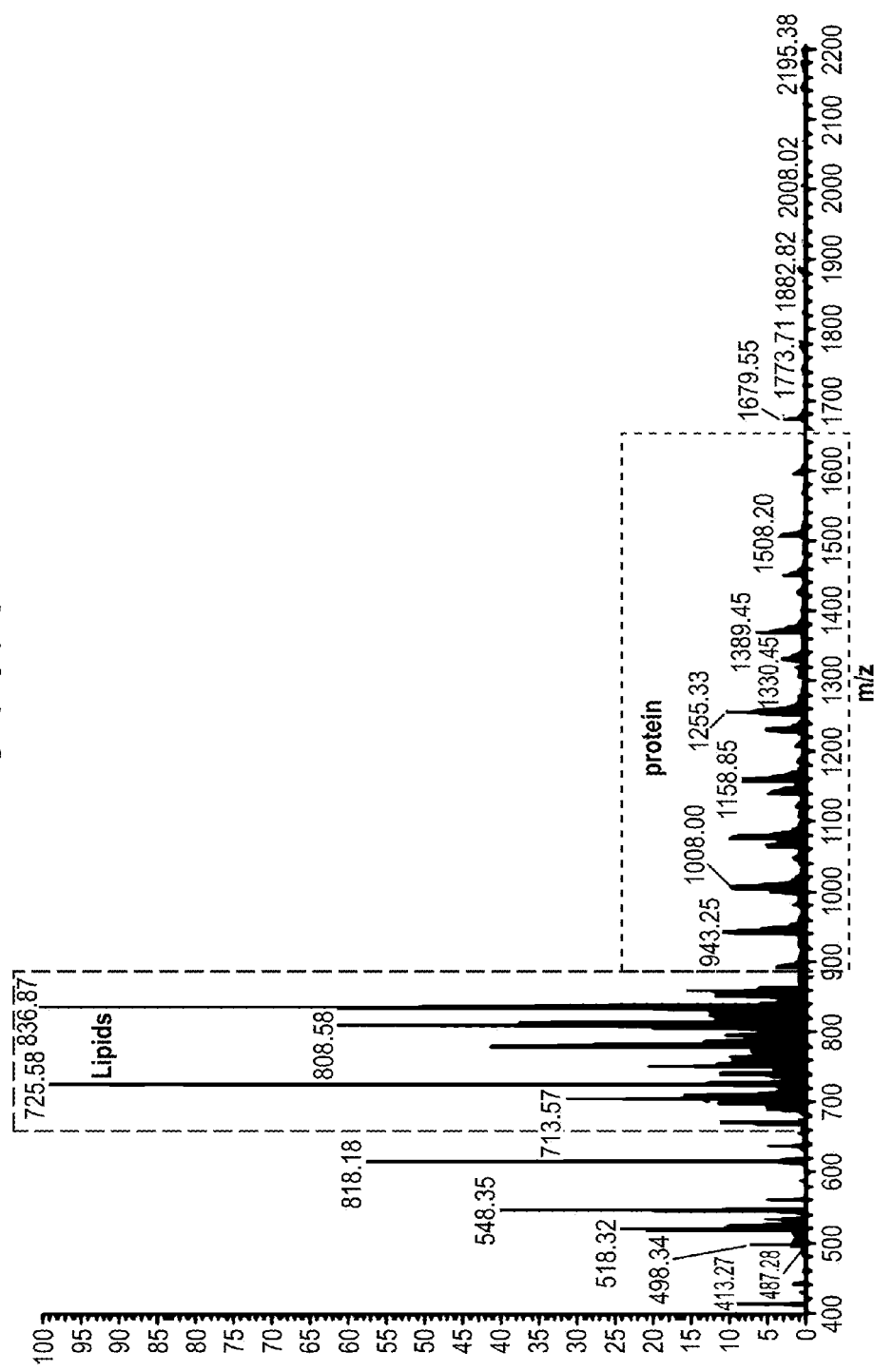
FIGS. 46A-C are a set of mass spectra showing detection of protein hemoglobin from fresh bovine whole blood using different paper substrates (FIG. 46A) Grade 1 chromatography paper, (FIG. 46B) printer paper, and (FIG. 46C) silanized paper were used as paper substrates accordingly.
Figure 46B:
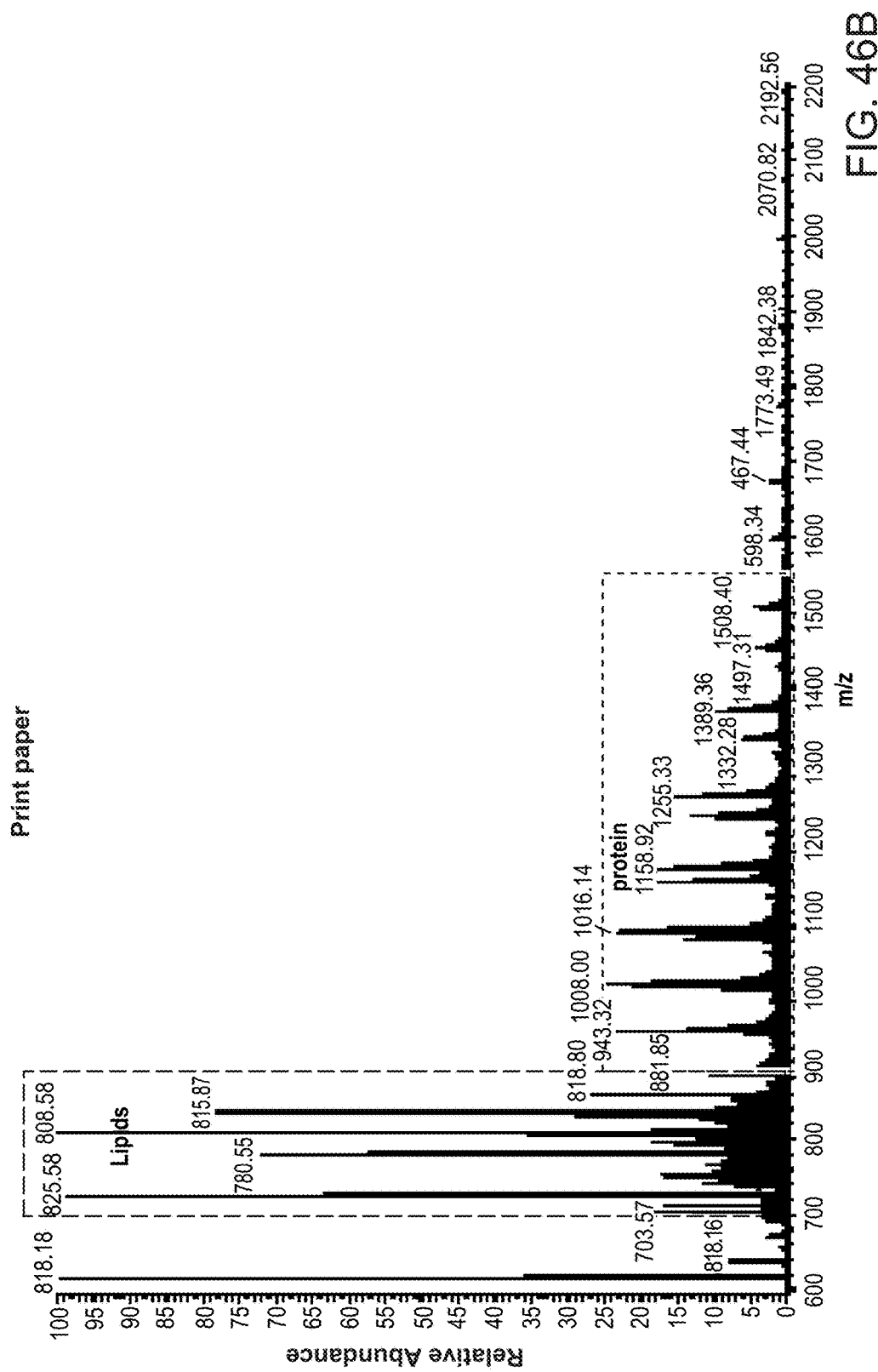
Figure 46C:
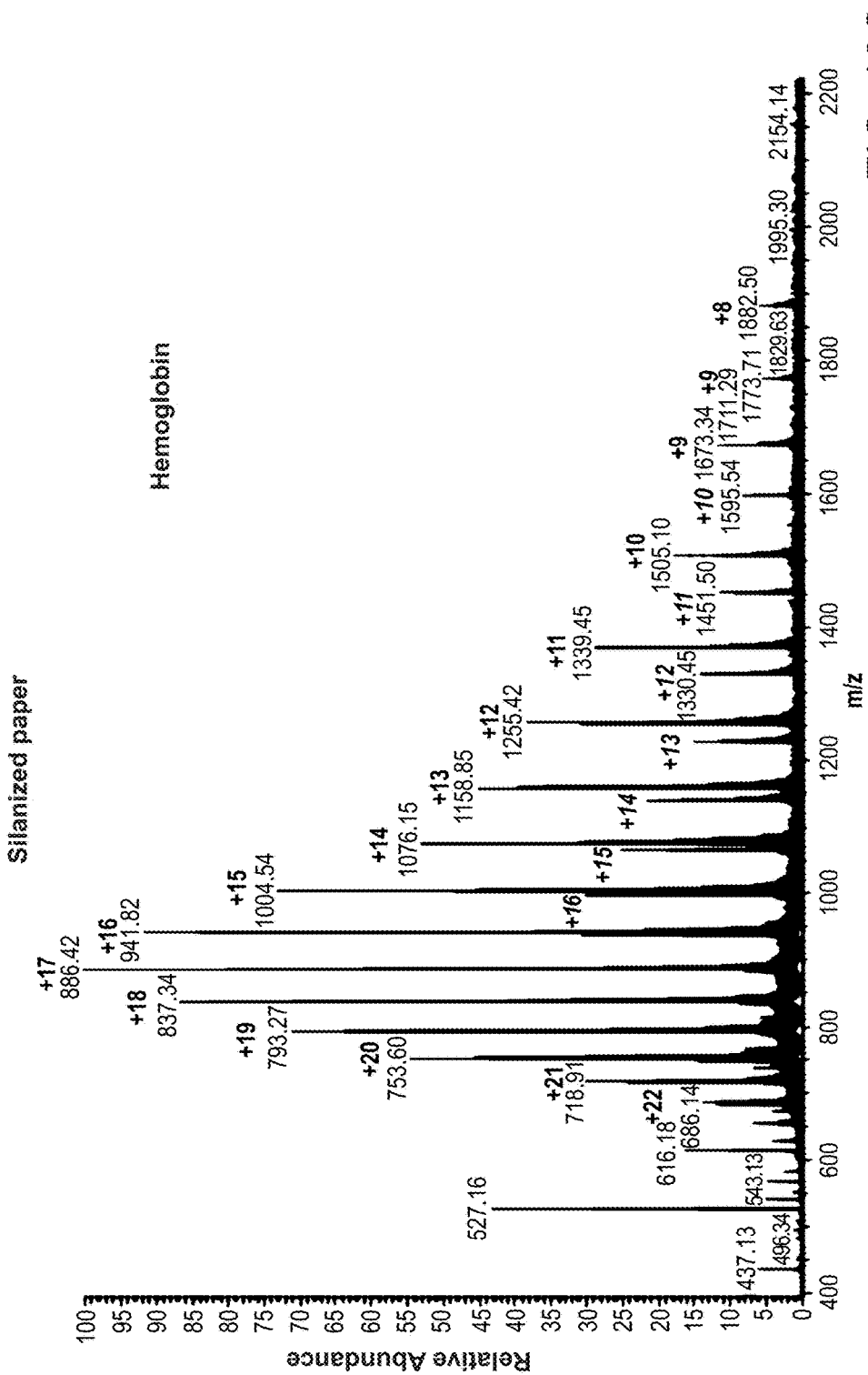
Figure 47A:
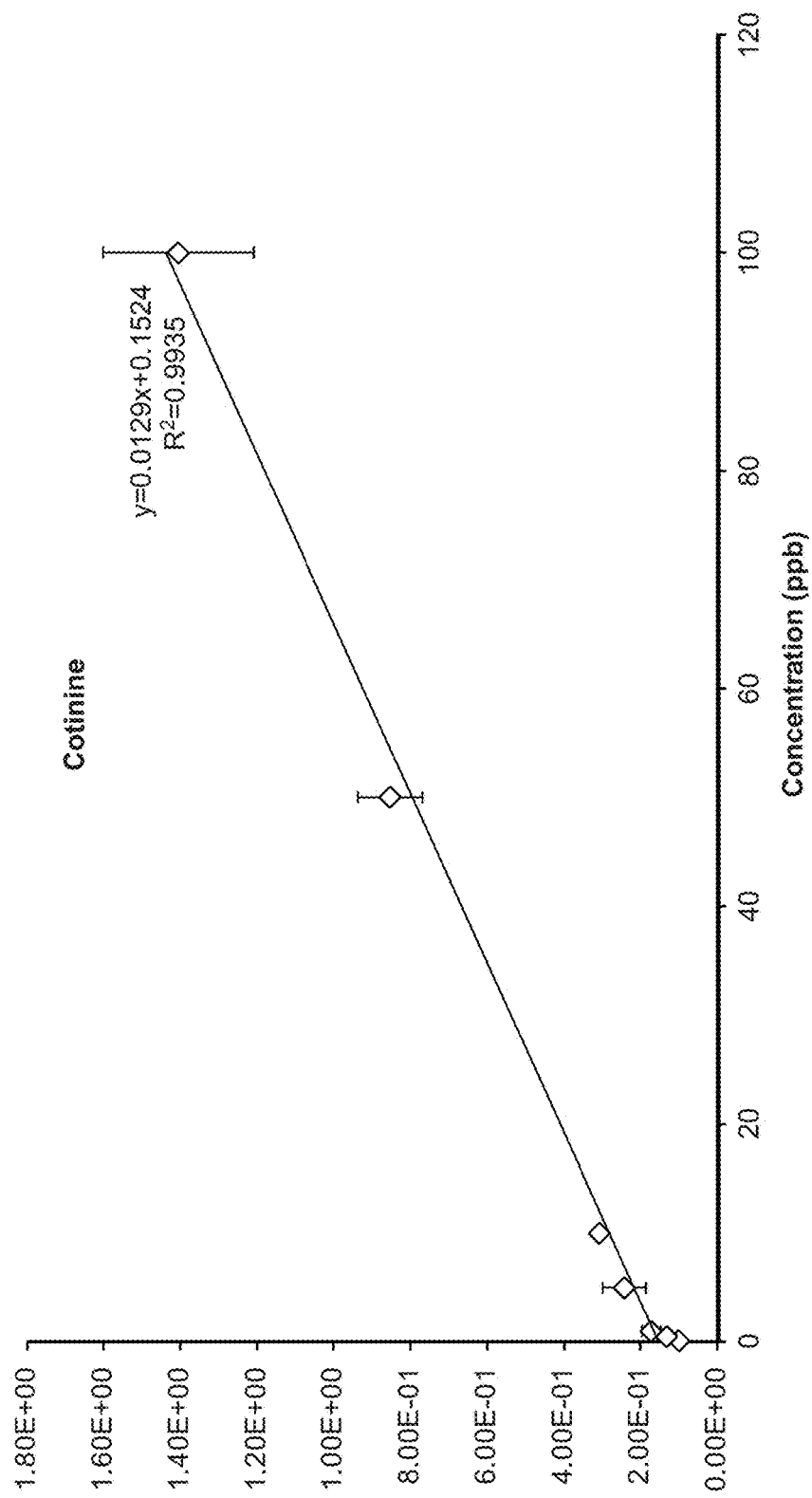
FIG. 47A is a graph showing quantitation of cotinine, the major metabolite of nicotine, from fresh bovine whole blood.

10 µL of bovine whole blood was dropped onto a paper surface. Then 50 µL methanol with 1% acetic acid was applied as solvent. 4 kV DC voltage was applied on the copper clip to produce spray. FIG. 46 shows that protein spectra could be detected from all the three paper substrates when fresh whole blood was used, especially for silanized paper which is quite hydrophobic. α and β subunits of hemoglobin could be detected as the dominated peaks in the spectra. The peak at m/z 616 represents the heme group from the hemoglobin. When chromatography paper and printer paper were used, the spectra were dominated by lipid peaks and the protein peaks have a low relative intensity. When silanized paper substrate was used, there is intense hemoglobin signal. The two sets of protein spectra in FIG. 46C represents α and β subunits of hemoglobin, respectively. The spectra was recorded using an Exactive Orbitrap mass spectrometer.

c. Extraction of Chemicals from Fresh Whole Blood Using Organic Solvents that are not Miscible with Blood FIG. 47A shows quantitation of cotinine, the major metabolite of nicotine, from fresh bovine whole blood. Printer paper was used as the substrate and 10 µL of bovine whole blood was dropped onto the paper surface. Then 30 µL 90% dichloromethane and 10% isopropanol was applied as solvent, which has been shown to be an effective solvent to extract cotinine from whole blood (F. Baumann, R. Regenthal, I. L. Burgos-Guerrero, U. Hegerl, R. Preiss, J Chromatogr B878, 107 (Jan. 1, 2010)). 4 kV DC voltage was applied on the copper clip to produce spray. The calibration curve was obtained by spiking different concentrations of cotinine into the blood sample and 100 ppb cotinine-d3 was used as internal standard for each sample. LOQ of 1 ppb could be reached. The spectra were recorded using TSQ mass spectrometer. As shown in FIG. 47, printer paper was used since it was less hydrophilic compared with Grade 1 chromotography paper.

Figure 47B:
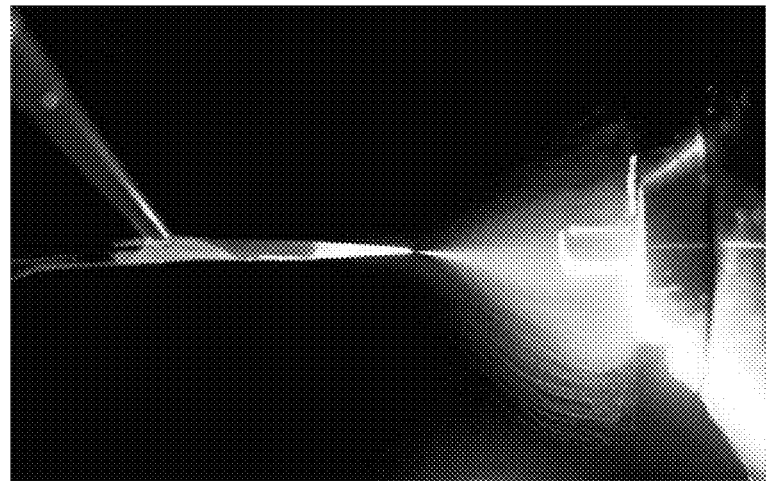
FIG. 47B is a photograph of the spray plume using 90% dichloromethane and 10% isopropanol as solvent.

Most of the blood sample stayed on top of the paper substrate forming a film of liquid blood instead of being absorbed into the paper. When the solvent was applied, it went through the blood sample to the tip. When high voltage is applied, a strong spray plum was produced from the tip of the paper triangle (FIG. 47B). During the whole process, the blood sample stayed in the original position. Since the solvent was not miscible with blood sample, the analytes in the blood were extracted through a liquid-liquid extraction process.

d. Extraction of Chemicals from Fresh Whole Blood Using Organic Solvents which are Miscible with Blood FIG. 48A shows quantitation of nicotine from fresh bovine whole blood. Print paper was used as the substrate and 10 µL of bovine whole blood was dropped onto the paper surface. Then acetonitrile was applied as solvent to extract nicotine from fresh whole blood. 4 kV DC voltage was applied on the copper clip to produce spray. The calibration curve was obtained by spiking different concentrations of nicotine into the blood sample and 100 ppb nicotine-d3 was used as internal standard for each sample. LOQ of 0.1 ppb was reached. The spectra were recorded using TSQ mass spectrometer. Printer paper was used since it was less hydrophilic compared with Grade 1 chromotography paper.

Figure 48B:
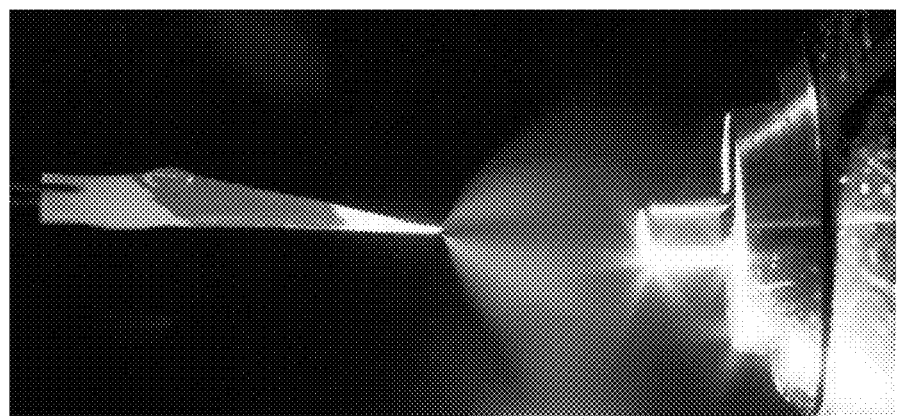
FIG. 48B is a photograph of the spray plume using acetonitrile as solvent.

When high voltage was applied, a strong spray plum was produced from the tip of the paper triangle (FIG. 48B). Even though acetonitrile is miscible with water in blood, most of the blood sample still stays in the original position during the spray.

e. Applying Sample Extraction to Make Dried Sample Spots for Later Analysis

Figure 49:
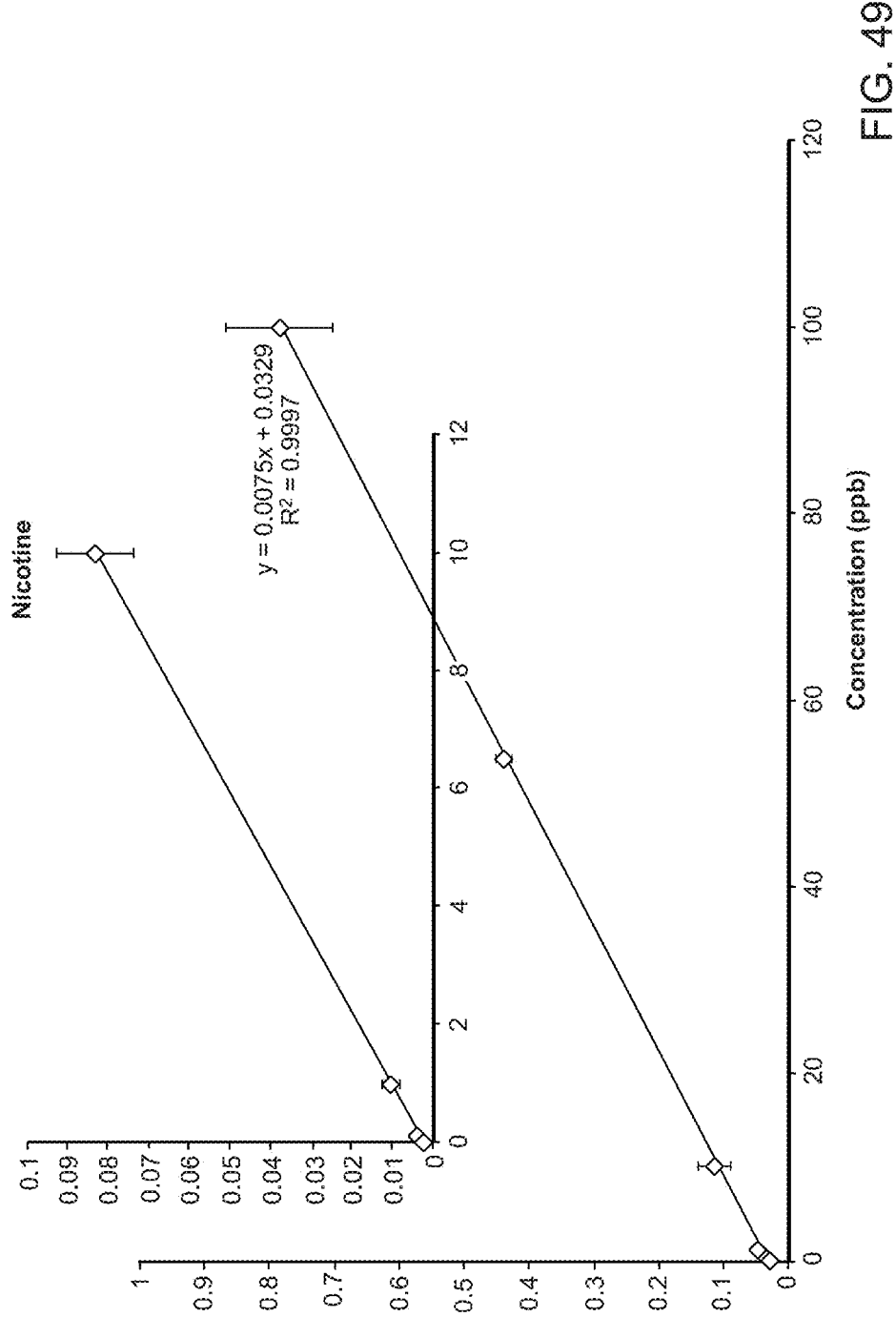
FIG. 49 is a graph showing 10 μL whole fresh blood is spotted on to the print paper.

10 µL whole fresh blood was spotted on to the print paper. Then 10 µL acetonitrile was applied onto the blood sample before it dried to extract nicotine from the blood sample. After the sample and solvent were dried on the paper, another 20 µL acetonitrile was applied as spray solvent and 4 kV DC was applied to generate paper spray. LOQ of 1 ppb could be achieved. The spectra were recorded using TSQ mass spectrometer (FIG. 49).

Example 24: Analysis of Tobacco Nicotine Alkaloids from Biofluids Using a Wetted Porous Substrate that Substantially Prevents Diffusion of Sample into the Substrate The determination of tobacco nicotine alkaloids from biofluids is of great importance for a smoking test, to tobacco cessation treatment, and to the study of exposure to secondhand smoke and effect of tobacco use on individual health. Paper spray mass spectrometry has been developed for direct, quantitative analysis of tobacco nicotine alkaloids from dried and liquid biofluids such as blood, urine and saliva. Limit of quantitation as low as several ng/mL were obtained for nicotine, cotinine, trans-3'-hydroxycotinine and anabasine. Due to the fast and convenient characteristics of this method, it shows potential for significantly improving the analytical efficiency in clinical labs and also for point-of-care tobacco use assessment.

a. Introduction

Tobacco use is the chief preventable cause of disease and death in the US (Centers for Disease Control and Prevention. Annual Smoking-Attributable Mortality, Years of Potential Life Lost, and Economic Costs—United States, 1995-1999. Morbidity and Mortality Weekly Report 2002; 51(14):300-3). However, due to it addiction nature, to quit smoking is extremely difficult. Based on the data from CDC, in 2010, about 19.3% of all adults are smokers in the US (Centers for Disease Control and Prevention. Vital Signs: Current Cigarette Smoking Among Adults Aged ≥18 Years—United States, 2005-2010. Morbidity and Mortality Weekly Report 2011; 60(33):1207-12) and only less than 10 percent who quit smoking for a day remain abstinent one year later (M. C. Fiore, Med. Clin. N. Am. 1992, 76, 289-303). Smokers have much higher health risks for a series of serious diseases, such as coronary heart disease, stroke, and lung cancer. The adverse health effects of smoking accounts for about one fifth deaths each year (Centers for Disease Control and Prevention. Annual Smoking-Attributable Mortality, Years of Potential Life Lost, and Economic Costs—United States, 1995-1999. Morbidity and Mortality Weekly Report 2002; 51(14):300-3) and $193 billion were spent annually due to cigarette smoking caused health-related economic losses in the US (Centers for Disease Control and Prevention. Smoking-Attributable Mortality, Years of Potential Life Lost, and Productivity Losses—United States, 2000-2004. Morbidity and Mortality Weekly Report 2008; 57(45):1226-8).

Because of the significant adverse health effects of tobacco use, more and more insurance companies request life insurance buyers to do smoking tests. Different rating categories will be given based on the smoking status. Many employers also use smoking testing to evaluate prospective employees for tobacco use.

For tobacco use assessment and other tobacco use related clinical diagnosis, nicotine and its metabolites are most frequently analyzed chemicals (I. Kim, M. A. Huestis, J. Mass Spectrom. 2006, 41, 815-821; and J. Hukkanen, P. Jacob, N. L. Benowitz, Pharmacol. Rev. 2005, 57, 79-115). Nicotine is the major addictive chemical in tobacco which makes people difficult to quit smoking once started (N. L. Benowitz, Annu. Rev. Pharmacol. Toxicol. 2009, 49, 57-71; and N. L. Benowitz, N. Engl. J. Med. 2010, 362, 2295-2303). Nicotine is also the major component in the pharmacotherapy for smoking cessation (J. E. Henningfield, N. Engl. J. Med. 1995, 333, 1196-1203). To reduce the withdrawal symptoms during smoking cessation, nicotine medications such as nicotine gum are often utilized which provide lower, and more stable blood nicotine concentration.

Nicotine is mainly metabolized in the liver by an enzyme CYP2A6 (J. Hukkanen, P. Jacob, N. L. Benowitz, Pharmacol. Rev. 2005, 57, 79-115). The half-life of nicotine is relatively short (about 2 hours), thus the assessment of nicotine in biofluids cannot reflect the status of tobacco use accurately. Cotinine is the major metabolite of nicotine with a much longer half-life (about 16 hours). Because of the long half-life, cotinine is being used as the biomarker for cigarette smoking and environmental tobacco smoke exposure. Cotinine is further metabolized by the same enzyme CYP2A6 to trans-3'-hydroxycotinine (3HC). Recent study showed that the ratio of 3HC to cotinine could provide a convenient measure to phenotype individuals for CYP2A6 activity which is a biomarker of nicotine metabolism guiding dosage in nicotine medication (N. L. Benowitz, O. F. Pomerleau, C. S. Pomerleau, P. Jacob, Nicotine & Tobacco Research 2003, 5, 621-624; P. Jacob, L. S. Yu, M. J. Duan, L. Ramos, O. Yturralde, N. L. Benowitz, Journal of Chromatography B-Analytical Technologies in the Biomedical and Life Sciences 2011, 879, 267-276; and D. Dempsey, P. Tutka, P. Jacob, F. Allen, K. Schoedel, R. F. Tyndale, N. L. Benowitz, Clin. Pharmacol. Ther. 2004, 76, 64-72). Although nicotine and its metabolites are widely used for tobacco use assessment, they cannot be used to distinguish smokers from persons taking nicotine medications. In such a condition, another tobacco alkaloid anabasine can be used which only exists in tobacco but not in nicotine-medication products (P. Jacob, L. Yu, A. T. Shulgin, N. L. Benowitz, Am. J. Public Health 1999, 89, 731-736; and P. Jacob, D. Hatsukami, H. Severson, S. Hall, L. Yu, N. L. Benowitz, Cancer Epidemiol. Biomark. Prev. 2002, 11, 1668-1673).

This Example shows the power of this technique for direct quantitation of biomarkers of tobacco use from biofluids, including blood, urine and saliva. Besides the testing them in dried spots, the Example also demonstrates the direct analysis of fresh liquid samples.

b. Materials

Bovine whole blood was purchased from Innovative Research (Novi, Mich.). Synthetic urine sample was purchase from CST Technologies (Great Neck, N.Y.). Saliva sample was donated by Dr. Ouyang who is the PI of this study.

Nicotine, cotinine, and anabasine were purchased from Sigma-Aldrich (St. Louis, Mo.). Trans-3'-hydroxycotinine and trans-3'-hydroxycotinine-d3 were purchased from Santa Cruz Biotechnology (Santa Cruz, Calif.). Nicotine-d3 and cotinine-d3 were purchased from CDN Isotopes (Quebec, Canada). Anabasine-d4 was purchased from United States Biological (Swampscott, Mass.).

All experiments were performed using a TSQ Quantum Access Max mass spectrometer (Thermo Scientific, San Jose, Calif.). All analytes were monitored in the selected reaction monitoring (SRM) mode. The SRM transitions are shown in Table 5 below.

TABLE 5

SRM transitions

| Analyte | Parent ion m/z | Fragment ion m/z |
|---|---|---|
| nicotine | 163, $(M + H)^+$ | 130 |
| nicotine-d3 | 166, $(M + H)^+$ | 130 |
| cotinine | 177, $(M + H)^+$ | 80 |
| cotinine-d3 | 180, $(M + H)^+$ | 80 |
| trans-3'-hydroxycotinine | 193, $(M + H)^+$ | 80 |
| trans-3'-hydroxycotinine-d3 | 196, $(M + H)^+$ | 80 |
| anabasine | 163, $(M + H)^+$ | 118 |
| anabasine-d4 | 167, $(M + H)^+$ | 122 |

To get the calibration curves, bovine whole blood was spiked with each chemical and corresponding isotope labeled internal standard. For dried blood spot analysis, the paper was loaded with 5 μL whole blood, placed in the open air overnight, and then stored in a sealed plastic bag containing desiccant at room temperature.

Grade 31ET chromatography paper was purchased from Whatman (Piscataway, N.J.). Printer paper (letter size, 75 g/m2) was purchased from Xerox (Norwalk, Conn.).

For this Example, the paper was cut into a triangle (base 7 mm, height 12 mm). A copper clip was used to hold the paper triangle in front of the mass spectrometer. 4 kV DC high voltage was applied through the copper clip to induce paper spray ionization from tip of the paper triangle. Unless otherwise noted, 90% acetonitrile with 10% water was used as the spray solvent.

For the calibration curves, 3 samples were repeated at each concentration. The lower limit of quantitation (LLOQ) was calculated as 10 times of standard deviation of blank samples only with internal standards divided by the slope of the calibration curve.

c. Results

Figure 50:
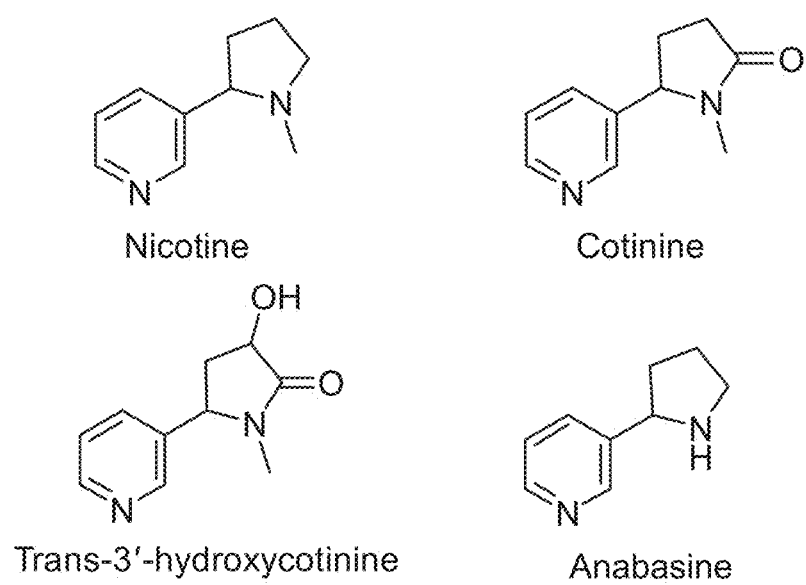
FIG. 50 shows structures of nicotine, cotinine, trans-3'-hydroxycotinine, and anabasine.
Figure 51A:
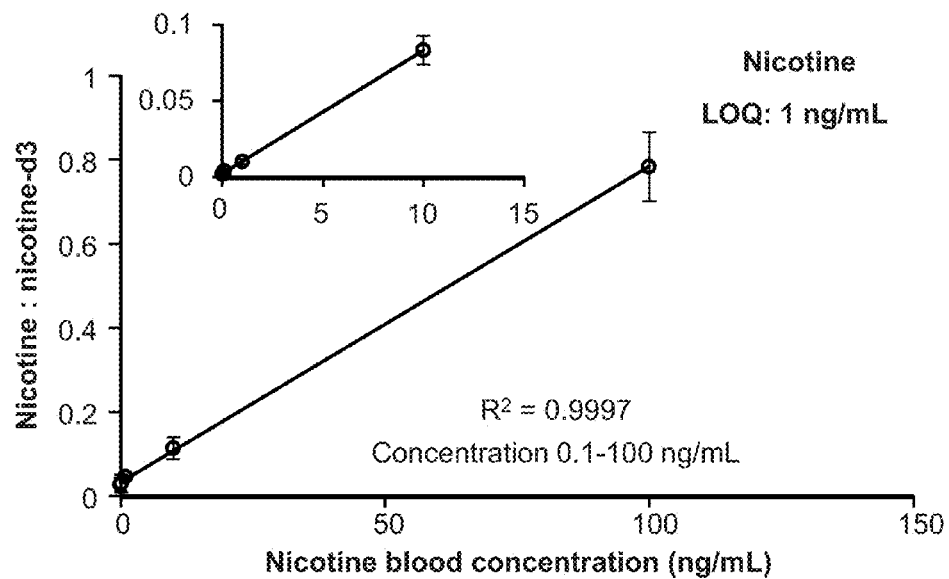
FIGS. 51A-D are a set of graphs showing calibration curves of nicotine (FIG. 51A), cotinine (FIG. 51B), 3HC (FIG. 51C) and anabasine (FIG. 51D) in dried blood spots. The blood samples were spiked with each chemical and its isotope labeled internal standard (100 ng/mL). Inset plot shows low concentration range. The bars represent the standard deviation of analysis for three replicates at different concentrations.
Figure 51B:
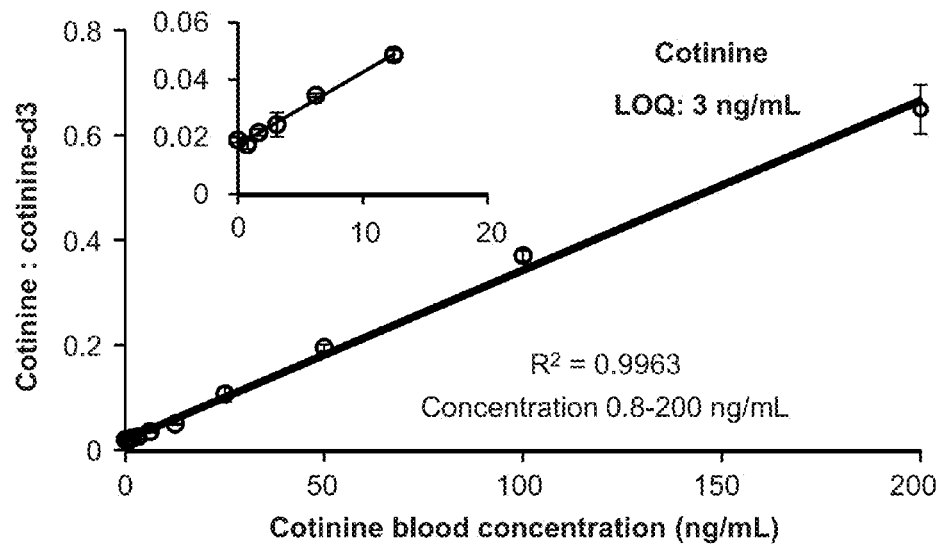
Figure 51C:
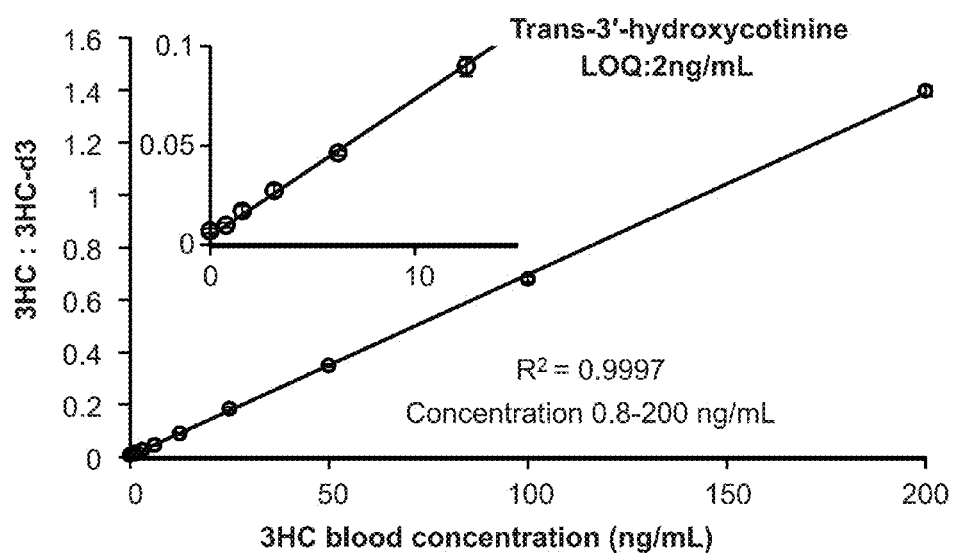
Figure 51D:
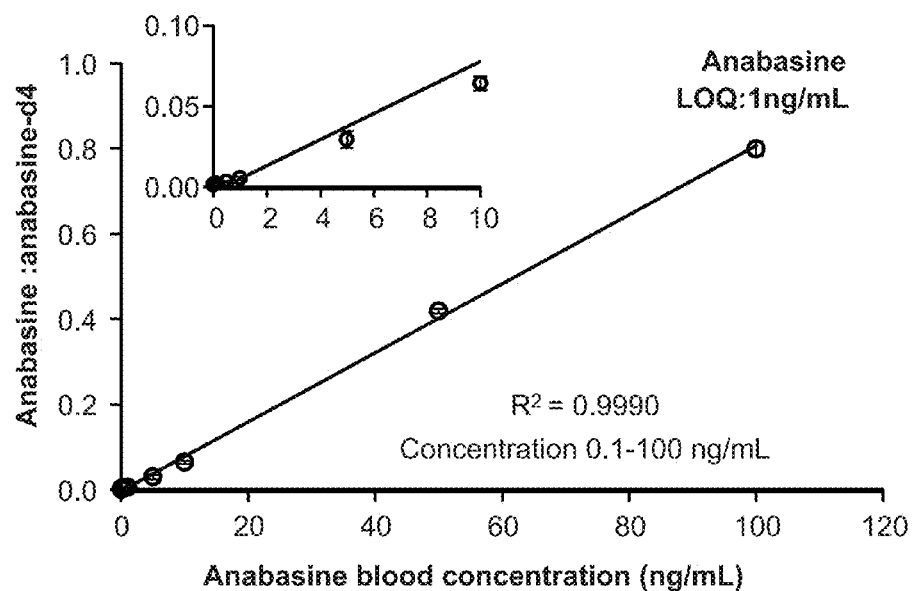

Nicotine, cotinine, 3HC, and anabasine (FIG. 50) were tested directly from dried blood spots using paper spray ionization. The calibration curves of the four chemicals are shown in FIG. 51. Good linarites were obtained throughout the whole concentration range tested. The LOQs of these four chemicals are between 1~3 ng/mL. As one of the major tobacco use biomarkers, the cut-off value of cotinine is ~14 ng/mL between smokers and non-smokers (M. J. Jarvis, H. Tunstallpedoe, C. Feyerabend, C. Vesey, Y. Saloojee, Am. J. Public Health 1987, 77, 1435-1438).

Different paper substrates were tested trying to minimize the matrix interference from the paper substrates and improve the LOQ. Chromatography paper with different thickness (grade 1 0.18 mm and 31 ET 0.5 mm), silica coated paper, and printer paper were tested. Interestingly, it was found that printer paper was one of the best paper substrates for these four chemicals. For 3HC and cotinine, similar results were obtained using chromatography paper and printer paper. However, for nicotine and anabasine, printer paper provided much lower background signal than chromatography paper thus significantly improved the LOQ. It was found that when organic solvent was continuously applied on printer paper, the background was low for the first several minutes, and then the background will gradually increase. It was observed that organic solvent are more difficult to penetrate through the paper substrate to the reverse side of the paper. These observations suggest that the lower background from printer paper may be because matrix chemicals were more slowly extracted from the printer paper substrate. The slow extraction of matrix chemicals may be due to the smaller pore size of the printer paper.

Figure 52A:
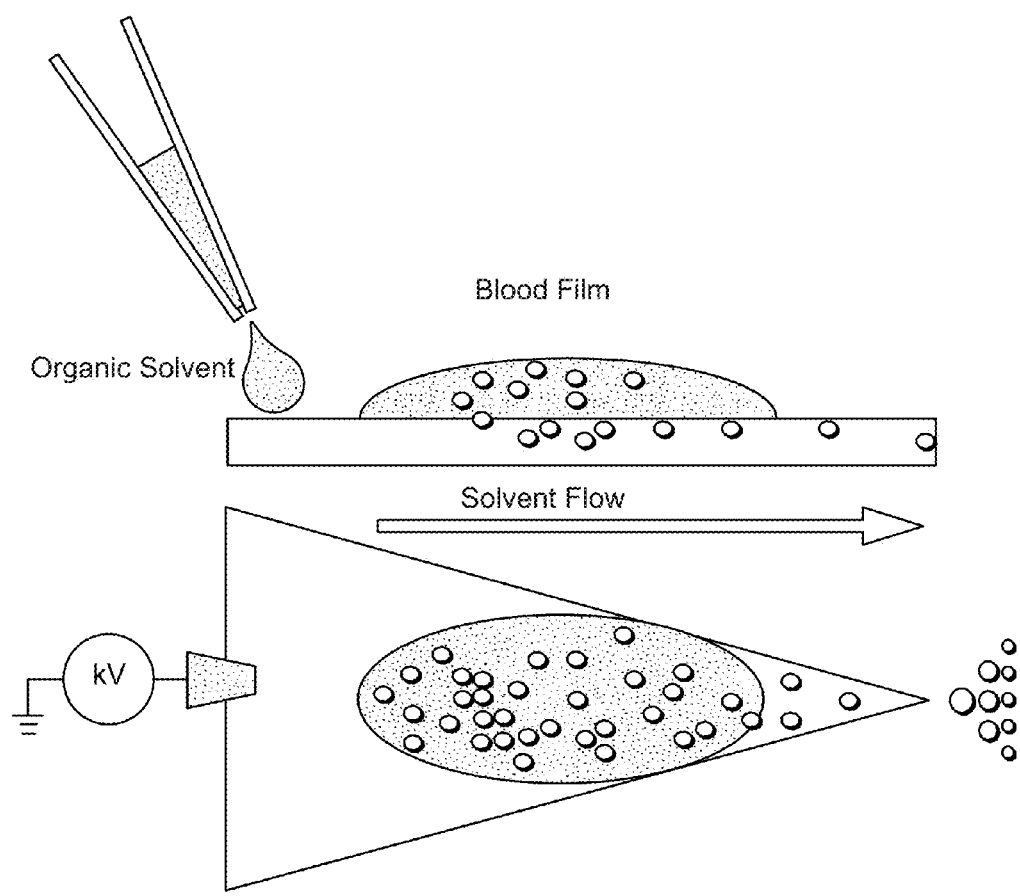
FIG. 52A Chemical extraction during paper spray ionization from fresh liquid blood.
Figure 53:
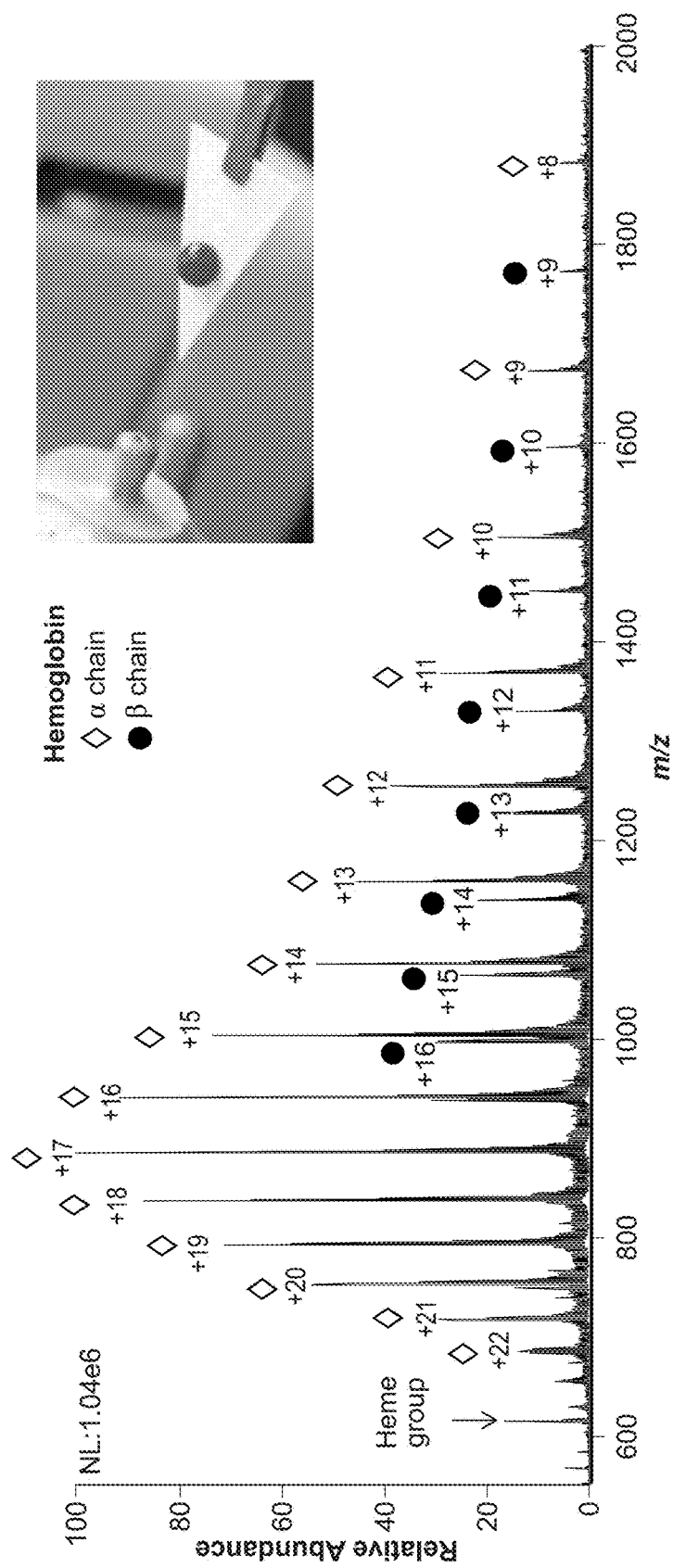
FIG. 53 shows the direct detection of protein hemoglobin from fresh liquid blood on hydrophobic paper substrate. 5 μL blood was applied on the hydrophobic paper forming a blood droplet. 10 μL methanol was applied as spray solvent. The alpha and beta chain and the heme group from hemoglobin could be directly detected.

For point-of-care test, people may want to get the results as fast as possible. Even though the analysis of dried blood spot using paper spray can be done within one minute, the time to allow the blood dry on the paper can take hours. Addition of the coagulant alum has been shown to allow paper spray analysis before the blood is dried. See Examples above. Here, paper spray was also tested for direct analysis of liquid blood samples without any additive. As shown in FIGS. 52A-B, 5 µL fresh bovine blood was added onto the printer paper and smeared by a pipette tip forming a thin blood film. Then 20 µL acetonitrile was added immediately and 3.5 kV DC high voltage was applied. It was observed that the spray plume was produced from the tip. It was interesting to see that during the spray the blood cells with red color were still trapped in their original position and would not contaminate the instrument (FIGS. 52B-D). It was observed that no protein spectra were obtained during the spray of fresh blood sample from the cellulose based paper substrates which could be due to the strong combination of the protein molecules to the paper substrates. However, by changing the hydrophobicity of the paper substrate, protein spectra could also be observed (FIG. 53). Different concentrations of nicotine and its isotope-labeled internal standard were spiked into bovine blood to get the calibration curve from the fresh blood. The LOQ of nicotine in this way was even better than dried blood spot, which is 0.1 ppb.

Figure 54:
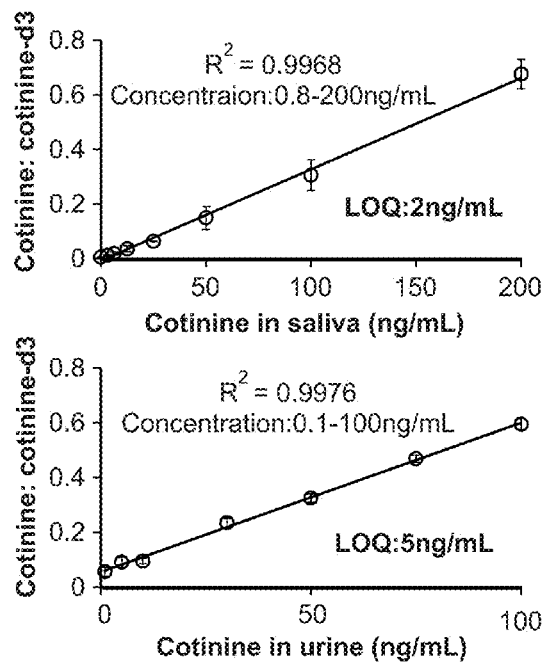
FIG. 54 shows the calibration curves of cotinine in fresh liquid saliva (1 ng/mL-200 ng/mL) and urine (1 ng/mL-100 ng/mL) using printer paper. The bars represent the standard deviation of analysis for three replicates at different nicotine concentrations.
Figure 55A:
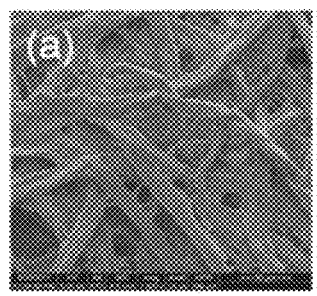
FIGS. 55A-I are a set of SEM and photographic images of Grade 4 chromatography and silica coated papers without and with dried blood spots: SEM images of (FIG. 55A) chromatography and (FIG. 55B) silica coated paper, and (FIG. 55C) close-up image of the selected area in (FIG. 55B) without dried blood spots; top view of (FIG. 55D) chromatography and (FIG. 55E) silica coated paper with dried blood spots; photograph images of the (FIG. 55F) top and (FIG. 55G) back sides of chromatography paper, and (FIG. 55H) top and (FIG. 55I) back sides of silica coated paper with blood spots.
Figure 55B:
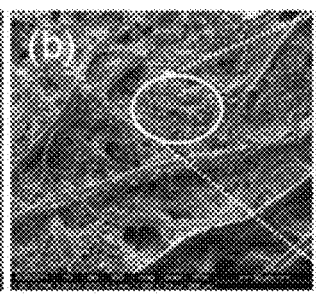
Figure 55C:
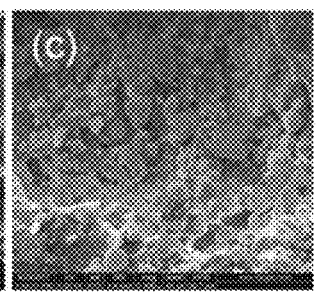
Figure 55D:
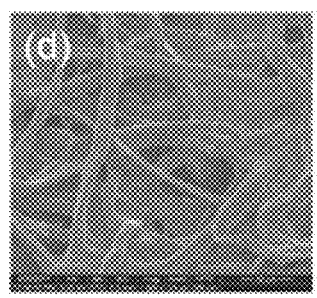
Figure 55E:
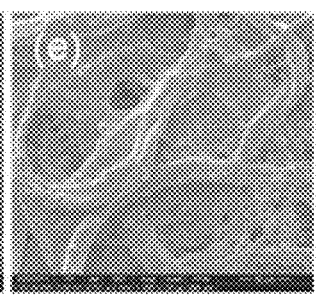
Figure 55F:
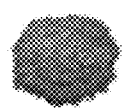
Figure 55G:
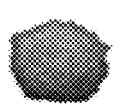
Figure 55H:
Figure 55I:
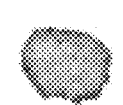

Besides blood, cotinine was also tested directly from fresh liquid saliva and urine. 5 µL saliva sample was added onto Grade 1 chromatography paper, and then 30 µL acetonitrile was applied as solvent. The calibration curve is shown in FIG. 54. The LOQ was 2 ng/mL which is lower than its cut-off values 14 ng/mL (M. J. Jarvis, H. Tunstallpedoe, C. Feyerabend, C. Vesey, Y. Saloojee, Am. J. Public Health 1987, 77, 1435-1438). For the urine sample, it was found that the matrix effect was more serious compared with the blood and saliva sample due to its high concentration of metal salts. No cotinine could be detected under 30 ng/mL using acetonitrile as the solvent. It has been found that the addition of high levels of ammonium acetate can significantly counteract the signal suppression of protein solutions caused by metal ions (A. T. Iavarone, O. A. Udekwu, E. R. Williams, Anal. Chem. 2004, 76, 3944-3950). This is presumably because of the precipitation of metal ions from solution within the evaporating electrospray droplets. Similar improvement was found herein. By adding 20 mM ammonium acetate into the urine solution, the LOQ could reach as low as 5 ng/mL with the cut-off value to be 50 ng/mL.

d. Conclusion

Data herein show direct quantitation of tobacco nicotine alkaloids from biological fluids in the form of both dried spots and fresh liquid. This method shows potential in quantitating human exposure to tobacco and in studying the nicotine metabolism.

Example 25: Ion Generation Using a Wetted Porous Substrate in which at Least a Portion of the Porous Substrate Includes a Material that Modifies an Interaction Between a Sample and the Substrate In this Example, paper spray was coupled with a commercial TSQ and a home-made MINI 11 for analysis of different target drugs in dried blood spots, respectively. Different from previous reports, silica coated paper was used for paper spray, rather than chromatography paper or filter paper, in order to improve the analysis of therapeutic drugs in dried blood spots (DBS).

Dichloromethane/isopropanol solvent was identified as an optimal spray solvent for the analysis. The comparison was made with paper spray using chromatography paper as substrate with methanol/water as solvent for the analysis of verapamil, citalopram, amitriptyline, lidocaine and sunitinib in dried blood spots. It was demonstrated that the efficiency of recovery of the analytes was notably improved with the silica coated paper and the limit of quantitation (LOQ) for the drug analysis was 0.1 ng mL$^{-1}$ using a commercial triple quadrupole mass spectrometer. The use of silica paper substrate also resulted in a sensitivity improvement of 5-50 fold in comparison with chromatography papers, including the Whatmann ET31 paper used for blood card. Analysis using a handheld miniature mass spectrometer Mini 11 gave LOQs of 10~20 ng mL−1 for the tested drugs, which is sufficient to cover the therapeutic ranges of these drugs.

a. Introduction

Accurate measurement of therapeutic drugs and their metabolites in blood plays an important role in drug discovery and disease therapy. Storing whole blood samples as the dried blood spots (DBS) on paper is being adopted for the analysis of drugs in blood. In comparison with conventional way of collecting blood with test tubes, DBS has some special advantages including small sample volume (typically less than 50 µL), improved chemical stability for many analytes in blood and easy sample storage and transfer at ambient temperatures (Rao, R. N.; Maurya, P. K.; Ramesh, M.; Srinivas, R.; Agwane, S. B. Biomed. Chromat. 2010, 24, 1356-1364; and Li, W. K.; Zhang, J.; Tse, F. L. S. Biomed. Chromat. 2011, 25, 258-277). DBS analysis can be used for a wide range of applications, including toxicology (Barfield, M.; Spooner, N.; Lad, R.; Parry, S.; Fowles, S. J. Chromatogr. B: Analyt. Technol. Biomed. Life Sci. 2008, 870, 32-37) and pharmacokinetics studies (Lawson, G.; Tanna, S.; Mulla, H.; Pandya, H. J. Pharm. Pharmacol. 2009, 61, A33; Suyagh, M. F.; Laxman, K. P.; Millership, J.; Collier, P.; Halliday, H.; McElnay, J. C. J. Chromatogr. B: Analyt. Technol. Biomed. Life Sci. 2010, 878, 769-776; and Spooner, N.; Lad, R.; Barfield, M. Anal. Chem. 2009, 81, 1557-1563) for drug discovery as well as therapeutic drug monitoring (TDM) to assist in dosage optimization during therapy (Ntale, M.; Mahindi, M.; Ogwal-Okeng, J. W.; Gustafsson, L. L.; Beck, O. J. Chromatogr. B: Anal. Technol.

Biomed. Life Sci. 2007, 859, 137-140; Lejeune, D.; Souletie, I.; Houze, S.; Le Bricon, T.; Le Bras, J.; Gourmel, B.; Houze, P. J. Pharm. Biomed. Anal. 2007, 43, 1106-1115; Ronn, A. M.; Lemnge, M. M.; Angelo, H. R.; Bygbjerg, I. C. Therap. Drug Monitor. 1995, 17, 79-83; Tawa, R.; Hirose, S.; Fujimoto, T. J. Chromatogr. B: Biomed. Appl. 1989, 490, 125-132; Croes, K.; McCarthy, P. T.; Flanagan, R. J. J. Anal. Toxicol. 1994, 18, 255-260; Heine, R.; Rosing, H.; van Gorp, E. C. M.; Mulder, J. W.; van der Steeg, W. A.; Beijnen, J. H.; Huitema, A. D. R. J. Chromatogr. B: Analyt. Technol. Biomed. Life Sci. 2008, 867, 205-212; Koal, T.; Burhenne, H.; Romling, R.; Svoboda, M.; Resch, K.; Kaever, V. Rapid Commun. Mass Spectrom. 2005, 19, 2995-3001; Cheung, C. Y.; van der Heijden, J.; Hoogtanders, K.; Christiaans, M.; Liu, Y. L.; Chan, Y. H.; Choi, K. S.; van de Plas, A.; Shek, C. C.; Chau, K. F.; Li, C. S.; van Hooff, J.; Stolk, L. Transplant Int. 2008, 21, 140-145; Coombes, E. J.; Gamlen, T. R.; Batstone, G. F.; Leigh, P. N. Ann. Clin. Biochem. 1984, 21, 519-522; Fujimoto, T.; Tsuda, Y.; Tawa, R.; Hirose, S. Clin. Chem. 1989, 35, 867-869; and Li, P. K.; Lee, J. T.; Conboy, K. A.; Ellis, E. F. Clin. Chem. 1986, 32, 552-555).

Regardless of how blood samples are collected or stored, similar procedures have been applied for the chemical analysis of the therapeutic drugs in blood. The analytes are extracted from the blood sample using organic solvents, then separated using chromatography and analyzed using mass spectrometry (MS), ultraviolet (UV), fluorescence (FL), or immunoassay. Liquid chromatography-tandem mass spectrometry (LC-MS/MS) has been the mainstream method for the quantitation of drugs in blood (Taylor, P. J.; Tai, C.-H.; Franklin, M. E.; Pillans, P. I. Clin. Biochem. 2011, 44, 14-20; Saint-Marcoux, F.; Sauvage, F.-L.; Marquet, P. Anal. Bioanal. Chem. 2007, 388, 1327-1349; Korecka, M.; Shaw, L. M. Ann. Transplant. 2009, 14, 61-72; and Checa, A.; Oliver, R.; Hernandez-Cassou, S.; Saurina, J. Anal. Chim. Acta 2009, 647, 1-13). High sensitivity and selectivity are obtained with LC-MS/MS for quantitative analysis of therapeutic drugs in blood. The standard procedure involves complex sample preparation and analyte separation prior to the MS analysis. These steps are essential for minimizing matrix effects and improving the detection limits (Breadmore, M. C.; Theurillat, R.; Thormann, W. Electrophoresis 2004, 25, 1615-1622; and Lee, E. D.; Henion, J. D. Rapid Commun. Mass Spectrom. 1992, 6, 727-733), but could take about 30 minutes to several hours. This time frame might not be rate determining for in-lab analysis of many samples where parallel high throughput approaches can be used, but could be so when small numbers of samples are analyzed and rapid decision making is required. Used in this way, LC-MS/MS can be applied to a wide range of drug compounds; however, this method must be performed in analytical laboratories and only by experienced chemists.

For analysis of therapeutic drugs in DBS using paper spray, the drug compounds are extracted from the blood matrix by the wetting solution. The extent of the extraction, relative to other compounds eluting from the DBS, has a direct impact on the sensitivity of the analysis. The affinity of the drug compounds to a paper substrate also affects the extraction efficiency and causes loss of compound during transport to the paper tip by the spray solvent and inefficiency in ionization. The chemical properties of the solvent need to be optimized for the extraction and transfer process, but they also need to be suitable for the spray ionization process, which is important to the MS analysis sensitivity. The selection of the combination of a paper substrate and a solvent is important to the overall performance of the paper spray MS analysis.

Generally, chromatography paper has mainly been used for paper spray substrates with methanol/water as the wetting and spray solvent. This Example investigates the use of silica-coated paper for the analysis of therapeutic drugs in dried blood spots. Silica is by far the most widely used matrix for chromatographic separation owing to its chemical and mechanical stability, variable pore size, well documented chemistry for surface modification, and excellent demonstrated performance for separations. Silica-coated paper is an excellent substrate for resolving a wide variety of compounds (Marinetti, G. V. In Lipid Chromatographic Analysis; Wuthier, R. E., Ed.; Marcel Dekker: New York, 1976; Vol. 1, pp 59-109; Valadon, L. R. G.; Mummery, R. S. Phytochemistry 1972, 11, 413-414; and Egan, R. W. Anal. Biochem. 1975, 68, 654-657).

In this Example, paper coated with silica gel was adopted as the paper spray substrate and relatively less polar solvents were used. The selection of the substrate/solvent systems was first optimized for drug analysis using a commercial triple quadrupole mass spectrometer and the performance using a handheld ion trap mass spectrometer (Mini 11; Gao, L.; Sugiarto, A.; Harper, J. D.; Cooks, R. G.; Ouyang, Z. Anal. Chem. 2008, 80, 7198-7205; Hou, K. Y.; Xu, W.; Xu, J. A.; Cooks, R. G.; Ouyang, Z. Anal. Chem. 2011, 83, 1857-1861; and Sokol, E.; Noll, R. J.; Cooks, R. G.; Beegle, L. W.; Kim, H. I.; Kanik, I. Int. J. Mass Spectrom. 2011, In Press, Corrected Proof) was then characterized for a set of therapeutic drugs from DBSs. The combination of the paper spray with a miniature mass spectrometer is of a great interest for point-of-care applications where small-size equipment and simple operational procedures are highly desirable. In the Mini 11 handheld mass spectrometer, a single stage discontinuous atmospheric pressure interface (DAPI; Gao, L.; Cooks, R. G.; Ouyang, Z. Anal. Chem. 2008, 80, 4026-4032) was used with an ion trap. A TSQ (Thermo Scientific, Inc., San Jose, Calif.) with multiple differential pumping stages and triple quadrupole mass analyzers can provide 50 times better LOQ for the analysis of therapeutic drugs in blood using paper spray.

b. Materials

The procedure of paper spray used in this Example was similar to that previously reported (Wang, H.; Liu, J. J.; Cooks, R. G.; Ouyang, Z. Angew. Chem., Int. Ed. 2010, 49, 877-880; Wang, H.; Manicke, N. E.; Yang, Q.; Zheng, L.; Shi, R.; Cooks, R. G.; Ouyang, Z. Anal. Chem. 2011, 83, 1197-1201; Manicke, N. E.; Yang, Q. A.; Wang, H.; Oradu, S.; Ouyang, Z.; Cooks, R. G. Int. J. Mass Spectrom. 2011, 300, 123-129; and Liu, J.; Wang, H.; Manicke, N. E.; Lin, J.-M.; Cooks, R. G.; Ouyang, Z. Anal. Chem. 2010, 82, 2463-2471). Briefly, the standards used herein, including verapamil, sunitinib, citalopram, amitriptyline, and lidocaine, were prepared as follows: drug solutions at 100× concentration were prepared by dilution of the stock solutions into 1:1 methanol/water. The 100× standards were then spiked into bovine whole blood (with sodium citrate as anticoagulant, Innovative Research, Novi, Mich.) by pipetting 5 μL of the standard into 495 μL of blood. The blood samples with lower concentrations of drugs were prepared serially by diluting 40 μL of higher drug content blood samples with 360 μL of blood. The concentrations of the drugs in the final blood samples were 0.01, 0.1, 1, 10, 1000, and 10,000 ng mL$^{-1}$, respectively. DBS samples were prepared by spotting a fixed volume (5 μL) of blood onto the paper substrate and drying for at least 4 h at room temperature. Samples were stored at room temperature in a sealed plastic bag containing desiccant.

For paper spray, the DBS substrate was cut into a triangle (10 mm height and 5 mm base width). A copper clip was used to hold the paper triangle and to apply the high voltage needed for the spray. The distance between the tip of the paper triangle and the inlet to the mass spectrometer was about 5 mm. The silica-coated ion-exchange paper Grade SG81 (0.27 mm thick) and the chromatography paper Grade 4 (0.21 mm thick) and Grade ET31 (0.50 mm thick) were purchased from Whatman International Ltd. (Maidstone, England) and used without further chemical treatment. The Grade 4 chromatography paper is of similar thickness to the silica-coated paper while the thicker Grade ET31 is used for making the commercial blood cards (Whatman FTA DMPK-C card). The 9:1 methanol/water (v/v) solvent has been found to be generally optimal for analysis of drugs in DBS on the cellulose filter papers. The MS analysis was carried out in positive ion mode with a spray voltage at 3.5 kV. The LOQ value for each drug was defined as the lowest concentration within the set of linear responses. Three replicate measurements were made for each sample.

Images of surfaces of the chromatography paper (Whatman Grade 4, 0.21 mm thick) and the silica-coated paper (Whatman Grade SG81, 0.27 mm thick)) were recorded using a FEI NOVA nanoSEM field emission scanning electron microscope (SEM, FEI Company, Hillsboro, Oreg.). The substrates were sputter-coated with platinum for 1.0 min before the analysis and the accelerating voltage for the Everhart-Thornley detector (ETD, routine imaging) or through-the-lens detector (TLD, high magnification/resolution imaging) was 5 kV with a working distance of about 5.0 mm.

A TSQ Quantum Access Max (Thermo Scientific, San Jose, Calif.), operated in the selected reaction monitoring (SRM) mode was used and specific product ions produced by collision-induced dissociation (CID) were monitored. The XCALIBUR software (MS control software) was used for control of the TSQ Quantum Access Max MS system and data acquisition. Argon gas (99.995% purity) was used as collision gas. The temperature MS inlet capillary was 300° C. The SRM and instrumental parameters used for the drug compounds were as follows: verapamil: m/z 455→303, tube lens 97 V, Q2 offset (collision energy) 28 V; sunitinib: m/z 399→283, tube lens 116 V, Q2 offset 28 V; citalopram: m/z 325→109, tube lens 121 V, Q2 offset 28 V; amitriptyline: m/z 278→233, tube lens 108 V, Q2 offset 17 V; lidocaine: m/z 235→86, tube lens 94 V, Q2 offset 18 V.

The Mini 11 (Gao, L.; Sugiarto, A.; Harper, J. D.; Cooks, R. G.; Ouyang, Z. Anal. Chem. 2008, 80, 7198-7205; Hou, K. Y.; Xu, W.; Xu, J. A.; Cooks, R. G.; Ouyang, Z. Anal. Chem. 2011, 83, 1857-1861; and Sokol, E.; Noll, R. J.; Cooks, R. G.; Beegle, L. W.; Kim, H. I.; Kanik, I. Int. J. Mass Spectrom. 2011, In Press, Corrected Proof) a handheld rectilinear ion trap mass spectrometer, has a discontinuous atmospheric pressure interface (DAPI; Gao, L.; Sugiarto, A.; Harper, J. D.; Cooks, R. G.; Ouyang, Z. Anal. Chem. 2008, 80, 7198-7205; and Hou, K. Y.; Xu, W.; Xu, J. A.; Cooks, R. G.; Ouyang, Z. Anal. Chem. 2011, 83, 1857-1861) and a pumping system with a 10 L/s trubomolecular pump (Pfeiffer HiPace 10, Pfeiffer Vacuum Inc., Nashua, N.H.) and a 5 L/min diaphragm pump (1091-N84.0-8.99, KNF Neuberger Inc., Trenton, N.J.). The flow restricting capillary in the DAPI is of 5 cm length and 250 μm I.D. The DAPI was opened for 12 ms to introduce the ions generated by paper spray and the mass analysis was performed 600 ms after the DAPI was closed and the vacuum had reached an approximate level. The precursor ions were trapped at an RF voltage of 275 $V_{p-p}$ at 1.0 MHz and the product ions were analyzed with a RF scan from 206 $V_{p-p}$ to 4,500 $V_{p-p}$ and a resonance ejection at q=0.70. The frequency and the amplitude of the excitation signal for the CID were as follows: amitriptyline, 99.40 kHz and 0.39 $V_{p-p}$; citalopram: 84.60 kHz and 0.63 $V_{p-p}$; lidocaine: 78.76 kHz and 1.22 $V_{p-p}$; sunitinib: 84.89 kHz and 0.73 $V_{p-p}$; verapamil: 80.58 kHz and 0.37 $V_{p-p}$.

c. Results

SEM images of the substrate surfaces are shown in FIG. 55. The chromatography paper (FIG. 55A) was shown to have a framework of cellulosic fibers, each of a diameter 10-20 μm. As previously reported by Roberts (The Chemistry of Paper; The Royal Society of Chemistry: Letchworth, UK, 1996) strong connections at the points of contact between two cellulose fibers were observed, which are due to the hydrogen bonding between the polysaccharides at the fiber surfaces. The silica-coated paper (FIG. 55B) has a similar cellulosic framework but the pores are filled with silica gel particles of diameters 1-5 μm (FIG. 55C). Bovine blood of 5.0 μL was deposited onto the paper substrates to form dried blood spots (ca. 7.0 mm diameter). The cellulosic framework in the chromatography paper could still be seen except that some small pores were blocked by the dried blood (FIG. 55D); however, the surface of the silica coated paper was completely covered by the dried blood (FIG. 55E). Diffusion of the blood through the paper substrates was also examined as shown in FIGS. 55F-55I. The colors of the top and bottom sides of the paper substrate within the DBS area are similar for the chromatography paper (FIGS. 55F and 55G), but significantly different for the silica-coated paper (FIGS. 55H and 55I). The color of the top side of the silica-coated paper substrate is much darker than that of the bottom side, which is due to a poor diffusion of the blood through the substrate with the framework pores blocked by the silica gel particles. A relatively large percentage of the blood sample stayed on the top side of the silica-coated paper substrate, which helped to improve the efficiency of analyte elution during the paper spray process. Though the blood distribution was less homogenous on this substrate, no unexpected sample degradation was observed after they had been stored in a sealed plastic bag for days.

As discussed herein, the paper spray process involves analyte elution as well as spray ionization. The solvent properties affect not only the extraction of the analytes from the dried blood spots, but also their transfer across the paper as well as the ion formation during the spray. For the silica-coated paper, pure solvents with a range of polarities were first investigated, including water, hexane, dichloromethane, methanol, ethanol, isopropanol, butyl alcohol. FIG. 56A compares efficiency of sampling and ionization of verapamil ((M+H)$^+$, m/z 455) in dried blood spots (500 ng mL$^{-1}$) using the silica-coated paper substrate. The intensity of the fragment ion m/z 303 was monitored using the triple quadrupole operated in SRM mode. With a spray voltage of 3.5 kV, the lowest signal intensities were observed with water and hexane, which have the highest and lowest solvent polarities, respectively. Signal intensities two orders of magnitude greater were observed with dichloromethane, while the best intensities were obtained with the alcohols, viz. methanol, ethanol, isopropanol, and butyl alcohol. Among these solvents, isopropanol was the best as a pure solvent for the efficient extraction and spray ionization of verapamil.

It is well-known that the electrospray process is highly dependent on the polarity and the volatility of the solvent.

Typically solvent mixtures are used to optimize the spray process for analysis of target analytes (Tian, Z. X.; Kass, S. R. J. Am. Chem. Soc. 2008, 130, 10842-1084; Lavarone, A. T.; Jurchen, J. C.; Williams, E. R. J. Am. Soc. Mass Spectrom. 2000, 11, 976-985; Venter, A. R.; Kamali, A.; Jain, S.; Baku, S. Anal. Chem. 2010, 82, 1674-1679; and Li, J. W.; Dewald, H. D.; Chen, H. Anal. Chem. 2009, 81, 9716-9722). Addition of a non- or less-polar solvent component of low boiling point helps to enhance the generation of droplets of suitable size during the spray and facilitates their subsequent desolvation (Kebarle, P.; Tang, L. Anal. Chem. 1993, 65, A972-A986). Paper spray is expected to share similar spray characteristics with electrospray but the efficiency of the analyte extraction step needs also to be considered in the selection of solvent composition. After finding isopropanol as the best pure solvent for paper spray with silica-coated substrates, dichloromethane was mixed with isopropanol to produce solvents with increased volatility. The direct sampling ionization of the verapamil in the dried blood spots was performed using a set of isopropanol/dichloromethane solvents in different ratios, as shown in FIG. 56B. The best signal intensity was observed with 10% (v/v) of isopropanol in the solvent mixture for the silica-coated paper. Mixtures of dichloromethane with methanol, ethanol, and butyl alcohol have also been tested and similar trends were observed. Among these solvents, 9:1 dichloromethane/isopropanol (v/v) gave the optimal performance with silica-coated paper for verapamil, citalopram, amitriptyline, lidocaine and sunitinib. These solvents were also tested with chromatography paper substrates (Grade 4 and ET31 papers) but the signal intensity was one order of magnitude lower than that with 9:1 methanol/water solvent in this case.

Figures 57D, 57E, 57F:
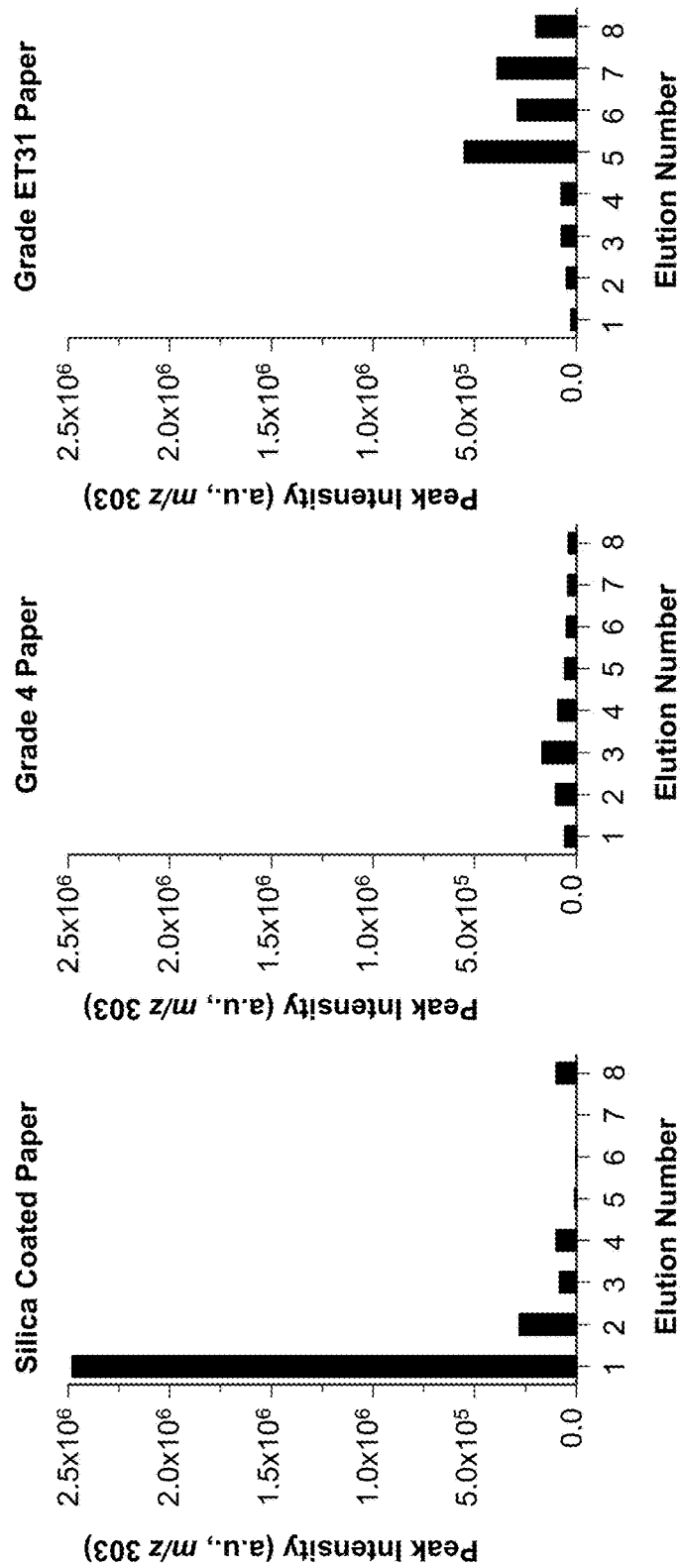

The elution efficiency was also characterized for the three solvent/substrate systems, 9:1 dichloromethane/isopropanol (v/v) for silica-coated paper and 9:1 methanol/water (v/v) for Grade 4 and Grade ET31 chromatography papers, using both pure verapamil sample spots and dried blood spots containing verapamil. The pure verapamil sample spots were prepared by dropping 5 µL water solution containing verapamil (500 ng mL$^{-1}$) onto the paper and drying the substrate completely. The voltage was applied and solvent added multiple times to produce many paper spray events using the same substrate bearing a single sample spot while the signal of fragment ion m/z 303 was monitored. Spray solvent of 25 µL was used each time and the solvent was not added until the monitored ion signal decreased to a minimum, when the spray solvent was also exhausted. Solvent consumption took 5-8 s for dichloromethane/isopropanol on silica-coated paper but 40-70 s for methanol/water on chromatography paper substrates. For both pure analytes and blood samples, much higher peak intensities were observed for the silica-coated paper substrate (FIGS. 57A and 57D). Most (~70%) of the verapamil, was eluted during the first elution step of the paper spray process. A relatively even elution pattern was observed for the Grade 4 chromatography paper with low peak intensities for verapamil (FIGS. 57B and 57E), although an increasing and then decreasing trend exists. Interestingly, a significant increase in analyte in the $2^{nd}$ (FIG. 57C) and $5^{th}$ (FIG. 57F) elution was observed with the Grade ET31 paper for the pure and the blood samples, respectively. Presumably, this is due to the relatively larger substrate volume, which requires sufficient wetting of the substrate and transfer of the analytes to the substrate tip for the paper spray.

Similar procedure was applied to dried blood spots containing verapamil. The blood spots were each prepared with 5 µL of blood sample containing 500 ng mL$^{-1}$ verapamil. The matrix in the dried blood spots is much more complex than that in the pure verapamil sample spots. For silica-coated paper with 9:1 dichloromethane/isopropanol, analyte release during the first paper spray event was still dominant, although the peak intensity for verapamil decreased about 3 times, presumably due to the matrix effect. For chromatography papers with methanol/water, no significant difference in elution pattern was observed except that the maxima of the verapamil detected appeared at later elutions (FIGS. 57D and 57F). There was also about an order of magnitude difference in the best signal intensities observed for these three systems in favor of the hydrophobic substrate.

Without be limited by any particular theory or mechanism of action, several factors could account for the difference between these two substrate/solvent systems and the improvement with the silica-coated paper substrate. The blocking of the pores in the cellulosic framework by the silica resulted in a more concentrated sample on the top surface of the substrate and also a less binding interaction between the analyte and the cellulose. This helps to improve analyte elution during the paper spray process. The polarity of the solvent systems might also play an important role. The polarity of methanol/water solvent (9:1, v/v) is higher than that of dichloromethane/isopropanol solvent (9:1, v/v) (polarity index: water 10.2, methanol 5.1, isopropanol 3.9 and dichloromethane 3.1). Low polarity organic compounds, such as verapamil, dissolve better in dichloromethane/isopropanol solvent, which makes the extraction of these chemicals from dried blood more efficient.

Figures 58A, 58B, 58C:
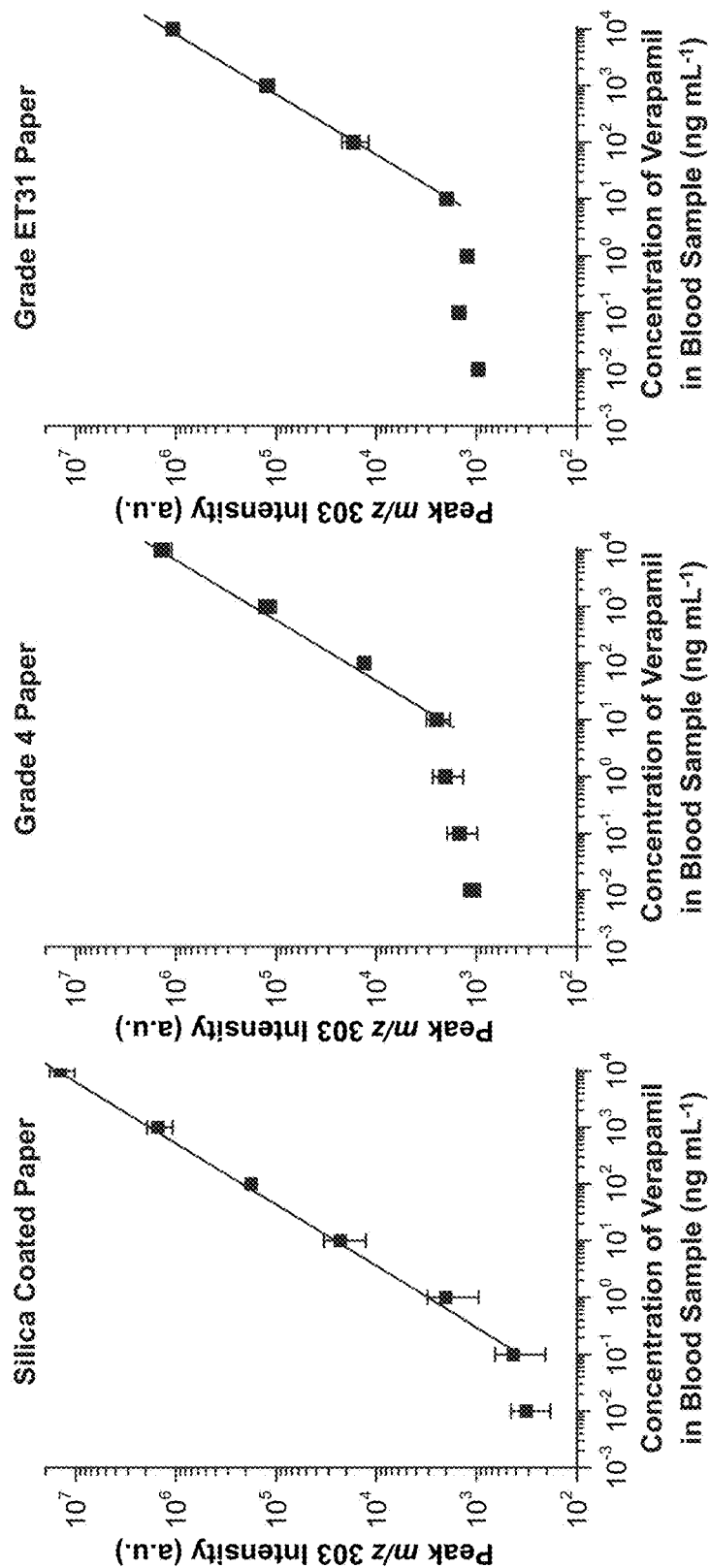
FIGS. 58A-C are graphs showing a comparison of the LOQ and linear dynamic range of verapamil with (FIG. 58A) silica coated paper (0.27 mm thick; 9:1 dichloromethane/isopropanol), (FIG. 58B) Grade 4 chromatography paper (0.21 mm thick; 9:1 methanol/water), and (FIG. 58C) Grade ET31 chromatography paper (0.50 mm thick; 9:1 methanol/water). Note: 5 μl of blood sample was used, product ion m/z 303 of verapamil was monitored.

The performance of the improved substrate/solvent system was characterized for quantitative analysis of therapeutic drugs in whole blood samples using paper spray. Dried blood spots on paper spray substrates were prepared by depositing 5 µL whole blood containing verapamil at a concentration from 0.01 ng mL$^{-1}$ to 10,000 ng mL$^{-1}$ and drying the sample on substrate completely. MS analysis was performed using the triple quadrupole mass spectrometer and the peak intensity of m/z 303 from verapamil ((M+H)$^+$, m/z 455) was recorded. As shown in FIG. 58A, an LOQ of 0.1 ng mL$^{-1}$ was observed for silica-coated substrate with 9:1 (v/v) dichloromethane/isopropanol, which is about two orders of magnitude better than that for Grade 4 (FIG. 58B) and Grade ET31 (FIG. 58C) chromatography papers with 9:1 (v/v) methanol/water. Other therapeutic drugs in whole blood, including sunitinib, citalopram, amitriptyline, and lidocaine, were also analyzed and an LOQ of 0.1 ng mL$^{-1}$ was obtained for each of them using paper spray with silica-coated paper.

In this Example, paper spray using the silica paper substrates was also characterized using a miniature rectilinear ion trap mass spectrometer, Mini 11. This was done by quantitative analysis of verapamil, sunitinib, citalopram, amitriptyline, and lidocaine in dried blood spots. MS/MS analysis was performed using the procedure previously described (Gao, L.; Sugiarto, A.; Harper, J. D.; Cooks, R. G.; Ouyang, Z. Anal. Chem. 2008, 80, 7198-7205; Hou, K. Y.; Xu, W.; Xu, J. A.; Cooks, R. G.; Ouyang, Z. Anal. Chem. 2011, 83, 1857-1861; and Sokol, E.; Noll, R. J.; Cooks, R. G.; Beegle, L. W.; Kim, H. I.; Kanik, I. Int. J. Mass Spectrom. 2011, In Press, Corrected Proof) to acquire the intensities of the characteristic fragment ions from the drug compounds.

Figure 59B:
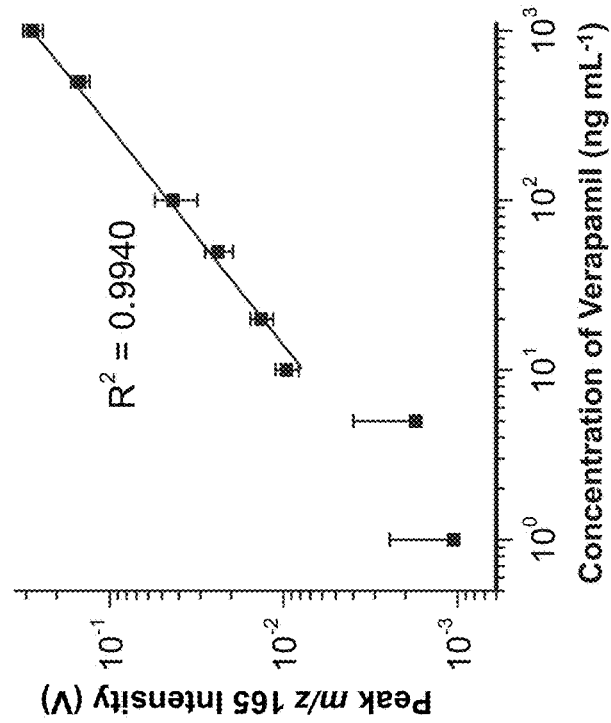
FIGS. 59A-B are graphs showing a linear dynamic range for (FIG. 59A) lidocaine and (FIG. 59A) verapamil, and typical spectra of lidocaine (FIG. 59C) and verapamil (FIG. 59D) with concentrations in blood of 20 ng mL−1 and 10 ng mL−1, respectively, obtained with Mini 11. Silica-coated paper (0.27 mm thick) with 9:1 dichloromethane/isopropanol.
Figure 59A:
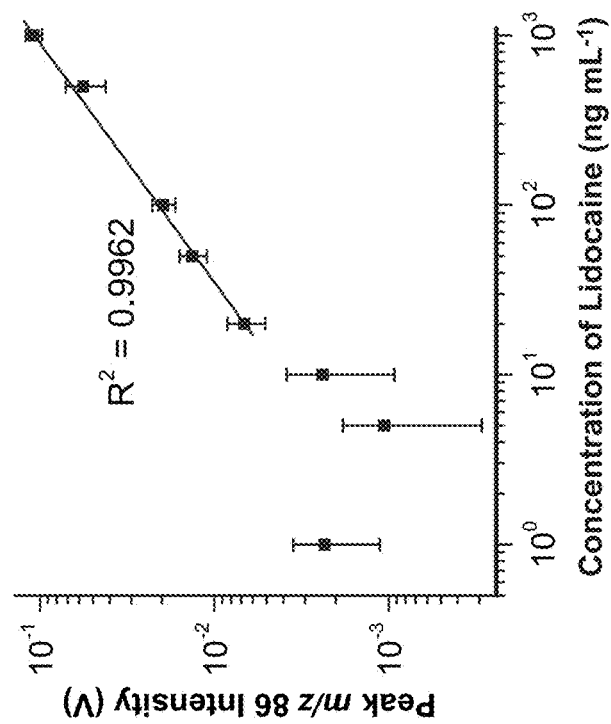

FIGS. 59A-59B shows the low concentration regions (1 ng mL$^{-1}$ to 1,000 ng mL$^{-1}$) of the linear ranges for quantitation of lidocaine (fragment ion m/z 86) and verapamil (fragment ion m/z 165). LOQ values for lidocaine and verapamil are 20 ng mL$^{-1}$ and 10 ng mL$^{-1}$, respectively, approximately two orders of magnitude higher than achieved using the benchtop triple quadruple. The spectra recorded at LOQs for these two drugs are shown in FIGS. 59C-59D. Good linearity was also obtained in the ranges from their LOQs to 1 µg/mL.

A comparison study was done for silica-coated paper and chromatography paper (Whatman Grade ET31, 0.50 mm thick) using paper spray and the Mini 11 for analysis of therapeutic drugs in dried blood spots. The LOQs obtained and the therapeutic windows for lidocaine, amitriptyline, sunitinib, verapamil, and citalopram are listed in Table 6.

TABLE 6

Comparison of LOQ values[a] for some typical drugs between ET 31 chromatography paper and silica coated paper with Mini 11.

| Drug | Precursor ion | Product ion | LOQ with Chromatography paper (ng mL$^{-1}$) | LOQ with silica coated paper (ng mL$^{-1}$) | Therapeutic range (ng mL$^{-1}$) |
|---|---|---|---|---|---|
| lidocaine | 235 | 86 | 100 | 20 | 1,000-6,000 |
| amitriptyline | 278 | 233 | 100 | 10 | 50-200 |
| sunitinib | 399 | 326 | 500 | 10 | 20-200 |
| verapamil | 455 | 165 | 100 | 10 | 50-250 |
| citalopram | 325 | 109 | 100 | 10 | 10-200 |

[a]LOQ for each drug is defined as the lowest concentration within the set of linear responses in the sensitivity plot as shown in FIGS. 58 and 59A-59B. Three replicates for each sample.

Using the chromatography paper with 9:1 methanol/water, the performance of the paper spray/Mini 11 system was only good enough to cover the therapeutic range for lidocaine, but not for the other 5 drugs in DBSs. With the silica paper substrate and 9:1 dichloramethane/isopropanol, improvements of 5-50 fold were obtained in LOQs for these drugs, which made the performance of the miniature systems adequate for their quantitative analysis from dried blood spots.

d. Conclusions

Paper spray with a silica coated paper substrate was characterized using a commercial triple quadrupole and a home-built miniature ion trap mass spectrometer for analysis of therapeutic drugs in dried blood spots. The overall analysis efficiency can be greatly improved by using low boiling and low polarity solvent, 9:1 dichloromethane/isopropanol (v/v). The LOQ of analysis of a set of therapeutic drugs in dried blood spots, including verapamil, citalopram, amitriptyline, lidocaine, and sunitinib, was obtained as low as 0.1 ng mL$^{-1}$ with the commercial triple quadrupole and 10~20 ng mL$^{-1}$ with a miniature ion trap mass spectrometer. The triple quadrupole is inherently better suited to SRM analysis than is an ion trap instrument so this factor as well as the reduced performance of the Mini MS is responsible for the difference. Compared to chromatography paper, in each case there is a 5-50 fold improvement with the silica paper substrate.

What is claimed is:

1. A sample analysis system comprising:
a cartridge comprising a porous substrate that tapers to a tip and an electrode connected to the porous substrate, wherein the cartridge further comprises a bottom portion and a detachable cover, and the cartridge is configured such that the bottom portion is configured to hold the porous substrate and the cartridge is configured such that voltage is not supplied to the porous substrate in the cartridge until the detachable cover is connected to the bottom portion; and
a mass spectrometer.

2. The system according to claim 1, wherein the cartridge is configured such that the tip of the porous substrate does not extend beyond an end of the cartridge.

3. The system according to claim 1, wherein the cartridge further comprises a solvent port.

4. The system according to claim 3, wherein the solvent port is configured for continuous supply of solvent to the porous substrate.

5. The system according to claim 3, wherein the solvent port is configured for supply of only a discrete amount of solvent to the porous substrate such that porous substrate is discrete from a flow of solvent.

6. The system according to claim 1, wherein the system is configured such that the cartridge is positioned with respect to an inlet of the mass spectrometer so that the tip of the porous substrate is aligned with the inlet of the mass spectrometer.

7. The system according to claim 1, wherein the porous substrate is paper.

8. The system according to claim 7, wherein the paper is filter paper.

9. A method for analyzing a sample, the method comprising:
applying a sample to a porous substrate that tapers to a tip;
loading the porous substrate into a cartridge comprising an electrode such that the electrode is connected to the porous substrate, wherein the cartridge further comprises a bottom portion and a detachable cover, and the cartridge is configured such that the bottom portion is configured to hold the porous substrate and the cartridge is configured such that voltage is not supplied to the porous substrate in the cartridge until the detachable cover is connected to the bottom portion;
applying voltage to the porous substrate after the detachable cover is connected to the bottom portion to generate sample ions; and
analyzing the sample ions.

10. The method according to claim 9, wherein the cartridge is configured such that the tip of the porous substrate does not extend beyond an end of the cartridge.

11. The method according to claim 9, wherein the cartridge further comprises a solvent port.

12. The method according to claim 11, wherein the method further comprises supplying solvent via the solvent port to the porous substrate in the cartridge prior to applying the voltage to the porous substrate.

13. The method according to claim 9, wherein the method further comprises supplying solvent to the porous substrate prior to the porous substrate being loading into the cartridge.

14. The method according to claim 9, wherein analyzing comprising introducing the sample ions into a mass spectrometer and analyzing the sample ions in the mass spectrometer.

15. The method according to claim 9, wherein the porous substrate is paper.

16. The system according to claim 15, wherein the paper is filter paper.

* * * * *